(12) United States Patent
Hashimoto et al.

(10) Patent No.: US 7,939,302 B2
(45) Date of Patent: *May 10, 2011

(54) PROCESS FOR PRODUCING DIPEPTIDES

(75) Inventors: Shin-ichi Hashimoto, Hofu (JP);
Kazuhiko Tabata, Machida (JP)

(73) Assignee: Kyowa Hakko Bio Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/400,996

(22) Filed: Mar. 10, 2009

(65) Prior Publication Data

US 2009/0269806 A1 Oct. 29, 2009

Related U.S. Application Data

(62) Division of application No. 11/165,211, filed on Jun. 24, 2005, now Pat. No. 7,514,243.

(30) Foreign Application Priority Data

Jun. 25, 2004 (JP) ................................. 2004-189011

(51) Int. Cl.
C12P 1/00 (2006.01)
C12P 13/00 (2006.01)
C12P 7/40 (2006.01)

(52) U.S. Cl. ........................... 435/128; 435/41; 435/136

(58) Field of Classification Search .......................... None
See application file for complete search history.

(56) References Cited

U.S. PATENT DOCUMENTS

| 6,319,696 B1 * | 11/2001 | Kishino et al. | |
|---|---|---|---|
| 7,112,425 B2 * | 9/2006 | Gondry et al. | |
| 7,514,242 B2 * | 4/2009 | Hashimoto et al. | 435/128 |
| 2002/0064834 A1 * | 5/2002 | Doekel et al. | |
| 2004/0171106 A1 * | 9/2004 | Hashimoto et al. | |

FOREIGN PATENT DOCUMENTS

| CA | 2 334 079 | | 1/2000 |
|---|---|---|---|
| EP | 1 096 011 | | 5/2001 |
| EP | 1 529 837 | | 5/2005 |
| WO | 00/03009 | * | 1/2000 |
| WO | 2004/000879 | | 12/2003 |

OTHER PUBLICATIONS

Takahashi et al., "Cloning of L-Amino Acid Deaminase Gene from Proteus vulgaris", Biosci. Biotech. J. Biochem., vol. 63, No. 12 (1999) 2244-47.
Tanizawa, et al., "Thermostable D-Amino Acid Aminotransferase from a Thermophilic Bacillus Species", J. Bio. Chem., vol. 264, No. 5 (1989) 2445-49.
Yazgan, et al., "Bacilysin biosynthesis by a partially-purified enzyme fraction from Bacillus subtilis", Enzyme and Microbial Technology, vol. 29 (2001) 400-06.
Sakajoh, et al., "Cell-free synthesis of the dipeptide antibiotic bacilysin", Journal of Industrial Microbiology, vol. 2 (1987) 201-08.
Kunst, et al., "The complete genome sequence of the Gram-positive bacterium Bacillus subtilis", Nature, vol. 390 (1997) 249-56.
Database Unitprot, Feb. 1, 1995, XP002314261, Database Accession No. P39641.
Database Uniprot, Oct. 1, 2002, XP002314262, Database Accesion No. Q8KWT3.
Khumtaveeporn, et al., "Expanded structural and stereospecificity in peptide synthesis with chemically modified mutants of subtilisin", Tetrahedron: Asymmetry, vol. 10 (1999) 2563-72.
NCBI Accession No. AAM90576, version AAM90576.1 GI:22085777, submitted Jul. 2, 2001 BacD [Bacillus amyloliquefaciens].
NCBI Accession No. AAM90571, version AAM90571.1 GI:22085769, submitted Jul. 2, 2001 BacD [Bacillus subtilis].
Henrich, et al., "Peptidase D Gene (pepD) of *Escherichia coli* K-12: Nucleotide Sequence, Transcript Mapping and Comparison with Other Peptidase Genes", Journal of Bacteriology, vol. 172, No. 8 (1990) 4641-51.
Olson, et al., "Identification and Characterization of dppA, an *Escherichia coli* Gene Encoding a Periplasmic Dipeptide Transport Protein", Journal of Bacteriology, vol. 173, No. 1 (1991) 234-44.
Steinborn, et al., EMBL Accession No. AF396778, created Aug. 2, 2002.
Asano, et al., "Properties of a Novel D-Stereospecific Aminopeptidase from Ochrobactrum anthropi", J. Biol. Chem., vol. 264, No. 24 (1989) 14233-39.

* cited by examiner

*Primary Examiner* — Anand U Desai
*Assistant Examiner* — Iqbal H Chowdhury
(74) *Attorney, Agent, or Firm* — Fitzpatrick, Cella, Harper & Scinto

(57) ABSTRACT

The present invention provides a process for producing a dipeptide which comprises culturing in a medium a microorganism which has the ability to produce a protein having the activity to form the dipeptide from one or more kinds of amino acids and which has the ability to produce at least one of said one or more kinds of amino acids, allowing the dipeptide to form and accumulate in the medium, and recovering the dipeptide from the medium.

11 Claims, 6 Drawing Sheets

PROCESS FOR PRODUCING DIPEPTIDES

This application is a division of application Ser. No. 11/165,211 filed Jun. 24, 2005, which in turn claims benefit of JP 2004-189011, filed Jun. 25, 2004, the entire contents of both of which are incorporated herein by reference.

BACKGROUND OF THE INVENTION

The present invention relates to a process for producing a dipeptide which comprises culturing in a medium a microorganism which has the ability to produce a protein having the activity to form the dipeptide from one or more kinds of amino acids and which has the ability to produce at least one of said one or more kinds of amino acids, allowing the dipeptide to form and accumulate in the medium, and recovering the dipeptide from the medium.

At present, many of the amino acids are produced by the so-called fermentation method (Hiroshi Soda, et al., Amino Acid Fermentation, Gakkai Shuppan Center (1986) and Biotechnology 2nd ed., Vol. 6, Products of Primary Metabolism, VCH Verlagsgesellschaft mbH, Weinheim (1996)). The fermentation method as used herein refers to a method in which a microorganism is cultured in a medium comprising inexpensive substances such as glucose, acetic acid, methanol, ammonia, ammonium sulfate and corn steep liquor to obtain a desired amino acid by utilizing the metabolic activity of the microorganism. The fermentation method is excellent as a method for producing amino acids from inexpensive materials with light burdens on the environment.

As for the method for large-scale peptide synthesis, chemical synthesis methods (liquid phase method and solid phase method), enzymatic synthesis methods and biological synthesis methods utilizing recombinant DNA techniques are known. Currently, the enzymatic synthesis methods and biological synthesis methods are employed for the synthesis of long-chain peptides longer than 50 residues, and the chemical synthesis methods and enzymatic synthesis methods are mainly employed for the synthesis of dipeptides.

In the synthesis of dipeptides by the chemical synthesis methods, operations such as introduction and removal of protective groups for functional groups are necessary, and racemates are also formed. The chemical synthesis methods are thus considered to be disadvantageous in respect of cost and efficiency. They are unfavorable also from the viewpoint of environmental hygiene because of the use of large amounts of organic solvents and the like.

As to the synthesis of dipeptides by the enzymatic methods, the following methods are known: a method utilizing reverse reaction of protease (J. Biol. Chem., 119, 707-720 (1937)); methods utilizing thermostable aminoacyl t-RNA synthetase (Japanese Published Unexamined Patent Application No. 146539/83, Japanese Published Unexamined Patent Application No. 209991/83, Japanese Published Unexamined Patent Application No. 209992/83 and Japanese Published Unexamined Patent Application No. 106298/84); a method utilizing reverse reaction of proline iminopeptidase (WO03/010307 pamphlet); and methods utilizing non-ribosomal peptide synthetase (hereinafter referred to as NRPS) (Chem. Biol., 7, 373-384 (2000), FEBS Lett., 498, 42-45 (2001), U.S. Pat. No. 5,795,738 and U.S. Pat. No. 5,652,116).

However, the method utilizing reverse reaction of protease requires introduction and removal of protective groups for functional groups of amino acids used as substrates, which causes difficulties in raising the efficiency of peptide-forming reaction and in preventing peptidolytic reaction. The methods utilizing thermostable aminoacyl t-RNA synthetase have the defects that the expression of the enzyme and the prevention of side reactions forming by-products other than the desired products are difficult. The method utilizing proline iminopeptidase requires amidation of one of the amino acids used as substrates. The methods utilizing NRPS are inefficient in that the supply of coenzyme 4'-phosphopantetheine is necessary.

In addition to the above defects, these methods are disadvantageous in respect of production cost because all of them use amino acids or derivatives thereof as substrates.

On the other hand, there exist a group of peptide synthetases that have enzyme molecular weight lower than that of NRPS and do not require coenzyme 4'-phosphopantetheine; for example, γ-glutamylcysteine synthetase, glutathione synthetase, D-alanyl-D-alanine (D-Ala-D-Ala) ligase, and poly-γ-glutamate synthetase. Most of these enzymes utilize D-amino acids as substrates or catalyze peptide bond formation at the γ-carboxyl group. Because of such properties, they can not be used for the synthesis of dipeptides by peptide bond formation at the α-carboxyl group of L-amino acid.

It is reported that a protein bearing no similarity to NRPS (albC gene product) is responsible for the synthesis of the cyclo(L-phenylalanyl-L-leucine) structure in *Streptomyces noursei* ATCC 11455 known as a strain producing the antibiotic albonoursin and that albonoursin was detected when cyclo dipeptide oxidase was made to act on the culture broth of *Escherichia coli* and *Streptomyces lividans* into which the albC gene was introduced (Chemistry & Biol., 9, 1355-1364 (2002)). However, there is no report that the albC gene product forms a straight-chain dipeptide.

The only known example of an enzyme capable of dipeptide synthesis by the activity to form a peptide bond at the α-carboxyl group of L-amino acid is bacilysin (dipeptide antibiotic derived from a microorganism belonging to the genus *Bacillus*) synthetase. Bacilysin synthetase is known to have the activity to synthesize bacilysin [L-alanyl-L-anticapsin (L-Ala-L-anticapsin)] and L-alanyl-L-alanine (L-Ala-L-Ala), but there is no information about its activity to synthesize other dipeptides (J. Ind. Microbiol., 2, 201-208 (1987) and Enzyme. Microbial. Technol., 29, 400-406 (2001)).

As for the bacilysin biosynthetase genes in *Bacillus subtilis* 168 whose entire genome information has been clarified (Nature, 390, 249-256 (1997)), it is known that the productivity of bacilysin is increased by amplification of bacilysin operons containing ORFs ywfA-F (WO00/03009 pamphlet). However, it is not known whether an ORF encoding a protein having the activity to ligate two or more amino acids by peptide bond is contained in these ORFs, and if contained, which ORF encodes the protein.

That is, no method has so far been known for producing a dipeptide consisting of one or more kinds of amino acids by fermentation.

An object of the present invention is to provide a process for producing a dipeptide which comprises culturing in a medium a microorganism which has the ability to produce a protein having the activity to form the dipeptide from one or more kinds of amino acids and which has the ability to produce at least one of said one or more kinds of amino acids, allowing the dipeptide to form and accumulate in the medium, and recovering the dipeptide from the medium.

SUMMARY OF THE INVENTION

The present invention relates to the following (1) to (15).
(1) A process for producing a dipeptide, which comprises: culturing in a medium a microorganism which has the ability to produce a protein having the activity to form the dipeptide from one or more kinds of amino acids and which has the ability to produce at least one of said one or more kinds of amino acids; allowing the dipeptide to form and accumulate in the medium; and recovering the dipeptide from the medium.

(2) The process according to the above (1), wherein the protein having the activity to form the dipeptide from one or more kinds of amino acids is a protein selected from the group consisting of the following [1] to [11]:
  [1] a protein having the amino acid sequence shown in any of SEQ ID NOS: 1 to 8;
  [2] a protein consisting of an amino acid sequence wherein one or more amino acid residues are deleted, substituted or added in the amino acid sequence shown in any of SEQ ID NOS: 1 to 8 and having the activity to form the dipeptide from one or more kinds of amino acids;
  [3] a protein consisting of an amino acid sequence which has 65% or more homology to the amino acid sequence shown in any of SEQ ID NOS: 1 to 8 and having the activity to form the dipeptide from one or more kinds of amino acids;
  [4] a protein having an amino acid sequence which has 80% or more homology to the amino acid sequence shown in SEQ ID NO: 17 and having the activity to form the dipeptide from one or more kinds of amino acids;
  [5] a protein having the amino acid sequence shown in SEQ ID NO: 37 or 38;
  [6] a protein consisting of an amino acid sequence wherein one or more amino acid residues are deleted, substituted or added in the amino acid sequence shown in SEQ ID NO: 37 or 38 and having the activity to form the dipeptide from one or more kinds of amino acids;
  [7] a protein consisting of an amino acid sequence which has 65% or more homology to the amino acid sequence shown in SEQ ID NO: 37 or 38 and having the activity to form the dipeptide from one or more kinds of amino acids;
  [8] a protein having non-ribosomal peptide synthetase (hereinafter referred to as NRPS) activity;
  [9] a protein having the amino acid sequence shown in SEQ ID NO: 43;
  [10] a protein consisting of an amino acid sequence wherein one or more amino acid residues are deleted, substituted or added in the amino acid sequence shown in SEQ ID NO: 43 and having the activity to form the dipeptide from one or more kinds of amino acids; and
  [11] a protein consisting of an amino acid sequence which has 65% or more homology to the amino acid sequence shown in SEQ ID NO: 43 and having the activity to form the dipeptide from one or more kinds of amino acids.

(3) The process according to the above (1) or (2), wherein the protein having the activity to form the dipeptide from one or more kinds of amino acids is a protein encoded by DNA selected from the group consisting of the following [1] to [8]:
  [1] DNA having the nucleotide sequence shown in any of SEQ ID NOS: 9 to 16 and 36;
  [2] DNA which hybridizes with DNA having a nucleotide sequence complementary to the nucleotide sequence shown in any of SEQ ID NOS: 9 to 16 and 36 under stringent conditions and which encodes a protein having the activity to form the dipeptide from one or more kinds of amino acids;
  [3] DNA having a nucleotide sequence which has 80% or more homology to the nucleotide sequence shown in SEQ ID NO: 18 and encoding a protein having the activity to form the dipeptide from one or more kinds of amino acids;
  [4] DNA having the nucleotide sequence shown in SEQ ID NO: 39 or 40;
  [5] DNA which hybridizes with DNA having a nucleotide sequence complementary to the nucleotide sequence shown in SEQ ID NO: 39 or 40 under stringent conditions and which encodes a protein having the activity to form the dipeptide from one or more kinds of amino acids;
  [6] DNA encoding a protein having NRPS activity;
  [7] DNA having the nucleotide sequence shown in SEQ ID NO: 44; and
  [8] DNA which hybridizes with DNA having a nucleotide sequence complementary to the nucleotide sequence shown in SEQ ID NO: 44 under stringent conditions and which encodes a protein having the activity to form the dipeptide from one or more kinds of amino acids.

(4) The process according to the above (1), wherein the microorganism which has the ability to produce a protein having the activity to form the dipeptide from one or more kinds of amino acids is a microorganism carrying a recombinant DNA comprising the DNA selected from the group consisting of [1] to [8] of the above (3).

(5) The process according to any of the above (1) to (4), wherein the ability to produce an amino acid is acquired by a method selected from the group consisting of the following [1] to [5]:
  [1] a method in which at least one of the regulation of the biosynthesis of the amino acid is reduced or eliminated;
  [2] a method in which the expression of at least one of the enzymes involved in the biosynthesis of the amino acid is enhanced;
  [3] a method in which the copy number of at least one of the enzyme genes involved in the biosynthesis of the amino acid is increased;
  [4] a method in which at least one of the metabolic pathways branching from the biosynthetic pathway of the amino acid into metabolites other than the amino acid is weakened or blocked; and
  [5] a method in which a cell strain having a higher resistance to an analogue of the amino acid as compared with a wild-type strain is selected.

(6) The process according to any of the above (1) to (5), wherein the microorganism is a microorganism belonging to the genus *Escherichia, Corynebacterium, Bacillus, Serratia, Pseudomonas* or *Streptomyces*.

(7) The process according to the above (6), wherein the microorganism belonging to the genus *Escherichia, Corynebacterium, Bacillus, Serratia, Pseudomonas* or *Streptomyces* is *Escherichia coli, Corynebacterium glutamicum, Corynebacterium ammoniagenes, Corynebacterium lactofermentum, Corynebacterium flavum, Corynebacterium efficiens, Bacillus subtilis, Bacillus megaterium, Serratia marcescens, Pseudomonas putida, Pseudomonas aeruginosa, Streptomyces coelicolor* or *Streptomyces lividans*.

(8) The process according to any of the above (1) to (5), wherein the microorganism is a microorganism in which the activities of one or more kinds of peptidases and one or more kinds of proteins having peptide-permeating/transporting activity (hereinafter referred to also as peptide-permeating/transporting proteins) are reduced or lost.

(9) The process according to any of the above (1) to (5), wherein the microorganism is a microorganism in which the activities of three or more kinds of peptidases are reduced or lost.

(10) The process according to the above (8) or (9), wherein the peptidase is a protein having the amino acid sequence shown in any of SEQ ID NOS: 45 to 48, or a protein having an amino acid sequence which has 80% or more homology to the amino acid sequence shown in any of SEQ ID NOS: 45 to 48 and having peptidase activity.

(11) The process according to the above (8) or (10), wherein the peptide-permeating/transporting protein is a protein having the amino acid sequence shown in any of SEQ ID NOS: 49 to 53, or a protein having an amino acid sequence which has 80% or more homology to the amino acid sequence shown in any of SEQ ID NOS: 49 to 53 and having peptide-permeating/transporting activity.

(12) The process according to any of the above (8) to (11), wherein the microorganism is a microorganism belonging to the genus *Escherichia, Bacillus* or *Corynebacterium*.

(13) The process according to the above (12), wherein the microorganism belonging to the genus *Escherichia, Bacillus* or *Corynebacterium* is *Escherichia coli, Corynebacterium glutamicum, Corynebacterium ammoniagenes, Corynebacterium lactofermentum, Corynebacterium flavum, Corynebacterium efficiens, Bacillus subtilis* or *Bacillus megaterium*.

(14) The process according to any of the above (1) to (13), wherein the amino acid is an amino acid selected from the group consisting of L-alanine, L-glutamine, L-glutamic acid, glycine, L-valine, L-leucine, L-isoleucine, L-proline, L-phenylalanine, L-tryptophan, L-methionine, L-serine, L-threonine, L-cysteine, L-asparagine, L-tyrosine, L-lysine, L-arginine, L-histidine, L-aspartic acid, L-α-aminobutyric acid, L-4-hydroxyproline, L-3-hydroxyproline, L-ornithine and L-citrulline.

(15) The process according to any of the above (1) to (14), wherein the dipeptide is a dipeptide represented by formula (I):

$$R^1\text{-}R^2 \quad (I)$$

(wherein $R^1$ and $R^2$, which may be the same or different, each represent an amino acid selected from the group consisting of L-alanine, L-glutamine, L-glutamic acid, glycine, L-valine, L-leucine, L-isoleucine, L-proline, L-phenylalanine, L-tryptophan, L-methionine, L-serine, L-threonine, L-cysteine, L-asparagine, L-tyrosine, L-lysine, L-arginine, L-histidine, L-aspartic acid, L-α-aminobutyric acid, L-4-hydroxyproline, L-3-hydroxyproline, L-ornithine and L-citrulline.

The present invention provides a process for producing a dipeptide which comprises culturing in a medium a microorganism which has the ability to produce a protein having the activity to form the dipeptide from one or more kinds of amino acids and which has the ability to produce at least one of said one or more kinds of amino acids, allowing the dipeptide to form and accumulate in the medium, and recovering the dipeptide from the medium.

Figure 1:
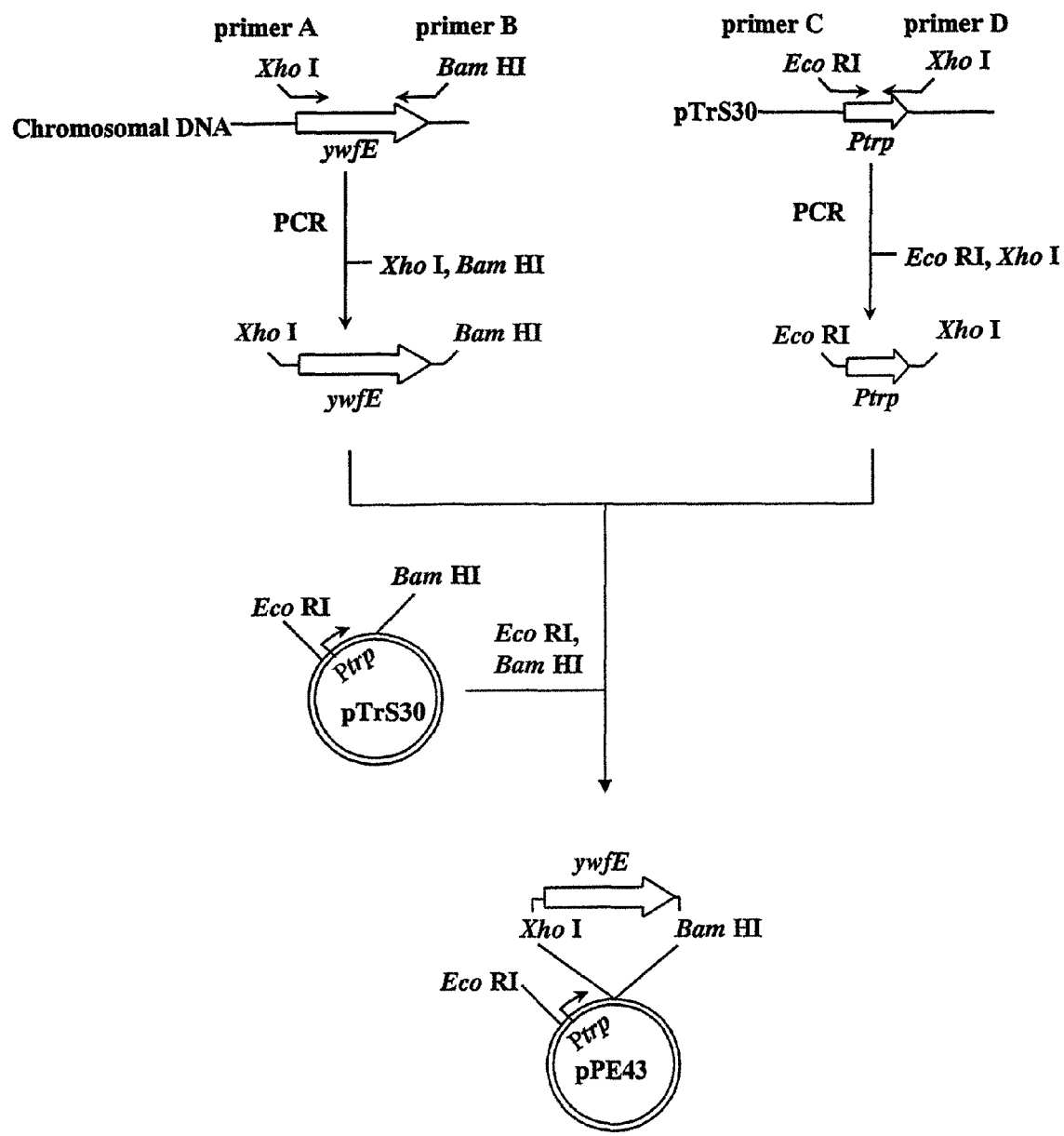
FIG. 1 shows the steps for constructing plasmid pPE43.

EXPLANATION OF SYMBOLS ywfE: ywfE gene derived from *Bacillus subtilis* 168
Ptrp: Tryptophan promoter gene
PT5: T5 promoter
$Amp^r$: Ampicillin resistance gene
$lacI^q$ Lactose repressor gene
albC: albC gene or albC-analogous gene
ald: ald gene
$pheA^{fbr}$: feedback-resistant pheA gene
$aroF^{fbr}$: feedback-resistant aroF gene

DETAILED DESCRIPTION OF THE INVENTION

The protein having the activity to form a dipeptide from one or more kinds of amino acids used in the production process of the present invention may be any protein that has the activity to form a dipeptide wherein the same or different amino acids are linked by peptide bond from one or more kinds of amino acids. Examples of the proteins include:

[1] a protein having the amino acid sequence shown in any of SEQ ID NOS: 1 to 8;

[2] a protein consisting of an amino acid sequence wherein one or more amino acid residues are deleted, substituted or added in the amino acid sequence shown in any of SEQ ID NOS: 1 to 8 and having the activity to form a dipeptide from one or more kinds of amino acids;

[3] a protein consisting of an amino acid sequence which has 65% or more homology to the amino acid sequence shown in any of SEQ ID NOS: 1 to 8 and having the activity to form a dipeptide from one or more kinds of amino acids;

[4] a protein having an amino acid sequence which has 80% or more homology to the amino acid sequence shown in SEQ ID NO: 17 and having the activity to form a dipeptide from one or more kinds of amino acids;

[5] a protein having the amino acid sequence shown in SEQ ID NO: 37 or 38;

[6] a protein consisting of an amino acid sequence wherein one or more amino acid residues are deleted, substituted or added in the amino acid sequence shown in SEQ ID NO: 37 or 38 and having the activity to form a dipeptide from one or more kinds of amino acids;

[7] a protein consisting of an amino acid sequence which has 65% or more homology to the amino acid sequence shown in SEQ ID NO: 37 or 38 and having the activity to form a dipeptide from one or more kinds of amino acids;

[8] a protein having NRPS activity;

[9] a protein having the amino acid sequence shown in SEQ ID NO: 43;

[10] a protein consisting of an amino acid sequence wherein one or more amino acid residues are deleted, substituted or added in the amino acid sequence shown in SEQ ID NO: 43 and having the activity to form a dipeptide from one or more kinds of amino acids; and

[11] a protein consisting of an amino acid sequence-which has 65% or more homology to the amino acid sequence shown in SEQ ID NO: 43 and having the activity to form a dipeptide from one or more kinds of amino acids.

In the present invention, the amino acids are those which are produced by the microorganisms used in the production process of the present invention described below, preferably L-amino acids and glycine, more preferably L-alanine, L-glutamine, L-glutamic acid, L-valine, L-leucine, L-isoleucine, L-proline, L-phenylalanine, L-tryptophan, L-methionine, L-serine, L-threonine, L-cysteine, L-asparagine, L-tyrosine, L-lysine, L-arginine, L-histidine, L-aspartic acid, L-α-aminobutyric acid, L-4-hydroxyproline, L-3-hydroxyproline, L-ornithine, L-citrulline and glycine, further preferably L-alanine, L-glutamine, L-glutamic acid, L-valine, L-leucine, L-isoleucine, L-proline, L-phenylalanine, L-tryptophan, L-methionine, L-serine, L-threonine, L-cysteine, L-asparagine, L-tyrosine, L-lysine, L-arginine, L-histidine, L-aspartic acid, L-α-aminobutyric acid and glycine.

The above protein consisting of an amino acid sequence wherein one or more amino acid residues are deleted, substituted or added and having the activity to form a dipeptide from one or more kinds of amino acids can be obtained, for example, by introducing a site-directed mutation into DNA encoding a protein consisting of the amino acid sequence shown in any of SEQ ID NOS: 1 to 8, 37, 38 and 43 by site-directed mutagenesis described in Molecular Cloning, A Laboratory Manual, Third Edition, Cold Spring Harbor Laboratory Press (2001) (hereinafter referred to as Molecular Cloning, Third Edition); Current Protocols in Molecular Biology, John Wiley & Sons (1987-1997) (hereinafter referred to as Current Protocols in Molecular Biology); Nucleic Acids Research, 10, 6487 (1982); Proc. Natl. Acad. Sci. USA, 79, 6409 (1982); Gene, 34, 315 (1985); Nucleic Acids Research, 13, 4431 (1985); Proc. Natl. Acad. Sci. USA, 82, 488 (1985), etc.

The number of amino acid residues which are deleted, substituted or added is not specifically limited, but is within the range where deletion, substitution or addition is possible by known methods such as the above site-directed mutagenesis. The suitable number is 1 to dozens, preferably 1 to 20, more preferably 1 to 10, further preferably 1 to 5.

The expression "one or more amino acid residues are deleted, substituted or added in any of the amino acid sequences shown in any of SEQ ID NOS: 1 to 8, 37, 38 and 43" means that the amino acid sequence may contain deletion, substitution or addition of a single or plural amino acid residues at an arbitrary position therein.

Amino acid residues that may be substituted are, for example, those which are not conserved in all of the amino acid sequences shown in SEQ ID NOS: 1 to 8, 37 and 38, or both of the amino acid sequence of a known NRPS and that shown in SEQ ID NO: 43 when the sequences are compared using known alignment software. An example of known alignment software is alignment analysis software contained in gene analysis software Genetyx (Software Development Co., Ltd.). As analysis parameters for the analysis software, default values can be used.

Deletion or addition of amino acid residues may be contained, for example, in the N-terminal region or the C-terminal region of the amino acid sequence shown in any of SEQ ID NOS: 1 to 8, 37, 38 and 43.

Deletion, substitution and addition may be simultaneously contained in one sequence, and amino acids to be substituted or added may be either natural or not. Examples of the natural amino acids are L-alanine, L-asparagine, L-aspartic acid, L-glutamine, L-glutamic acid, glycine, L-arginine, L-histidine, L-isoleucine, L-leucine, L-lysine, L-methionine, L-phenylalanine, L-proline, L-serine, L-threonine, L-tryptophan, L-tyrosine, L-valine and L-cysteine.

The following are examples of the amino acids capable of mutual substitution. The amino acids in the same group can be mutually substituted.

Group A: leucine, isoleucine, norleucine, valine, norvaline, alanine, 2-aminobutanoic acid, methionine, O-methylserine, t-butylglycine, t-butylalanine, cyclohexylalanine Group B: aspartic acid, glutamic acid, isoaspartic acid, isoglutamic acid, 2-aminoadipic acid, 2-aminosuberic acid Group C: asparagine, glutamine Group D: lysine, arginine, ornithine, 2,4-diaminobutanoic acid, 2,3-diaminopropionic acid Group E: proline, 3-hydroxyproline, 4-hydroxyproline Group F: serine, threonine, homoserine Group G: phenylalanine, tyrosine In order that the protein of the present invention may have the activity to form a dipeptide from one or more kinds of amino acids, it is desirable that the homology of its amino acid sequence to the amino acid sequence shown in any of SEQ ID NOS: 1 to 8, 37, 38 and 43, preferably the amino acid sequence shown in SEQ ID NO: 1, is 65% or more, preferably 75% or more, more preferably 85% or more, further preferably 90% or more, particularly preferably 95% or more, and most preferably 98% or more.

The homology among amino acid sequences and nucleotide sequences can be determined by using algorithm BLAST by Karlin and Altschul [Proc. Natl. Acad. Sci. USA, 90, 5873 (1993)] and FASTA [Methods Enzymol., 183, 63 (1990)]. On the basis of the algorithm BLAST, programs such as BLASTN and BLASTX have been developed [J. Mol. Biol., 215, 403 (1990)]. When a nucleotide sequence is analyzed by BLASTN on the basis of BLAST, the parameters, for instance, are as follows: score=100 and wordlength=12. When an amino acid sequence is analyzed by BLASTX on the basis of BLAST, the parameters, for instance, are as follows: score=50 and wordlength=3. When BLAST and Gapped BLAST programs are used, default parameters of each program are used. The specific techniques for these analyses are known.

The amino acid sequence shown in SEQ ID NO: 17 is a region conserved among the proteins having the amino acid sequences shown in SEQ ID NOS: 1 to 7 and is also a region corresponding to the consensus sequence of proteins having Ala-Ala ligase activity derived from various microorganisms.

Proteins having an amino acid sequence which has 80% or more, preferably 90% or more, further preferably 95% or more homology to the amino acid sequence shown in SEQ ID NO: 17 and having the activity to form a dipeptide from one or more kinds of amino acids are also included in the proteins produced by the microorganisms used in the production process of the present invention.

In order that the protein having an amino acid sequence which has 80% or more, preferably 90% or more, further preferably 95% or more homology to the amino acid sequence shown in SEQ ID NO: 17 may have the activity to form a dipeptide from one or more kinds of amino acids, it is desirable that the homology of its amino acid sequence to the amino acid sequence shown in any of SEQ ID NOS: 1 to 8 is at least 80% or more, usually 90% or more, and particularly 95% or more.

The homology among amino acid sequences can be determined by using BLAST or FASTA as described above.

It is possible to confirm that the proteins of the above [1] to [11] are proteins having the activity to form a dipeptide from one or more kinds of amino acids, for example, in the following manner. That is, a transformant expressing the protein is prepared by recombinant DNA techniques, the protein of the present invention is produced using the transformant, and then the protein of the present invention, one or more kinds of amino acids and ATP are allowed to be present in an aqueous medium, followed by HPLC analysis or the like to know whether a dipeptide is formed and accumulated in the aqueous medium.

The DNA used in the production process of the present invention may be any DNA encoding a protein having the activity to form a dipeptide wherein the same or different amino acids are linked by peptide bond from one or more kinds of amino acids. Examples of the DNAs include:

[12] DNA having the nucleotide sequence shown in any of SEQ ID NOS: 9 to 16 and 36;

[13] DNA which hybridizes with DNA having a nucleotide sequence complementary to the nucleotide sequence shown in any of SEQ ID NOS: 9 to 16 and 36 under stringent conditions and which encodes a protein having the activity to form a dipeptide from one or more kinds of amino acids;

[14] DNA having a nucleotide sequence which has 80% or more homology to the nucleotide sequence shown in SEQ ID NO: 18 and encoding a protein having the activity to form a dipeptide from one or more kinds of amino acids;

[15] DNA having the nucleotide sequence shown in SEQ ID NO: 39 or 40;

[16] DNA which hybridizes with DNA having a nucleotide sequence complementary to the nucleotide sequence shown in SEQ ID NO: 39 or 40 under stringent conditions and which encodes a protein having the activity to form a dipeptide from one or more kinds of amino acids;

[17] DNA encoding a protein having NRPS activity;

[18] DNA having the nucleotide sequence shown in SEQ ID NO: 44; and

[19] DNA which hybridizes with DNA having a nucleotide sequence complementary to the nucleotide sequence shown in SEQ ID NO: 44 under stringent conditions and which encodes a protein having the activity to form a dipeptide from one or more kinds of amino acids.

The above DNA capable of hybridization under stringent conditions refers to DNA which is obtained by colony hybridization, plaque hybridization, Southern blot hybridization, or the like using a part or the whole of the DNA having a nucleotide sequence complementary to the nucleotide sequence shown in any of SEQ ID NOS: 9 to 16, 36, 39, 40 and 44 as a probe. A specific example of such DNA is DNA which can be identified by performing hybridization at 65° C. in the presence of 0.7 to 1.0 mol/l, preferably 0.9 mol/l sodium chloride using a filter with colony- or plaque-derived DNA immobilized thereon, and then washing the filter at 65° C. with a 0.1 to 2-fold conc., preferably 0.1-fold conc. SSC solution (1-fold conc. SSC solution: 150 mmol/l sodium chloride and 15 mmol/l sodium citrate). Hybridization can be carried out according to the methods described in Molecular Cloning, Third Edition; Current Protocols in Molecular Biology; DNA Cloning 1: Core Techniques, A Practical Approach, Second Edition, Oxford University (1995), etc. Specifically, the hybridizable DNA includes DNA having at least 75% or more homology, preferably 85% or more homology, further preferably 90% or more homology, particularly preferably 95% or more homology to the nucleotide sequence shown in any of SEQ ID NOS: 9 to 16, 36; 39, 40 and 44 as calculated by use of BLAST or FASTA described above based on the above parameters.

The DNA samples to be subjected to hybridization include, for example, chromosomal DNAs of microorganisms belonging to the same genus, preferably the same species as those having the nucleotide sequence shown in any of SEQ ID NOS: 9 to 16, 36, 39, 40 and 44 on their chromosomal DNAs. It is possible to confirm that the DNA which hybridizes with DNA having the nucleotide sequence shown in any of SEQ ID NOS: 9 to 16, 36, 39, 40 and 44 under stringent conditions is DNA encoding a protein having the activity to form a dipeptide from one or more kinds of amino acids, for example, by producing a protein encoded by the DNA by recombinant DNA techniques and measuring the activity of the protein as described above.

(i) Preparation of DNA Used in the Production Process of the Present Invention

The DNAs used in the production process of the present invention can be obtained by:

(a) Southern hybridization of a chromosomal DNA library from a microorganism, preferably a microorganism belonging to the genus *Bacillus*, using a probe designed based on the nucleotide sequence shown in any of SEQ ID NOS: 9 to 16 and 36, or by PCR [PCR Protocols, Academic Press (1990)] using primer DNAs designed based on the nucleotide sequence shown in any of SEQ ID NOS: 9 to 16 and 36 and, as a template, the chromosomal DNA of a microorganism, preferably a microorganism belonging to the genus *Bacillus*;

(b) Southern hybridization of a chromosomal DNA library from a microorganism, preferably a microorganism belonging to the genus *Streptomyces*, using a probe designed based on the nucleotide sequence shown in SEQ ID NO: 39 or 40, or by PCR using primer DNAs designed based on the nucleotide sequence shown in SEQ ID NO: 3 or 4 and, as a template, the chromosomal DNA of a microorganism, preferably a microorganism belonging to the genus *Streptomyces*; and (c) Southern hybridization of a chromosomal DNA library from a microorganism, preferably a microorganism belonging to the genus *Bacillus, Streptomyces, Pseudomonas* or *Xanthomonas*, using DNA encoding known NRPS, for example, NRPS described in Eur. J. Biochem., 270, 4555 (2003), PCT National Publication No. 512835/03, U.S. Pat. No. 5,795,738 or U.S. Pat. No. 5,652,116, or a probe designed based on the nucleotide sequence shown in SEQ ID NO: 44, or by PCR using primer DNAs designed based on the nucleotide sequence of DNA encoding the above NRPS and, as a template, the chromosomal DNA of a microorganism, preferably a microorganism belonging to the genus *Bacillus, Streptomyces, Pseudomonas* or *Xanthomonas*.

The DNA used in the production process of the present invention can also be obtained by conducting a search through various gene sequence databases for a sequence having 75% or more homology, preferably 85% or more homology, more preferably 90% or more homology, further preferably 95% or more homology, particularly preferably 98% or more homology to the nucleotide sequence of DNA encoding the amino acid sequence shown in any of SEQ ID NOS: 1 to 8, 17, 37, 38 and 43, and obtaining the desired DNA, based on the nucleotide sequence obtained by the search, from a chromosomal DNA or cDNA library of an organism having the nucleotide sequence according to the above-described method.

The obtained DNA, as such or after cleavage with appropriate restriction enzymes, is inserted into a vector by a conventional method, and the obtained recombinant DNA is introduced into a host cell. Then, the nucleotide sequence of the DNA can be determined by a conventional sequencing method such as the dideoxy method [Proc. Natl. Acad. Sci., USA, 74, 5463 (1977)] or by using a nucleotide sequencer such as 373A DNA Sequencer (Perkin-Elmer Corp.).

In cases where the obtained DNA is found to be a partial DNA by the analysis of nucleotide sequence, the full length DNA can be obtained by Southern hybridization of a chromosomal DNA library using the partial DNA as a probe.

It is also possible to prepare the desired DNA by chemical synthesis using a DNA synthesizer (e.g., Model 8905, PerSeptive Biosystems) based on the determined nucleotide sequence of the DNA.

Examples of the DNAs that can be obtained by the above-described method are DNAs having the nucleotide sequences shown in SEQ ID NOS: 9 to 16, 36, 39, 40 and 44.

Examples of the vectors for inserting the above DNA include pBluescriptII KS(+) (Stratagene), pDIRECT [Nucleic Acids Res., 18, 6069 (1990)], pCR-Script Amp SK(+) (Stratagene), pT7 Blue (Novagen, Inc.), pCR II (Invitrogen Corp.) and pCR-TRAP (Genhunter Corp.).

The above host cells include microorganisms belonging to the genus Escherichia. Examples of the microorganisms belonging to the genus Escherichia include Escherichia coli XL1-Blue, Escherichia coli XL2-Blue, Escherichia coli DH1, Escherichia coli MC1000, Escherichia coli ATCC 12435, Escherichia coli W1485, Escherichia coli JM109, Escherichia coli HB101, Escherichia coli No. 49, Escherichia coli W3110, Escherichia coli NY49, Escherichia coli MP347, Escherichia coli NM522 and Escherichia coli ME8415.

Introduction of the recombinant DNA can be carried out by any of the methods for introducing DNA into the above host cells, for example, the method using calcium ion [Proc. Natl. Acad. Sci. USA, 69, 2110 (1972)], the protoplast method (Japanese Published Unexamined Patent Application No. 248394/88) and electroporation [Nucleic Acids Res., 16, 6127 (1988)].

An example of the microorganism carrying the DNA used in the production process of the present invention obtained by the above method is Escherichia coli NM522/pPE43, which is a microorganism carrying a recombinant DNA comprising DNA having the sequence shown in SEQ ID NO: 1.

(ii) Preparation of Microorganisms Having the Ability to Produce Amino Acids

The microorganisms having the ability to produce amino acids used in the process for producing a dipeptide of the present invention include any microorganisms having the ability to produce one or more kinds of amino acids, for example, a strain isolated from nature which inherently has the ability and a microorganism to which the ability to produce at least one kind of amino acid among amino acids constituting a desired dipeptide was artificially imparted by a known method.

Examples of the known methods are:
(a) a method in which at least one of the regulation of the biosynthesis of an amino acid is reduced or eliminated;
(b) a method in which the expression of at least one of the enzymes involved in the biosynthesis of an amino acid is enhanced;
(c) a method in which the copy number of at least one of the enzyme genes involved in the biosynthesis of an amino acid is increased;
(d) a method in which at least one of the metabolic pathways branching from the biosynthetic pathway of an amino acid into metabolites other than the amino acid is weakened or blocked; and
(e) a method in which a cell strain having a higher resistance to an analogue of an amino acid as compared with a wild-type strain is selected.

The above known methods can be used alone or in combination.

The method of the above (a) is specifically described in Agric. Biol. Chem., 43, 105-111 (1979); J. Bacteriol., 110, 761-763 (1972); Appl. Microbiol. Biotechnol., 39, 318-323 (1993), etc. The method of the above (b) is specifically described in Agric. Biol. Chem., 43, 105-111 (1979); J. Bacteriol., 110, 761-763 (1972), etc. The method of the above (c) is specifically described in Appl. Microbiol. Biotechnol., 39, 318-323 (1993); Agric. Biol. Chem., 39, 371-377 (1987), etc. The method of the above (d) is specifically described in Appl. Environ. Microbiol., 38, 181-190 (1979); Agric. Biol. Chem., 42, 1773-1778 (1978), etc. The method of the above (e) is specifically described in Agric. Biol. Chem., 36, 1675-1684 (1972); Agric. Biol. Chem., 41, 109-116 (1977); Agric. Biol. Chem., 37, 2013-2023 (1973), Agric. Biol. Chem., 51, 2089-2094 (1987), etc. Microorganisms having the ability to produce various amino acids can be prepared by referring to the above publications.

Further, as for the preparation of microorganisms having the ability to produce amino acids by the methods of the above (a) to (e), alone or in combination, many examples are described in Biotechnology 2nd ed., Vol. 6, Products of Primary Metabolism (VCH Verlagsgesellschaft mbH, Weinheim, 1996) section 14a and 14b; Advances in Biochemical Engineering/Biotechnology 79, 1-35 (2003); Hiroshi Soda, et al., Amino Acid Fermentation, Gakkai Shuppan Center (1986), etc. In addition to the above, many reports have been made on the methods for preparation of microorganisms having the ability to produce specific amino acids: for example, Japanese Published Unexamined Patent Application No. 164297/03; Agric. Biol. Chem., 39, 153-160 (1975); Agric. Biol. Chem., 39, 1149-1153 (1975); Japanese Published Unexamined Patent Application No. 13599/83; J. Gen. Appl. Microbiol., 4, 272-283 (1958); Japanese Published Unexamined Patent Application No. 94985/88; Agric. Biol. Chem., 37, 2013-2023 (1973); WO 97/15673; Japanese Published Unexamined Patent Application No. 18596/81; Japanese Published Unexamined Patent Application No. 144092/81 and PCT National Publication No. 511086/03. Microorganisms having the ability to produce one or more kinds of amino acids can be prepared by referring to the above publications.

Examples of the microorganisms having the ability to produce amino acids prepared by the above methods include. L-glutamine-producing strains (e.g. a microorganism wherein the glnE gene and/or the glnB gene are deleted), L-alanine-producing strains [e.g. a microorganism wherein the expression of alanine dehydrogenase gene (ald gene) is enhanced], and L-phenylalanine-producing microorganisms (e.g. a microorganism expressing the phenylalanine-feedback-resistant pheA gene and/or the tyrosine-feedback-resistant aroF gene).

The above microorganisms which produce amino acids include any microorganisms to which the methods of the above (a) to (e) can be applied or microorganisms having the above genotypes, preferably procaryotes, more preferably bacteria.

The procaryotes include microorganisms belonging to the genera Escherichia, Serratia, Bacillus, Brevibacterium, Corynebacterium, Microbacterium, Pseudomonas, Agrobacterium, Alicyclobacillus, Anabaena, Anacystis, Arthrobacter, Azotobacter, Chromatium, Erwinia, Methylobacterium, Phormidium, Rhodobacter, Rhodopseudomonas, Rhodospirillum, Scenedesmus, Streptomyces, Synechoccus and Zymomonas, for example, Escherichia coli, Bacillus subtilis, Bacillus megaterium, Bacillus amyloliquefaciens, Bacillus coagulans, Bacillus licheniformis, Bacillus pumilus, Brevibacterium ammoniagenes, Brevibacterium immariophilum, Brevibacterium saccharolyticum, Brevibacterium flavum, Brevibacterium lactofermentum, Corynebacterium glutamicum, Corynebacterium acetoacidophilum, Microbacterium ammoniaphilum, Serratia ficaria, Serratia fonticola, Serratia liquefaciens, Serratia marcescens, Pseudomonas aeruginosa, Pseudomonas putida, Agrobacterium radiobacter, Agrobacterium rhizogenes, Agrobacterium rubi, Anabaena cylindrica, Anabaena doliolum, Anabaena flosaquae, Arthrobacter aurescens, Arthrobacter citreus, Arthrobacter globformis, Arthrobacter hydrocarboglutamicus, Arthrobacter mysorens, Arthrobacter nicotianae, Arthrobacter paraffineus, Arthrobacter protophormiae, Arthrobacter roseoparaffinus, Arthrobacter sulfureus, Arthrobacter ureafaciens, Chromatium buderi, Chromatium tepidum, Chromatium vinosum, Chromatium warmingii, Chromatium fluviatile, Erwinia uredovora, Erwinia carotovora, Erwinia ananas, Erwinia herbicola, Erwinia punctata, Erwinia tereus, Methylobacterium rhodesianum, Methylobacterium extorquens, Phormidium sp. ATCC 29409, Rhodobacter capsulatus, Rhodobacter sphaeroides, Rhodopseudomonas blastica, Rhodopseudomonas marina, Rhodopseudomonas palustris, Rhodospirillum rubrum, Rhodospirillum salexigens, Rhodospirillum salinarum, Streptomyces ambofaciens, Streptomyces aureofaciens, Streptomyces aureus, Streptomyces fungicidicus, Streptomyces griseochromogenes, Streptomyces griseus, Streptomyces lividans, Streptomyces olivogriseus, Streptomyces rameus, Streptomyces tanashiensis, Streptomyces vinaceus and Zymomonas mobilis. Preferred procaryotes include bacteria belonging to the genera Escherichia, Serratia, Bacillus, Brevibacterium, Corynebacterium, Pseudomonas and Streptomyces, for example, the above-mentioned species belonging to the genera Escherichia, Serratia, Bacillus, Brevibacterium, Corynebacterium, Pseudomonas and Streptomyces. More preferred bacteria include Escherichia coli, Corynebacterium glutamicum, Corynebacterium ammoniagenes, Corynebacterium lactofermentum, Corynebacterium flavum, Corynebacterium efficiens, Bacillus subtilis, Bacillus megaterium, Serratia marcescens, Pseudomonas putida, Pseudomonas aeruginosa, Streptomyces coelicolor and Streptomyces lividans, among which Escherichia coli is particularly preferred.

Specific examples of the microorganisms producing amino acids include Escherichia coli JGLE1 and Escherichia coli JGLBE1, which are L-glutamine-producing strains, Escherichia coli JM101 carrying an ald gene expression plasmid, which is an L-alanine-producing strain, Escherichia coli JM101 carrying pPHEA2 and/or an aroF gene expression plasmid, which are L-phenylalanine-producing strains, Escherichia coli JGLE1 and Escherichia coli JGLBE1 carrying an ald gene expression plasmid, which are L-glutamine- and L-alanine-producing strains, Escherichia coli JM101 carrying an ald gene expression plasmid and pPHEA2 and/or an aroF gene expression plasmid, which are L-alanine- and L-phenylalanine-producing strains, and ATCC 21277 strains carrying pPHEA and/or an aroF gene expression plasmid, which are L-threonine- and L-phenylalanine-producing strains.

Further, specific examples of the microorganisms having the ability to produce amino acids include FERM BP-5807 and ATCC 13032 strains producing L-glutamic acid, FERM P-4806 and ATCC 14751 strains producing L-glutamine, ATCC 21148, ATCC 21277 and ATCC 21650 strains producing L-threonine, FERM P-5084 and ATCC 13286 strains producing L-lysine, FERM P-5479, VKPM B-2175 and ATCC 21608 strains producing L-methionine, FERM BP-3757 and ATCC 14310 strains producing L-isoleucine, ATCC 13005 and ATCC 19561 strains producing L-valine, FERM BP-4704 and ATCC 21302 strains producing L-leucine, FERM BP-4121 and ATCC 15108 strains producing L-alanine, ATCC 21523 and FERM BP-6576 strains producing L-serine, FERM BP-2807 and ATCC 19244 strains producing L-proline, FERM P-5616 and ATCC 21831 strains producing L-arginine, ATCC 13232 strain producing L-ornithine, FERM BP-6674 and ATCC 21607 strains producing L-histidine, DSM 10118, DSM 10121, DSM 10123 and FERM BP-1777 strains producing L-tryptophan, ATCC 13281 and ATCC 21669 strains producing L-phenylalanine, ATCC 21652 strain producing L-tyrosine, W3110/pHC34 strain producing L-cysteine (PCT National Publication No. 511086/03), Escherichia coli SOLR/pRH71 producing L-4-hydroxyproline described in WO96/27669, FERM BP-5026 and FERM BP-5409 strains producing L-3-hydroxyproline, and FERM P-5643 and FERM P-1645 strains producing L-citrulline.

The above strains designated by FERM Nos., ATCC Nos., VKPM Nos. and DSM Nos. are available from International Patent Organism Depositary, National Institute of Advanced Industrial Science and Technology (Japan), American Type Culture Collection (U.S.A.), Russian National Collection of Industrial Microorganisms (Russia) and Deutsche Sammlung von Mikroorganismen und Zellkulturen (Germany), respectively.

(iii) Preparation of Microorganisms which have the Ability to Produce a Protein Having the Activity to Form a Dipeptide from One or More Kinds of Amino Acids and which have the Ability to Produce at Least One of Said One or More Kinds of Amino Acids The microorganisms which have the ability to produce a protein having the activity to form a dipeptide from one or more kinds of amino acids and which have the ability to produce at least one of said one or more kinds of amino acids can be prepared by the following methods:

(a) a method of introducing DNA encoding a protein having the activity to form a dipeptide from one or more kinds of amino acids prepared by the method of the above (i) into a microorganism having the ability to produce one or more kinds of amino acids prepared by the method of the above (ii);

(b) a method of imparting, by the method of the above (ii), the ability to produce one or more kinds of amino acids to a microorganism carrying DNA encoding a protein having the activity to form a dipeptide from one or more kinds of amino acids prepared by the method of the above (i);

(c) a method of introducing DNA encoding a protein having the activity to form a dipeptide from one or more kinds of amino acids into a microorganism inherently having the ability to produce one or more kinds of amino acids by the method of the above (i); and (d) a method of imparting the ability to produce one or more kinds of amino acids to a microorganism inherently having the ability to produce a protein having the activity to form a dipeptide from one or more kinds of amino acids by the method of the above (ii).

Introduction of DNA encoding a protein having the activity to form a dipeptide from one or more kinds of amino acids prepared by the method of the above (i) into a microorganism can impart the ability to produce a protein having the activity to form a dipeptide from one or more kinds of amino acids to the microorganism. The ability to produce a protein having the activity to form a dipeptide from one or more kinds of amino acids can be imparted to a microorganism by expressing the DNA prepared by the method of the above (i) in a host cell utilizing the methods described in Molecular Cloning, Third Edition, Current Protocols in Molecular Biology, or the like, for example, in the following manner.

On the basis of the DNA prepared by the method described in the above (i), a DNA fragment of an appropriate length comprising a region encoding the protein is prepared according to need. The productivity of the protein can be enhanced by replacing a nucleotide in the nucleotide sequence of the region encoding the protein so as to make a codon most suitable for the expression in a host cell.

The DNA fragment is inserted downstream of a promoter in an appropriate expression vector to prepare a recombinant DNA.

A transformant producing the protein can be obtained by introducing the recombinant DNA into a host cell suited for the expression vector.

As the host cell, any microorganisms that are capable of expressing the desired gene can be used. Preferred are procaryotes, and more preferred are bacterial cells. Examples of the preferred procaryotes are the procaryotes mentioned in the above (ii).

The microorganism may or may not have the ability to produce one or more kinds of amino acids. When a microorganism without the ability is used as the host cell, a microorganism used in the production process of the present invention can be obtained by preparing a transformant by introducing the recombinant DNA obtained by the above method into the microorganism by the following method, and then imparting the ability to produce one or more kinds of amino acids to the transformant by the method of the above (ii).

The expression vectors that can be employed are those capable of autonomous replication or integration into the chromosome in microorganism cells and comprising a promoter at a position appropriate for the transcription of the DNA used in the production process of the present invention.

When a prokaryote is used as the host cell, it is preferred that the recombinant DNA comprising the DNA used in the production process of the present invention is a recombinant DNA which is capable of autonomous replication in the prokaryote and which comprises a promoter, a ribosome binding sequence, the DNA used in the production process of the present invention, and a transcription termination sequence. The recombinant DNA may further comprise a gene regulating the promoter.

Examples of suitable expression vectors are pBTrp2, pBTac1 and pBTac2 (products of Boehringer Mannheim GmbH), pHelix1 (Roche Diagnostics Corp.), pKK233-2 (Amersham Pharmacia Biotech), pSE280 (Invitrogen Corp.), pGEMEX-1 (Promega Corp.), pQE-8 (Qiagen, Inc.), pET-3 (Novagen, Inc.), pKYP10 (Japanese Published Unexamined Patent Application, No. 110600/83), pKYP200 [Agric. Biol. Chem., 48, 669 (1984)], pLSA1 [Agric. Biol. Chem., 53, 277 (1989)], pGEL1 [Proc. Natl. Acad. Sci. USA, 82, 4306 (1985)], pBluescript II SK(+), pBluescript II KS(−) (Stratagene), pTrS30 [prepared from *Escherichia coli* JM109/pTrS30 (FERM BP-5407)], pTrS32 [prepared from *Escherichia coli* JM109/pTrS32 (FERM BP-5408)], pPAC31 (WO98/12343), pUC19 [Gene, 33, 103 (1985)], pSTV28 (Takara Bio Inc.), pUC118 (Takara Bio Inc.), pPA1 (Japanese Published Unexamined Patent Application No. 233798/88), pWH1520 (MoBiTec), pCS299P (WO00/63388), pVLT31 [Gene, 123, 17 (1993)] and pIJ702 (Genetic Manipulation of *Streptomyces*: a Laboratory Manual: John Innes Foundation).

When a microorganism belonging to the genus *Escherichia* is used as the host cell, any promoters capable of functioning in *Escherichia coli* can be used as the promoter. For example, promoters derived from *Escherichia coli* or phage, such as trp promoter ($P_{trp}$), lac promoter ($P_{lac}$), $P_L$ promoter, $P_R$ promoter and $P_{SE}$ promoter, SPO1 promoter, SPO2 promoter and penP promoter can be used. Artificially designed and modified promoters such as a promoter in which two $P_{trp}$s are combined in tandem, tac promoter, lacT7 promoter and letI promoter, etc. can also be used.

Also useful are promoters such as xylA promoter for the expression in microorganisms belonging to the genus *Bacillus* [Appl. Microbiol. Biotechnol., 35, 594-599 (1991)], P54-6 promoter for the expression in microorganisms belonging to the genus *Corynebacterium* [Appl. Microbiol. Biotechnol., 53, 674-679 (2000)], tac promoter for the expression in microorganisms belonging to the genus *Pseudomonas* [Gene, 123, 17-24 (1993)] and xylA promoter for the expression in microorganisms belonging to the genus *Streptomyces* (Genetic Manipulation of *Streptomyces*: a Laboratory Manual: John Innes Foundation).

It is preferred to use a plasmid in which the distance between the Shine-Dalgarno sequence (ribosome binding sequence) and the initiation codon is adjusted to an appropriate length (e.g., 6 to 18 nucleotides).

In the recombinant DNA wherein the DNA used in the production process of the present invention is ligated to an expression vector, the transcription termination sequence is not essential, but it is preferred to place the transcription termination sequence immediately downstream of the structural gene.

An example of such recombinant DNA is pPE43.

Introduction of the recombinant DNA into microorganism cells can be carried out by any of the methods for introducing DNA into the cells, for example, the method using calcium ion [Proc. Natl. Acad. Sci. USA, 69, 2110 (1972)], the protoplast method (Japanese Published Unexamined Patent Application No. 248394/88) and electroporation [Nucleic Acids Res., 16, 6127 (1988)].

Examples of the microorganisms inherently having the ability to produce one or more kinds of amino acids used in the above method (c) include known strains having the ability to produce amino acids described in the above (ii).

Examples of the microorganisms inherently having the ability to produce a protein having the activity to form a dipeptide from one or more kinds of amino acids used in the above method (d) include: (A) microorganisms belonging to the genus *Bacillus*, more preferably, microorganisms belonging to the genus *Bacillus* which have bacilysin-synthesizing activity, further preferably, microorganisms belonging to a species selected from the group consisting of *Bacillus subtilis*, *Bacillus amyloliquefaciens*, *Bacillus coagulans*, *Bacillus licheniformis*, *Bacillus megaterium* and *Bacillus pumilus*, most preferably, microorganisms selected from the group consisting of the strains *Bacillus subtilis* ATCC 15245, *Bacillus subtilis* ATCC 6633, *Bacillus subtilis* IAM 1213, *Bacillus subtilis* IAM 1107, *Bacillus subtilis* IAM 1214, *Bacillus subtilis* ATCC 9466, *Bacillus subtilis* IAM 1033, *Bacillus subtilis* ATCC 21555, *Bacillus amyloliquefaciens* IFO 3022 and *Bacillus pumilus* NRRL B-12025; and (B) microorganisms belonging to the genus *Streptomyces*, preferably, microorganisms belonging to the genus *Streptomyces* which have the ability to produce albonoursin, more preferably, microorganisms belonging to the species *Streptomyces albulus* or *Streptomyces noursei*.

(iv) Microorganisms in which the Activities of Peptidases And Proteins Having Peptide-Permeating/Transporting Activity are Reduced or Lost The microorganisms used in the production process of the present invention include microorganisms prepared by the method of the above (iii) in which the activities of one or more kinds of peptidases and one or more kinds of proteins having peptide-permeating/transporting activity (hereinafter referred to as peptide-permeating/transporting proteins) are reduced or lost, and those in which the activities of three or more kinds of peptidases are reduced or lost.

Such microorganisms can be obtained, for example, by the following methods: (a) a method of imparting, by the method of the above (iii), the ability to produce a protein having the activity to form a dipeptide from one or more kinds of amino acids and the ability to produce at least one of said one or more kinds of amino acids to a microorganism in which the functions of one or more kinds of peptidases and one or more kinds of peptide-permeating/transporting proteins are reduced or lost, or a microorganism in which the functions of three or more kinds of peptidases are reduced or lost; and (b) a method of reducing or causing loss of the functions of a) one or more kinds of peptidases and one or more kinds of peptide-permeating/transporting proteins or b) three or more kinds of peptidases of a microorganism having the ability to produce a protein having the activity to form a dipeptide from one or more kinds of amino acids and the ability to produce at least one of said one or more kinds of amino acids which can be prepared by the method of the above (iii).

The microorganisms in which the activities of one or more kinds of peptidases and one or more kinds of peptide-permeating/transporting proteins are reduced or lost include microorganisms in which the activities of one or more arbitrary kinds of peptidases and one or more arbitrary kinds of peptide-permeating/transporting proteins are reduced or lost provided that the microorganisms can normally grow, specifically, microorganisms in which the activities of preferably one to nine kinds, more preferably one to seven kinds, further preferably one to four kinds of peptidases and preferably one to five kinds, more preferably one to three kinds, further preferably one or two kinds, particularly preferably one kind of peptide-permeating/transporting protein are reduced or lost.

Examples of such microorganisms are microorganisms in which the activities of one or more kinds of peptidases and one or more kinds of peptide-permeating/transporting proteins are reduced or lost because the nucleotide sequences of one or more kinds of genes encoding peptidases (hereinafter referred to as peptidase genes) and one or more kinds of genes encoding peptide-permeating/transporting proteins (hereinafter referred to as peptide-permeating/transporting protein genes) among the peptidase genes and peptide-permeating/transporting protein genes existing on the genomic DNA of the microorganisms are entirely or partially deleted or said nucleotide sequences contain nucleotide substitutions or additions.

The expression "the activity of peptidase is reduced" means that the peptidolytic activity is reduced, or reduced to normally 80% or less, preferably 50% or less, more preferably 30% or less, further preferably 20% or less, particularly preferably 10% or less, most preferably 5% or less compared with peptidase having none of the above deletions, substitutions and additions of nucleotides.

The peptidolytic activity of a microorganism can be measured by allowing a peptide as a substrate and microorganism cells to be present in an aqueous medium, thereby performing peptidolytic reaction, and then determining the amount of the remaining peptide by a known method, e.g., HPLC analysis.

The above peptidases may be any proteins having peptidolytic activity. Preferred are proteins having high dipeptide-hydrolyzing activity. More preferred are dipeptidases.

Examples of peptidases include: those existing in *Escherichia coli* such as PepA having the amino acid sequence shown in SEQ ID NO: 45, PepB having the amino acid sequence shown in SEQ ID NO: 46, PepD having the amino acid sequence shown in SEQ ID NO: 47, PepN having the amino acid sequence shown in SEQ ID NO: 48, PepP [GenBank accession No. (hereinafter abbreviated as Genbank) AAC75946], PepQ (GenBank AAC76850), PepE (GenBank AAC76991), PepT (GenBank AAC74211), Dcp (GenBank AAC74611) and IadA (GenBank AAC77284); those existing in *Bacillus subtilis* such as AmpS (GenBank AF012285), PepT (GenBank X99339), YbaC (GenBank Z99104), YcdD (GenBank Z99105), YjbG (GenBank Z99110), YkvY (GenBank Z99111), YqjE (GenBank Z99116) and YwaD (GenBank Z99123); and those existing in *Corynebacterium glutamicum* such as proteins having the amino acid sequences represented by BAB97732, BAB97858, BAB98080, BAB98880, BAB98892, BAB99013, BAB99598 and BAB99819 (registration Nos. of DNA Data Bank of Japan). Examples of dipeptidases include PepA, PepB, PepD and PepN having the amino acid sequences shown in SEQ ID NOS: 45 to 48, PepQ, PepE and IadA. Proteins having amino acid sequences which have 80% or more, preferably 90% or more, more preferably 95% or more homology to the amino acid sequence shown in any of SEQ ID NOS: 45 to 48 and having peptidase activity are also included in the proteins having high dipeptide-hydrolyzing activity. The homology among amino acid sequences and nucleotide sequences can be determined by using BLAST, FASTA or the like described above.

The expression "the activity of a peptide-permeating/transporting protein is reduced" means that the peptide-uptaking activity is reduced, or reduced to normally 80% or less, preferably 50% or less, more preferably 30% or less, further preferably 20% or less, particularly preferably 10% or less, most preferably 5% or less compared with a peptide-permeating/transporting protein having none of the above deletions, substitutions and additions of nucleotides.

The peptide-uptaking activity of a microorganism can be measured by allowing a peptide as a substrate and microorganism cells to be present in an aqueous medium, thereby performing peptide-uptaking reaction, and then determining the amount of the remaining peptide by a known method, e.g., HPLC analysis.

The above peptide-permeating/transporting proteins may be any proteins involved in peptide permeation or transport of microorganisms, for example, proteins encoded by genes forming an operon on chromosomal DNA which form a complex on cell membrane to express peptide-uptaking activity and those which have peptide-uptaking activity as individual proteins. Preferred are proteins having high dipeptide-uptaking activity.

Examples of the peptide-permeating/transporting proteins include: those existing in *Escherichia coli* such as DppA having the amino acid sequence shown in SEQ ID NO: 49, DppB having the amino acid sequence shown in SEQ ID NO: 50, DppC having the amino acid sequence shown in SEQ ID NO: 51, DppD having the amino acid sequence shown in SEQ ID NO: 52, DppF having the amino acid sequence shown in SEQ ID NO: 53, OppA (GenBank AAC76569), OppB (GenBank AAC76568), OppC (GenBank AAC76567), OppD (GenBank AAC76566), OppF (GenBank AAC76565), YddO (GenBank AAC74556), YddP (GenBank AAC74557), YddQ (GenBank AAC74558), YddR (GenBank AAC74559), YddS (GenBank AAC74560), YbiK (GenBank AAC73915), MppA (GenBank AAC74411), SapA (GenBank AAC74376), SapB (GenBank AAC74375), SapC (GenBank AAC74374), SapD (GenBank AAC74373) and SapF (GenBank AAC74372); those existing in *Bacillus subtilis* such as DppA (GenBank CAA40002), DppB (GenBank CAA40003), DppC (GenBank CAA40004), DppD (GenBank CAA40005), DppE (GenBank CAA40006), OppA (GenBank CAA39787), OppB (GenBank CAA39788), OppC (GenBank CAA39789), OppD (GenBank CAA39790), OppF (GenBank CAA39791), AppA (GenBank CAA62358), AppB (GenBank CAA62359), AppC (GenBank CAA62360), AppD (GenBank CAA62356), AppF (GenBank CAA62357), YclF (GenBank CAB12175) and YkfD (GenBank CAB13157); and those existing in *Corynebacterium glutamicum* such as proteins having the amino acid sequences represented by BAB99048, BAB99383, BAB99384, BAB99385, BAB99713, BAB99714, BAB99715, BAB99830, BAB99831 and BAB99832 (registration Nos. of DNA Data Bank of Japan). Examples of the proteins having high dipeptide-uptaking activity include DppA, DppB, DppC, DppD and DppF having the amino acid sequences shown in SEQ ID NOS: 49 to 53, and proteins having amino acid sequences which have 80% or more, preferably 90% or more, more preferably 95% or more homology to the amino acid sequence shown in any of SEQ ID NOS: 49 to 53.

The homology among amino acid sequences can be determined by using programs such as BLAST and FASTA described above.

The microorganisms in which the activities of three or more kinds of peptidases are reduced or lost include microorganisms in which the activities of three or more arbitrary kinds of peptidases are reduced or lost provided that the microorganisms can normally grow, specifically, microorganisms in which the activities of preferably three to nine kinds, more preferably three to six kinds, further preferably three or four kinds of peptidases are reduced or lost.

Examples of peptidases include the above-described peptidases and dipeptidases existing in *Escherichia coli, Bacillus subtilis* and *Corynebacterium glutamicum*. Proteins consisting of amino acid sequences which have 80% or more, preferably 90% or more, more preferably 95% or more homology to the amino acid sequence shown in any of SEQ ID NOS: 45 to 48 and having peptidase activity are also included in the proteins having high dipeptide-hydrolyzing activity.

The homology among amino acid sequences can be determined by using programs such as BLAST and FASTA described above.

(v) Preparation of Microorganisms in which the Activities of Peptidases and Peptide-Permeating/Transporting Proteins are Reduced or Lost The microorganisms in which the activities of peptidases and peptide-permeating/transporting proteins are reduced or lost may be obtained by any method capable of preparing such microorganisms. For example, they can be obtained by introducing a deletion, substitution or addition of a nucleotide into peptidase genes and peptide-permeating/transporting protein genes on chromosomal DNAs of microorganisms as described below.

The methods for introducing a deletion, substitution or addition of a nucleotide into a gene on the chromosomal DNA of a microorganism include methods utilizing homologous recombination. An example of the methods utilizing general homologous recombination is a method using a plasmid for homologous recombination prepared by ligating a mutant gene having an introduced nucleotide deletion, substitution or addition to a plasmid DNA incapable of autonomous replication in a host cell into which the nucleotide deletion or the like is to be introduced and carrying a drug resistance gene.

The plasmid for homologous recombination is introduced into a host cell by an ordinary method, followed by selection of a transformant in which the plasmid for homologous recombination has been integrated into the chromosomal DNA by homologous recombination using the drug resistance as a marker. The obtained transformant is cultured using a medium which does not contain the drug for several hours to one day, and then spread on an agar medium containing the drug and on an agar medium without the drug. By selecting a strain which does not grow on the former medium but can grow on the latter medium, the strain in which second homologous recombination occurred on the chromosomal DNA can be obtained. Introduction of a nucleotide deletion, substitution or addition into a desired gene on the chromosomal DNA can be confirmed by determining the nucleotide sequence of a region of the chromosomal DNA containing the gene into which the deletion or the like has been introduced.

By use of the above method, a nucleotide deletion, substitution or addition can be introduced into desired genes on chromosomal DNAs of microorganisms such as those belonging to the genera *Escherichia, Bacillus* and *Corynebacterium*.

Further, a nucleotide deletion, substitution or addition can be efficiently introduced into plural genes by utilizing homologous recombination according to a method using a straight-chain DNA.

Specifically, a straight-chain DNA containing a gene into which a nucleotide deletion, substitution or addition is to be introduced is incorporated into a cell to cause homologous recombination between chromosomal DNA and the introduced straight-chain DNA. This method is applicable to any microorganisms capable of efficiently incorporating a straight-chain DNA. Preferred microorganisms are those belonging to the genera *Escherichia* and *Bacillus*. *Escherichia coli* is more preferred, and *Escherichia coli* expressing a group of recombinant proteins derived from λ phage (Red recombination system) is further preferred.

An example of *Escherichia coli* expressing λ Red recombination system is *Escherichia coli* JM101 carrying pKD46, which is a plasmid DNA comprising a λ Red recombination system gene (available from *Escherichia coli* Genetic Stock Center, Yale University, U.S.A.).

Examples of the DNAs useful for homologous recombination are as follows:

(a) straight-chain DNA in which DNAs having homology to the DNAs present on the outside of a region of chromosomal DNA to be subjected to introduction of a nucleotide deletion, substitution or addition are present at both termini of a drug resistance gene;

(b) straight-chain DNA in which DNAs having homology to the DNAs present on the outside of a region of chromosomal DNA to be subjected to introduction of a nucleotide deletion, substitution or addition are directly ligated to each other;

(c) straight-chain DNA having a drug resistance gene and a gene that can be used for negative selection and in which DNAs having homology to the DNAs present on the outside of a region of chromosomal DNA to be subjected to introduction of a nucleotide deletion, substitution or addition are present at both termini; and (d) straight-chain DNA of the above (a) in which a nucleotide sequence recognized by yeast-derived Flp recombinase [Proc. Natl. Acad. Sci. USA., 82, 5875 (1985)] is additionally present between the drug resistance gene and the DNAs having homology to the DNAs present on the outside of a region of chromosomal DNA.

As the drug resistance gene, any drug resistance genes that impart resistance to a drug to which the host microorganism shows sensitivity can be used. When *Escherichia coli* is used as the host microorganism, examples of the drug resistance genes are kanamycin resistance gene, chloramphenicol resistance gene, gentamicin resistance gene, spectinomycin resistance gene, tetracycline resistance gene and ampicillin resistance gene.

The "gene that can be used for negative selection" refers to a gene that is fatal to a host microorganism under certain culture conditions when the gene is expressed in the host microorganism. Examples of the genes are sacB gene derived from a microorganism belonging to the genus *Bacillus* [Appl. Environ. Microbiol., 59, 1361-1366 (1993)] and rpsL gene derived from a microorganism belonging to the genus *Escherichia* [Genomics, 72, 99-104 (2001)].

The DNAs having homology to the DNAs present on the outside of a region of chromosomal DNA to be subjected to introduction of a substitution or deletion, which exist at both ends of the above straight-chain DNAs, are located in the same direction as that on the chromosomal DNA, and their length is preferably about 10 bp to 100 bp, more preferably about 20 bp to 50 bp, and further preferably about 30 bp to 40 bp.

The nucleotide sequence recognized by yeast-derived Flp recombinase is not specifically limited so long as it is a nucleotide sequence recognized by the said protein and catalyzing homologous recombination. Preferred examples are DNA having the nucleotide sequence shown in SEQ ID NO: 54, and DNA having a nucleotide sequence wherein one to several nucleotides are deleted, substituted or added in the said DNA and having a nucleotide sequence recognized by yeast-derived Flp recombinase and catalyzing homologous recombination.

The expression "having homology" means that the above straight-chain DNA has such a degree of homology that allows occurrence of homologous recombination between the subject region of chromosomal DNA and the straight-chain DNA, specifically, 80% or more homology, preferably 90% or more homology, more preferably 95% or more homology, further preferably 100% homology.

The homology among nucleotide sequences can be determined by using programs such as BLAST and FASTA described above.

The above straight-chain DNA can be prepared by PCR. The desired straight-chain DNA can also be obtained by constructing DNA containing the above straight-chain DNA on plasmid and then carrying out treatment with restriction enzymes.

Examples of the methods for introducing a nucleotide deletion, substitution or addition into the chromosomal DNA of a microorganism include the following Methods 1 to 4.

Method 1:
 A method which comprises introducing the straight-chain DNA of the above (a) or (d) into a host microorganism and selecting a transformant carrying the straight-chain DNA inserted on its chromosomal DNA by homologous recombination using the drug resistance as a marker.

Method 2:
 A method which comprises introducing the straight-chain DNA of the above (b) into the transformant obtained according to the above Method 1 and eliminating the drug resistance gene inserted on its chromosomal DNA by Method 1 to substitute or delete a region of the chromosomal DNA of the microorganism.

Method 3:
 A method which comprises:
 [1] introducing the straight-chain DNA of the above (c) into a host microorganism and selecting a transformant carrying the straight-chain DNA inserted on its chromosomal DNA by homologous recombination using the drug resistance as a marker;

[2] synthesizing DNA by ligating DNAs having homology to the DNAs present on the outside of a region of chromosomal DNA to be subjected to introduction of a substitution or deletion in the same direction as that on the chromosomal DNA, and introducing the synthesized DNA into the transformant obtained in the above [1]; and

[3] culturing the transformant subjected to the operation of the above [2] under conditions such that the gene that can be used for negative selection is expressed, and selecting a strain capable of growing by the culturing as a strain in which the drug resistance gene and the gene that can be used for negative selection are eliminated from the chromosomal DNA.

Method 4:
 A method which comprises:
 [1] introducing the straight-chain DNA of the above (d) into a host microorganism and selecting a transformant carrying the straight-chain DNA inserted on its chromosomal DNA by homologous recombination using the drug resistance as a marker; and

[2] introducing a Flp recombinase gene expression plasmid into the transformant obtained in the above [1], and after expression of the gene, obtaining a strain sensitive to the drug used in the above [1].

In the above methods, introduction of the straight-chain DNA into a host microorganism can be carried out by any of the methods for introducing DNA into the microorganism, for example, the method using calcium ion [Proc. Natl. Acad. Sci. USA, 69, 2110 (1972)], the protoplast method (Japanese Published Unexamined Patent Application No. 248394/88) and electroporation [Nucleic Acids Res., 16, 6127 (1988)].

By using a straight-chain DNA in which an arbitrary gene to be inserted to chromosomal DNA is incorporated in the center part of the straight-chain DNA used in Method 2 or Method 3 [2], it is possible to eliminate the drug resistance gene and at the same time to insert an arbitrary gene to the chromosomal DNA.

The above Methods 2 to 4 are methods that leave no foreign genes such as a drug resistance gene and a gene usable for negative selection on the chromosomal DNA of the transformant to be finally obtained. Therefore, it is possible to readily produce a microorganism having nucleotide deletions, substitutions or additions in two or more different regions of the chromosomal DNA by repeating the operations of Methods 1 and 2, Method 3 [1] to [3], and Method 4 [1] and [2] using the same drug resistance gene and the same gene usable for negative selection.

(vi) Process for Producing a Dipeptide of the Present Invention

A dipeptide can be produced by culturing in a medium a microorganism obtained by the methods of the above (iii) and (v), allowing the dipeptide to form and accumulate in the culture, and recovering the dipeptide from the culture.

Culturing of the microorganism in a medium can be carried out according to an ordinary method used for culturing of a microorganism.

That is, any of natural media and synthetic media can be used insofar as it contains carbon sources, nitrogen sources, inorganic salts, etc. which can be assimilated by the microorganism and is a medium suitable for efficient culturing of the microorganism.

The medium does not necessarily contain amino acids which constitute the desired dipeptide; however, some of natural media and media for culturing an amino acid-requiring strain contain said amino acids. The medium used in the production process of the present invention may contain an amino acid in an amount required for the growth of a microorganism used in the present invention. That is, the amount of amino acid contained in an ordinary medium is very small compared with that of the amino acid produced by the microorganism used in the production process of the present invention and the presence of the amino acid contained in an ordinary medium does not affect the amount of a dipeptide produced by the present invention; consequently, the medium used in the production process of the present invention may contain the amino acid in such a degree of amount.

For example, a natural medium used in the present invention may contain the amino acid usually in an amount of less than 2.5 g/l, preferably 0.5 g/l or less, more preferably 0.1 g/l or less, further preferably 20 mg/l or less, and a synthetic medium may contain the amino acid usually in an amount of 1 g/l or less, preferably 50 mg/l or less, more preferably 1 mg/l or less, further preferably 0.5 mg/l or less. When a dipeptide consisting of two different kinds of amino acids is produced according to the production process of the present invention and the microorganism used has the ability to produce only one of the amino acids constituting the dipeptide, the other amino acid which can not be produced by the microorganism may be added to the medium used in the present invention. In this case, the amino acid is added usually in an amount of 0.5 g/l to 100 g/l, preferably 2 g/l to 50 g/l.

As the carbon sources, any carbon sources that can be assimilated by the microorganism can be used. Examples of suitable carbon sources include carbohydrates such as glucose, fructose, sucrose, molasses containing them, starch and starch hydrolyzate; organic acids such as acetic acid and propionic acid; and alcohols such as ethanol and propanol.

As the nitrogen sources, ammonia, ammonium salts of organic or inorganic acids such as ammonium chloride, ammonium sulfate, ammonium acetate and ammonium phosphate, and other nitrogen-containing compounds can be used as well as peptone, meat extract, yeast extract, corn steep liquor, casein hydrolyzate, soybean cake, soybean cake hydrolyzate, and various fermented microbial cells and digested products thereof.

Examples of the inorganic salts include potassium dihydrogenphosphate, dipotassium hydrogenphosphate, magnesium phosphate, magnesium sulfate, sodium chloride, ferrous sulfate, manganese sulfate, copper sulfate and calcium carbonate.

Culturing is usually carried out under aerobic conditions, for example, by shaking culture or submerged spinner culture under aeration. The culturing temperature is preferably 15 to 40° C., and the culturing period is usually 5 hours to 7 days. The pH is maintained at 3.0 to 9.0 during the culturing. The pH adjustment is carried out by using an organic or inorganic acid, an alkali solution, urea, calcium carbonate, ammonia, etc.

If necessary, antibiotics such as ampicillin and tetracycline may be added to the medium during the culturing.

When a microorganism transformed with an expression vector comprising an inducible promoter is cultured, an inducer may be added to the medium, if necessary. For example, in the case of a microorganism transformed with an expression vector comprising lac promoter, isopropyl-β-D-thiogalactopyranoside or the like may be added to the medium; and in the case of a microorganism transformed with an expression vector comprising trp promoter, indoleacrylic acid or the like may be added.

The dipeptides produced by the above process include dipeptides in which one or two kinds of amino acids are linked by the α-bond. Preferred are those in which the amino acids are L-amino acids or glycine. More preferred are those represented by formula (I):

$$R^1\text{-}R^2 \qquad (I)$$

(wherein $R^1$ and $R^2$, which may be the same or different, each represent an amino acid selected from the group consisting of L-alanine (L-Ala), L-glutamine (L-Gln), L-glutamic acid (L-Glu), glycine (Gly), L-valine (L-Val), L-leucine (L-Leu), L-isoleucine (L-Ile), L-proline (L-Pro), L-phenylalanine (L-Phe), L-tryptophan (L-Trp), L-methionine (L-Met), L-serine (L-Ser), L-threonine (L-Thr), L-cysteine (L-Cys), L-asparagine (L-Asn), L-tyrosine (L-Tyr), L-lysine (L-Lys), L-arginine (L-Arg), L-histidine (L-His), L-aspartic acid (L-Asp), L-α-aminobutyric acid (L-α-AB), L-4-hydroxyproline (L-4-HYP), L-3-hydroxyproline (L-3-HYP), L-ornithine (L-Orn) and L-citrulline (L-Cit). Further preferred are dipeptides wherein $R^1$ is L-Ala, Gly, L-Met, L-Ser or L-Thr and $R^2$ is L-Gln, L-Glu, Gly, L-Val, L-Leu, L-Ile, L-Pro, L-Phe, L-Trp, L-Met, L-Ser, L-Thr, L-Cys, L-Asn, L-Tyr, L-Lys, L-Arg, L-His, L-Asp, L-α-AB, L-4-HYP, L-3-HYP, L-Orn or L-Cit. Particularly preferred dipeptides are: dipeptides wherein $R^1$ is L-Ala and $R^2$ is L-Gln, Gly, L-Val, L-Leu, L-Ile, L-Phe, L-Trp, L-Met, L-Ser, L-Thr, L-Cys, L-Asn, L-Tyr, L-Lys, L-Arg, L-His, L-α-AB or L-Cit; dipeptides wherein $R^1$ is Gly and $R^2$ is L-Gln, Gly, L-Phe, L-Trp, L-Met, L-Ser, L-Thr, L-Cys, L-Tyr, L-Lys, L-Arg, L-α-AB or L-Cit; dipeptides wherein $R^1$ is L-Met and $R^2$ is L-Phe, L-Met, L-Cys, L-Tyr, L-Lys or L-His; dipeptides wherein $R^1$ is L-Ser and $R^2$ is L-Gln, Gly, L-Phe, L-Met, L-Ser, L-Thr, L-Tyr, L-His or L-α-AB; dipeptides wherein $R^1$ is L-Thr and $R^2$ is L-Gln, L-Leu, L-Phe, L-Met, L-Ser, L-Thr or L-α-AB; dipeptides wherein $R^1$ is L-Gln and $R^2$ is L-Phe or L-α-AB; a dipeptide wherein $R^1$ is L-Phe and $R^2$ is L-Gln; a dipeptide wherein $R^1$ is L-Trp and $R^2$ is Gly; dipeptides wherein $R^1$ is L-Cys and $R^2$ is L-Ala, L-Gln, Gly or L-Met; dipeptides wherein $R^1$ is L-Lys and $R^2$ is L-Ala, Gly or L-Met; a dipeptide wherein $R^1$ is L-Arg and $R^2$ is L-α-AB; a dipeptide wherein $R^1$ is L-His and $R^2$ is L-Met; and dipeptides wherein $R^1$ is L-α-AB and $R^2$ is L-Ala, L-Gln, Gly, L-Ser, L-Thr, L-Arg or L-α-AB. Most preferred are L-alanyl-L-alanine (L-Ala-L-Ala), L-alanyl-L-glutamine (L-Ala-L-Gln), L-alanyl-L-phenylalanine (L-Ala-L-Phe), L-threonyl-L-phenylalanine (L-Thr-L-Phe), L-alanyl-L-tyrosine(L-Ala-L-Tyr), L-Alanyl-L-methionine(L-Ala-L-Met), L-Alanyl-L-valine(L-Ala-L-Val), L-Alanyl-L-isoleucine(L-Ala-L-Ile), L-Alanyl-L-Leucine(L-Ala-L-Leu) and L-Serinyl-L-phenylalanine(L-Ser-L-Phe).

Recovery of the dipeptide formed and accumulated in the culture can be carried out by ordinary methods using active carbon, ion-exchange resins, etc. or by means such as extraction with an organic solvent, crystallization, thin layer chromatography and high performance liquid chromatography.

The method for obtaining DNA encoding a protein having the activity to form a dipeptide from one or more kinds of amino acids and the like are illustrated in the following experimental examples, but the method for obtaining the DNA and the like are not limited to the following experimental examples.

Experimental Example 1

Search for a Protein Having the Dipeptide-Synthesizing Activity Utilizing a Database By using, as a query, the amino acid sequence of D-Ala-D-Ala ligase gene derived from *Bacillus subtilis* 168 [Nature, 390, 249-256 (1997)], a search for a gene encoding a protein having homology which is present in the genomic DNA sequences of *Bacillus subtilis* 168 was carried out using the homology search function of Subtilist which is a database of the genomic DNA of *Bacillus subtilis* 168.

From the sequences obtained as a result of the search, genes encoding the amino acid sequences shown in SEQ ID NOS: 33, 34 and 35 which are D-Ala-D-Ala ligase motifs [Biochemistry, 30, 1673 (1991)] and encoding proteins whose function had already been clarified were excluded. Of the remaining sequences, the sequence showing the highest homology (29.1%) to the D-Ala-D-Ala ligase motif was selected as a gene of unknown function, ywfE.

The nucleotide sequence of ywfE gene is shown in SEQ ID NO: 9, and the amino acid sequence of the protein encoded by the nucleotide sequence is shown in SEQ ID NO: 1.

Experimental Example 2

Construction of a Strain Expressing the ywfE Gene

On the basis of the information on the nucleotide sequence obtained in Experimental Example 1, a ywfE gene fragment of *Bacillus subtilis* was obtained in the following manner.

That is, *Bacillus subtilis* 168 (ATCC 23857) was inoculated into LB medium [10 g/l Bacto-tryptone (Difco), 5 g/l yeast extract (Difco) and 5 g/l sodium chloride] and subjected to static culture overnight at 30° C. After the culturing, the chromosomal DNA of the microorganism was isolated and purified according to the method using saturated phenol described in Current Protocols in Molecular Biology.

By using a DNA synthesizer (Model 8905, PerSeptive Biosystems, Inc.), DNAs having the nucleotide sequences shown in SEQ ID NOS: 19 to 22 (hereinafter referred to as primer A, primer B, primer C and primer D, respectively) were synthesized. Primer A has a sequence wherein a nucleotide sequence containing the XhoI recognition sequence is added to the 5' end of a region of the *Bacillus subtilis* chromosomal DNA containing the initiation codon of ywfE gene. Primer B has a sequence wherein a nucleotide sequence containing the BamHI recognition sequence is added to the 5' end of a nucleotide sequence complementary to a sequence containing the termination codon of ywfE gene. Primer C has a sequence wherein a nucleotide sequence containing the EcoRI recognition sequence is added to the 5' end of the nucleotide sequence of trp promoter region of expression vector pTrS30 containing trp promoter [prepared from *Escherichia coli* JM109/pTrS30 (FERM BP-5407)]. Primer D has a sequence wherein a nucleotide sequence containing the XhoI recognition sequence is added to the 5' end of a sequence complementary to the sequence of trp promoter region of expression vector pTrS30 containing trp promoter.

A ywfE gene fragment was amplified by PCR using the above primer A and primer B, and the chromosomal DNA of *Bacillus subtilis* as a template. A trp promoter region fragment was amplified by PCR using primer C and primer D, and pTrS30 as a template. PCR was carried out by 30 cycles, one cycle consisting of reaction at 94° C. for one minute, reaction at 55° C. for 2 minutes and reaction at 72° C. for 3 minutes, using 40 µl of a reaction mixture comprising 0.1 µg of the chromosomal DNA or 10 ng of pTrS30 as a template, 0.5 µmol/l each of the primers, 2.5 units of Pfu DNA polymerase (Stratagene), 4 µl of buffer for Pfu DNA polymerase (10×) (Stratagene) and 200 µmol/l each of dNTPs (dATP, dGTP, dCTP and dTTP).

One-tenth of each of the resulting reaction mixtures was subjected to agarose gel electrophoresis to confirm that a ca. 1.4 kb DNA fragment corresponding to the ywfE gene fragment and a ca. 0.3 kb DNA fragment corresponding to the trp promoter region fragment were respectively amplified in the PCR using primer A and primer B and the PCR using primer C and primer D. Then, the remaining reaction mixture was mixed with an equal amount of phenol/chloroform (1 vol/1 vol) saturated with TE [10 mmol/l Tris-HCl (pH 8.0), 1 mmol/l EDTA]. The resulting solution was centrifuged, and the obtained upper layer was mixed with a two-fold volume of cold ethanol and allowed to stand at −80° C. for 30 minutes. The resulting solution was centrifuged to precipitate DNA, and the obtained DNA was dissolved in 20 µl of TE.

The thus obtained solutions (5 µl each) were respectively subjected to reaction to cleave the DNA amplified using primer A and primer B with restriction enzymes XhoI and BamHI and to reaction to cleave the DNA amplified using primer C and primer D with restriction enzymes EcoRI and XhoI. DNA fragments were separated by agarose gel electrophoresis, and a 1.4 kb fragment containing ywfE gene and a 0.3 kb fragment containing trp promoter region were respectively recovered using GENECLEAN II Kit (BIO 101).

Expression vector pTrS30 containing trp promoter [prepared from *Escherichia coli* JM109/pTrS30 (FERM BP-5407)] (0.2 µg) was cleaved with restriction enzymes EcoRI and BamHI. DNA fragments were separated by agarose gel electrophoresis and a 4.5 kb DNA fragment was recovered in the same manner as above.

The 1.4 kb fragment containing ywfE gene, the 0.3 kb fragment containing trp promoter region and the 4.5 kb DNA fragment obtained above were subjected to ligation reaction using a ligation kit (Takara Bio Inc.) at 16° C. for 16 hours.

*Escherichia coli* NM522 (Stratagene) was transformed using the reaction mixture according to the method using calcium ion [Proc. Natl. Acad. Sci. USA, 69, 2110 (1972)], spread on LB agar medium containing 50 µg/ml ampicillin, and cultured overnight at 30° C.

A plasmid was extracted from a colony of the transformant that grew on the medium according to a known method and the structure of the plasmid was analyzed using restriction enzymes, whereby it was confirmed that expression vector pPE43 containing ywfE gene ligated downstream of the trp promoter was obtained (FIG. 1).

Experimental Example 3

Production of a Dipeptide

*Escherichia coli* NM522 carrying pPE43 (*Escherichia coli* NM522/pPE43) obtained in Experimental Example 2 was inoculated into 8 ml of LB medium containing 50 µg/ml ampicillin in a test tube, and cultured at 28° C. for 17 hours. The resulting culture was centrifuged to obtain wet cells.

A reaction mixture (0.1 ml) comprising 60 mg/ml (final concentration) wet cells, 120 mmol/l potassium phosphate buffer (pH 7.4), 60 mmol/l magnesium chloride, 60 mmol/l ATP, 30 mmol/l L-Ala, 30 mmol/l L-Gln and 0.4% Nymeen S-215 was prepared, and reaction was carried out at 37° C. for 3 minutes.

After the completion of reaction, the reaction product was derivatized by the dinitrophenol method and then analyzed by HPLC. The HPLC analysis was carried out using, as a separation column, Lichrosorb-RP-18 column (Kanto Kagaku) and, as an eluent, 1% (v/v) phosphoric acid and 25% (v/v) acetonitrile at a flow rate of 0.7 ml/min. As a result, it was confirmed that 120 mg/l L-alanyl-L-glutamine (L-Ala-L-Gln) was formed and accumulated in the reaction mixture.

Formation of L-Ala-L-Gln was not observed when the reaction was carried out using cells of *Escherichia coli* NM522/pTrS30, which is a control strain carrying only a vector.

Experimental Example 4

Purification of C-Terminal His-Tagged Recombinant Dipeptide Synthetase

By using the above DNA synthesizer, DNAs having the nucleotide sequences shown in SEQ ID NOS: 23 and 24 (hereinafter referred to as primer E and primer F, respectively) were synthesized. Primer E has a nucleotide sequence containing a region wherein the initiation codon of ywfE gene (atg) is substituted by the NcoI recognition sequence (cc atgg). Primer F has a nucleotide sequence containing a region wherein the termination codon of ywfE gene is substituted by the BamHI recognition sequence (ggatcc).

PCR was carried out using the chromosomal DNA of *Bacillus subtilis* 168 (ATCC 23857) as a template and the above primer E and primer F as a set of primers. That is, PCR was carried out by 30 cycles, one cycle consisting of reaction at 94° C. for one minute, reaction at 55° C. for 2 minutes and reaction at 72° C. for 3 minutes, using 40 μl of a reaction mixture comprising 0.1 μg of the chromosomal DNA, 0.5 μmol/l each of the primers, 2.5 units of Pfu DNA polymerase, 4 μl of buffer for Pfu DNA polymerase (10×) and 200 μmol/l each of dNTPs.

One-tenth of the resulting reaction mixture was subjected to agarose gel electrophoresis to confirm that a ca. 1.4 kb fragment corresponding to the ywfE gene fragment was amplified. Then, the remaining reaction mixture was mixed with an equal amount of phenol/chloroform saturated with TE. The resulting solution was centrifuged, and the obtained upper layer was mixed with a two-fold volume of cold ethanol and allowed to stand at −80° C. for 30 minutes. The resulting solution was centrifuged, and the obtained DNA precipitate was dissolved in 20 μl of TE.

The thus obtained solution (5 μl) was subjected to reaction to cleave the amplified DNA with restriction enzymes NcoI and BamHI. DNA fragments were separated by agarose gel electrophoresis, and a 1.4 kb DNA fragment containing ywfE gene was recovered using GENECLEAN II Kit.

C-Terminal His-tagged recombinant expression vector pQE60 (Qiagen, Inc.) (0.2 μg) was cleaved with restriction enzymes NcoI and BamHI. DNA fragments were separated by agarose gel electrophoresis, and a 3.4 kb DNA fragment was recovered in the same manner as above.

The 1.4 kb DNA fragment containing ywfE gene and the 3.4 kb DNA fragment obtained above were subjected to ligation reaction using a ligation kit at 16° C. for 16 hours.

*Escherichia coli* NM522 was transformed using the ligation reaction mixture according to the method using calcium ion, spread on LB agar medium containing 50 μg/ml ampicillin, and cultured overnight at 30° C.

Figure 2:
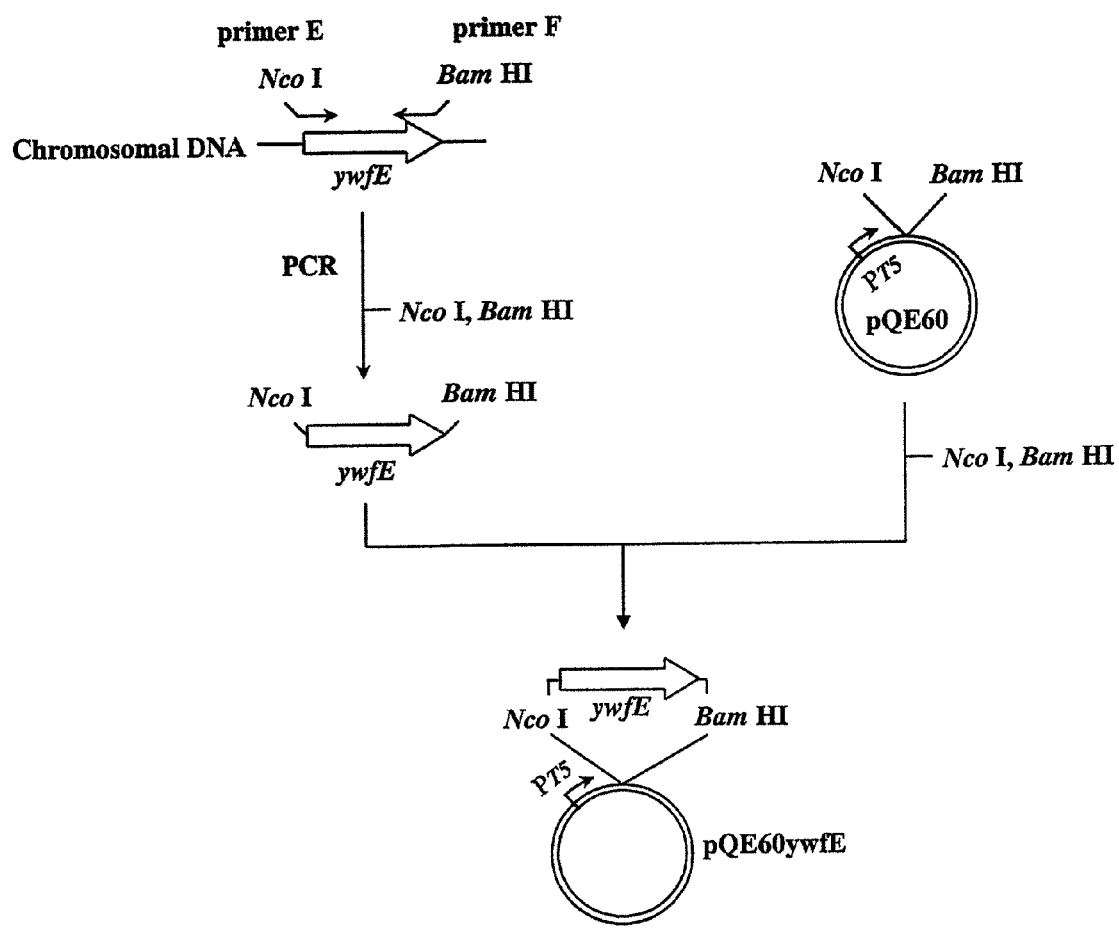
FIG. 2 shows the steps for constructing plasmid pQE60ywfE.

A plasmid was extracted from a colony of the transformant that grew on the medium according to a known method and the structure of the plasmid was analyzed using restriction enzymes, whereby it was confirmed that pQE60ywfE, which is a C-terminal His-tagged ywfE gene expression vector, was obtained (FIG. 2).

*Escherichia coli* NM522 carrying pQE60ywfE (*Escherichia coli* NM522/pQE60ywfE) was inoculated into 8 ml of LB medium containing 50 μg/ml ampicillin in a test tube, and cultured at 28° C. for 17 hours. The resulting culture was inoculated into 50 ml of LB medium containing 50 μg/ml ampicillin in a 250-ml Erlenmeyer flask, and cultured at 30° C. for 3 hours. Then, isopropyl-β-D-thiogalactopyranoside (IPTG) was added to give a final concentration of 1 mmol/l, followed by further culturing at 30° C. for 4 hours. The resulting culture was centrifuged to obtain wet cells, and a His-tagged recombinant enzyme was purified from the wet cells using HisTrap (His-tagged protein purification kit, Amersham Pharmacia Biotech) according to the instructions attached thereto.

Experimental Example 5

Production of Dipeptides Using the His-Tagged Recombinant Enzyme (1)

(i) A reaction mixture (0.1 ml) comprising 0.04 mg of the purified His-tagged recombinant enzyme obtained in Experimental Example 4, 100 mmol/l Tris-HCl (pH 8.0), 60 mmol/l magnesium chloride, 60 mmol/l ATP, 30 mmol/l L-Ala and 30 mmol/l L-Gln was prepared, and reaction was carried out at 37° C. for 16 hours.

After the completion of reaction, the reaction product was analyzed in the same manner as in Experimental Example 3 above, whereby it was confirmed that 3.7 g/l L-Ala-L-Gln and 0.3 g/l L-alanyl-L-alanine (L-Ala-L-Ala) were formed and accumulated in the reaction mixture.

(ii) Reactions were carried out under the same conditions as in the above (i) using reaction mixtures having the same composition as that of the reaction mixture of the above (i) except that 0.01 mg of the enzyme was used and L-Phe, L-Met, L-Leu and L-Val, respectively, were used in place of L-Gln.

After the completion of reactions, the reaction products were analyzed in the same manner as in Experimental Example 3 above, whereby it was confirmed that the following dipeptides were formed and accumulated in the respective reaction mixtures: 7.0 g/l L-alanyl-L-phenylalanine (L-Ala-L-Phe) alone; 7.0 g/l L-alanyl-L-methionine (L-Ala-L-Met) and 0.03 g/l L-Ala-L-Ala; 5.0 g/l L-alanyl-L-leucine (L-Ala-L-Leu) and 0.2 g/l L-Ala-L-Ala; and 1.6 g/l L-alanyl-L-valine (L-Ala-L-Val) and 0.3 g/l L-Ala-L-Ala.

(iii) Reactions were carried out under the same conditions as in the above (i) using reaction mixtures having the same composition as that of the reaction mixture of the above (i) except that 0.01 mg of the enzyme was used, Gly was used in place of L-Ala, and L-Phe and L-Met, respectively, were used in place of L-Gln.

After the completion of reactions, the reaction products were analyzed in the same manner as in Experimental Example 3 above, whereby it was confirmed that 5.2 g/l glycyl-L-phenylalanine (Gly-L-Phe) and 1.1 g/l glycyl-L-methionine (Gly-L-Met) were formed and accumulated in the respective reaction mixtures.

When ATP was excluded from the compositions of the above reaction mixtures, no dipeptide was formed.

The above results revealed that the ywfE gene product has the activity to produce, in the presence of ATP, the following dipeptides: L-Ala-L-Gln plus L-Ala-L-Ala, L-Ala-L-Phe, L-Ala-L-Met plus L-Ala-L-Ala, L-Ala-L-Leu plus L-Ala-L-Ala, or L-Ala-L-Val plus L-Ala-L-Ala from L-Ala plus L-Gln, L-Phe, L-Met, L-Leu or L-Val; and Gly-L-Phe or Gly-L-Met from Gly plus L-Phe or L-Met.

Experimental Example 6

Production of Dipeptides Using the His-Tagged Recombinant Enzyme (2)

A reaction mixture (0.1 ml) comprising 0.04 mg of the purified His-tagged recombinant enzyme obtained in Experimental Example 4, 100 mmol/l Tris-HCl (pH 8.0), 60 mmol/l magnesium chloride and 60 mmol/l ATP was prepared. To this mixture were respectively added combinations of various L-amino acids, Gly and β-Ala selected from the amino acids shown in the first row of Table 1 and in the leftmost column of Table 1 to give a concentration of 30 mmol/l each, and the resulting mixtures were subjected to reaction at 37° C. for 16 hours. After the completion of reactions, the reaction products were analyzed by HPLC, whereby it was confirmed that the dipeptides shown in Table 1 were formed.

TABLE 1

|   | Ala | Gln | Glu | Gly | Val | Leu | Ile | Pro |
|---|---|---|---|---|---|---|---|---|
| Ala | AlaAla | AlaGln AlaAla | AlaAla | AlaGly AlaAla | AlaVal AlaAla | AlaLeu AlaAla | AlaIle AlaAla | AlaAla |
| Gln |  | X | X | GlyGln GlyGly | X | X | X | X |
| Glu |  |  |  | GlyGly |  |  |  |  |
| Gly |  |  |  | GlyGly |  |  |  | GlyGly |
| Val |  |  |  |  |  |  |  |  |
| Leu |  |  |  |  |  |  |  |  |
| Ile |  |  |  |  |  |  |  |  |
| Pro |  |  |  |  |  |  |  |  |
| Phe |  |  |  |  |  |  |  |  |
| Trp |  |  |  |  |  |  |  |  |
| Met |  |  |  |  |  |  |  |  |
| Ser |  |  |  |  |  |  |  |  |
| Thr |  |  |  |  |  |  |  |  |
| Cys |  |  |  |  |  |  |  |  |
| Asn |  |  |  |  |  |  |  |  |
| Tyr |  |  |  |  |  |  |  |  |
| Lys |  |  |  |  |  |  |  |  |
| Arg |  |  |  |  |  |  |  |  |
| His |  |  |  |  |  |  |  |  |
| Asp |  |  |  |  |  |  |  |  |
| αAB |  |  |  |  |  |  |  |  |
| β-Ala |  |  |  |  |  |  |  |  |
| Cit |  |  |  |  |  |  |  |  |

|   | Phe | Trp | Met | Ser | Thr | Cys | Asn | Tyr |
|---|---|---|---|---|---|---|---|---|
| Ala | AlaPhe AlaAla | AlaTrp AlaAla | AlaMet | AlaSer AlaAla | AlaThr AlaAla | AlaAla ○ | AlaAsn AlaAla | AlaTyr AlaAla |
| Gln | ○ | X | MetMet | SerGln SerSer | ThrGln ThrThr | ○ | X | X |
| Glu |  |  |  |  |  |  |  |  |
| Gly | GlyPhe | GlyGly ○ | GlyMet GlyGly | GlySer GlyGly SerGly SerSer | GlyThr GlyGly ThrGly ThrThr | GlyGly ○ | GlyGly | GlyTyr GlyGly |
| Val |  |  | X |  |  |  |  |  |
| Leu |  |  | MetMet |  | ThrLeu |  |  |  |
| Ile |  |  | MetMet |  |  |  |  |  |
| Pro |  |  | MetMet | SerSer | ThrThr |  |  |  |
| Phe |  |  | MetPhe MetMet | SerPhe | ThrPhe ThrThr |  |  |  |
| Trp |  |  |  |  |  |  |  |  |
| Met |  |  | MetMet | SerMet | ThrMet ThrThr | MetMet ○ |  | MetTyr MetMet |
| Ser |  |  |  | SerSer | SerThr SerSer ThrSer ThrThr |  |  | SerTyr SerSer |
| Thr |  |  |  |  | ThrThr |  |  |  |
| Cys |  |  |  |  |  |  |  |  |
| Asn |  |  |  |  |  |  |  |  |
| Tyr |  |  |  |  |  |  |  |  |
| Lys |  |  |  |  |  |  |  |  |
| Arg |  |  |  |  |  |  |  |  |
| His |  |  |  |  |  |  |  |  |
| Asp |  |  |  |  |  |  |  |  |
| α-AB |  |  |  |  |  |  |  |  |
| β-Ala |  |  |  |  |  |  |  |  |
| Cit |  |  |  |  |  |  |  |  |

|   | Lys | Arg | His | Asp | α-AB | β-Ala | Cit | Azaserine | Theanine |
|---|---|---|---|---|---|---|---|---|---|
| Ala | AlaAla ○ | AlaArg AlaAla | AlaHis AlaAla | AlaAla | AlaAla ○ |  | AlaAla ○ | AlaAla ○ | AlaAla ○ |
| Gln | X | X | X | X | ○ |  |  |  |  |
| Glu |  |  |  |  |  |  |  |  |  |
| Gly | GlyGly ○ | GlyArg GlyGly | GlyGly | GlyGly | GlyGly ○ |  | ○ |  |  |

TABLE 1-continued

| | | | | | |
|---|---|---|---|---|---|
| Val | | | | | |
| Leu | | | | | |
| Ile | | | | | |
| Pro | | | | | |
| Phe | | X | | ○ | |
| Trp | | | | | |
| Met | MetMet | MetMet | | ○ | |
| | ○ | ○ | | | |
| Ser | | SerHis | SerSer | | |
| | | | ○ | | |
| Thr | | | ThrThr | | |
| | | | ○ | | |
| Cys | | | | | |
| Asn | | | | | |
| Tyr | | | | | |
| Lys | | | | | |
| Arg | | | ○ | | |
| His | | | | β-AlaHis | |
| Asp | | | | | |
| α-AB | | | ○ | | |
| β-Ala | | | | | |
| Cit | | | ○ | | |

The dipeptides formed by the reaction using, as substrates, two (or one) kinds of L-amino acids, Gly and β-Ala shown in the first row and the leftmost column of Table 1 are shown in the respective cells of the table. In the table, ○ means that a dipeptide was formed though its sequence was unidentified; X means that formation of a dipeptide was not confirmed; and a blank means that reaction was not carried out.

Experimental Example 7

Production of a Dipeptide Using a Strain Expressing the His-Tagged Recombinant Enzyme

*Escherichia coli* NM522/pQE60ywfE obtained in Experimental Example 4 was inoculated into 8 ml of LB medium containing 50 μg/ml ampicillin in a test tube, and cultured at 28° C. for 17 hours. The resulting culture was inoculated into 50 ml of LB medium containing 50 μg/ml ampicillin in a 250-ml Erlenmeyer flask, and cultured at 30° C. for 3 hours. Then, IPTG was added to give a final concentration of 1 mmol/l, followed by further culturing at 30° C. for 4 hours. The resulting culture was centrifuged to obtain wet cells.

A reaction mixture (20 ml, pH 7.2) comprising 200 g/l wet cells, 50 g/l glucose, 5 g/l phytic acid (diluted to neutrality with 33% conc. sodium hydroxide solution), 15 g/l potassium dihydrogenphosphate, 5 g/l magnesium sulfate heptahydrate, 4 g/l Nymeen S-215, 10 ml/l xylene, 200 mmol/l L-Ala and 200 mmol/l L-Gln was put in a 50-ml beaker, and reaction was carried out at 32° C. at 900 rpm for 2 hours. During the reaction, the pH of the reaction mixture was maintained at 7.2 by using 2 mol/l potassium hydroxide.

The reaction product was analyzed by the same method as in Experimental Example 3, whereby it was confirmed that 25 mg/l L-Ala-L-Gln was accumulated.

Experimental Example 8

Cloning of Genes Corresponding to the ywfE Gene from Various Microorganisms of the Genus *Bacillus* and Analysis Thereof On the basis of the nucleotide sequence shown in SEQ ID NO: 9, genes corresponding to the ywfE gene which exist in *Bacillus subtilis* ATCC 15245, ATCC 6633, IAM 1213, IAM 1107, IAM 1214, ATCC 9466, IAM 1033 and ATCC 21555, *Bacillus amyloliquefaciens* IFO 3022 and *Bacillus pumilus* NRRL B-12025 were obtained in the following manner.

That is, *Bacillus subtilis* ATCC 15245, ATCC 6633, IAM 1213, IAM 1107, IAM 1214, ATCC 9466, IAM 1033 and ATCC 21555, *Bacillus amyloliquefaciens* IFO 3022 and *Bacillus pumilus* NRRL B-12025 were respectively inoculated into LB medium and subjected to static culture overnight at 30° C. After the culturing, the chromosomal DNAs of the respective microorganisms were isolated and purified according to the method using saturated phenol described in Current Protocols in Molecular Biology.

By using a DNA synthesizer (Model 8905, PerSeptive Biosystems, Inc.), DNAs having the nucleotide sequences shown in SEQ ID NOS: 25 and 26 (hereinafter referred to as primer G and primer H, respectively) were synthesized. Primer G has a sequence containing a region upstream of the initiation codon of ywfE gene on the chromosomal DNA of *Bacillus subtilis* 168, and primer H has a sequence complementary to a sequence containing a region downstream of the termination codon of ywfE gene.

PCR was carried out using each of the chromosomal DNAs of *Bacillus subtilis* ATCC 15245, ATCC 6633, IAM 1213, IAM 1107, IAM 1214, ATCC 9466, IAM 1033 and ATCC 21555 and *Bacillus amyloliquefaciens* IFO 3022 as a template and the above primer G and primer H as a set of primers. That is, PCR was carried out by 30 cycles, one cycle consisting of reaction at 94° C. for one minute, reaction at 55° C. for 2 minutes and reaction at 72° C. for 3 minutes, using 40 μl of a reaction mixture comprising 0.1 μg of the chromosomal DNA, 0.5 μmol/l each of the primers, 2.5 units of Pfu DNA polymerase, 4 μl of buffer for Pfu DNA polymerase (10×) and 200 μmol/l each of dNTPs.

One-tenth of each of the resulting reaction mixtures was subjected to agarose gel electrophoresis to confirm that a ca. 1.4 kb fragment corresponding to the ywfE gene fragment was amplified. Then, the remaining reaction mixture was mixed with an equal amount of phenol/chloroform saturated with TE. The resulting solution was centrifuged, and the obtained upper layer was mixed with a two-fold volume of cold ethanol and allowed to stand at −80° C. for 30 minutes. The resulting solution was centrifuged, and the obtained DNA precipitate was dissolved in 20 μl of TE.

Each of the thus obtained 1.4 kb DNA fragments derived from the chromosomal DNAs of the respective strains and pCR-blunt (Invitrogen Corp.) were subjected to ligation reaction using a ligation kit at 16° C. for 16 hours.

*Escherichia coli* NM522 was transformed using each ligation reaction mixture according to the method using calcium ion, spread on LB agar medium containing 50 µg/ml ampicillin, and cultured overnight at 30° C.

A plasmid was extracted from a colony of each transformant that grew on the medium according to a known method and the structure of each plasmid was analyzed using restriction enzymes. As a result, it was confirmed that the following plasmids containing a gene corresponding to the ywfE gene were obtained: pYWFE1 (derived from ATCC 15245, DNA having the nucleotide sequence shown in SEQ ID NO: 36), pYWFE2 (derived from ATCC 6633, DNA having the nucleotide sequence shown in SEQ ID NO: 10), pYWFE3 (derived from IAM 1213, DNA having the nucleotide sequence shown in SEQ ID NO: 11), pYWFE4 (derived from IAM 1107, DNA having the nucleotide sequence shown in SEQ ID NO: 12), pYWFE5 (derived from IAM 1214, DNA having the nucleotide sequence shown in SEQ ID NO: 13), pYWFE6 (derived from ATCC 9466, DNA having the nucleotide sequence shown in SEQ ID NO: 9), pYWFE7 (derived from IAM 1033, DNA having the nucleotide sequence shown in SEQ ID NO: 36), pYWFE8 (derived from ATCC 21555, DNA having the nucleotide sequence shown in SEQ ID NO: 14) and pYWFE9 (derived from IFO 3022, DNA having the nucleotide sequence shown in SEQ ID NO: 15).

On the other hand, a gene corresponding to ywfE gene derived from *Bacillus pumilus* NRRL B-12025 (DNA having the nucleotide sequence shown in SEQ ID NO: 16) was obtained in the following manner.

PCR was carried out using the chromosomal DNA of the NRRL B-12025 strain prepared above as a template and DNAs respectively consisting of the nucleotide sequences shown in SEQ ID NOS: 27 and 28 as a set of primers. That is, PCR was carried out by 30 cycles, one cycle consisting of reaction at 98° C. for 5 seconds, reaction at 55° C. for 30 seconds and reaction at 72° C. for one minute, using 50 µl of a reaction mixture comprising 0.1 µg of the chromosomal DNA, 0.5 µmol/l each of the primers, 2.5 units of Z-taq polymerase (Takara Bio Inc.), 5 µl of buffer for Z-taq polymerase (10×) (Takara Bio Inc.) and 200 µmol/l each of dNTPs.

One-tenth of the resulting reaction mixture was subjected to agarose gel electrophoresis to confirm that a ca. 0.8 kb fragment was amplified. Then, the remaining reaction mixture was mixed with an equal amount of phenol/chloroform saturated with TE. The resulting mixture was centrifuged, and the obtained upper layer was mixed with a two-fold volume of cold ethanol and allowed to stand at −80° C. for 30 minutes. The resulting solution was centrifuged, and the obtained DNA precipitate was dissolved in 20 µl of TE.

The thus obtained 0.8 kb DNA fragment and pGEM T-easy (Promega Corp.) were subjected to ligation reaction using a ligation kit at 16° C. for 16 hours.

*Escherichia coli* DH5a was transformed using the reaction mixture according to the method using calcium ion, spread on LB agar medium containing 50 µg/ml ampicillin, and cultured overnight at 30° C.

A plasmid was extracted from the transformant obtained above and the nucleotide sequence of the ca. 0.8 kb DNA insert was determined, whereby a sequence from nucleotides 358 to 1160 in the nucleotide sequence shown in SEQ ID NO: 16 was confirmed.

The above plasmid was cleaved with EcoRI and then subjected to agarose gel electrophoresis to separate a DNA fragment. The DNA fragment was purified using GENECLEAN II Kit, and ca. 0.5 µg of the purified DNA fragment was DIG-labeled using DIG-High Prime DNA Labeling & Detection Starter Kit I (Roche Diagnostics Corp.) according to the instructions attached thereto.

Southern analysis of the chromosomal DNA of the NRRL B-12025 strain was carried out using the DIG-labeled DNA obtained above.

The chromosomal DNA of the NRRL B-12025 strain was completely digested with BamHI, EcoRI, HindIII, KpnI, PstI, SacI, SalI and SphI, respectively, and subjected to agarose gel electrophoresis to separate DNA fragments, followed by transfer to nylon membrane plus charge (Roche Diagnostics Corp.) according to an ordinary method.

After the DNA fragments were fixed on the nylon membrane by UV irradiation, Southern hybridization was carried out using the above probe DNA and the nylon membrane.

The hybridization was carried out by bringing the nylon membrane into contact with the probe DNA at 65° C. for 16 hours, washing the nylon membrane twice with a solution consisting of 0.1% SDS and 2×SSC at room temperature for 5 minutes, and further washing the membrane twice with a solution consisting of 0.1% SDS and 0.5×SSC at 65° C. for 15 minutes. The other operations and conditions and detection of the hybridized DNA were carried out according to the instructions attached to the above-mentioned DIG-High Prime DNA Labeling & Detection Starter Kit I.

As a result, color development was observed at around 3.5 kbp of the fragments completely digested with HindIII and PstI.

Subsequently, the chromosomal DNA of the NRRL B-12025 strain was completely digested with HindIII and PstI, respectively, and subjected to agarose gel electrophoresis to separate DNA fragments. From the respective restriction enzyme-digested DNAs, 3-4 kbp fragments were purified using GENECLEAN II Kit, followed by autocyclization using a ligation kit.

On the basis of the nucleotide sequence of the 0.8 kb DNA fragment determined above, the nucleotide sequences shown in SEQ ID NOS: 29 and 30 were designed and synthesized, and they were used in PCR using the cyclized DNA obtained above as a template. PCR was carried out by 30 cycles, one cycle consisting of reaction at 98° C. for 5 seconds, reaction at 55° C. for 30 seconds and reaction at 72° C. for 3 minutes and 30 seconds, using 50 µl of a reaction mixture comprising 10 ng of the cyclized DNA, 0.5 µmol/l each of the primers, 2.5 units of pyrobest polymerase (Takara Bio Inc.), 5 µl of buffer for pyrobest polymerase (10×) (Takara Bio Inc.) and 200 µmol/l each of dNTPs.

One-tenth of the resulting reaction mixture was subjected to agarose gel electrophoresis to confirm that a ca. 3.0 kb fragment was amplified. Then, the remaining reaction mixture was mixed with an equal amount of phenol/chloroform saturated with TE. The resulting mixture was centrifuged, and the obtained upper layer was mixed with a two-fold volume of cold ethanol and allowed to stand at −80° C. for 30 minutes. The resulting solution was centrifuged, and the obtained DNA precipitate was dissolved in 20 µl of TE.

The thus obtained DNA fragment and Zero Blunt PCR Cloning Kit (Invitrogen Corp.) were subjected to ligation reaction using a ligation kit.

*Escherichia coli* NM522 was transformed using the reaction mixture according to the method using calcium ion, spread on LB agar medium containing 50 µg/ml ampicillin, and cultured overnight at 30° C.

A plasmid was extracted from a colony of the transformant that grew on the medium according to a known method and the structure of the plasmid was analyzed using restriction enzymes. As a result, it was confirmed that plasmid pYWFE10 (derived from NRRL B-12025, DNA having the nucleotide sequence shown in SEQ ID NO: 16) containing a gene corresponding to the ywfE gene was obtained.

The nucleotide sequences of the genes corresponding to the ywfE gene which are respectively contained in the plasmids pYWFE1 to pYWFE10 obtained above were determined using 373A DNA Sequencer.

The amino acid sequences of the proteins encoded by the genes respectively contained in pYWFE1, pYWFE6 and pYWFE7 were identical with the amino acid sequence of the protein encoded by the ywfE gene, whereas those of the proteins encoded by the genes respectively contained in pYWFE2, pYWFE3, pYWFE4, pYWFE5, pYWFE8, pYWFE9 and pYWFE10 were different from the amino acid sequence of the protein encoded by the ywfE gene.

The amino acid sequences of the proteins encoded by the genes corresponding to the ywfE gene which are contained in pYWFE2, pYWFE3, pYWFE4, pYWFE5, pYWFE8, pYWFE9 and pYWFE10, and pYWFE1 and pYWFE7 are shown in SEQ ID NOS: 2 to 8 and 1, respectively, and the nucleotide sequences of these genes are shown in SEQ ID NOS: 10 to 16 and 36, respectively.

Experimental Example 9

Purification of C-Terminal His-Tagged Recombinant Dipeptide Synthetase

PCR was carried out using each of the chromosomal DNAs of *Bacillus subtilis* ATCC 15245, ATCC 6633, IAM 1213, IAM 1107, IAM 1214, ATCC 9466, IAM 1033 and ATCC 21555 and *Bacillus amyloliquefaciens* IFO 3022 as a template and primer A and primer B described in Experimental Example 2 as a set of primers. That is, PCR was carried out by 30 cycles, one cycle consisting of reaction at 94° C. for one minute, reaction at 55° C. for 2 minutes and reaction at 72° C. for 3 minutes, using 40 µl of a reaction mixture comprising 0.1 µg of the chromosomal DNA, 0.5 µmol/l each of the primers, 2.5 units of Pfu DNA polymerase, 4 µl of buffer for Pfu DNA polymerase (10×) and 200 µmol/l each of dNTPs.

When the chromosomal DNA of *Bacillus pumilus* NRRL B-12025 was used as a template, PCR was carried out using DNAs respectively having the nucleotide sequences shown in SEQ ID NOS: 31 and 32 as a set of primers under the same conditions as above.

One-tenth of each of the resulting reaction mixtures was subjected to agarose gel electrophoresis to confirm that a ca. 1.4 kb DNA fragment corresponding to the ywfE gene fragment was amplified. Then, the remaining reaction mixture was mixed with an equal amount of phenol/chloroform saturated with TE. The resulting mixture was centrifuged, and the obtained upper layer was mixed with a two-fold volume of cold ethanol and allowed to stand at −80° C. for 30 minutes. The resulting solution was centrifuged, and the obtained DNA precipitate was dissolved in 20 µl of TE.

Each of the thus obtained solutions (5 µl) was subjected to reaction to cleave the amplified DNA with restriction enzymes NcoI and BamHI. DNA fragments were separated by agarose gel electrophoresis, and a 1.4 kb DNA fragment containing a gene corresponding to the ywfE gene was recovered using GENECLEAN II Kit.

Subsequently, 0.2 µg of the C-terminal His-tagged recombinant expression vector pQE60 was cleaved with restriction enzymes NcoI and BamHI. DNA fragments were separated by agarose gel electrophoresis, and a 3.4 kb DNA fragment was recovered in the same manner as above.

Each of the 1.4 kb DNA fragments containing a gene corresponding to the ywfE gene of *Bacillus subtilis* 168 and the 3.4 kb DNA fragment obtained above were subjected to ligation reaction using a ligation kit at 16° C. for 16 hours.

*Escherichia coli* NM522 was transformed using each ligation reaction mixture according to the method using calcium ion, spread on LB agar medium containing 50 µg/ml ampicillin, and cultured overnight at 30° C.

A plasmid was extracted from a colony of each transformant that grew on the medium according to a known method and the structure of each plasmid was analyzed using restriction enzymes. As a result, it was confirmed that the following C-terminal His-tagged gene expression vectors were obtained: pQE60ywfE1 (a vector containing the gene derived from ATCC 15245), pQE60ywfE2 (a vector containing the gene derived from ATCC 6633), pQE60ywfE3 (a vector containing the gene derived from IAM 1213), pQE60ywfE4 (a vector containing the gene derived from IAM 1107), pQE60ywfE5 (a vector containing the gene derived from IAM 1214), pQE60ywfE6 (a vector containing the gene derived from ATCC 9466), pQE60ywfE7 (a vector containing the gene derived from IAM 1033), pQE60ywfE8 (a vector containing the gene derived from ATCC 21555), pQE60ywfE9 (a vector containing the gene derived from IFO 3022) and pQE60ywfE10 (a vector containing the gene derived from NRRL B-12025).

*Escherichia coli* NM522/pQE60ywfE1 to NM522/pQE60ywfE10 strains obtained above were respectively inoculated into 8 ml of LB medium containing 50 µg/ml ampicillin in a test tube, and cultured at 28° C. for 17 hours. Each of the resulting cultures was inoculated into 50 ml of LB medium containing 50 µg/ml ampicillin in a 250-ml Erlenmeyer flask, and cultured at 30° C. for 3 hours. Then, IPTG was added to give a final concentration of 1 mmol/l, followed by further culturing at 30° C. for 4 hours. The resulting culture was centrifuged to obtain wet cells, and His-tagged recombinant enzymes were purified from the respective wet cells using HisTrap according to the instructions attached thereto.

Experimental Example 10

Production of Dipeptides Using Purified Enzymes

Reaction mixtures (0.1 ml each) comprising 0.04 mg of the respective recombinant enzymes obtained in Experimental Example 9, 100 mmol/l Tris-HCl (pH 8.0), 60 mmol/l magnesium chloride, 60 mmol/l ATP, 30 mmol/l L-Ala and 30 mmol/l L-Gln were prepared, and reactions were carried out at 37° C. for 16 hours.

After the completion of reactions, the reaction mixtures were analyzed by the method described in Experimental Example 3, whereby it was confirmed that 3.0 to 3.5 g/l L-Ala-L-Gln and 0.25 to 0.3 g/l L-Ala-L-Ala were formed and accumulated.

When ATP was excluded from the compositions of the above reaction mixtures, L-Ala-L-Gln or L-Ala-L-Ala was not formed at all.

The above results revealed that all of the products of the genes obtained in Experimental Example 8 have the activity to produce L-Ala-L-Gln and L-Ala-L-Ala from L-Ala and L-Gln in the presence of ATP.

Experimental Example 11

Acquisition of the albC Gene and its Analogous Gene

The albC gene and its analogous gene were obtained from *Streptomyces noursei* and *Streptomyces albulus* based on the nucleotide sequence of the albC gene of *Streptomyces noursei* [Chemistry & Biol., 9, 1355 (2002)] in the following manner.

*Streptomyces noursei* IFO15452 and *Streptomyces albulus* IFO14147 were inoculated into KM73 medium [2 g/l yeast extract (Difco) and 10 g/l soluble starch (Wako Pure Chemical Industries, Ltd.)] containing 1% glycine and KP medium [15 g/l glucose, 10 g/l glycerol, 10 g/l polypeptone (Nihon Pharmaceutical Co., Ltd.), 10 g/1 meat extract (Kyokuto Pharmaceutical Industrial Co., Ltd.) and 4 g/l calcium carbonate], respectively, and subjected to shaking culture overnight at 28° C. *Streptomyces noursei* IFO15452 and *Streptomyces albulus* IFO14147 were distributed by National Institute of Technology and Evaluation (NITE) Biological Resource Center (BRC) (2-5-8, Kazusakamatari, Kisarazu-shi, Chiba 292-0818 Japan).

After the culturing, the chromosomal DNAs of the respective microorganisms were isolated and purified according to the method described in Genetic Manipulation of *Streptomyces*: a Laboratory Manual: John Innes Foundation.

On the basis of the nucleotide sequence of the albC gene, DNAs having the nucleotide sequences shown in SEQ ID NOS: 41 and 42 (hereinafter referred to as primer J and primer K, respectively) were synthesized by using a DNA synthesizer (Model 8905, PerSeptive Biosystems, Inc.). Primer J has a sequence wherein a sequence containing the NcoI recognition sequence is added to the 5' end of a region containing the initiation codon of the albC gene on the chromosomal DNA of *Streptomyces noursei*. Primer K has a sequence wherein a sequence containing the BglII recognition sequence is added to the 5' end of a sequence complementary to a sequence containing the termination codon of the albC gene.

PCR was carried out using each of the chromosomal DNAs of *Streptomyces noursei* and *Streptomyces albulus* as a template and the above primer J and primer K as a set of primers. That is, PCR was carried out by 30 cycles, one cycle consisting of reaction at 94° C. for one minute, reaction at 55° C. for 30 seconds and reaction at 72° C. for one minute, using 50 µl of a reaction mixture comprising 0.1 µg of the chromosomal DNA as a template, 0.5 µmol/l each of the primers, 2.5 units of Ex Taq DNA polymerase (Takara Bio Inc.), 5 µl of buffer for Ex Taq DNA polymerase (10×) (Takara Bio Inc.), 200 µmol/l each of dNTPs and 5 µl of dimethyl sulfoxide.

One-tenth of each of the resulting reaction mixtures was subjected to agarose gel electrophoresis to confirm that a ca. 0.7 kb DNA fragment was amplified. Then, the remaining reaction mixture was mixed with an equal amount of phenol/chloroform saturated with TE. The resulting solution was centrifuged, and the obtained upper layer was mixed with a two-fold volume of cold ethanol and allowed to stand at −80° C. for 30 minutes. The resulting solution was centrifuged to precipitate DNA, and the obtained DNA was dissolved in 20 µl of TE.

Each of the thus obtained solutions (5 µl) was subjected to reaction to cleave the amplified DNA with restriction enzymes NcoI and BglII. DNA fragments were separated by agarose gel electrophoresis, and a 700 bp DNA fragment was recovered using GENECLEAN II Kit.

Subsequently, 0.2 µg of the expression vector pQE60 containing phage T5 promoter was cleaved with restriction enzymes NcoI and BglII. DNA fragments were separated by agarose gel electrophoresis, and a 3.4 kb DNA fragment was recovered in the same manner as above.

Each of the actinomycetes-derived 0.7 kb DNA fragments and the pQE60-derived 3.4 kb DNA fragment obtained above were subjected to ligation reaction using a ligation kit at 16° C. for 16 hours.

*Escherichia coli* NM522 was transformed using each ligation reaction mixture according to the method using calcium ion, spread on LB agar medium containing 50 µg/ml ampicillin, and cultured overnight at 30° C.

Figure 3:
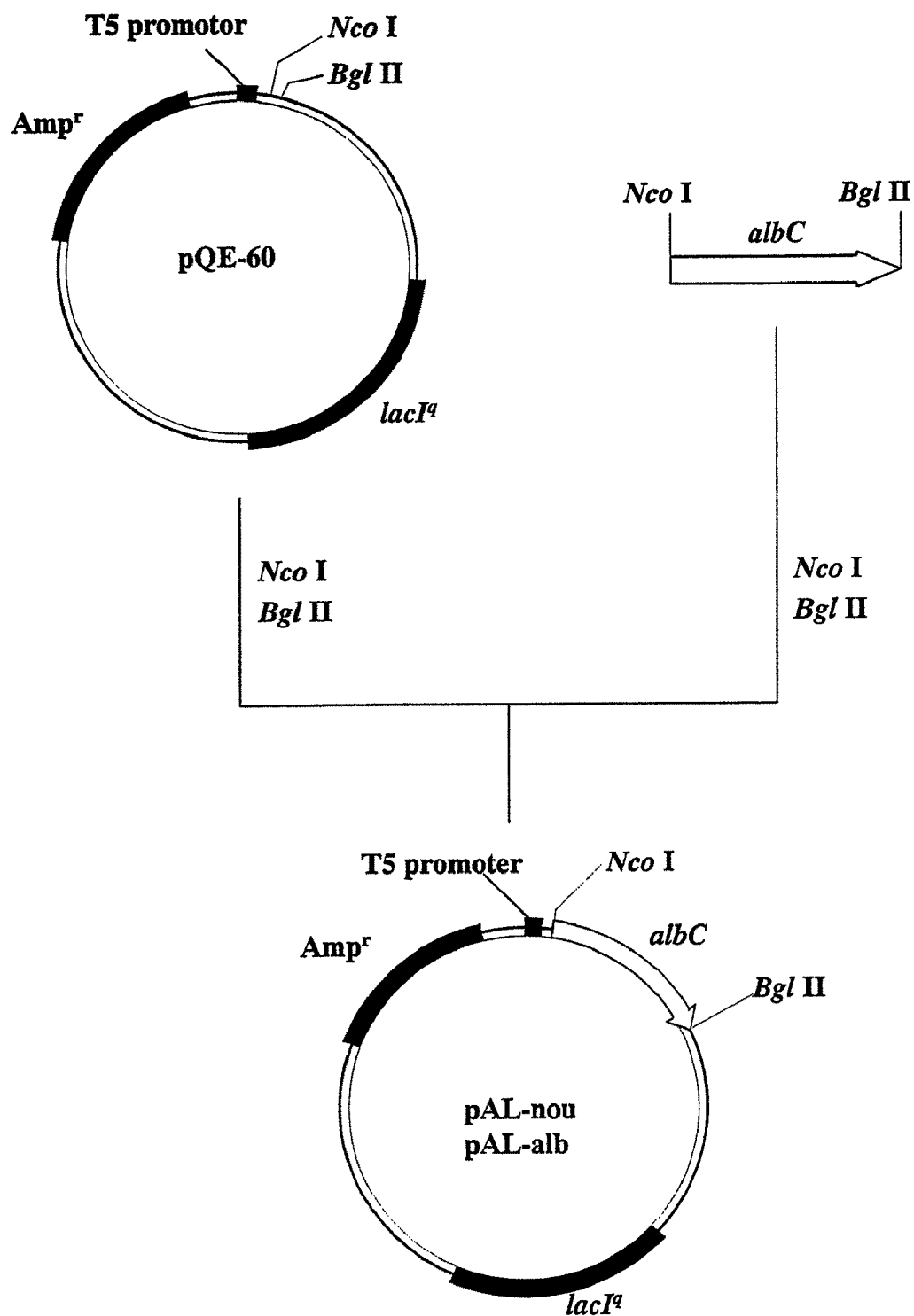
FIG. 3 shows the steps for constructing pAL-nou and pAL-albC, which are plasmid vectors for the expression of proteins having the activity to synthesize a straight-chain dipeptide.

A plasmid was extracted from a colony of each transformant that grew on the medium according to a known method, and the structure of each plasmid was analyzed using restriction enzymes. As a result, it was confirmed that expression vector pAL-nou containing the DNA derived from *Streptomyces noursei* at a position downstream of the phage T5 promoter and expression vector pAL-alb containing the DNA derived from *Streptomyces albulus* were obtained (FIG. 3).

The nucleotide sequence of each actinomycete-derived DNA inserted into the respective plasmid was determined by using a nucleotide sequencer (373A DNA Sequencer), whereby it was confirmed that pAL-alb contained DNA encoding a protein having the amino acid sequence shown in SEQ ID NO: 37, i.e. DNA having the nucleotide sequence shown in SEQ ID NO: 39, and pAL-nou contained DNA encoding a protein having the amino acid sequence shown in SEQ ID NO: 38, i.e. DNA having the nucleotide sequence shown in SEQ ID NO: 40.

Experimental Example 12

Production of Straight-Chain Dipeptides by the Use of Cells as an Enzyme Source

*Escherichia coli* NM522 carrying pAL-nou or pAL-alb obtained in Experimental Example 11 (*Escherichia coli* NM522/pAL-nou or NM522/pAL-alb) and *Escherichia coli* NM522 without a plasmid were respectively inoculated into 10 ml of LB medium containing 50 µg/ml ampicillin in a test tube (no addition of ampicillin in the case of a strain carrying no plasmid, hereinafter the same shall apply), and cultured at 30° C. for 17 hours. Each of the resulting cultures (0.5 ml) was inoculated into 50 ml of LB medium in a 250-ml Erlenmeyer flask and subjected to shaking culture at 30° C. for one hour. Then, IPTG was added to give a final concentration of 1 mmol/l, followed by further culturing for 4 hours. The resulting culture was centrifuged to obtain wet cells.

A reaction mixture (3.0 ml) comprising 100 mg/ml (final concentration) wet cells, 60 mmol/l potassium phosphate buffer (pH 7.2), 10 mmol/1 magnesium chloride, 10 mmol/l ATP, 1 g/l L-Leu and 1 g/l L-Phe was prepared, and reaction was carried out at 30° C. One hour after the start of the reaction, the reaction mixture was sampled and acetonitrile was added thereto to a concentration of 20% (v/v). Then, the obtained reaction product was analyzed by HPLC. The HPLC analysis was carried out by using ODS-HA column (YMC Co., Ltd.) as a separation column and 30% (v/v) acetonitrile as an eluent at a flow rate of 0.6 ml/min, and by measuring ultraviolet absorption at 215 nm.

As a result, it was confirmed that 36.7 mg/l cyclo(L-leucyl-L-phenylalanine) [cyclo(L-Leu-L-Phe)] was accumulated in the reaction mixture of *Escherichia coli* NM522/pAL-nou. However, no cyclo(L-Leu-L-Phe) was detected in the reaction mixture of *Escherichia coli* NM522. The same reaction mixtures were analyzed by HPLC under the following conditions to measure straight-chain dipeptides (hereinafter, "straight-chain dipeptide" is referred simply as "dipeptide") L-leucyl-L-phenylalanine (L-Leu-L-Phe) and L-phenylalanyl-L-leucine (L-Phe-L-Leu).

Both the dipeptides were derivatized by the F-moc method and then analyzed by HPLC. The HPLC analysis was carried out by using ODS-HG5 (Nomura Kagaku Co., Ltd.) as a separation column and solution A (6 ml/l acetic acid and 20%

(v/v) acetonitrile, pH adjusted to 4.8 with triethylamine) and solution B (6 ml/l acetic acid and 70% (v/v) acetonitrile, pH adjusted to 4.8 with triethylamine) as eluents at a flow rate of 0.6 ml/min, and by detecting the dipeptides at an excitation wavelength of 254 nm and a fluorescence wavelength of 630 nm. The ratio of solution A to solution B was 8:2 during the first 5 minutes of elution and thereafter changed with a linear gradient so that the ratio became 1:1 at 20 minutes after the start of elution.

As a result, it was confirmed that 21.9 mg/l L-Leu-L-Phe and 12.0 mg/l L-Phe-L-Leu were accumulated in the reaction mixture of *Escherichia coli* NM522/pAL-nou and no dipeptide was detected in the reaction mixture of *Escherichia coli* NM522 used as a control strain.

The above result revealed that the cyclodipeptide-synthesizing enzyme obtained in Experimental Example 11 has the ability to synthesize dipeptides.

Experimental Example 13

Production of Dipeptides Using the Purified Enzyme (1)

*Escherichia coli* NM522/pAL-nou was cultured in the same manner as in Experimental Example 12. After the completion of the culturing, centrifugation was carried out to obtain wet cells. The obtained wet cells were washed with a 60 mmol/l potassium phosphate buffer (pH 7.2) and suspended in a 20 mmol/l potassium phosphate buffer containing 10 mmol/l imidazole. The resulting suspension was subjected to ultrasonication at 4° C. to obtain a disrupted cell suspension. The obtained suspension (10 ml: containing 0.863 mg of protein) was passed through a His-tag purification column (Amersham Biosciences K.K.) and then 15 ml of a 20 mmol/l potassium phosphate buffer containing 10 mmol/l imidazole was passed through the column for washing to purify a His-tagged albC protein in the column. Then, 2 ml of a reaction mixture having the same composition as that in Experimental Example 12 [composition: 60 mmol/l potassium phosphate buffer (pH 7.2), 10 mmol/l magnesium chloride, 10 mmol/l ATP, 1 g/l L-Leu, 1 g/l L-Phe] was put into the column containing the His-tagged albC protein, followed by incubation at 30° C., during which the substrates were held in the column. After 24 hours, the reaction mixture in the column was eluted with 3 ml of a reaction mixture having the same composition, and the cyclodipeptide and dipeptides in the reaction mixture were determined in the same manner as in Experimental Example 12.

As a result, it was confirmed that 6.8 mg/l cyclo(L-Leu-L-Phe), 28.7 mg/l L-Leu-L-Phe and 18.5 mg/l L-Phe-L-Leu were formed. No cyclodipeptide or dipeptide was detected in the reaction mixture when without ATP incubated in the same manner.

Experimental Example 14

Production of Dipeptides Using the Purified Enzyme (2)

Enzymatic reaction was carried out in the same manner as in Experimental Example 13 except that the amino acids as substrates were replaced by another amino acid, and the obtained product was analyzed. As the reaction mixture, a mixture having the same composition as that of Experimental Example 13 except that the amino acids as the substrates were replaced by 1 g/l L-Ala, L-Leu or L-Phe was used.

As a result, it was revealed that 9.41 mg/l L-Ala-L-Ala, 7.85 mg/l L-Leu-L-Leu and 5.20 mg/l L-Phe-L-Phe were respectively formed in 24 hours after the start of the reaction.

Experimental Example 15

Construction of *Escherichia coli* for Enhanced Expression of the ywfE Gene

By using a DNA synthesizer (Model 8905, PerSeptive Biosystems, Inc.), DNAs having the sequences shown in SEQ ID NOS: 84 to 87 (hereinafter referred to as primer L, primer M, primer N and primer 0, respectively) were synthesized. The sequence of SEQ ID NO: 84 is a sequence wherein a sequence containing the XhoI recognition sequence is added to the 5' end of a region containing the Shine-Dalgarno sequence (ribosome binding sequence) of the ywfE gene on the plasmid pQE60ywfE. The sequence of SEQ ID NO: 85 is a sequence wherein a sequence containing the BamHI recognition sequence is added to the 5' end of a sequence complementary to a sequence containing the termination codon of the ywfE gene. The sequence of SEQ ID NO: 86 is a sequence wherein a sequence containing the EcoRI recognition sequence is added to the 5' end of the sequence of trp promoter region of expression vector pTrS30 containing trp promoter. The sequence of SEQ ID NO: 87 is a sequence wherein a sequence containing the XhoI recognition sequence is added to the 5' end of a sequence complementary to the sequence of trp promoter region of expression vector pTrS30 containing trp promoter.

A ywfE gene fragment and a trp promoter region fragment were amplified by PCR using the above primers L and M, and primers N and O as a set of primers, respectively, and the plasmid pQE60ywfE as a template. PCR was carried out by 30 cycles, one cycle consisting of reaction at 94° C. for one minute, reaction at 55° C. for 2 minutes and reaction at 72° C. for 3 minutes, using 40 µl of a reaction mixture comprising 10 ng of pQE60ywfE, 0.5 µmol/l each of the primers, 2.5 units of Pfu DNA polymerase, 4 µl of buffer for Pfu DNA polymerase (10×) and 200 µmol/l each of dNTPs.

One-tenth of each of the resulting reaction mixtures was subjected to agarose gel electrophoresis to confirm that a ca. 1.4 kb fragment corresponding to the ywfE gene fragment and a ca. 0.3 kb fragment corresponding to the trp promoter region fragment were respectively amplified in the PCR using primer L and primer M and the PCR using primer N and primer 0. Then, the remaining reaction mixture was mixed with an equal amount of phenol/chloroform saturated with TE. The resulting solution was centrifuged, and the obtained upper layer was mixed with a two-fold volume of cold ethanol and allowed to stand at −80° C. for 30 minutes. The resulting solution was centrifuged, and the obtained DNA was dissolved in 20 µl of TE.

The thus obtained DNA solutions (5 µl each) were respectively subjected to reaction to cleave the DNA amplified using primer L and primer M with restriction enzymes XhoI and BamHI and to reaction to cleave the DNA amplified using primer N and primer O with restriction enzymes EcoRI and XhoI. DNA fragments were separated by agarose gel electrophoresis, and a 1.4 kb fragment containing the ywfE gene and a 0.3 kb fragment containing trp promoter region were respectively recovered using GENECLEAN II Kit.

Expression vector pTrs30 containing trp promoter (0.2 µg) was cleaved with restriction enzymes EcoRI and BamHI. DNA fragments were separated by agarose gel electrophoresis and a 4.5 kb DNA fragment was recovered in the same manner as above.

The 1.4 kb fragment containing the ywfE gene, the 0.3 kb fragment containing trp promoter region and the 4.5 kb DNA fragment obtained above were subjected to ligation reaction using a ligation kit at 16° C. for 16 hours.

*Escherichia coli* NM522 was transformed using the reaction mixture according to the method using calcium ion, spread on LB agar medium containing 50 µg/ml ampicillin, and cultured overnight at 30° C.

Figure 4:
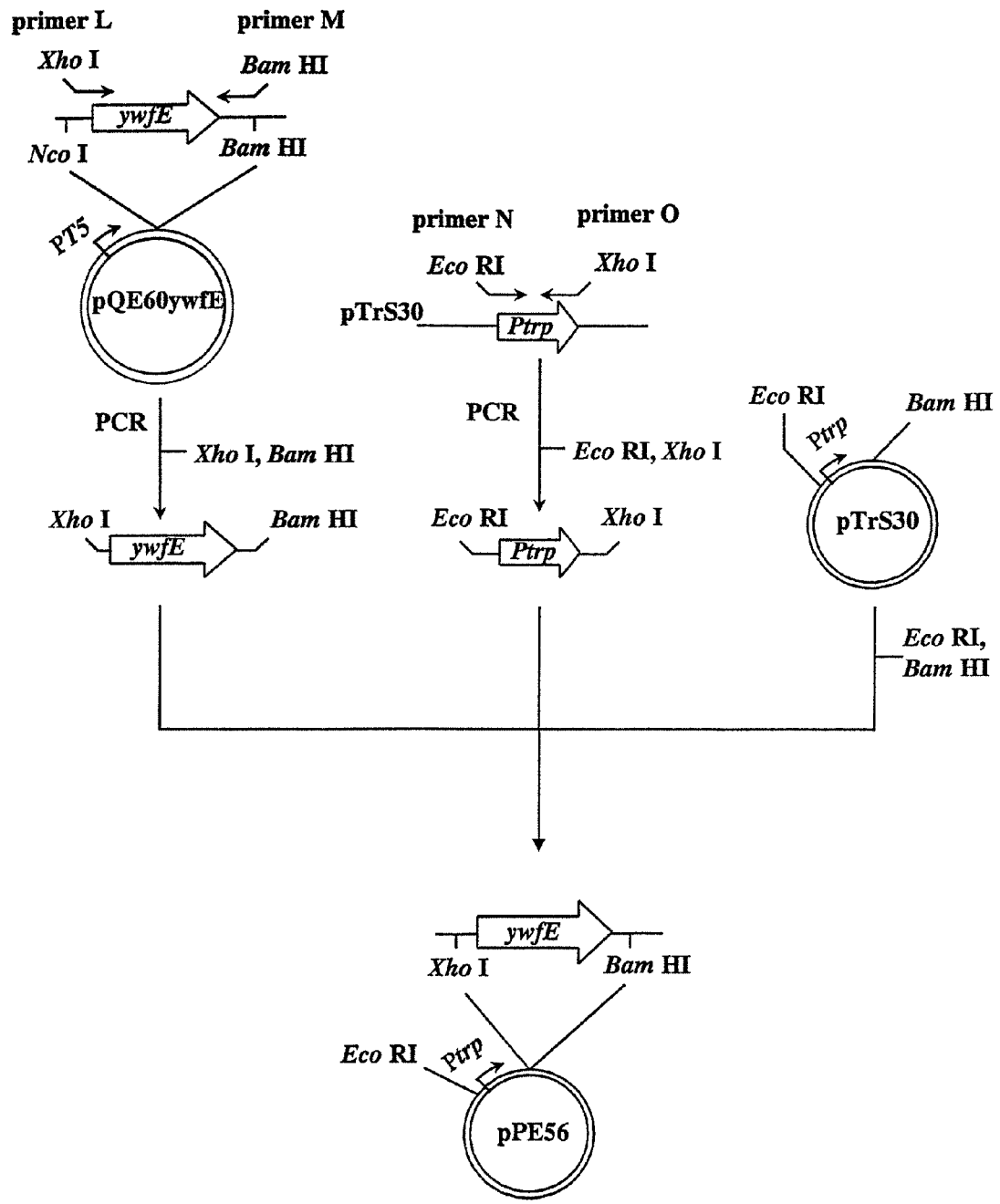
FIG. 4 shows the steps for constructing ywfE gene expression-enhanced vector pPE56.

A plasmid was extracted from a colony of the transformant that grew on the medium according to a known method, whereby expression vector pPE56 containing the ywfE gene at a position downstream of the trp promoter was obtained. The structure of the vector was confirmed by digestion with restriction enzymes (FIG. 4)

Experimental Example 16

Preparation of Strains Having Deletions of the pepD, pepN, pepB and pepA Genes and the dpp Operon Strains in which specific genes on *Escherichia coli* chromosomal DNA are deleted were prepared according to the method utilizing the homologous recombination system of lambda phage [Proc. Natl. Acad. Sci. USA, 97, 6641-6645 (2000)].

Plasmids pKD46, pKD3 and pCP20 used below were prepared by extraction, according to a known method, from *Escherichia coli* strains carrying them which were obtained from *Escherichia coli* Genetic Stock Center, Yale University, U.S.A.

(1) Cloning of DNA Fragments for Gene Deletion

For the purpose of deleting the following genes existing on the chromosomal DNA of *Escherichia coli* K12, DNAs having nucleotide sequences homologous to 36-bp nucleotide sequences that lie upstream and downstream of the respective genes to be deleted on the chromosomal DNA of *Escherichia coli* K12 and the nucleotide sequence shown in SEQ ID NO: 54 which is recognized by yeast-derived Flp recombinase were synthesized using a DNA synthesizer (Model 8905, PerSeptive Biosystems, Inc.). The genes to be deleted are the pepD gene having the nucleotide sequence shown in SEQ ID NO: 55, the pepN gene having the nucleotide sequence shown in SEQ ID NO: 56, the pepB gene having the nucleotide sequence shown in SEQ ID NO: 57, the pepA gene having the nucleotide sequence shown in SEQ ID NO: 58, the dppA gene having the nucleotide sequence shown in SEQ ID NO: 59, the dppB gene having the nucleotide sequence shown in SEQ ID NO: 60, the dppC gene having the nucleotide sequence shown in SEQ ID NO: 61, the dppD gene having the nucleotide sequence shown in SEQ ID NO: 62 and the dppF gene having the nucleotide sequence shown in SEQ ID NO: 63. In the case of the dppA, dppB, dppC, dppD and dppF genes, which form an operon, DNAs having nucleotide sequences homologous to the nucleotide sequences that lie upstream and downstream of the operon were synthesized.

That is, DNAs consisting of the following nucleotide sequences were synthesized as respective sets of primers for amplification of DNA fragments for gene deletion: SEQ ID NOS: 64 and 65 for pepD gene deletion; SEQ ID NOS: 66 and 67 for pepN gene deletion; SEQ ID NOS: 68 and 69 for pepA gene deletion; SEQ ID NOS: 70 and 71 for pepB gene deletion; and SEQ ID NOS: 72 and 73 for dpp operon deletion.

Subsequently, PCR was carried out using each set of the above synthetic DNAs as a set of primers and pKD3 DNA as a template. That is, PCR was carried out by 30 cycles, one cycle consisting of reaction at 94° C. for one minute, reaction at 55° C. for 2 minutes and reaction at 72° C. for 3 minutes, using 40 µl of a reaction mixture comprising 10 ng of the plasmid DNA, 0.5 µmol/l each of the primers, 2.5 units of Pfu DNA polymerase, 4 µl of buffer for Pfu DNA polymerase (10×) and 200 µmol/l each of deoxyNTPs.

One-tenth of each of the resulting reaction mixtures was subjected to agarose gel electrophoresis to confirm that the desired fragment was amplified. Then, the remaining reaction mixture was mixed with an equal amount of phenol/chloroform saturated with TE.

The resulting mixture was centrifuged, and the obtained upper layer was mixed with a two-fold volume of cold ethanol and allowed to stand at −80° C. for 30 minutes, followed by centrifugation. By this procedure, chloramphenicol resistance gene-containing DNA fragments for deletion of the pepD, pepN, pepB and pepA genes and the dpp operon were obtained.

(2) Preparation of *Escherichia coli* JM101 Having pepD Gene Deletion

*Escherichia coli* JM101 was transformed with pKD46, spread on LB agar medium containing 100 mg/l ampicillin, and cultured at 30° C. to select *Escherichia coli* JM101 carrying pKD46 (hereinafter referred to as *Escherichia coli* JM101/pKD46).

The plasmid pKD46 carries λ Red recombinase gene the expression of which can be induced by L-arabinose. Accordingly, when *Escherichia coli* carrying pKD46 grown in the presence of L-arabinose is transformed using a straight-chain DNA, homologous recombination occurs with high frequency. Further, as pKD46 has a thermosensitive replication origin, curing of the plasmid can be readily caused by culturing the strain at 42° C.

The chloramphenicol resistance gene-containing DNA fragment for pepD gene deletion obtained above was introduced into *Escherichia coli* JM101/pKD46 obtained by culturing in the presence of 10 mmol/l L-arabinose and 50 µg/ml ampicillin by electroporation. The resulting cells were spread on LB agar medium (10 g/l Bacto-tryptone, 5 µg/l Bacto-yeast extract, 5 g/l sodium chloride and 15 g/l agar) containing 25 mg/l chloramphenicol and cultured at 30° C. to select a transformant in which the chloramphenicol resistance gene-containing DNA fragment for pepD gene deletion was integrated into the chromosomal DNA of *Escherichia coli* JM101 by homologous recombination.

The selected chloramphenicol-resistant strain was inoculated onto LB agar medium containing 25 mg/l chloramphenicol and cultured at 42° C. for 14 hours, followed by single colony isolation. Replicas of the obtained colonies were made on LB agar medium containing 25 mg/l chloramphenicol and LB agar medium containing 100 mg/l ampicillin, followed by culturing at 37° C. By selecting a colony showing chloramphenicol resistance and ampicillin sensitivity, a pKD46-cured strain was obtained.

The pKD46-cured strain thus obtained was transformed using pCP20, followed by selection on LB agar medium containing 100 mg/l ampicillin to obtain a pKD46-cured strain carrying pCP20.

The plasmid pCP20 carries a yeast-derived Flp recombinase gene the expression of which can be induced at a temperature of 42° C.

The chloramphenicol resistance gene-containing DNA fragments for deletion of the pepD, pepN, pepB and pepA genes and the dpp operon prepared above contain nucleotide sequences recognized by Flp recombinase at both termini of the chloramphenicol resistance gene. Therefore, the resistance gene can be readily deleted by homologous recombination catalyzed by Flp recombinase.

Further, as pCP20 has a thermosensitive replication origin, expression of Flp recombinase and curing of pCP20 can be simultaneously induced by culturing the pCP20-carrying strain at 42° C.

The pCP20-carrying pKD46-cured strain obtained above was inoculated onto drug-free LB agar medium and cultured at 42° C. for 14 hours, followed by single colony isolation. Replicas of the obtained colonies were made on drug-free LB agar medium, LB agar medium containing 25 mg/l chloramphenicol and LB agar medium containing 100 mg/l ampicillin, followed by culturing at 30° C. Then, colonies showing chloramphenicol sensitivity and ampicillin sensitivity were selected.

Chromosomal DNAs were prepared from the respective strains selected above according to an ordinary method [Seibutsukogaku Jikkensho (Experiments in Biotechnology), edited by The Society for Biotechnology, Japan, p. 97-98, Baifukan (1992)]. PCR was carried out using, as a set of primers, DNAs having the nucleotide sequences shown in SEQ ID NOS: 74 and 75 which were designed based on an inner nucleotide sequence of the pepD gene to be deleted, and using each of the chromosomal DNAs as a template. That is, PCR was carried out by 30 cycles, one cycle consisting of reaction at 94° C. for one minute, reaction at 55° C. for 2 minutes and reaction at 72° C. for 3 minutes, using 40 μl of a reaction mixture comprising 0.1 μg of the chromosomal DNA, 0.5 μmol/l each of the primers, 2.5 units of Pfu DNA polymerase, 4 μl of buffer for Pfu DNA polymerase (10×) and 200 μmol/l each of deoxyNTPs.

A strain with which no amplified DNA fragment was detected in the above PCR was identified as a strain having pepD gene deletion and was designated as *Escherichia coli* JPD1.

(3) Preparation of a Strain in which the pepD and pepN Genes on the Chromosomal DNA of *Escherichia coli* JM101 are Deleted

*Escherichia coli* JPD1 obtained in the above (2) was transformed with pKD46, spread on LB agar medium containing 100 mg/l ampicillin, and cultured at 30° C. to select *Escherichia coli* JPD1 carrying pKD46 (hereinafter referred to as *Escherichia coli* JPD1/pKD46). The chloramphenicol resistance gene-containing DNA fragment for pepN gene deletion was introduced into *Escherichia coli* JPD1/pKD46 by electroporation to obtain a transformant in which the chloramphenicol resistance gene-containing DNA fragment for pepN gene deletion was integrated into the chromosomal DNA of *Escherichia coli* JPD1/pKD46 by homologous recombination.

Subsequently, the same procedure as in the above (2) was carried out to obtain a strain in which the chloramphenicol resistance gene was deleted from the chromosomal DNA, which was designated as *Escherichia coli* JPDN2.

(4) Preparation of Strains in which the pepN, pepA or pepB Gene or the dpp Operon on the Chromosomal DNA of *Escherichia coli* JM101 is Deleted and Strains Having Multiple Gene Deletion The strains having pepN, pepA or pepB gene or dpp operon deletion were prepared according to the same procedure as in the above (2) using the respective chloramphenicol resistance gene-containing DNA fragments for gene or operon deletion prepared in the above (1).

Acquisition of the strains having gene deletions by the above method was confirmed by carrying out PCR in the same manner as in the above (2) using, as sets of primers, DNAs having the nucleotide sequences shown in SEQ ID NOS: 76 to 83 which were designed and synthesized based on inner nucleotide sequences of the respective genes to be deleted. That is, DNAs having the following nucleotide sequences were used as respective sets of primers for the confirmation of gene deletion: SEQ ID NOS: 76 and 77 for pepN deletion; SEQ ID NOS: 78 and 79 for pepA deletion; SEQ ID NOS: 80 and 81 for pepB deletion; and SEQ ID NOS: 82 and 83 for dpp operon deletion.

The thus obtained dpp operon-deleted strain, pepN gene-deleted strain, pepA gene-deleted strain and pepB gene-deleted strain were designated as *Escherichia coli* JDPP1, *Escherichia coli* JPN1, *Escherichia coli* JPA1 and *Escherichia coli* JPB7, respectively.

Further, strains having multiple gene deletions, i.e., deletions of two or more genes or operon selected from the group consisting of the pepD, pepN, pepA and pepB genes and the dpp operon were prepared according to the method of the above (3). Acquisition of the strains having multiple gene deletions was confirmed by PCR similar to that in the above (2). The thus obtained double gene-deleted strain having pepD gene and dpp operon deletions was designated as *Escherichia coli* JPDP49, triple gene-deleted strain having pepB, pepD and pepN gene deletions as *Escherichia coli* JPDNB43, triple gene-deleted strain having pepD and pepN gene and dpp operon deletions as *Escherichia coli* JPNDDP36, quadruple gene-deleted strain having pepA, pepD and pepN gene and dpp operon deletions as *Escherichia coli* JPNDAP5, and quadruple gene-deleted strain having pepB, pepD and pepN gene and dpp operon deletions as *Escherichia coli* JPNDBP7. The genes deleted in the gene-deleted strains are shown in Table 2.

TABLE 2

| Strain | Deleted gene |
| --- | --- |
| JM101 | none |
| JDPP1 | dpp operon |
| JPN1 | pepN |
| JPA1 | pepA |
| JPB7 | pepB |
| JPD1 | pepD |
| JPDN2 | pepD, pepN |
| JPNDB43 | pepB, pepD, pepN |
| JPDP49 | pepD, dpp operon |
| JPNDDP36 | pepD, pepN, dpp operon |
| JPNDAP5 | pepA, pepD, pepN, dpp operon |
| JPNDBP7 | pepB, pepD, pepN, dpp operon |

Experimental Example 17

Evaluation of Productivity of L-Ala-L-Gln and L-Ala-L-Ala by *Escherichia coli* Strains in which Peptidase and Dipeptide-Permeating/Transporting Protein Activities are Lost The strains having deletions of genes encoding various peptidases and dipeptide-permeating/transporting protein which were obtained in Experimental Example 16 were transformed using the plasmid pPE56 constructed in Experimental Example 15 to obtain ampicillin-resistant transformants.

Each of the obtained transformants was inoculated into 8 ml of LB medium containing 50 μg/ml ampicillin in a test tube and cultured at 28° C. for 17 hours. The resulting culture was added to 8 ml of an aqueous medium [16 g/l dipotassium hydrogenphosphate, 14 g/l potassium dihydrogenphosphate, 5 g/l ammonium sulfate, 1 g/l citric acid (anhydrous), 0.5 g/l Casamino acid (Difco), 1 g/l L-Pro, 2.5 g/l L-Ala, 2.5 g/l L-Gln, 10 g/l glucose, 10 mg/l vitamin $B_1$, 25 mg/l magnesium sulfate heptahydrate and 50 mg/l ferrous sulfate heptahydrate; pH adjusted to 7.2 with 10 mol/l sodium hydroxide solution; L-Gln was added after sterilization by filtration of a 10-fold conc. solution; glucose, vitamin B$_1$, magnesium sulfate heptahydrate and ferrous sulfate heptahydrate were added after separate steam sterilization] containing 100 μg/ml ampicillin in a test tube in an amount of 1% and subjected to reaction at 30° C. for 24 hours. The resulting aqueous medium was centrifuged to obtain a supernatant.

The product in the supernatant was derivatized by the F-moc method and then analyzed by HPLC. The HPLC analysis was carried out using ODS-HG5 (Nomura Kagaku Co., Ltd.) as a separation column and solution A (6 ml/l acetic acid and 20% (v/v) acetonitrile, pH adjusted to 4.8 with triethylamine) and solution B (6 ml/l acetic acid and 70% (v/v) acetonitrile, pH adjusted to 4.8 with triethylamine) as eluents. The ratio of solution A to solution B was 8:2 during the first 5 minutes of elution and thereafter changed with a linear gradient so that the ratio became 1:1 at 20 minutes after the start of elution. The results of analysis are shown in Table 3.

TABLE 3

| Strain | Deleted gene | L-Ala-L-Gln (g/l) | L-Ala-L-Ala (g/l) |
|---|---|---|---|
| JM101 | none | 0 | 0 |
| JDPP1 | dpp operon | 0.02 | 0.01 |
| JPN1 | pepN | 0.01 | 0.01 |
| JPA1 | pepA | 0.01 | 0.01 |
| JPB7 | pepB | 0.01 | 0.01 |
| JPD1 | pepD | 0.01 | 0.01 |
| JPDN2 | pepD, pepN | 0.02 | 0.03 |
| JPNDB43 | pepB, pepD, pepN | 0.05 | 0.12 |
| JPDP49 | pepD, dpp operon | 0.11 | 0.08 |
| JPNDDP36 | pepD, pepN, dpp operon | 0.16 | 0.21 |
| JPNDAP5 | pepA, pepD, pepN, dpp operon | 0.28 | 0.26 |
| JPNDBP7 | pepB, pepD, pepN, dpp operon | 0.43 | 0.22 |

As can be seen from Table 3, small amounts of dipeptides were formed and accumulated by use of the microorganisms having deletions of two or less kinds of peptidase genes or one operon encoding a peptide-permeating/transporting protein, whereas the amounts of dipeptides formed and accumulated were greatly increased by use of the microorganisms having deletions of one or more kinds of peptidase genes and one operon encoding a peptide-permeating/transporting protein or microorganisms having deletions of three or more kinds of peptidase genes.

Experimental Example 18

Evaluation of Productivity of L-Alanyl-L-valine (Hereinafter Referred to as L-Ala-L-Val) by *Escherichia coli* Strains in which Peptidase and Peptide-Permeating/Transporting Protein Activities are Lost Similarly to Experimental Example 17, the *Escherichia coli* strains having deletions of genes encoding various peptidases and peptide-permeating/transporting protein were transformed using pPE56. Each of the obtained transformants was added to 8 ml of LB medium containing 50 μg/ml ampicillin in a test tube and cultured at 28° C. for 17 hours. The resulting culture was added to 8 ml of an aqueous medium [16 g/l dipotassium hydrogenphosphate, 14 g/l potassium dihydrogenphosphate, 5 g/l ammonium sulfate, 1 g/l citric acid (anhydrous), 0.5 g/l Casamino acid (Difco), 1 g/l L-Pro, 2.5 g/l L-Ala, 2.5 g/l L-Val, 10 g/l glucose, 10 mg/l vitamin B$_1$, 25 mg/l magnesium sulfate heptahydrate and 50 mg/l ferrous sulfate heptahydrate; pH adjusted to 7.2 with 10 mol/l sodium hydroxide solution; glucose, vitamin B$_1$, magnesium sulfate heptahydrate and ferrous sulfate heptahydrate were added after separate steam sterilization] containing 100 μg/ml ampicillin in a test tube in an amount of 1% and subjected to reaction at 30° C. for 24 hours. The resulting aqueous medium was centrifuged to obtain a supernatant.

The product in the supernatant was analyzed by the method described in Experimental Example 17. The results are shown in Table 4.

TABLE 4

| Strain | Deleted gene | L-Ala-L-Val (g/l) |
|---|---|---|
| JM101 | none | 0 |
| JDPP1 | dpp operon | 0 |
| JPN1 | pepN | 0 |
| JPA1 | pepA | 0 |
| JPB7 | pepB | 0 |
| JPD1 | pepD | 0 |
| JPDN2 | pepD, pepN | 0 |
| JPNDB43 | pepB, pepD, pepN | 0.04 |
| JPDP49 | pepD, dpp operon | 0.11 |
| JPNDDP36 | pepD, pepN, dpp operon | 0.22 |
| JPNDBP7 | pepB, pepD, pepN, dpp operon | 0.20 |

As can be seen from Table 4, the dipeptide was not produced by use of the microorganisms having deletions of two or less kinds of peptidase genes or one operon encoding a peptide-permeating/transporting protein, whereas the dipeptide was produced by use of the microorganisms having deletions of three or more kinds of peptidase genes or microorganisms having deletions of one or more kinds of peptidase genes and one operon encoding a peptide-permeating/transporting protein.

Experimental Example 19

Evaluation of Productivity of Glycyl-L-glutamine (Hereinafter Referred to as Gly-L-Gln) by *Escherichia coli* Strains in which Peptidase and Dipeptide-Permeating/Transporting Protein Activities are Lost Similarly to Experimental Example 17, the strains having deletions of various peptidase genes and an operon encoding a dipeptide-permeating/transporting protein were transformed using pPE56. Each of the obtained transformants was inoculated into 8 ml of LB medium containing 50 μg/ml ampicillin in a test tube and cultured at 28° C. for 17 hours.

The resulting culture was added to 8 ml of an aqueous medium [16 g/l dipotassium hydrogenphosphate, 14 g/l potassium dihydrogenphosphate, 5 g/l ammonium sulfate, 1 g/l citric acid (anhydrous), 0.5 g/l Casamino acid (Difco), 1 g/l L-Pro, 2.5 g/l Gly, 2.5 g/l L-Gln, 10 g/l glucose, 10 mg/l vitamin B$_1$, 25 mg/l magnesium sulfate heptahydrate and 50 mg/l ferrous sulfate heptahydrate; pH adjusted to 7.2 with 10 mol/l sodium hydroxide solution; L-Gln was added after sterilization by filtration of a 10-fold conc. solution; glucose, vitamin B$_1$, magnesium sulfate heptahydrate and ferrous sulfate heptahydrate were added after separate steam sterilization] containing 100 μg/ml ampicillin in a test tube in an amount of 1% and subjected to reaction at 30° C. for 24 hours. The resulting aqueous medium was centrifuged to obtain a supernatant.

The product in the supernatant was analyzed by the method described in Experimental Example 17. The results are shown in Table 5.

TABLE 5

| Strain | Deleted gene | Gly-L-Gln (g/l) |
|---|---|---|
| JM101 | none | 0 |
| JDPP1 | dpp operon | 0 |
| JPDN2 | pepD, pepN | 0 |
| JPNDB43 | pepB, pepD, pepN | 0.01 |
| JPNDDP36 | pepD, pepN, dpp operon | 0.02 |
| JPNDBP7 | pepB, pepD, pepN, dpp operon | 0.03 |

As can be seen from Table 5, the dipeptide was not produced by use of the microorganisms having deletions of two or less kinds of peptidase genes or one operon encoding a peptide-permeating/transporting protein, whereas the dipeptide was produced by use of the microorganisms having deletions of three or more kinds of peptidase genes or microorganisms having deletions of two or more kinds of peptidase genes and one operon encoding a peptide-permeating/transporting protein.

Certain embodiments of the present invention are illustrated in the following examples. These examples are not to be construed as limiting the scope of the invention.

Example 1

Preparation of a Microorganism Having Deletions of the glnE and glnB Genes Involved in the Regulation of L-Glutamine Biosynthesis Deletion of specific genes on *Escherichia coli* chromosomal DNA was carried out according to the method utilizing the homologous recombination system of lambda phage [Proc. Natl. Acad. Sci. USA, 97, 6641-6645 (2000)].
(1) Cloning of Drug Resistance Gene-Containing DNA Fragments for Gene Deletion The nucleotide sequences of the glnE gene and the glnB gene of *Escherichia coli* K12 were already disclosed [Science, 5331, 1453-1474 (1997)]. On the basis of the reported nucleotide sequences, DNAs consisting of the nucleotide sequences shown in SEQ ID NOS: 88 and 89 to be used as primer DNAs for glnE gene deletion and DNAs consisting of the nucleotide sequences shown in SEQ ID NOS: 90 and 91 to be used as primer DNAs for glnB gene deletion were synthesized using a DNA synthesizer (Model 8905, PerSeptive Biosystems, Inc.). The synthesized primer DNAs were designed based on the 36-bp nucleotide sequences that lie upstream and downstream of the respective target genes to be deleted.

PCR was carried out using each set of the above synthetic DNAs as a set of primers and pKD3 DNA as a template. That is, PCR was carried out by 30 cycles, one cycle consisting of reaction at 94° C. for one minute, reaction at 55° C. for 2 minutes and reaction at 72° C. for 3 minutes, using 40 µl of a reaction mixture comprising 10 ng of the plasmid DNA, 0.5 µmol/l each of the primers, 2.5 units of Pfu DNA polymerase, 4 µl of buffer for Pfu DNA polymerase (10×) and 200 µmol/l each of deoxyNTPs.

One-tenth of each of the resulting reaction mixtures was subjected to agarose gel electrophoresis to confirm that the desired fragment was amplified. Then, the remaining reaction mixture was mixed with an equal amount of phenol/chloroform saturated with TE.

The resulting mixture was centrifuged, and the obtained upper layer was mixed with a two-fold volume of cold ethanol and allowed to stand at −80° C. for 30 minutes, followed by centrifugation to precipitate DNA. Then, the DNA precipitate was dissolved in 20 µl of TE. By this procedure, chloramphenicol resistance gene-containing DNA fragments for deletion of the glnE gene and the glnB gene were obtained.
(2) Preparation of *Escherichia coli* JM101 in which the glnE Gene on the Chromosomal DNA is Deleted

*Escherichia coli* JM101 was transformed with pKD46, and *Escherichia coli* JM101 carrying pKD46 (hereinafter referred to as *Escherichia coli* JM101/pKD46) was selected on LB agar medium containing 100 mg/l ampicillin. *Escherichia coli* JM101/pKD46 cultured in the presence of 10 mmol/l L-arabinose and 50 µg/ml ampicillin was transformed by electroporation using the chloramphenicol resistance gene-containing DNA fragment for glnE gene deletion, and a recombinant strain in which the chloramphenicol resistance gene was inserted into the glnE gene on the chromosomal DNA of JM101 strain and the glnE structural gene was deleted was selected on LB agar medium containing 25 mg/l chloramphenicol.

Replicas of the obtained chloramphenicol-resistant strain were made on LB agar medium containing 25 mg/l chloramphenicol, followed by single colony isolation at 42° C. Then, replicas of the obtained colonies were made on LB agar medium containing 25 mg/l chloramphenicol and LB agar medium containing 100 mg/l ampicillin to select a colony showing chloramphenicol resistance and ampicillin sensitivity. The selected pKD46-cured strain was transformed using pCP20, spread on LB agar medium containing 100 mg/l ampicillin, and cultured overnight at 30° C.

Replicas of the ampicillin-resistant strain that grew on the medium were made on drug-free LB agar medium, followed by single colony isolation at 42° C. Then, replicas of the obtained colonies were made on drug-free LB agar medium, LB agar medium containing 25 mg/l chloramphenicol and LB agar medium containing 100 mg/l ampicillin to select colonies showing chloramphenicol sensitivity and ampicillin sensitivity. Chromosomal DNAs were prepared from the respective strains thus obtained according to an ordinary method [Seibutsukogaku Jikkensho (Experiments in Biotechnology), edited by The Society for Biotechnology, Japan, p. 97-98, Baifukan (1992)]. Colony PCR was carried out using primer DNAs consisting of the nucleotide sequences shown in SEQ ID NOS: 92 and 93 which were designed based on an inner nucleotide sequence of the glnE gene to be deleted. That is, colony PCR was carried out by 30 cycles, one cycle consisting of reaction at 94° C. for one minute, reaction at 55° C. for 2 minutes and reaction at 72° C. for 3 minutes, using 40 µl of a reaction mixture comprising the cells in an amount obtained by contacting a 200-µl pipette tip with the colony, 0.5 µmol/l each of the primers, 2.5 units of Pfu DNA polymerase, 4 µl of buffer for Pfu DNA polymerase (10×) and 200 µmol/l each of deoxyNTPs.

Of the strains subjected to PCR, a strain with which no gene amplification was detected was identified as a strain having glnE gene deletion and was designated as *Escherichia coli* JGLE1.
(3) Preparation of *Escherichia coli* JM101 in which the glnE and glnB Genes on the Chromosomal DNA are Deleted

*Escherichia coli* JGLE1 obtained in the above (2) was transformed with pKD46, spread on LB agar medium containing 100 mg/l ampicillin, and cultured overnight at 30° C. to obtain *Escherichia coli* JGLE1 carrying pKD46 (hereinafter referred to as *Escherichia coli* JGLE1/pKD46). *Escherichia coli* JGLE1/pKD46 was transformed by electroporation using the chloramphenicol resistance gene-containing DNA fragment for glnB gene deletion to obtain a recombinant strain in which the chloramphenicol resistance gene was inserted into the glnB gene on the chromosomal DNA and the glnB structural gene was deleted. Colony PCR was carried out under the same conditions as in the above (2) using primer DNAs consisting of the nucleotide sequences shown in SEQ ID NOS: 94 and 95 which were designed based on an inner nucleotide sequence of the glnB gene. A strain with which no gene amplification was detected in the above PCR was identified as a strain having glnB gene deletion and was designated as *Escherichia coli* JGLBE1.

Example 2

Construction of a Plasmid Expressing the ywfE Gene and an Alanine Dehydrogenase Gene (ald Gene) Derived from *Bacillus subtilis*

Figure 5:
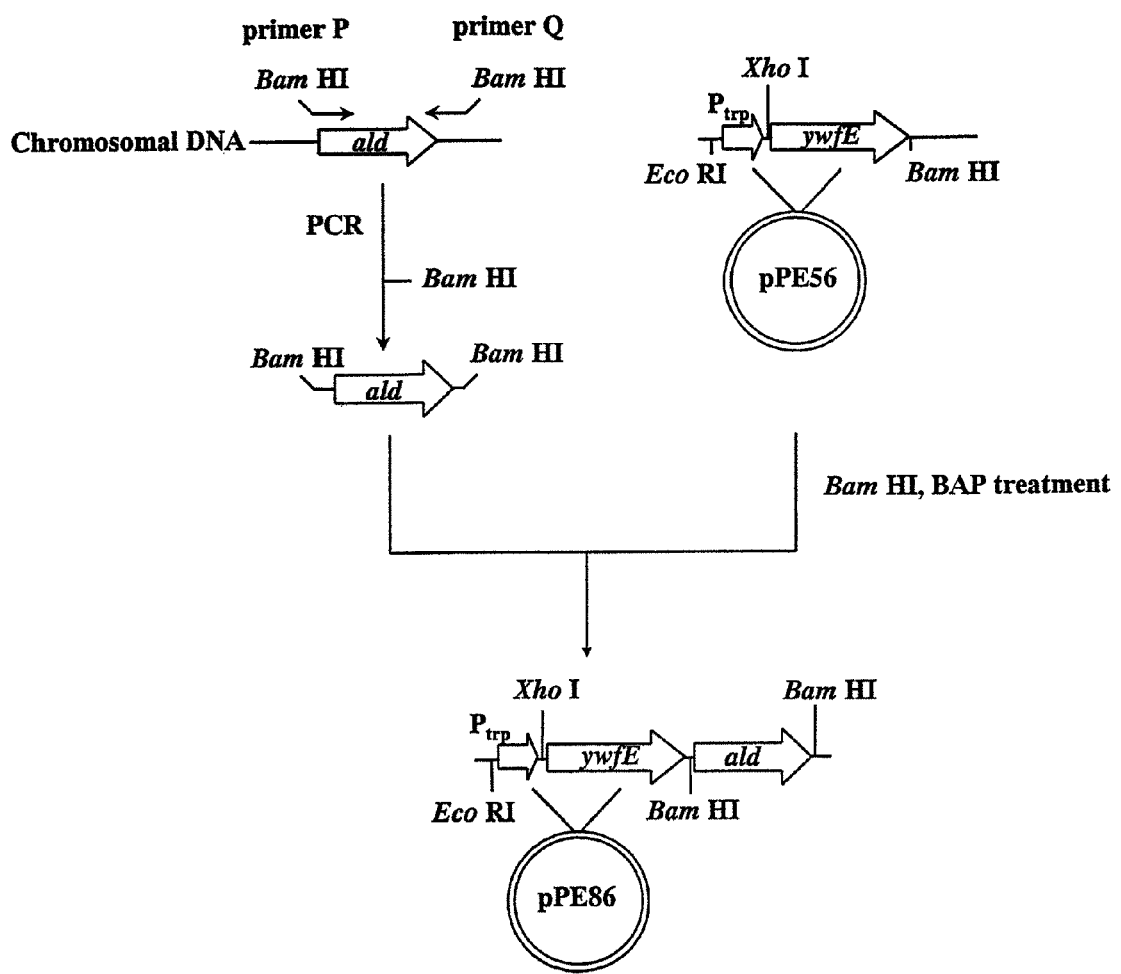
FIG. 5 shows the steps for constructing ywfE gene and ald gene expression vector pPE86.

On the basis of the ywfE gene expression plasmid pPE56 constructed in Experimental Example 15, an expression plasmid which constitutively expresses an alanine dehydrogenase gene (ald gene) derived from *Bacillus subtilis* at the same time was constructed by the method shown in FIG. 5.

By using a DNA synthesizer (Model 8905, PerSeptive Biosystems, Inc.), DNAs having the nucleotide sequences shown in SEQ ID NOS: 96 and 97 (hereinafter referred to as primer P and primer Q, respectively) were synthesized. The sequence shown in SEQ ID NO: 96 is a sequence wherein a sequence containing the BamHI recognition sequence is added to the 5' end of a region containing the Shine-Dalgarno sequence (ribosome binding sequence) of the ald gene. The sequence shown in SEQ ID NO: 97 is a sequence wherein a sequence containing the BamHI recognition sequence is added to the 5' end of a sequence complementary to a sequence containing the termination codon of the ald gene.

PCR was carried out using the chromosomal DNA of *Bacillus subtilis* obtained in Experimental Example 2 as a template and the above primer P and primer Q as a set of primers. That is, PCR was carried out by 30 cycles, one cycle consisting of reaction at 94° C. for one minute, reaction at 55° C. for 2 minutes and reaction at 72° C. for 3 minutes, using 40 µl of a reaction mixture comprising 0.1 µg of the chromosomal DNA, 0.5 µmol/l each of the primers, 2.5 units of Pfu DNA polymerase, 4 µl of buffer for Pfu DNA polymerase (10×) and 200 µmol/l each of dNTPs.

One-tenth of the resulting reaction mixture was subjected to agarose gel electrophoresis to confirm that a ca. 1.2 kb fragment corresponding to the ald gene fragment was amplified. Then, the remaining reaction mixture was mixed with an equal amount of phenol/chloroform saturated with TE. The resulting mixture was centrifuged, and the obtained upper layer was mixed with a two-fold volume of cold ethanol and allowed to stand at −80° C. for 30 minutes. The resulting solution was centrifuged, and the obtained DNA precipitate was dissolved in 20 µl of TE.

The thus obtained solution (5 µl) was subjected to reaction to cleave the amplified DNA with restriction enzyme BamHI. DNA fragments were separated by agarose gel electrophoresis, and a 1.2 kb DNA fragment containing the ald gene was recovered using GENECLEAN II Kit.

pPE56 (0.2 µg) was cleaved with restriction enzyme BamHI. DNA fragments were separated by agarose gel electrophoresis, and a 6.3 kb DNA fragment was recovered in the same manner as above. Dephosphorylation of the end of the 6.3 kb DNA fragment was carried out by treatment with alkaline phosphatase (*E. coli* C75, Takara Bio Inc.) at 60° C. for 30 minutes. The reaction mixture was mixed with an equal amount of phenol/chloroform saturated with TE. The resulting mixture was centrifuged, and the obtained upper layer was mixed with a two-fold volume of cold ethanol and allowed to stand at −80° C. for 30 minutes. The resulting solution was centrifuged, and the obtained DNA precipitate was dissolved in 20 µl of TE.

The 1.2 kb DNA fragment containing the ald gene and the alkaline phosphatase-treated 6.3 kb DNA fragment obtained above were subjected to ligation reaction using a ligation kit at 16° C. for 16 hours.

*Escherichia coli* NM522 was transformed using the ligation reaction mixture according to the method using calcium ion, spread on LB agar medium containing 50 µg/ml ampicillin, and cultured overnight at 30° C.

A plasmid was extracted from a colony of the transformant that grew on the medium according to a known method. By restriction enzyme digestion, it was confirmed that a plasmid into which the ald gene was inserted in the same direction as the ywfE gene was obtained, and the plasmid was designated as pPE86 (FIG. 5).

Example 3

Construction of a Plasmid Expressing a Feedback-Resistant pheA Gene and a Feedback-Resistant aroF Gene Derived from *Escherichia coli*

(1) Construction of a Plasmid Expressing a Desensitized pheA Gene

A feedback-resistant pheA gene was obtained from plasmid pE pheA 22 expressing the phenylalanine-desensitized pheA gene obtained by introduction of a phenylalanine analogue resistance mutation (Japanese Published Unexamined Patent Application No. 260892/86) and a feedback-resistant aroF gene was obtained from plasmid pE aroF 18 expressing the tyrosine-feedback-resistant aroF gene obtained by introduction of a tyrosine resistance mutation (Japanese Published Unexamined Patent Application No. 65691/87), and an expression plasmid was constructed in the following manner.

By using a DNA synthesizer (Model 8905, PerSeptive Biosystems, Inc.), DNAs having the nucleotide sequences shown in SEQ ID NOS: 98 and 99 (hereinafter referred to as primer R and primer S, respectively) were synthesized. The sequence shown in SEQ ID NO: 98 is a sequence wherein a sequence containing the ClaI recognition sequence is added to the 5' end of a region containing the Shine-Dalgarno sequence (ribosome binding sequence) of the pheA gene. The sequence shown in SEQ ID NO: 99 is a sequence wherein a sequence containing the BamHI recognition sequence is added to the 5' end of a sequence complementary to a sequence containing the termination codon of the pheA gene. PCR was carried out using the plasmid pE pheA 22 as a template and the above primer R and primer S as a set of primers. That is, PCR was carried out by 30 cycles, one cycle consisting of reaction at 94° C. for one minute, reaction at 55° C. for 2 minutes and reaction at 72° C. for 3 minutes, using 40 µl of a reaction mixture comprising 10 ng of the plasmid DNA, 0.5 µmol/l each of the primers, 2.5 units of Pfu DNA polymerase, 4 µl of buffer for Pfu DNA polymerase (10×) and 200 µmol/l each of dNTPs.

One-tenth of the resulting reaction mixture was subjected to agarose gel electrophoresis to confirm that a ca. 1.1 kb fragment corresponding to the pheA gene fragment was amplified. Then, the remaining reaction mixture was mixed with an equal amount of phenol/chloroform saturated with TE. The resulting mixture was centrifuged, and the obtained upper layer was mixed with a two-fold volume of cold ethanol and allowed to stand at −80° C. for 30 minutes. The resulting solution was centrifuged, and the obtained DNA precipitate was dissolved in 20 μl of TE.

The thus obtained solution (5 μl) was subjected to reaction to cleave the amplified DNA with restriction enzymes ClaI and BamHI. DNA fragments were separated by agarose gel electrophoresis, and a 1.1 kb DNA fragment containing the pheA gene was recovered using GENECLEAN II Kit.

Expression vector pTrS30 containing trp promoter [preparable from *Escherichia coli* JM109/pTrS30 (FERM BP-5407)] (0.2 μg) was cleaved with restriction enzymes ClaI and BamHI. DNA fragments were separated by agarose gel electrophoresis, and a 4.6 kb DNA fragment was recovered in the same manner as above.

The 1.1 kb DNA fragment containing the pheA gene and the 4.6 kb DNA fragment obtained above were subjected to ligation reaction using a ligation kit at 16° C. for 16 hours.

*Escherichia coli* NM522 was transformed using the ligation reaction mixture according to the method using calcium ion, spread on LB agar medium containing 50 μg/ml ampicillin, and cultured overnight at 30° C.

A plasmid was extracted from a colony of the transformant that grew on the medium according to a known method. By restriction enzyme digestion, it was confirmed that a plasmid expressing the feedback-resistant pheA gene was obtained, and the plasmid was designated as pPHEA1.

The obtained pPHEA1 (0.2 μg) was cleaved with restriction enzymes EcoRI and BamHI. DNA fragments were separated by agarose gel electrophoresis, and a 1.5 kb DNA fragment containing the trp promoter and the desensitized pheA gene was recovered using GENECLEAN II Kit.

Then, plasmid vector pSTV28 having the replication origin of pACYC184 and containing a chloramphenicol resistance gene (Takara Bio Inc.) (0.2 μg) was cleaved with restriction enzymes EcoRI and BamHI. DNA fragments were separated by agarose gel electrophoresis, and a 3.0 kb DNA fragment was recovered in the same manner as above.

The 1.5 kb DNA fragment containing the trp promoter and the feedback-resistant pheA gene and the 3.0 kb DNA fragment obtained above were subjected to ligation reaction using a ligation kit at 16° C. for 16 hours.

*Escherichia coli* NM522 was transformed using the ligation reaction mixture according to the method using calcium ion, spread on LB agar medium containing 30 μg/ml chloramphenicol, and cultured overnight at 30° C.

Figure 6:
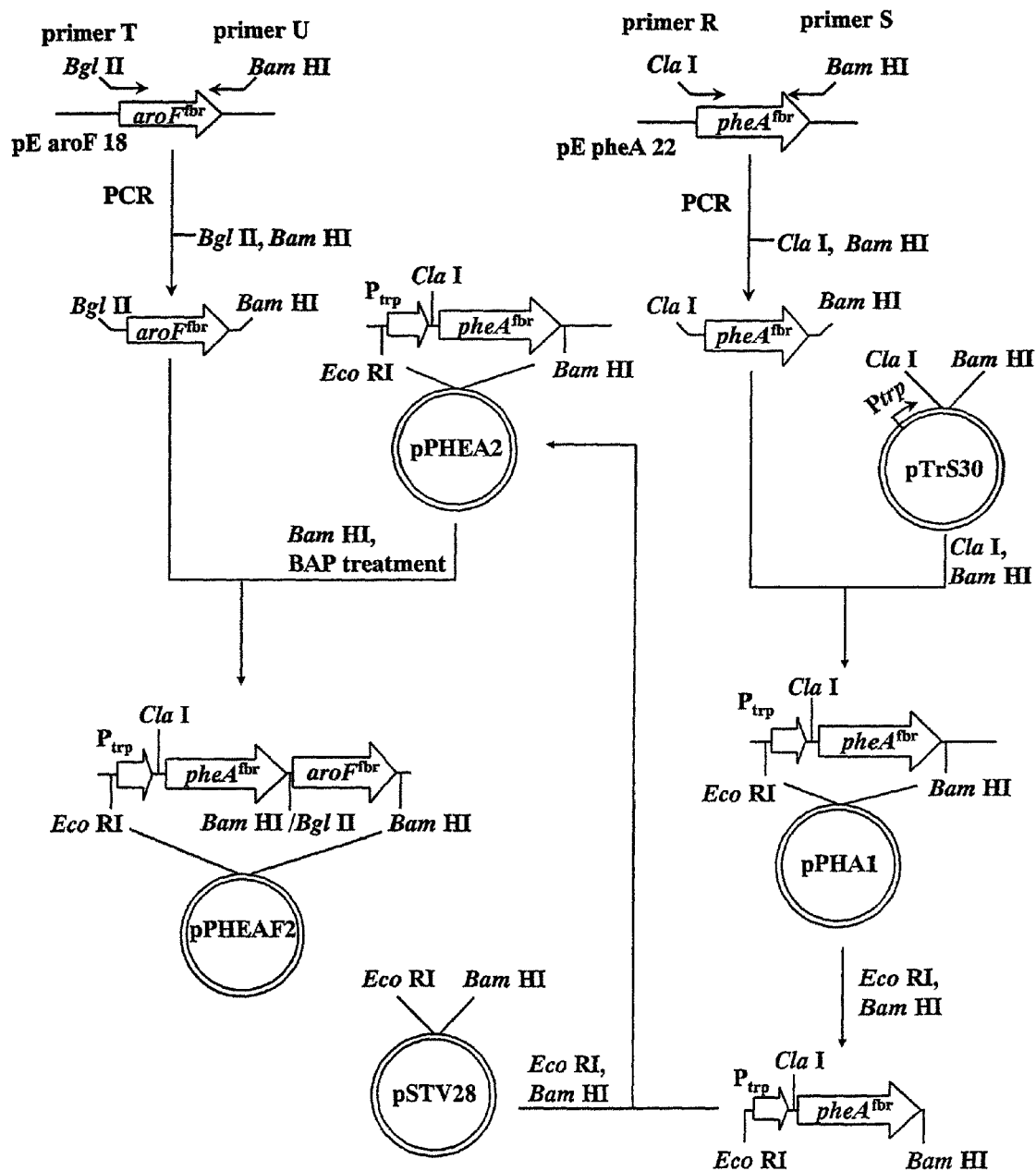
FIG. 6 shows the steps for constructing desensitized pheA gene expression vector pPHEA2, and feedback-resistant pheA gene and feedback-resistant aroF gene expression plasmid vector pPHEAF2.

A plasmid was extracted from a colony of the transformant that grew on the medium according to a known method. By restriction enzyme digestion, it was confirmed that a vector expressing the feedback-resistant pheA gene was obtained, and the plasmid was designated as pPHEA2 (FIG. 6).

(2) Construction of a Plasmid Expressing the Feedback-Resistant pheA Gene and the Feedback-Resistant aroF Gene By using a DNA synthesizer (Model 8905, PerSeptive Biosystems, Inc.), DNAs having the nucleotide sequences shown in SEQ ID NOS: 100 and 101 (hereinafter referred to as primer T and primer U, respectively) were synthesized. The sequence shown in SEQ ID NO: 100 is a sequence wherein a sequence containing the BglII recognition sequence is added to the 5' end of a region containing the Shine-Dalgarno sequence (ribosome binding sequence) of the aroF gene. The sequence shown in SEQ ID NO: 101 is a sequence wherein a sequence containing the BamHI recognition sequence is added to the 5' end of a sequence complementary to a sequence containing the termination codon of the aroF gene. PCR was carried out using the plasmid pE aroF 18 as a template and the above primer T and primer U as a set of primers. That is, PCR was carried out by 30 cycles, one cycle consisting of reaction at 94° C. for one minute, reaction at 55° C. for 2 minutes and reaction at 72° C. for 3 minutes, using 40 μl of a reaction mixture comprising 10 ng of the plasmid pE aroF 18, 0.5 μmol/l each of the primers, 2.5 units of Pfu DNA polymerase, 4 μl of buffer for Pfu DNA polymerase (10×) and 200 μmol/l each of dNTPs.

One-tenth of the resulting reaction mixture was subjected to agarose gel electrophoresis to confirm that a ca. 1.1 kb fragment corresponding to the aroF gene fragment was amplified. Then, the remaining reaction mixture was mixed with an equal amount of phenol/chloroform saturated with TE. The resulting mixture was centrifuged, and the obtained upper layer was mixed with a two-fold volume of cold ethanol and allowed to stand at −80° C. for 30 minutes. The resulting solution was centrifuged, and the obtained DNA precipitate was dissolved in 20 μl of TE.

The thus obtained solution (5 μl) was subjected to reaction to cleave the amplified DNA with restriction enzymes BglII and BamHI. DNA fragments were separated by agarose gel electrophoresis, and a 1.1 kb DNA fragment containing the desensitized aroF gene was recovered using GENECLEAN II Kit.

The plasmid pPHEA2 expressing the feedback-resistant pheA gene obtained in the above (1) (0.2 μg) was cleaved with restriction enzyme BamHI. DNA fragments were separated by agarose gel electrophoresis, and a 4.5 kb DNA fragment was recovered in the same manner as above. Dephosphorylation of the end of the 4.5 kb DNA fragment was carried out by treatment with alkaline phosphatase at 60° C. for 30 minutes. The reaction mixture was mixed with an equal amount of phenol/chloroform saturated with TE. The resulting mixture was centrifuged, and the obtained upper layer was mixed with a two-fold volume of cold ethanol and allowed to stand at −80° C. for 30 minutes. The resulting solution was centrifuged, and the obtained DNA precipitate was dissolved in 20 μl of TE.

The 1.1 kb DNA fragment containing the feedback-resistant aroF gene and the alkaline phosphatase-treated 4.5 kb DNA fragment obtained above were subjected to ligation reaction using a ligation kit at 16° C. for 16 hours.

*Escherichia coli* NM522 was transformed using the ligation reaction mixture according to the method using calcium ion, spread on LB agar medium containing 30 μg/ml chloramphenicol, and cultured overnight at 30° C.

A plasmid was extracted from a colony of the transformant that grew on the medium according to a known method. By restriction enzyme digestion, it was confirmed that a plasmid expressing the feedback-resistant aroF gene and the feedback-resistant pheA gene in which the feedback-resistant aroF gene was inserted in the same direction as the feedback-resistant pheA gene was obtained, and the plasmid was designated as pPHEAF2 (FIG. 6).

Example 4

Construction of a Plasmid Expressing an aroF-tyrA Operon which Exhibits Tyrosine Resistance Derived from *Escherichia coli*

(1) Construction of a Plasmid Expressing an aroF-tyrA Operon which Exhibits Tyrosine Resistance An aroF-tyrA operon exhibiting tyrosine resistance was obtained from plasmid pKm1aroFm-18 expressing the aroF-tyrA operon obtained by introduction of a tyrosine resistance mutation (Japanese Published Unexamined Patent Application No. 034197/85) and an expression plasmid was constructed in the following manner.

By using a DNA synthesizer (Model 8905, PerSeptive Biosystems, Inc.), DNAs consisting of the nucleotide sequences shown in SEQ ID NOS: 102 and 103 were synthesized. The sequence shown in SEQ ID NO: 102 is a sequence wherein a sequence containing the ClaI recognition sequence is added to the 5' end of a region containing the Shine-Dalgarno sequence (ribosome binding sequence) of the aroF gene. The sequence shown in SEQ ID NO: 103 is a sequence wherein a sequence containing the SphI recognition sequence is added to the 5' end of a sequence complementary to a sequence containing the termination codon of the tyrA gene.

PCR was carried out using the plasmid pKm1aroFm-18 as a template and the DNAs consisting of the nucleotide sequences shown in SEQ ID NOS: 102 and 103 as a set of primers. That is, PCR was carried out by 30 cycles, one cycle consisting of reaction at 94° C. for one minute, reaction at 55° C. for 2 minutes and reaction at 72° C. for 3 minutes, using 40 µl of a reaction mixture comprising 10 ng of the plasmid DNA, 0.5 µmol/l each of the primers, 2.5 units of Pfu DNA polymerase, 4 µl of buffer for Pfu DNA polymerase (10×) and 200 µmol/l each of dNTPs.

One-tenth of the resulting reaction mixture was subjected to agarose gel electrophoresis to confirm that a ca. 2.2 kb fragment corresponding to the aroF-tyrA gene fragment was amplified. Then, the remaining reaction mixture was mixed with an equal amount of phenol/chloroform saturated with TE. The resulting mixture was centrifuged, and the obtained upper layer was mixed with a two-fold volume of cold ethanol and allowed to stand at −80° C. for 30 minutes. The resulting solution was centrifuged, and the obtained DNA precipitate was dissolved in 20 µl of TE.

The thus obtained solution (5 µl) was subjected to reaction to cleave the amplified DNA with restriction enzymes ClaI and SphI. DNA fragments were separated by agarose gel electrophoresis, and a 2.2 kb DNA fragment containing the aroF-tyrA operon was recovered using GENECLEAN II Kit.

Expression vector pTrS30 containing trp promoter [preparable from *Escherichia coli* JM109/pTrS30 (FERM BP-5407)] (0.2 µg) was cleaved with restriction enzymes ClaI and SphI. DNA fragments were separated by agarose gel electrophoresis, and a 4.6 kb DNA fragment was recovered in the same manner as above.

The 2.2 kb DNA fragment containing the aroF-tyrA operon and the 4.6 kb DNA fragment obtained above were subjected to ligation reaction using a ligation kit at 16° C. for 16 hours.

*Escherichia coli* NM522 was transformed using the ligation reaction mixture according to the method using calcium ion, spread on LB agar medium containing 50 µg/ml ampicillin, and cultured overnight at 30° C.

A plasmid was extracted from a colony of the transformant that grew on the medium according to a known method. By restriction enzyme digestion, it was confirmed that a plasmid expressing the aroF-tyrA operon which exhibits tyrosine resistance was obtained, and the plasmid was designated as pTY1.

The obtained pTY1 (0.2 µg) was cleaved with restriction enzymes EcoRI and SphI. DNA fragments were separated by agarose gel electrophoresis, and a 2.6 kb DNA fragment containing the trp promoter and the aroF-tyrA operon exhibiting tyrosine resistance was recovered using GENECLEAN II Kit.

Then, plasmid vector pSTV28 having the replication origin of pACYC184 and containing a chloramphenicol resistance gene (Takara Bio Inc.) (0.2 µg) was cleaved with restriction enzymes EcoRI and SphI. DNA fragments were separated by agarose gel electrophoresis, and a 3.0 kb DNA fragment was recovered in the same manner as above.

The 2.6 kb DNA fragment containing the trp promoter and the aroF-tyrA operon exhibiting tyrosine resistance and the 3.0 kb DNA fragment obtained above were subjected to ligation reaction using a ligation kit at 16° C. for 16 hours.

*Escherichia coli* NM522 was transformed using the ligation reaction mixture according to the method using calcium ion, spread on LB agar medium containing 30 µg/ml chloramphenicol, and cultured overnight at 30° C.

A plasmid was extracted from a colony of the transformant that grew on the medium according to a known method. By restriction enzyme digestion, it was confirmed that a vector expressing the aroF-tyrA operon which exhibits tyrosine resistance was obtained, and the plasmid was designated as pTY2.

Example 5

Preparation of a Strain Having metJ Gene Deletion (1) Cloning of a Drug Resistance Gene-Containing DNA Fragment for metJ Gene Deletion The nucleotide sequence of the metJ gene of *Escherichia coli* K12 was already disclosed [Science, 5331, 1453-1474 (1997)].

The metJ gene encodes a repressor of the L-methionine biosynthesis system of *Escherichia coli* and it is known that L-methionine producing-ability is enhanced by introducing a mutation to inhibit production of the repressor (Japanese Published Unexamined Patent Application No. 139471/00).

On the basis of the reported nucleotide sequence, DNAs consisting of the nucleotide sequences shown in SEQ ID NOS: 104 and 105 to be used as primer DNAs for preparation of a strain having metJ gene deletion were synthesized using a DNA synthesizer (Model 8905, PerSeptive Biosystems, Inc.).

The DNAs have nucleotide sequences homologous to 36-bp nucleotide sequences that lie upstream and downstream of the target gene to be deleted.

PCR was carried out using the DNAs as a set of primers and pKD3 DNA as a template to amplify a chloramphenicol resistance gene-containing DNA fragment for preparation of a strain having metJ gene deletion. That is, PCR was carried out by 30 cycles, one cycle consisting of reaction at 94° C. for one minute, reaction at 55° C. for 2 minutes and reaction at 72° C. for 3 minutes, using 40 µl of a reaction mixture comprising 10 ng of the plasmid DNA, 0.5 µmol/l each of the primers, 2.5 units of Pfu DNA polymerase, 4 µl of buffer for Pfu DNA polymerase (10×) and 200 µmol/l each of deoxyNTPs.

One-tenth of the resulting reaction mixture was subjected to agarose gel electrophoresis to confirm that the desired fragment was amplified. Then, the remaining reaction mixture was mixed with an equal amount of phenol/chloroform saturated with TE. The resulting mixture was centrifuged, and the obtained upper layer was mixed with a two-fold volume of cold ethanol and allowed to stand at −80° C. for 30 minutes. The resulting solution was centrifuged, and the obtained DNA precipitate was dissolved in 20 µl of TE.

(2) Preparation of *Escherichia coli* JM101 in which the Drug Resistance Gene is Inserted into the metJ Gene on the Chromosomal DNA By using *Escherichia coli* JM101 and the chloramphenicol resistance gene-containing DNA fragment for preparation of a strain having metJ gene deletion obtained in the above (1), a recombinant in which the chloramphenicol resistance gene was inserted into the metJ gene on the chromosomal DNA of *Escherichia coli* JM101 was prepared in the same manner as in Example 1 (2).

Insertion of the chloramphenicol resistance gene into the chromosome was confirmed by carrying out colony PCR in the same manner as in Example 1 (2) using, as a set of primers, DNAs consisting of the nucleotide sequences shown in SEQ ID NOS: 106 and 107, i.e., the nucleotide sequences located approximately 400 bp upstream and downstream of the site to which the chloramphenicol resistance gene was inserted.

Of the strains subjected to colony PCR, a strain with which a ca. 2 kb fragment containing the chloramphenicol resistance gene was amplified was identified as a strain having metJ gene deletion. Then, by using pCP20 expressing Flp recombinase, a strain in which the chloramphenicol resistance gene was cured from the chromosomal DNA was prepared in the same manner as in Example 7 (3), and was designated as *Escherichia coli* JMJ1.

Example 6

Construction of a Plasmid Expressing the ywfE Gene and a Feedback-Resistant 3-Phosphoglycerate Dehydrogenase Gene (serA Gene) Derived from *Escherichia coli*

It is known that mutation of the *Escherichia coli*-derived 3-phosphoglycerate dehydrogenase gene (serA gene) to substitute the codon at positions 1096-1098 of the structural gene by the termination codon (TAA) produces a gene encoding a mutant 3-phosphoglycerate dehydrogenase in which the C-terminal 45 amino acid residues are deleted and the substantial inhibition by serine is alleviated (hereinafter referred to as the feedback-resistant serA gene) (Japanese Patent No. 2584409).

As the primers for amplification of the feedback-resistant serA gene, DNA consisting of the nucleotide sequence shown in SEQ ID NO: 108 and DNA consisting of the nucleotide sequence shown in SEQ ID NO: 109 containing the codon-substituted mutant sequence were used.

The nucleotide sequence shown in SEQ ID NO: 108 is a sequence wherein a sequence containing the ClaI recognition sequence is added to the 5' end of a region containing the Shine-Dalgarno sequence (ribosome binding sequence) of the serA gene. The sequence shown in SEQ ID NO: 109 is a sequence wherein a sequence containing the SphI recognition sequence is added to the 5' end of a sequence complementary to a sequence containing the termination codon to delete the C-terminal 45 amino acid residues of the serA gene.

PCR was carried out to amplify the feedback-resistant serA gene using the above synthetic DNAs as a set of primers and the chromosomal DNA of *Escherichia coli* W3110 as a template. That is, PCR was carried out by 30 cycles, one cycle consisting of reaction at 94° C. for one minute, reaction at 55° C. for 2 minutes and reaction at 72° C. for 3 minutes, using 40 µl of a reaction mixture comprising 0.1 µg of the chromosomal DNA, 0.5 µmol/l each of the primers, 2.5 units of Pfu DNA polymerase, 4 µl of buffer for Pfu DNA polymerase (10×) and 200 µmol/l each of deoxyNTPs.

One-tenth of the resulting reaction mixture was subjected to agarose gel electrophoresis to confirm that a ca. 1.1 kb fragment corresponding to the feedback-resistant serA gene fragment was amplified. Then, the remaining reaction mixture was mixed with an equal amount of phenol/chloroform saturated with TE. The resulting mixture was centrifuged, and the obtained upper layer was mixed with a two-fold volume of cold ethanol and allowed to stand at −80° C. for 30 minutes.

The resulting solution was centrifuged, and the obtained DNA precipitate was dissolved in 20 µl of TE.

The thus obtained solution (5 µl) was subjected to reaction to cleave the amplified DNA with restriction enzymes ClaI and SphI. DNA fragments were separated by agarose gel electrophoresis, and a 1.1 kb DNA fragment containing the serA gene was recovered using GENECLEAN II Kit.

Expression vector pTrS30 containing trp promoter [preparable from *Escherichia coli* JM109/pTrS30 (FERM BP-5407)] (0.2 µg) was cleaved with restriction enzymes ClaI and SphI. DNA fragments were separated by agarose gel electrophoresis, and a 4.3 kb DNA fragment was recovered in the same manner as above.

The 1.1 kb DNA fragment containing the serA gene and the 4.3 kb DNA fragment obtained above were subjected to ligation reaction using a ligation kit at 16° C. for 16 hours.

*Escherichia coli* NM522 was transformed using the ligation reaction mixture according to the method using calcium ion, spread on LB agar medium containing 50 µg/ml ampicillin, and cultured overnight at 30° C.

A plasmid was extracted from a colony of the transformant that grew on the medium according to a known method and was designated as pSE15. The structure of the plasmid was confirmed by restriction enzyme digestion.

Amplification of a feedback-resistant serA gene fragment was carried out using the above-obtained plasmid pSE15 expressing the feedback-resistant serA gene derived from *Escherichia coli* as a template and DNAs consisting of the nucleotide sequences shown in SEQ ID NOS: 110 and 109 as a set of primers.

Separately, amplification of a ywfE gene fragment containing trp promoter was carried out using the plasmid pPE56 expressing the ywfE gene constructed in Experimental Example 15 as a template, and DNAs consisting of the nucleotide sequences shown in SEQ ID NOS: 111 and 112 as a set of primers. Both PCRs were carried out by 30 cycles, one cycle consisting of reaction at 94° C. for one minute, reaction at 55° C. for 2 minutes and reaction at 72° C. for 3 minutes, using 40 µl of a reaction mixture comprising 10 ng of the plasmid DNA, 0.5 µmol/l each of the primers, 2.5 units of Pfu DNA polymerase, 4 µl of buffer for Pfu DNA polymerase (10×) and 200 µmol/l each of deoxyNTPs.

One-tenth of each of the resulting reaction mixtures was subjected to agarose gel electrophoresis to confirm that the desired fragment was amplified. Then, the remaining reaction mixture was mixed with an equal amount of phenol/chloroform saturated with TE. The resulting mixture was centrifuged, and the obtained upper layer was mixed with a two-fold volume of cold ethanol and allowed to stand at −80° C. for 30 minutes. The resulting solution was centrifuged, and the obtained DNA precipitate was dissolved in 20 µl of TE.

By the above procedure, a feedback-resistant serA gene fragment and a ywfE gene fragment containing trp promoter were obtained. The feedback-resistant serA gene fragment was cleaved with restriction enzymes BglII and SphI. The ywfE gene fragment containing trp promoter was cleaved with restriction enzymes EcoRI and BamHI. DNA fragments were separated by agarose gel electrophoresis, and a 1.1 kb DNA fragment containing the serA gene and a 1.8 kb DNA fragment containing trp promoter and the ywfE gene were recovered using GENECLEAN II Kit.

Expression vector pTrS30 containing trp promoter (0.2 µg) was cleaved with restriction enzymes EcoRI and SphI. DNA fragments were separated by agarose gel electrophoresis, and a 3.9 kb DNA fragment was recovered in the same manner as above.

The 1.6 kb DNA fragment containing the serA gene, the 1.8 kb DNA fragment containing trp promoter and the ywfE gene and the 3.9 kb DNA fragment obtained above were subjected to ligation reaction using a ligation kit at 16° C. for 16 hours.

*Escherichia coli* NM522 was transformed using the ligation reaction mixture according to the method using calcium ion, spread on LB agar medium containing 50 µg/ml ampicillin, and cultured overnight at 30° C.

A plasmid was extracted from a colony of the transformant that grew on the medium according to a known method. By restriction enzyme digestion, it was confirmed that a plasmid into which the feedback-resistant serA gene was inserted in the same direction as the ywfE gene was obtained, and the plasmid was designated as pPE212.

Example 7

Preparation of a Strain Having ilvL Gene Deletion and a Strain Having Revertant ilvG Gene Substitution (1) Cloning of a Drug Resistance Gene-Containing DNA Fragment for Preparation of a Strain Having ilvL Gene Deletion and a DNA Fragment for Preparation of a Strain Having Revertant ilvG Gene Substitution The nucleotide sequences of the ilvL gene and the ilvG gene of *Escherichia coli* K12 were already disclosed [Science, 5331, 1453-1474 (1997)].

The attenuator region which regulates the expression of the ilvGMEDA operon of *Escherichia coli* K12 is located in the 5' upstream region of the operon and its nucleotide sequence is disclosed in Nucleic Acids Res., 15, 2137 (1987). It is known that removal of the attenuator region deactivates the attenuation function, which leads to constitutive expression of the ilvGMEDA operon (Japanese Published Unexamined Patent Application No. 473979/96). On the basis of this information, *Escherichia coli* K12 which constitutively expresses ilvGMEDA operon was prepared in the following manner.

As wild-type *Escherichia coli* K12 has the ilvG gene having a frameshift mutation, it does not express active acetohydroxy acid synthase isozyme II (AHASII) [Proc. Natl. Acad. Sci. USA, 78, 922 (1981)]. *Escherichia coli* K12 in which the activity of acetohydroxy acid synthase is restored was prepared in the following manner by introduction of a mutation to restore the frame by inserting two nucleotides (AA) between the 981st nucleotide and the 982nd nucleotide of the ilvG gene of *Escherichia coli* K12 by referring to the sequence of the ilvG gene existing on the chromosomal DNA of *Escherichia coli* O157:H7 in which AHASII is normally functioning.

On the basis of the reported nucleotide sequence, DNAs consisting of the nucleotide sequences shown in SEQ ID NOS: 113 and 114 were synthesized as a set of primers to amplify a drug resistance gene-containing DNA fragment for preparation of a strain having ilvL gene deletion using a DNA synthesizer (Model 8905, PerSeptive Biosystems, Inc.).

The DNAs have nucleotide sequences homologous to 36-bp nucleotide sequences that lie upstream and downstream of the target gene to be deleted.

Separately, DNA consisting of the nucleotide sequence shown in SEQ ID NO: 115 and DNA consisting of the nucleotide sequence shown in SEQ ID NO: 116 containing the two nucleotides-inserted mutant sequence were synthesized as a set of primers for amplification of an upstream region of the revertant ilvG gene, and DNA consisting of the nucleotide sequence shown in SEQ ID NO: 117 containing the two nucleotides-inserted mutant sequence and DNA consisting of the nucleotide sequence shown in SEQ ID NO: 118 were synthesized as a set of primers for amplification of a downstream region of the revertant ilvG gene.

PCR was carried out, using each set of the above DNAs as a set of primers, to amplify a chloramphenicol resistance gene-containing DNA fragment for deletion of the ilvL gene using pKD3 DNA as a template, and to amplify upstream and downstream regions of the revertant ilvG gene using the chromosomal DNA of *Escherichia coli* W3110 as a template. That is, PCR was carried out by 30 cycles, one cycle consisting of reaction at 94° C. for one minute, reaction at 55° C. for 2 minutes and reaction at 72° C. for 3 minutes, using 40 µl of a reaction mixture comprising 0.1 µg of the chromosomal DNA or 10 ng of the plasmid DNA, 0.5 µmol/l each of the primers, 2.5 units of Pfu DNA polymerase, 4 µl of buffer for Pfu DNA polymerase (10×) and 200 µmol/l each of deoxyNTPs.

One-tenth of each of the resulting reaction mixtures was subjected to agarose gel electrophoresis to confirm that the desired fragment was amplified. Then, the remaining reaction mixture was mixed with an equal amount of phenol/chloroform saturated with TE.

The resulting mixture was centrifuged, and the obtained upper layer was mixed with a two-fold volume of cold ethanol and allowed to stand at −80° C. for 30 minutes, followed by centrifugation to precipitate DNA. Then, the DNA precipitate was dissolved in 20 µl of TE. By this procedure, a chloramphenicol resistance gene-containing DNA fragment for preparation of a strain having ilvL gene deletion, an upstream region of the revertant ilvG gene and a downstream region of the revertant ilvG gene were obtained.

Then, crossover PCR [A. J. Link, D. Phillips, G. M. Church, J. Bacteriol., 179, 6228-6237 (1997)] was carried out using the upstream region of the revertant ilvG gene and the downstream region of the revertant ilvG gene as templates and DNAs having the nucleotide sequences shown in SEQ ID NOS: 115 and 118 as a set of primers. PCR was carried out under the same conditions as above.

The above PCR produced a DNA fragment for preparation of a revertant ilvG gene-substituted strain in which the upstream region of the revertant ilvG gene and the downstream region of the revertant ilvG gene are ligated.

(2) Preparation of *Escherichia coli* JM101 in which the ilvG Gene on the Chromosomal DNA is Substituted by the Revertant ilvG Gene

*Escherichia coli* JM101 was transformed with pKD46 according to a known method, spread on LB agar medium containing 100 mg/l ampicillin, and cultured overnight at 30° C. to obtain *Escherichia coli* JM101 carrying pKD46 (hereinafter referred to as *Escherichia coli* JM101/pKD46).

*Escherichia coli* JM101/pKD46 cultured in the presence of 10 mmol/l L-arabinose and 50 µg/ml ampicillin was transformed by electroporation using the DNA fragment for preparation of a revertant ilvG gene-substituted strain obtained in the above (1), and a strain in which the ilvG gene on the chromosomal DNA was substituted by the revertant ilvG gene was selected on agar medium containing M9 medium and glucose, containing 200 mg/l L-valine.

Replicas of the obtained L-valine-resistant strain were made on agar medium containing M9 medium and glucose, containing 200 mg/l L-valine, followed by single colony isolation at 42° C. Then, replicas of the obtained colonies were made on agar medium containing M9 medium and glucose, containing 200 mg/l L-valine and LB agar medium containing 100 mg/l ampicillin to select a colony showing L-valine resistance and ampicillin sensitivity. The obtained revertant ilvG gene-substituted strain was designated as *Escherichia coli* JM101G+1.

(3) Preparation of *Escherichia coli* JM101 in which the ilvG Gene on the Chromosomal DNA is Substituted by the Revertant ilvG Gene and the ilvL Gene is Deleted

*Escherichia coli* JM101G+1 obtained in the above (2) was transformed with pKD46, spread on LB agar medium containing 100 mg/l ampicillin, and cultured overnight at 30° C. to obtain *Escherichia coli* JM101G+1 carrying pKD46 (hereinafter referred to as *Escherichia coli* JM101G+1/pKD46).

*Escherichia coli* JM101G+1/pKD46 was transformed by electroporation using the chloramphenicol resistance gene-containing DNA fragment for preparation of a strain having ilvL gene deletion obtained in the above (1), and a recombinant strain in which the chloramphenicol resistance gene was inserted into the ilvL gene on the chromosomal DNA of JM101 strain was selected on LB agar medium containing 25 mg/l chloramphenicol.

Replicas of the obtained chloramphenicol-resistant strain were made on LB agar medium containing 25 mg/l chloramphenicol, followed by single colony isolation at 42° C. Then, replicas of the obtained colonies were made on LB agar medium containing 25 mg/l chloramphenicol and 100 mg/l ampicillin to select a pKD46-cured strain showing chloramphenicol resistance and ampicillin sensitivity.

The structure of the chromosomal DNA of the transformant obtained above was confirmed by synthesizing the nucleotide sequences shown in SEQ ID NOS: 119 and 120, i.e., the nucleotide sequences located approximately 400 bp upstream and downstream of the site to which the chloramphenicol resistance gene was inserted on the chromosomal DNA of *Escherichia coli*, and then carrying out colony PCR using the synthetic DNAs as a set of primers. Colony PCR was carried out by 30 cycles, one cycle consisting of reaction at 94° C. for one minute, reaction at 55° C. for 2 minutes and reaction at 72° C. for 3 minutes, using 40 µl of a reaction mixture comprising the cells in an amount obtained by contacting a 200-µl pipette tip with the colony, 0.5 µmol/l each of the primers, 2.5 units of Pfu DNA polymerase, 4 µl of buffer for Pfu DNA polymerase (10×) and 200 µmol/l each of deoxyNTPs.

Of the strains subjected to colony PCR, a strain with which a ca. 2 kb fragment containing the chloramphenicol resistance gene was amplified was identified as a strain having ilvL gene deletion and was designated as *Escherichia coli* JILG+Cm1.

The above-obtained *Escherichia coli* JILG+Cm1 was transformed using pCP20, followed by selection on LB agar medium containing 100 mg/l ampicillin to obtain *Escherichia coli* JILG+Cm1 carrying pCP20.

The plasmid pCP20 carries a yeast-derived Flp recombinase gene the expression of which can be induced at a temperature of 42° C.

The chloramphenicol resistance gene-containing DNA fragment for preparation of a strain having ilvL gene deletion prepared in the above (1) contains nucleotide sequences recognized by Flp recombinase at both termini of the chloramphenicol resistance gene. Therefore, the resistance gene can be readily deleted by homologous recombination catalyzed by Flp recombinase.

Further, as pCP20 has a thermosensitive replication origin, expression of Flp recombinase and curing of pCP20 can be simultaneously induced by culturing the pCP20-carrying strain at 42° C.

*Escherichia coli* JILG+Cm1 obtained above was inoculated onto drug-free LB agar medium and cultured at 42° C. for 14 hours, followed by single colony isolation. Replicas of the obtained colonies were made on drug-free LB agar medium, LB agar medium containing 25 mg/l chloramphenicol and LB agar medium containing 100 mg/l ampicillin, followed by culturing at 30° C. Then, colonies showing chloramphenicol sensitivity and ampicillin sensitivity were selected.

Each of the colonies selected above was subjected to colony PCR using DNAs consisting of the nucleotide sequences shown in SEQ ID NOS: 119 and 120 as a set of primers. Colony PCR was carried out by 30 cycles, one cycle consisting of reaction at 94° C. for one minute, reaction at 55° C. for 2 minutes and reaction at 72° C. for 3 minutes, using 40 µl of a reaction mixture comprising the cells in an amount obtained by contacting a 200-µl pipette tip with the colony, 0.5 µmol/l each of the primers, 2.5 units of Pfu DNA polymerase, 4 µl of buffer for Pfu DNA polymerase (10×) and 200 µmol/l each of deoxyNTPs.

Of the strains subjected to colony PCR, a strain with which a ca. 0.7 kb chloramphenicol resistance gene-cured fragment was amplified was identified as a strain having ilvL gene deletion and was designated as *Escherichia coli* JILG+1.

Example 8

Preparation of a Strain Having Feedback-Resistant ilvA Gene Substitution (1) Cloning of a Drug Resistance Gene-Containing DNA Fragment for Preparation of a Strain Having ilvA Gene Deletion and a DNA Fragment for Preparation of a Strain Having Feedback-Resistant ilvA Gene Substitution The nucleotide sequence of the ilvA gene of *Escherichia coli* K12 was already disclosed [Science, 5331, 1453-1474 (1997)].

It is known that the ilvA 219 gene encoding threonine deaminase of which the inhibition by L-isoleucine is substantially eliminated (hereinafter referred to as feedback-resistant ilvA gene) has a mutation in which leucine 447 is substituted by phenylalanine [Biochemistry, 34, 9403 (1995)].

On the basis of the reported nucleotide sequence, DNAs consisting of the nucleotide sequences shown in SEQ ID NOS: 121 and 122 were synthesized as primer DNAs to amplify a drug resistance gene-containing DNA fragment for preparation of a strain having ilvA gene deletion using a DNA synthesizer (Model 8905, PerSeptive Biosystems, Inc.).

The DNAs have nucleotide sequences homologous to 36-bp nucleotide sequences that lie upstream and downstream of the target gene to be deleted.

Separately, DNA consisting of the nucleotide sequence shown in SEQ ID NO: 123 and DNA consisting of the nucleotide sequence shown in SEQ ID NO: 124 containing the codon-substituted mutant sequence were synthesized as a set of primers for amplification of an upstream region of the feedback-resistant ilvA gene, and DNA consisting of the nucleotide sequence shown in SEQ ID NO: 125 containing the codon-substituted mutant sequence and DNA consisting of the nucleotide sequence shown in SEQ ID NO: 126 were synthesized as a set of primers for amplification of a downstream region of the feedback-resistant ilvA gene.

PCR was carried out, using each set of the above DNAs as a set of primers, to amplify a chloramphenicol resistance gene-containing DNA fragment for preparation of a strain having ilvA gene deletion using pKD3 DNA as a template, and to amplify upstream and downstream regions of the feedback-resistant ilvA gene using the chromosomal DNA of *Escherichia coli* W3110 as a template. That is, PCR was carried out by 30 cycles, one cycle consisting of reaction at 94° C. for one minute, reaction at 55° C. for 2 minutes and reaction at 72° C. for 3 minutes, using 40 µl of a reaction mixture comprising 0.1 µg of the chromosomal DNA or 10 ng of the plasmid DNA, 0.5 µmol/l each of the primers, 2.5 units of Pfu DNA polymerase, 4 µl of buffer for Pfu DNA polymerase (10×) and 200 µmol/l each of deoxyNTPs.

One-tenth of each of the resulting reaction mixtures was subjected to agarose gel electrophoresis to confirm that the desired fragment was amplified. Then, the remaining reaction mixture was mixed with an equal amount of phenol/chloroform saturated with TE.

The resulting mixture was centrifuged, and the obtained upper layer was mixed with a two-fold volume of cold ethanol and allowed to stand at −80° C. for 30 minutes, followed by centrifugation to precipitate DNA. Then, the DNA precipitate was dissolved in 20 µl of TE. By this procedure, a chloramphenicol resistance gene-containing DNA fragment for deletion of the ilvA gene, an upstream region of the feedback-resistant ilvA gene and a downstream region of the feedback-resistant ilvA gene were obtained.

Then, crossover PCR was carried out using, of the above PCR-amplified fragments, the upstream region of the feedback-resistant ilvA gene and the downstream region of the feedback-resistant ilvA gene as templates and using DNAs consisting of the nucleotide sequences shown in SEQ ID NOS: 123 and 126 as a set of primers. PCR was carried out under the same conditions as above.

The above PCR produced a DNA fragment for preparation of a feedback-resistant ilvA gene-substituted strain in which the upstream region of the feedback-resistant ilvA gene and the downstream region of the feedback-resistant ilvA gene are ligated.

(2) Preparation of *Escherichia coli* JM110 in which the Drug Resistance Gene is Inserted into the ilvA Gene on the Chromosomal DNA of *Escherichia coli*

*Escherichia coli* JM101/pKD46 cultured in the presence of 10 mmol/l L-arabinose and 50 µg/ml ampicillin was transformed by electroporation using the chloramphenicol resistance gene-containing DNA fragment for deletion of the ilvA gene obtained in the above (1). A recombinant strain in which the chloramphenicol resistance gene was inserted into the ilvA gene on the chromosomal DNA of *Escherichia coli* JM101 and the ilvA structural gene was deleted was selected on LB agar medium containing 25 mg/l chloramphenicol.

Replicas of the obtained chloramphenicol-resistant strain were made on LB agar medium containing 25 mg/l chloramphenicol, followed by single colony isolation at 30° C. Then, replicas of the obtained colonies were made on LB agar medium containing 25 mg/l chloramphenicol and 100 mg/l ampicillin to select colonies showing chloramphenicol resistance and ampicillin resistance.

Colony PCR was carried out on the obtained strains using, as a set of primers, DNAs having the nucleotide sequences shown in SEQ ID NOS: 123 and 126, i.e., the nucleotide sequences located approximately 400 bp upstream and downstream of the site to which the chloramphenicol resistance gene was inserted on the chromosomal DNA. That is, colony PCR was carried out by 30 cycles, one cycle consisting of reaction at 94° C. for one minute, reaction at 55° C. for 2 minutes and reaction at 72° C. for 3 minutes, using 40 µl of a reaction mixture comprising the cells in an amount obtained by contacting a 200-µl pipette tip with the colony, 0.5 µmol/l each of the primers, 2.5 units of Pfu DNA polymerase, 4 µl of buffer for Pfu DNA polymerase (10×) and 200 µmol/l each of deoxyNTPs.

Of the strains subjected to colony PCR, a strain with which a ca. 2 kb fragment containing the chloramphenicol resistance gene was amplified was identified as a strain having ilvA gene deletion and was designated as *Escherichia coli* JIACm1/pKD46.

(3) Preparation of *Escherichia coli* JM101 in which the ilvA Gene on the Chromosomal DNA is Substituted by the Feedback-Resistant ilvA Gene

*Escherichia coli* JIACm1/pKD46 prepared in the above (2) was cultured in the presence of 10 mmol/l L-arabinose and 50 µg/ml ampicillin and then transformed by electroporation using the DNA fragment for preparation of an feedback-resistant ilvA gene-substituted strain obtained in the above (1). A strain in which the ilvA gene on the chromosomal DNA of JIACm1 strain was substituted by the feedback-resistant ilvA gene was selected on agar medium containing M9 medium and glucose using recovery of isoleucine requirement as a marker.

Replicas of the ampicillin-resistant strain which grew were made on drug-free agar medium containing M9 medium and glucose, followed by single colony isolation at 42° C. Then, replicas of the obtained colonies were made on drug-free LB agar medium, LB agar medium containing 25 mg/l chloramphenicol and LB agar medium containing 100 mg/l ampicillin to select a colony showing chloramphenicol sensitivity and ampicillin sensitivity. It was confirmed that the obtained strain was the inhibition-released ilvA gene-substituted strain, which was designated as *Escherichia coli* JIA1.

(4) Preparation of *Escherichia coli* JILG+1 in which the ilvA Gene on the Chromosomal DNA is Substituted by the Inhibition-Released ilvA Gene The procedures of the above (1) to (3) were carried out using, as a parent strain, *Escherichia coli* JILG+1 prepared in Example 7 in place of *Escherichia coli* JM101 to obtain a strain in which the ilvL gene was deleted, the ilvG gene was substituted by the revertant ilvG gene and the ilvA gene was substituted by the feedback-resistant ilvA gene. The obtained strain was designated as *Escherichia coli* JILG+IA1.

Example 9

Preparation of a Strain Having Mutant leuA Gene Substitution (1) Cloning of a Drug Resistance Gene-Containing DNA Fragment for Preparation of a Strain Having leuA Gene Deletion and a DNA Fragment for Preparation of a Strain Having Mutant leuA Substitution The nucleotide sequence of the leuA gene of *Escherichia coli* K12 was already disclosed [Science, 5331, 1453-1474 (1997)].

*Escherichia coli* FERM BP-4704 is a leucine-producing strain selected by leucine analogue (4-azaleucine) resistance (Japanese Published Unexamined Patent Application No. 70879/96) and is considered to have the mutant leuA gene encoding isopropyl malate synthase substantially released from the inhibition by L-leucine.

On the basis of the reported nucleotide sequence, DNAs consisting of the nucleotide sequences shown in SEQ ID NOS: 127 and 128 were synthesized as a set of primers to amplify a drug resistance gene-containing DNA-fragment for preparation of a strain having leuA gene deletion using a DNA synthesizer (Model 8905, PerSeptive Biosystems, Inc.).

The DNAs have nucleotide sequences homologous to 36-bp nucleotide sequences that lie upstream and downstream of the target gene to be deleted.

Separately, DNA having the nucleotide sequence shown in SEQ ID NO: 129, i.e., the nucleotide sequence located approximately 200 bp upstream of the initiation codon of the leuA gene, and DNA having the nucleotide sequence shown in SEQ ID NO: 130, i.e., the nucleotide sequence located approximately 200 bp downstream of the termination codon of the leuA gene in reverse orientation were synthesized as a set of primers to amplify a DNA fragment for preparation of a strain having mutant leuA gene substitution.

PCR was carried out, using each set of the above DNAs as a set of primers, to amplify a chloramphenicol resistance gene-containing DNA fragment for preparation of a strain having leuA gene deletion using pKD3 DNA as a template, and to amplify a DNA fragment for preparation of a strain having mutant leuA gene substitution using the chromosomal DNA of FERM BP-4704 strain prepared by an ordinary method as a template.

That is, PCR was carried out by 30 cycles, one cycle consisting of reaction at 94° C. for one minute, reaction at 55° C. for 2 minutes and reaction at 72° C. for 3 minutes, using 40 µl of a reaction mixture comprising 0.1 µg of the chromosomal DNA or 10 ng of the plasmid DNA, 0.5 µmol/l each of the primers, 2.5 units of Pfu DNA polymerase, 4 µl of buffer for Pfu DNA polymerase (10×) and 200 µmol/l each of deoxyNTPs.

One-tenth of each of the resulting reaction mixtures was subjected to agarose gel electrophoresis to confirm that the desired fragment was amplified. Then, the remaining reaction mixture was mixed with an equal amount of phenol/chloroform saturated with TE.

The resulting mixture was centrifuged, and the obtained upper layer was mixed with a two-fold volume of cold ethanol and allowed to stand at −80° C. for 30 minutes, followed by centrifugation to precipitate DNA. Then, the DNA precipitate was dissolved in 20 µl of TE. By this procedure, a chloramphenicol resistance gene-containing DNA fragment for preparation of a strain having leuA gene deletion and a DNA fragment for preparation of a strain having mutant leuA gene substitution were obtained.

(2) Preparation of *Escherichia coli* JM101 in which the Drug Resistance Gene is Inserted into the leuA Gene on the Chromosomal DNA A mutant strain of *Escherichia coli* in which the chloramphenicol resistance gene was inserted into the leuA gene on the chromosomal DNA of *Escherichia coli* JM101 was prepared by the same procedure as in Example 8 (2).

Insertion of the chloramphenicol resistance gene into the chromosomal DNA was confirmed by carrying out colony PCR using, as a set of primers, DNAs consisting of the nucleotide sequences shown in SEQ ID NOS: 131 and 132, i.e., the nucleotide sequences located approximately 200 bp upstream and downstream of the site to which the chloramphenicol resistance gene was inserted.

PCR was carried out under the same conditions as in Example 8 (2). Of the strains subjected to colony PCR, a strain with which a ca. 2 kb fragment containing the chloramphenicol resistance gene was amplified was identified as a strain having leuA gene deletion in which the chloramphenicol resistance gene was inserted into the leuA gene, and was designated as *Escherichia coli* JLACm1/pKD46.

(3) Preparation of *Escherichia coli* JM101 in which the leuA Gene on the Chromosomal DNA is Substituted by the Mutant Gene Derived from *Escherichia coli* H-9070

The same procedure as in Example 8 (3) was carried out using the DNA fragment for preparation of a strain having mutant leuA gene substitution obtained in the above (1) and *Escherichia coli* JLACm1/pKD46 obtained in the above (2) to obtain a recombinant strain in which the leuA gene into which the chloramphenicol resistance gene was inserted on the chromosomal DNA of *Escherichia coli* JLACm1/pKD46 was substituted by the mutant leuA gene. The obtained strain was designated as *Escherichia coli* JLA1.

(4) Preparation of *Escherichia coli* JILG+1 in which the leuA Gene on the Chromosomal DNA is Substituted by the Mutant leuA Gene The procedures of the above (1) to (3) were carried out using, as a parent strain, *Escherichia coli* JILG+1 prepared in Example 7 in place of *Escherichia coli* JM101 to obtain a strain in which the ilvL gene was deleted, the ilvG gene was substituted by the revertant ilvG gene and the leuA gene was substituted by the mutant leuA gene. The obtained strain was designated as *Escherichia coli* JILG+LA1.

Example 10

Fermentative Production of L-Ala-L-Ala Using a Microorganism Having the Ability to Produce L-Alanine

*Escherichia coli* JM101 was transformed with the plasmid pPE86 expressing the ywfE gene and the ald gene both derived from *Bacillus subtilis* obtained in Example 2, spread on LB agar medium containing 50 µg/ml ampicillin, and cultured overnight at 30° C. A plasmid was extracted from the strain that grew on the medium according to a known method. By restriction enzyme digestion, it was confirmed that *Escherichia coli* JM101 carrying the plasmid pPE86 (hereinafter referred to as *Escherichia coli* JM101/pPE86) was obtained. *Escherichia coli* JM101 carrying the plasmid pTrS30 (hereinafter referred to as *Escherichia coli* JM101/pTrS30) and *Escherichia coli* JM101 carrying the plasmid pPE56 (hereinafter referred to as *Escherichia coli* JM101/pPE56) were also obtained in the same manner.

Each of the obtained transformants was inoculated into 8 ml of LB medium containing 50 µg/ml ampicillin in a test tube and cultured at 28° C. for 17 hours. The resulting culture was inoculated into 8 ml of a production medium [16 g/l dipotassium hydrogenphosphate, 14 g/l potassium dihydrogenphosphate, 5 g/l ammonium sulfate, 1 g/l citric acid (anhydrous), 5 g/l Casamino acid (Difco), 10 g/l glucose, 10 mg/l vitamin $B_1$, 25 mg/l magnesium sulfate heptahydrate and 50 mg/l ferrous sulfate heptahydrate; pH adjusted to 7.2 with 10 mol/l sodium hydroxide; glucose, vitamin $B_1$, magnesium sulfate heptahydrate and ferrous sulfate heptahydrate were added after separate steam sterilization] containing 100 µg/ml ampicillin in a test tube in an amount of 1% and cultured at 30° C. for 24 hours. The resulting culture was centrifuged to obtain a culture supernatant.

The product in the culture supernatant was derivatized by the F-moc method and then analyzed by HPLC. The HPLC analysis was carried out in the same manner as in Experimental Example 17. The results are shown in Table 6.

TABLE 6

|  | L-Ala-L-Ala (mg/l) | L-Ala (mg/l) |
|---|---|---|
| JM101/pTrS30 | 0 | 0 |
| JM101/pPE56 | 0 | 1 |
| JM101/pPE86 | 7 | 667 |

Example 11

Fermentative Production of L-Ala-L-Gln Using a Microorganism Having the Ability to Produce L-Ala and L-Gln

*Escherichia coli* JGLBE1 having double deletions of the glnE gene and the glnB gene obtained in Example 1 was transformed with the plasmid pPE86 obtained in Example 2, spread on LB agar medium containing 50 μg/ml ampicillin, and cultured overnight at 30° C. A plasmid was extracted from a colony that grew on the medium according to a known method. By restriction enzyme digestion, it was confirmed that *Escherichia coli* JGLBE1 carrying the plasmid pPE86 was obtained, and the strain was designated as *Escherichia coli* JGLBE1/pPE86. *Escherichia coli* JGLBE1 carrying the plasmid pTrS30 (hereinafter referred to as *Escherichia coli* JGLBE1/pTrS30) and *Escherichia coli* JGLBE1 carrying the plasmid pPE56 (hereinafter referred to as *Escherichia coli* JGLBE1/pPE56) were also obtained in the same manner.

Each of the obtained transformants was inoculated into 8 ml of LB medium containing 50 μg/ml ampicillin in a test tube and cultured at 28° C. for 17 hours. The resulting culture was inoculated into 8 ml of the production medium described in Example 10 containing 100 μg/ml ampicillin in a test tube in an amount of 1% and cultured at 30° C. for 24 hours. The resulting culture was centrifuged to obtain a culture supernatant.

The product in the culture supernatant was derivatized by the F-moc method and then analyzed by HPLC. The HPLC analysis was carried out in the same manner as in Experimental Example 17. The results are shown in Table 7.

TABLE 7

|  | L-Ala-L-Gln (mg/l) | L-Gln (mg/l) |
| --- | --- | --- |
| JGLBE1/pTrS30 | 0 | 183 |
| JGLBE1/pPE56 | 6 | 1063 |
| JGLBE1/pPE86 | 72 | 311 |

Example 12

Fermentative Production of L-Ala-L-Phe Using a Microorganism Having the Ability to Produce L-Ala and L-Phe

*Escherichia coli* JM101/pPE86 obtained in Example 10 was transformed with each of the plasmid pPHEA2 expressing the feedback-resistant pheA gene derived from *Escherichia coli* and the plasmid pPHEAF2 expressing the feedback-resistant pheA gene and feedback-resistant aroF gene derived from *Escherichia coli* constructed in Example 3, spread on LB agar medium containing 50 μg/ml ampicillin and 30 μg/ml chloramphenicol, and cultured overnight at 30° C. A plasmid was extracted from a colony of each strain that grew on the medium according to a known method, and it was confirmed that *Escherichia coli* JM101/pPE86 strains respectively carrying pPHEA2 and pPHEAF2 (hereinafter referred to as *Escherichia coli* JM101/pPE86/pPHEA2 and *Escherichia coli* JM101/pPE86/pPHEAF2, respectively) were obtained. In the same manner, *Escherichia coli* JM101/pTrS30 and *Escherichia coli* JM101/pPE56 obtained in Example 10 were transformed with each of pPHEA2 and pPHEAF2 to obtain *Escherichia coli* JM101/pTrS30 carrying pPHEA2 (hereinafter referred to as *Escherichia coli* JM101/pTrS30/pPHEA2), *Escherichia coli* JM101/pTrS30 carrying pPHEAF2 (hereinafter referred to as *Escherichia coli* JM101/pTrS30/pPHEAF2), *Escherichia coli* JM101/pPE56 carrying pPHEA2 (hereinafter referred to as *Escherichia coli* JM101/pPE56/pPHEA2) and *Escherichia coli* JM101/pPE56 carrying pPHEAF2 (hereinafter referred to as *Escherichia coli* JM101/pPE56/pPHEAF2).

Each of the obtained transformants was inoculated into 8 ml of LB medium containing 50 μg/ml ampicillin and 30 μg/ml chloramphenicol in a test tube and cultured at 28° C. for 17 hours. The resulting culture was inoculated into 8 ml of the production medium described in Example 10 containing 100 μg/ml ampicillin and 50 μg/ml chloramphenicol in a test tube in an amount of 1% and cultured at 30° C. for 24 hours. The resulting culture was centrifuged to obtain a culture supernatant.

The product in the culture supernatant was derivatized by the F-moc method and then analyzed by HPLC. The HPLC analysis was carried out in the same manner as in Experimental Example 17. The results are shown in Table 8.

TABLE 8

|  | L-Ala-L-Phe (mg/l) | L-Phe (mg/l) |
| --- | --- | --- |
| JM101/pTrS30/pPHEA2 | 0 | 37 |
| JM101/pTrS30/pPHEAF2 | 0 | 77 |
| JM101/pPE56/pPHEA2 | 129 | 54 |
| JM101/pPE56/pPHEAF2 | 294 | 104 |
| JM101/pPE86/pPHEA2 | 277 | 91 |
| JM101/pPE86/pPHEAF2 | 340 | 118 |

Example 13

Fermentative Production of L-Threonyl-L-phenylalanine (L-Thr-L-Phe) Using a Microorganism Having the Ability to Produce L-Thr and L-Phe

*Escherichia coli* βIM-4 (ATCC 21277) exhibiting proline-, methionine-, isoleucine- and thiamine-requirement, imparted with α-amino-β-hydroxyvaleric acid resistance and having the ability to produce L-Thr was transformed with the *Bacillus subtilis*-derived ywfE expression-enhanced plasmid pPE56 obtained in Experimental Example 15, spread on LB agar medium containing 50 μg/ml ampicillin, and cultured overnight at 30° C. A plasmid was extracted from a colony that grew on the medium according to a known method. By restriction enzyme digestion, it was confirmed that *Escherichia coli* ATCC 21277 carrying pPE56 (hereinafter referred to as *Escherichia coli* ATCC 21277/pPE56) was obtained.

Then, *Escherichia coli* ATCC 21277/pPE56 was transformed with each of pSTV28 (Takara Bio Inc.), and pPHEA2 and pPHEAF2 obtained in Example 3, spread on LB agar medium containing 50 μg/ml ampicillin and 30 μg/ml chloramphenicol, and cultured overnight at 30° C. A plasmid was extracted from a colony of each strain that grew on the medium according to a known method. By restriction enzyme digestion, it was confirmed that *Escherichia coli* ATCC 21277/pPE56 strains respectively carrying pSTV28, pPHEA2 and pPHEAF2 (hereinafter referred to as *Escherichia coli* ATCC 21277/pPE56/pSTV28, *Escherichia coli* ATCC 21277/pPE56/pPHEA2 and *Escherichia coli* ATCC 21277/pPE56/pPHEAF2, respectively) were obtained. In the same manner, *Escherichia coli* ATCC 21277 carrying pTrS30 and pSTV28 (hereinafter referred to as *Escherichia coli* ATCC 21277/pTrS30/pSTV28), *Escherichia coli* ATCC 21277 carrying pTrS30 and pPHEA2 (hereinafter referred to as *Escherichia coli* ATCC 21277/pTrS30/pPHEA2) and *Escherichia coli* ATCC 21277 carrying pTrS30 and pPHEAF2 (hereinafter referred to as *Escherichia coli* ATCC 21277/pTrS30/pPHEAF2) were obtained.

Each of the obtained transformants was inoculated into 8 ml of LB medium containing 50 μg/ml ampicillin and 30

µg/ml chloramphenicol in a test tube and cultured at 28° C. for 17 hours. The resulting culture was inoculated into 8 ml of the production medium described in Example 10 containing 100 µg/ml ampicillin and 50 µg/ml chloramphenicol in a test tube in an amount of 1% and cultured at 30° C. for 24 hours. The resulting culture was centrifuged to obtain a culture supernatant.

The product in the culture supernatant was derivatized by the F-moc method and then analyzed by HPLC. The HPLC analysis was carried out in the same manner as in Experimental Example 17. The results are shown in Table 9.

TABLE 9

|  | L-Thr-L-Phe (mg/l) | L-Thr (mg/l) | L-Phe (mg/l) |
| --- | --- | --- | --- |
| ATCC21277/pTrS30/pSTV28 | 0 | 180 | 80 |
| ATCC21277/pTrS30/pHEA2 | 0 | 30 | 210 |
| ATCC21277/pTrS30/pPHEAF2 | 0 | 30 | 170 |
| ATCC21277/pPE56/pSTV28 | 230 | 300 | 70 |
| ATCC21277/pPE56/pHEA2 | 410 | 250 | 110 |
| ATCC21277/pPE56/pPHEAF2 | 460 | 270 | 0 |

Example 14

Fermentative Production of L-Ala-L-Tyr Using a Microorganism Having the Ability to Produce L-Ala and L-Tyr

*Escherichia coli* JM101/pPE86 obtained in Example 10 was transformed with the plasmid pTY2 expressing the tyrosine-resistant mutant aroF-tyrA operon derived from *Escherichia coli* constructed in Example 4, spread on LB agar medium containing 50 µg/ml ampicillin and 30 µg/ml chloramphenicol, and cultured overnight at 30° C. A plasmid was extracted from a colony of the strain that grew on the medium according to a known method, and it was confirmed that *Escherichia coli* JM101/pPE86 carrying pTY2 (hereinafter referred to as *Escherichia coli* JM101/pPE86/pTY2) was obtained. In the same manner, *Escherichia coli* JM101/pTrS30 and *Escherichia coli* JM101/pPE56 obtained in Example 10 were transformed with pTY2 to obtain *Escherichia coli* JM101/pTrS30 carrying pTY2 (hereinafter referred to as *Escherichia coli* JM101/pTrS30/pTY2) and *Escherichia coli* JM101/pPE56 carrying pTY2 (hereinafter referred to as *Escherichia coli* JM101/pPE56/pTY2).

Each of the obtained transformants was inoculated into 8 ml of LB medium containing 50 µg/ml ampicillin and 30 µg/ml chloramphenicol in a test tube and cultured at 28° C. for 17 hours. The resulting culture was inoculated into 8 ml of the production medium described in Example 10 containing 100 µg/ml ampicillin and 50 µg/ml chloramphenicol in a test tube in an amount of 1% and cultured at 30° C. for 24 hours. The resulting culture was centrifuged to obtain a culture supernatant.

The product in the culture supernatant was derivatized by the F-moc method and then analyzed by HPLC. The HPLC analysis was carried out in the same manner as in Experimental Example 17. The results are shown in Table 10.

TABLE 10

|  | L-Ala-L-Tyr (mg/l) | L-Tyr (mg/l) |
| --- | --- | --- |
| JM101/pTrS30/pTY2 | 0 | 1 |
| JM101/pPE56/pTY2 | 51 | 6 |
| JM101/pPE86/pTY2 | 63 | 7 |

Example 15

Fermentative Production of L-Alanyl-L-methionine (L-Ala-L-Met) Using a Microorganism Having the Ability to Produce L-Ala and L-Met

*Escherichia coli* JMJ1 obtained in Example 5 was transformed with pPE86 obtained in Example 2, spread on LB agar medium containing 50 µg/ml ampicillin, and cultured overnight at 30° C. A plasmid was extracted from a colony of the strain that grew on the medium according to a known method. By restriction enzyme digestion, it was confirmed that *Escherichia coli* JMJ1 carrying pPE86 was obtained, and the strain was designated as *Escherichia coli* JMJ1/pPE86. In the same manner, *Escherichia coli* JMJ1 carrying pTrS30 (hereinafter referred to as *Escherichia coli* JMJ1/pTrS30) and *Escherichia coli* JMJ1 carrying pPE56 (hereinafter referred to as *Escherichia coli* JMJ1/pPE56) were obtained.

Each of the obtained transformants was inoculated into 8 ml of LB medium containing 50 µg/ml ampicillin in a test tube and cultured at 28° C. for 17 hours. The resulting culture was inoculated into 8 ml of the production medium described in Example 10 containing 100 µg/ml ampicillin in a test tube in an amount of 1% and cultured at 30° C. for 24 hours. The resulting culture was centrifuged to obtain a culture supernatant.

The product in the culture supernatant was derivatized by the F-moc method and then analyzed by HPLC. The HPLC analysis was carried out in the same manner as in Experimental Example 17. The results are shown in Table 11.

TABLE 11

|  | L-Ala-L-Met (mg/l) | L-Met (mg/l) |
| --- | --- | --- |
| JMJ1/pTrS30 | 0 | 16 |
| JMJ1/pPE56 | 0 | 61 |
| JMJ1/pPE86 | 113 | 180 |

The results shown in Examples 10 to 15 revealed that a microorganism which has the ability to produce a protein having the activity to form a dipeptide from one or more kinds of amino acids and the ability to produce one or more kinds of amino acids forms and accumulates the dipeptide in a medium when cultured therein, and the ability to produce the dipeptide of a microorganism which has the ability to produce two amino acids is higher than that of a microorganism which has the ability to produce one amino acids in the above microorganism.

Example 16

Fermentative Production of L-Ala-L-Ala Using a Microorganism Having the Ability to Produce L-Ala and Having Deletions of Peptidase Genes and a Dipeptide-Permeating/Transporting Protein Operon

*Escherichia coli* JPNDDP36 having deletions of the pepD and pepN genes and the dpp operon obtained in Experimental Example 16 (4) was transformed with each of pTrS30, and pPE56 and pPE86 obtained in Example 2, spread on LB agar medium containing 50 µg/ml ampicillin, and cultured overnight at 30° C. A plasmid was extracted from a colony of each strain that grew on the medium according to a known method. By restriction enzyme digestion, it was confirmed that *Escherichia coli* JPNDDP36 strains respectively carrying pTrS30, pPE56 and pPE86 (hereinafter referred to as *Escheri-* chia coli JPNDDP36/pTrS30, *Escherichia coli* JPNDDP36/pPE56 and *Escherichia coli* JPNDDP36/pPE86, respectively) were obtained.

Each of the obtained transformants was cultured in the same manner as in Example 10 and the product in the culture supernatant was analyzed in the same manner as in Experimental Example 17. The results are shown in Table 12.

TABLE 12

|  | L-Ala-L-Ala (mg/l) | L-Ala (mg/l) |
|---|---|---|
| JPNDDP36/pTrS30 | 0 | 0 |
| JPNDDP36/pPE56 | 0 | 1 |
| JPNDDP36/pPE86 | 10 | 2 |

Example 17

Fermentative Production of L-Ala-L-Gln Using a Microorganism Having the Ability to Produce L-Ala and L-Gln and Having Deletions of Peptidase Genes and a Dipeptide-Permeating/Transporting Protein Operon (1) Construction of a Microorganism Having the Ability to Produce L-Ala and L-Gln and Having Deletions of Peptidase Genes and a Dipeptide-Permeating/Transporting Protein Operon According to the same procedure as in Example 1, deletions of the glnE gene and the glnB gene were introduced into *Escherichia coli* JPNDDP36 obtained in Experimental Example 16 (4) to obtain *Escherichia coli* JPNDDPGBE1 having the ability to produce L-Ala and L-Gln and having deletions of peptidase genes and a dipeptide-permeating/transporting protein operon.

(2) Fermentative Production of L-Ala-L-Gln

*Escherichia coli* JPNDDPGBE1 obtained in the above (1) was transformed with each of pTrS30, pPE56 and pPE86 in the same manner as in Example 16 to obtain *Escherichia coli* JPNDDPGBE1 strains carrying the respective plasmids (hereinafter referred to as *Escherichia coli* JPNDDPGBE1/pTrS30, *Escherichia coli* JPNDDPGBE1/pPE56 and *Escherichia coli* JPNDDPGBE1/pPE86, respectively). Each of the obtained transformants was cultured in the same manner as in Example 10 and the product in the culture supernatant was analyzed in the same manner as in Experimental Example 17. The results are shown in Table 13.

TABLE 13

|  | L-Ala-L-Gln (mg/l) | L-Gln (mg/l) |
|---|---|---|
| JPNDDPGBE1/pTrS30 | 0 | 1329 |
| JPNDDPGBE1/pPE56 | 400 | 1625 |
| JPNDDPGBE1/pPE86 | 1053 | 504 |

Example 18

Fermentative Production of L-Ala-L-Tyr Using a Microorganism Having the Ability to Produce L-Ala and L-Tyr and Having Deletions of Peptidase Genes and a Dipeptide-Permeating/Transporting Protein Operon

*Escherichia coli* JPNDDP36 obtained in Experimental Example 16 was transformed with pPE86 obtained in Example 2, spread on LB agar medium containing 50 μg/ml ampicillin, and cultured overnight at 30° C. A plasmid was extracted from a colony of the strain that grew on the medium according to a known method. By restriction enzyme digestion, it was confirmed that *Escherichia coli* JPNDDP36 carrying pPE86 was obtained, and the strain was designated as *Escherichia coli* JPNDDP36/pPE86. In the same manner, *Escherichia coli* JPNDDP36 carrying pTrS30 (hereinafter referred to as *Escherichia coli* JPNDDP36/pTrS30) and *Escherichia coli* JPNDDP36 carrying pPE56 (hereinafter referred to as *Escherichia coli* JPNDDP36/pPE56) were obtained.

The obtained transformants were transformed with pTY2 obtained in Example 4 to obtain the following transformants carrying pTY2: *Escherichia coli* JPNDDP36/pTrS30/pTY2, *Escherichia coli* JPNDDP36/pPE56/pTY2 and *Escherichia coli* JPNDDP36/pPE86/pTY2.

Each of the obtained transformants was inoculated into 8 ml of LB medium containing 50 μg/ml ampicillin in a test tube and cultured at 28° C. for 17 hours. The resulting culture was inoculated into 8 ml of the production medium described in Example 10 containing 100 μg/ml ampicillin in a test tube in an amount of 1% and cultured at 30° C. for 24 hours. The resulting culture was centrifuged to obtain a culture supernatant.

The product in the culture supernatant was derivatized by the F-moc method and then analyzed by HPLC. The HPLC analysis was carried out in the same manner as in Experimental Example 17. The results are shown in Table 14.

TABLE 14

|  | L-Ala-L-Tyr (mg/l) | L-Tyr (mg/l) |
|---|---|---|
| JPNDDP36/pTrS30/pTY2 | 0 | 41 |
| JPNDDP36/pPE56/pTY2 | 301 | 16 |
| JPNDDP36/pPE86/pTY2 | 367 | 8 |

Example 19

Fermentative Production of L-Ala-L-Val Using a Microorganism Having the Ability to Produce L-Ala and L-Val and Having Deletions of Peptidase Genes and a Dipeptide-Permeating/Transporting Protein Operon

*Escherichia coli* JPNDDPILG+1 in which the ilvL gene was deleted and the frameshift mutation of the ilvG gene reverted was prepared using, as a parent strain, the mutant strain having deletions of peptidase genes and a peptide-permeating/transporting protein operon obtained in Experimental Example 16 according to the method described in Example 7.

*Escherichia coli* JPNDDPILG+1 was transformed with pPE86 obtained in Example 2, spread on LB agar medium containing 50 μg/ml ampicillin, and cultured overnight at 30° C. A plasmid was extracted from the strain that grew on the medium according to a known method. By restriction enzyme digestion, it was confirmed that *Escherichia coli* JPNDDPILG+1 carrying the plasmid pPE86 (hereinafter referred to as *Escherichia coli* JPNDDPILG+1/pPE86) was obtained. In the same manner, *Escherichia coli* JPNDDPILG+1 carrying the plasmid pTrS30 (hereinafter referred to as *Escherichia coli* JPNDDPILG+1/pTrS30) and *Escherichia coli*

JPNDDPILG+1 carrying the plasmid pPE56 (hereinafter referred to as *Escherichia coli* JPNDDPILG+1/pPE56) were obtained.

Each of the obtained transformants was inoculated into 8 ml of LB medium containing 50 µg/ml ampicillin in a test tube and cultured at 28° C. for 17 hours. The resulting culture was inoculated into 8 ml of a medium [16 g/l dipotassium hydrogenphosphate, 14 g/l potassium dihydrogenphosphate, 5 g/l ammonium sulfate, 1 g/l citric acid (anhydrous), 5 g/l Casamino acid (Difco), 10 g/l glucose, 10 mg/l vitamin $B_1$, 25 mg/l magnesium sulfate heptahydrate and 50 mg/l ferrous sulfate heptahydrate; pH adjusted to 7.2 with 10 mol/l sodium hydroxide; glucose, vitamin $B_1$, magnesium sulfate heptahydrate and ferrous sulfate heptahydrate were added after separate steam sterilization] containing 100 µg/ml ampicillin in a test tube in an amount of 1% and cultured at 30° C. for 24 hours. The resulting culture was centrifuged to obtain a culture supernatant.

The product in the culture supernatant was derivatized by the F-moc method and then analyzed by HPLC. The HPLC analysis was carried out in the same manner as in Experimental Example 17. The results are shown in Table 15.

TABLE 15

|  | L-Ala-L-Val (mg/l) | L-Val (mg/l) |
| --- | --- | --- |
| JPNDDPILG + 1/pTrS30 | 0 | 220 |
| JPNDDPILG + 1/pPE56 | 62 | 171 |
| JPNDDPILG + 1/pPE86 | 300 | 240 |

Example 20

Fermentative Production of L-Ala-L-Ile Using a Microorganism Having the Ability to Produce L-Ala and L-Ile and Having Deletions of Peptidase Genes and a Dipeptide-Permeating/Transporting Protein Operon

*Escherichia coli* JPNDDPILG+IA1 in which the ilvL gene was deleted, the frameshift mutation of the ilvG gene reverted and the ilvA gene was substituted by the inhibition-released ilvA gene was prepared using, as a parent strain, *Escherichia coli* JPNDDP36, the mutant strain having deletions of peptidase genes and a peptide-permeating/transporting protein operon obtained in Experimental Example 16 according to the methods described in Examples 7 and 8.

*Escherichia coli* JPNDDPILG+IA1 was transformed with pPE86 obtained in Example 2, spread on LB agar medium containing 50 µg/ml ampicillin, and cultured overnight at 30° C. A plasmid was extracted from a colony of the strain that grew on the medium according to a known method. By restriction enzyme digestion, it was confirmed that *Escherichia coli* JPNDDPILG+IA1 carrying pPE86 was obtained, and the strain was designated as *Escherichia coli* JPNDDPILG+IA1/pPE86. In the same manner, *Escherichia coli* JPNDDPILG+IA1 carrying pTrS30 (hereinafter referred to as *Escherichia coli* JPNDDPILG+IA1/pTrS30) and *Escherichia coli* JPNDDPILG+IA1 carrying pPE56 (hereinafter referred to as *Escherichia coli* JPNDDPILG+IA1/pPE56) were obtained.

Each of the obtained transformants was inoculated into 8 ml of LB medium containing 50 µg/ml ampicillin in a test tube and cultured at 28° C. for 17 hours. The resulting culture was inoculated into 8 ml of the production medium described in Example 10 containing 100 µg/ml ampicillin in a test tube in an amount of 1% and cultured at 30° C. for 24 hours. The resulting culture was centrifuged to obtain a culture supernatant.

The product in the culture supernatant was derivatized by the F-moc method and then analyzed by HPLC. The HPLC analysis was carried out in the same manner as in Experimental Example 17. The results are shown in Table 16.

TABLE 16

|  | L-Ala-L-Ile (mg/l) | L-Ile (mg/l) |
| --- | --- | --- |
| JPNDDPILG + IA1/pTrS30 | 0 | 124 |
| JPNDDPILG + IA1/pPE56 | 21 | 212 |
| JPNDDPILG + IA1/pPE86 | 159 | 189 |

Example 21

Fermentative Production of L-Ala-L-Leu Using a Microorganism Having the Ability to Produce L-Ala and L-Leu and Having Deletions of Peptidase Genes and a Dipeptide-Permeating/Transporting Protein Operon

*Escherichia coli* JPNDDPILG+LA1 in which the ilvL gene was deleted, the frameshift mutation of the ilvG gene reverted and the leuA gene was substituted by the mutant leuA gene was prepared using, as a parent strain, *Escherichia coli* JPNDDP36, the mutant strain having deletions of peptidase genes and a peptide-permeating/transporting protein operon obtained in Experimental Example 16 according to the methods described in Examples 7 and 9. The obtained strain was transformed with pPE86 obtained in Example 2, spread on LB agar medium containing 50 µg/ml ampicillin, and cultured overnight at 30° C. A plasmid was extracted from a colony of the strain that grew on the medium according to a known method. By restriction enzyme digestion, it was confirmed that *Escherichia coli* JPNDDPILG+LA1 carrying pPE86 was obtained, and the strain was designated as *Escherichia coli* JPNDDPILG+LA1/pPE86. In the same manner, *Escherichia coli* JPNDDPILG+LA1 carrying pTrS30 (hereinafter referred to as *Escherichia coli* JPNDDPILG+LA1/pTrS30) and *Escherichia coli* JPNDDPILG+LA1 carrying pPE56 (hereinafter referred to as *Escherichia coli* JPNDDPILG+LA1/pPE56) were obtained.

Each of the obtained transformants was inoculated into 8 ml of LB medium containing 50 µg/ml ampicillin in a test tube and cultured at 28° C. for 17 hours. The resulting culture was inoculated into 8 ml of the production medium described in Example 10 containing 100 µg/ml ampicillin in a test tube in an amount of 1% and cultured at 30° C. for 24 hours. The resulting culture was centrifuged to obtain a culture supernatant.

The product in the culture supernatant was derivatized by the F-moc method and then analyzed by HPLC. The HPLC analysis was carried out in the same manner as in Experimental Example 17. The results are shown in Table 17.

TABLE 17

|  | L-Ala-L-Leu (mg/l) | L-Leu (mg/l) |
| --- | --- | --- |
| JPNDDPILG + LA1/pTrS30 | 0 | 12 |
| JPNDDPILG + LA1/pPE56 | 78 | 66 |
| JPNDDPILG + LA1/pPE86 | 110 | 25 |

Example 22

Fermentative Production of L-Ser-L-Phe Using a Microorganism Having the Ability to Produce L-Ser and L-Phe and Having Deletions of Peptidase Genes and a Dipeptide-Permeating/Transporting Protein Operon

*Escherichia coli* JPNDDP36 obtained in Experimental Example 16 was transformed with pSE15 or pPE212 obtained in Example 3, spread on LB agar medium containing 50 μg/ml ampicillin, and cultured overnight at 30° C. A plasmid was extracted from a colony of each of the strains that grew on the medium according to a known method. By restriction enzyme digestion, it was confirmed that *Escherichia coli* JPNDDP36 carrying pSE15 and *Escherichia coli* JPNDDP36 carrying pPE212 were obtained, and the strain was designated as *Escherichia coli* JPNDDP36/pSE15 and *Escherichia coli* JPNDDP36/pPE212, respectively.

The obtained transformants were transformed with the plasmid pPHEAF2 expressing the feedback-resistant pheA gene and feedback-resistant aroF gene derived from *Escherichia coli* constructed in Example 3 to obtain the following transformants carrying pPHEAF2: *Escherichia coli* JPNDDP36/pSE15/pPHEAF2 and *Escherichia coli* JPNDDP36/pPE212/pPHEAF2.

*Escherichia coli* JPNDDP36/pSE15/pPHEAF2 and *Escherichia coli* JPNDDP36/pPE212/pPHEAF2 were inoculated into 8 ml of LB medium containing 50 μg/ml ampicillin and 30 μg/ml chloramphenicol in a test tube, respectively and cultured at 28° C. for 17 hours. The resulting culture was inoculated into 8 ml of the production medium described in Example 10 containing 100 μg/ml ampicillin in a test tube in an amount of 1% and cultured at 30° C. for 24 hours. The resulting culture was centrifuged to obtain a culture supernatant.

The product in the culture supernatant was derivatized by the F-moc method and then analyzed by HPLC. The HPLC analysis was carried out in the same manner as in Experimental Example 17. The results are shown in Table 18.

TABLE 18

|  | L-Ala-L-Tyr (mg/l) | L-Ser (mg/l) | L-Tyr (mg/l) |
|---|---|---|---|
| JPNDDP36/pSE15/pPHEAF2 | 0 | 7 | 31 |
| JPNDDP36/pSE212/pPHEAF2 | 7 | 7 | 10 |

The results shown in Examples 16 to 22 revealed that a microorganism which has the ability to produce a protein having the activity to form a dipeptide from one or more kinds of amino acids, which has the ability to produce one or more kinds of amino acids, and in which the activities of one or more kinds of peptidases and one or more kinds of peptide-permeating/transporting proteins are lost, or in which the activities of three or more kinds of peptidases are lost forms and accumulates the dipeptide in a medium when cultured therein, and the ability to produce the dipeptide of said microorganism is higher than that of a microorganism which has the ability to produce the protein having the activity to form the dipeptide from one or more kinds of amino acids and the ability to produce one or more kinds of amino acids, but in which the activities of any peptidase and peptide-permeating/transporting protein are not lost.

Sequence Listing Free Text

SEQ ID NO: 19—Description of Artificial Sequence: Synthetic DNA
SEQ ID NO: 20—Description of Artificial Sequence: Synthetic DNA
SEQ ID NO: 21—Description of Artificial Sequence: Synthetic DNA
SEQ ID NO: 22—Description of Artificial Sequence: Synthetic DNA
SEQ ID NO: 23—Description of Artificial Sequence: Synthetic DNA
SEQ ID NO: 24—Description of Artificial Sequence: Synthetic DNA
SEQ ID NO: 25—Description of Artificial Sequence: Synthetic DNA
SEQ ID NO: 26—Description of Artificial Sequence: Synthetic DNA
SEQ ID NO: 27—Description of Artificial Sequence: Synthetic DNA
SEQ ID NO: 28—Description of Artificial Sequence: Synthetic DNA
SEQ ID NO: 29—Description of Artificial Sequence: Synthetic DNA
SEQ ID NO: 30—Description of Artificial Sequence: Synthetic DNA
SEQ ID NO: 31—Description of Artificial Sequence: Synthetic DNA
SEQ ID NO: 32—Description of Artificial Sequence: Synthetic DNA
SEQ ID NO: 33—Description of Artificial Sequence: Amino acid sequence used in database search
SEQ ID NO: 34—Description of Artificial Sequence: Amino acid sequence used in database search
SEQ ID NO: 35—Description of Artificial Sequence: Amino acid sequence used in database search
SEQ ID NO: 41—Description of Artificial Sequence: Synthetic DNA
SEQ ID NO: 42—Description of Artificial Sequence: Synthetic DNA
SEQ ID NO: 54—Description of Artificial Sequence: Synthetic DNA
SEQ ID NO: 64—Description of Artificial Sequence: Synthetic DNA
SEQ ID NO: 65—Description of Artificial Sequence: Synthetic DNA
SEQ ID NO: 66—Description of Artificial Sequence: Synthetic DNA
SEQ ID NO: 67—Description of Artificial Sequence: Synthetic DNA
SEQ ID NO: 68—Description of Artificial Sequence: Synthetic DNA
SEQ ID NO: 69—Description of Artificial Sequence: Synthetic DNA
SEQ ID NO: 70—Description of Artificial Sequence: Synthetic DNA
SEQ ID NO: 71—Description of Artificial Sequence: Synthetic DNA
SEQ ID NO: 72—Description of Artificial Sequence: Synthetic DNA
SEQ ID NO: 73—Description of Artificial Sequence: Synthetic DNA
SEQ ID NO: 74—Description of Artificial Sequence: Synthetic DNA
SEQ ID NO: 75—Description of Artificial Sequence: Synthetic DNA
SEQ ID NO: 76—Description of Artificial Sequence: Synthetic DNA SEQ ID NO: 77—Description of Artificial Sequence: Synthetic DNA
SEQ ID NO: 78—Description of Artificial Sequence: Synthetic DNA
SEQ ID NO: 79—Description of Artificial Sequence: Synthetic DNA
SEQ ID NO: 80—Description of Artificial Sequence: Synthetic DNA
SEQ ID NO: 81—Description of Artificial Sequence: Synthetic DNA
SEQ ID NO: 82—Description of Artificial Sequence: Synthetic DNA
SEQ ID NO: 83—Description of Artificial Sequence: Synthetic DNA
SEQ ID NO: 84—Description of Artificial Sequence: Synthetic DNA
SEQ ID NO: 85—Description of Artificial Sequence: Synthetic DNA
SEQ ID NO: 86—Description of Artificial Sequence: Synthetic DNA
SEQ ID NO: 87—Description of Artificial Sequence: Synthetic DNA
SEQ ID NO: 88—Description of Artificial Sequence: Synthetic DNA
SEQ ID NO: 89—Description of Artificial Sequence: Synthetic DNA
SEQ ID NO: 90—Description of Artificial Sequence: Synthetic DNA
SEQ ID NO: 91—Description of Artificial Sequence: Synthetic DNA
SEQ ID NO: 92—Description of Artificial Sequence: Synthetic DNA
SEQ ID NO: 93—Description of Artificial Sequence: Synthetic DNA
SEQ ID NO: 94—Description of Artificial Sequence: Synthetic DNA
SEQ ID NO: 95—Description of Artificial Sequence: Synthetic DNA
SEQ ID NO: 96—Description of Artificial Sequence: Synthetic DNA
SEQ ID NO: 97—Description of Artificial Sequence: Synthetic DNA
SEQ ID NO: 98—Description of Artificial Sequence: Synthetic DNA
SEQ ID NO: 99—Description of Artificial Sequence: Synthetic DNA
SEQ ID NO: 100—Description of Artificial Sequence: Synthetic DNA
SEQ ID NO: 101—Description of Artificial Sequence: Synthetic DNA
SEQ ID NO: 102—Description of Artificial Sequence: Synthetic DNA
SEQ ID NO: 103—Description of Artificial Sequence: Synthetic DNA
SEQ ID NO: 104—Description of Artificial Sequence: Synthetic DNA
SEQ ID NO: 105—Description of Artificial Sequence: Synthetic DNA
SEQ ID NO: 106—Description of Artificial Sequence: Synthetic DNA
SEQ ID NO: 107—Description of Artificial Sequence: Synthetic DNA
SEQ ID NO: 108—Description of Artificial Sequence: Synthetic DNA
SEQ ID NO: 109—Description of Artificial Sequence: Synthetic DNA
SEQ ID NO: 110—Description of Artificial Sequence: Synthetic DNA
SEQ ID NO: 111—Description of Artificial Sequence: Synthetic DNA
SEQ ID NO: 112—Description of Artificial Sequence: Synthetic DNA
SEQ ID NO: 113—Description of Artificial Sequence: Synthetic DNA
SEQ ID NO: 114—Description of Artificial Sequence: Synthetic DNA
SEQ ID NO: 115—Description of Artificial Sequence: Synthetic DNA
SEQ ID NO: 116—Description of Artificial Sequence: Synthetic DNA
SEQ ID NO: 117—Description of Artificial Sequence: Synthetic DNA
SEQ ID NO: 118—Description of Artificial Sequence: Synthetic DNA
SEQ ID NO: 119—Description of Artificial Sequence: Synthetic DNA
SEQ ID NO: 120—Description of Artificial Sequence: Synthetic DNA
SEQ ID NO: 121—Description of Artificial Sequence: Synthetic DNA
SEQ ID NO: 122—Description of Artificial Sequence: Synthetic DNA
SEQ ID NO: 123—Description of Artificial Sequence: Synthetic DNA
SEQ ID NO: 124—Description of Artificial Sequence: Synthetic DNA
SEQ ID NO: 125—Description of Artificial Sequence: Synthetic DNA
SEQ ID NO: 126—Description of Artificial Sequence: Synthetic DNA
SEQ ID NO: 127—Description of Artificial Sequence: Synthetic DNA
SEQ ID NO: 128—Description of Artificial Sequence: Synthetic DNA
SEQ ID NO: 129—Description of Artificial Sequence: Synthetic DNA
SEQ ID NO: 130—Description of Artificial Sequence: Synthetic DNA
SEQ ID NO: 131—Description of Artificial Sequence: Synthetic DNA
SEQ ID NO: 132—Description of Artificial Sequence: Synthetic DNA

What is claimed is:

1. A process for producing a dipeptide represented by formula (I):

$$R^1\text{-}R^2 \quad (I)$$

wherein $R^1$ is L-alanine, glycine, L-methionine, L-serine, L-threonine, β-alanine, L-cysteine or L-α-aminobutyric acid, and $R^2$ is L-alanine, L-glutamine, L-glutamic acid, glycine, L-valine, L-leucine, L-isoleucine, L-proline, L-phenylalanine, L-tryptophan, L-methionine, L-serine, L-threonine, L-cysteine, L-asparagine, L-tyrosine, L-lysine, L-arginine, L-histidine, L-aspartic acid, L-α-aminobutyric acid, β-alanine, L-azaserine, L-theanine, L-4-hydroxyproline, L-3-hydroxyproline, L-ornithine, L-citrulline or L-6-diazo-5-oxo-norleucine, provided that both $R^1$ and $R^2$ cannot be L-alanine at the same time, said method comprising:

culturing in a medium a microorganism which produces a protein comprising the amino acid sequence of SEQ ID NO:2, or a protein consisting of an amino acid sequence which has 95% or more homology to the amino acid sequence of SEQ ID NO:2 and having the activity of forming said dipeptide, and which has the ability to produce at least one of $R^1$ or $R^2$;

allowing the dipeptide to form and accumulate in the medium; and recovering the dipeptide from the medium.

2. The process according to claim 1, wherein the protein is encoded by DNA selected from the group consisting of the following [1] to [3]:

[1] DNA comprising the nucleotide sequence of SEQ ID NO ID NO:10;

[2] DNA encoding a protein comprising the amino acid sequence of SEQ ID NO:2 or a protein consisting of an amino acid sequence which has 95% or more homology to the amino acid sequence of SEQ ID NO:2 and having the activity of forming the dipeptide from $R^1$ and $R^2$; and

[3] DNA which hybridizes with DNA having a nucleotide sequence completely complementary to the nucleotide sequence shown in SEQ ID NO:10 at 65° C. in the presence of 0.7 to 1.0 mol/l sodium chloride followed by washing at 65° C. with a 0.1 to 2-fold concentrated SSC solution, and which encodes a protein having the activity to form the dipeptide from $R^1$ and $R^2$.

3. The process according to claim 1, wherein the microorganism is transformed with a recombinant DNA comprising the DNA selected from the group consisting of [1] to [3];

[1] DNA comprising the nucleotide sequence of SEQ ID NO:10;

[2] DNA encoding a protein comprising the amino acid sequence of SEQ ID NO:2 or a protein consisting of an amino acid sequence which has 95% or more homology to the amino acid sequence of SEQ ID NO:2 and having the activity of forming the dipeptide from $R^1$ and $R^2$; and

[3] DNA which hybridizes with DNA having a nucleotide sequence completely complementary to the nucleotide sequence shown in SEQ ID NO:10 at 65° C. in the presence of 0.7 to 1.0 mol/l sodium chloride followed by washing at 65° C. with a 0.1 to 2-fold concentrated SSC solution, and which encodes a protein having the activity to form the dipeptide from $R^1$ and $R^2$.

4. The process according to claim 3, wherein the microorganism belongs to the genus Escherichia, Corynebacterium, Bacillus, Serratia, Pseudomonas or Streptomyces.

5. The process according to claim 4, wherein the microorganism is Escherichia coli, Corynebacterium glutamicum, Corynebacterium ammoniagenes, Corynebacterium lactofermentum, Corynebacterium flavum, Corynebacterium efficiens, Bacillus subtilis, Bacillus megaterium, Serratia marcescens, Pseudomonas putida, Pseudomonas aeruginosa, Streptomyces coelicolor or Streptomyces lividans.

6. The process according to claim 1, wherein the microorganism belongs to the genus Bacillus.

7. The process according to claim 6, wherein the microorganism is Bacillus subtilis.

8. The process according to claim 1, wherein the protein consists of said amino acid sequence which has 95% or more homology to the amino acid sequence of SEQ ID NO:2 and having the activity of forming a dipeptide from $R^1$ and $R^2$.

9. The process according to claim 2, wherein the DNA comprises SEQ ID NO:10.

10. The process according to claim 3, wherein the DNA comprises SEQ ID NO:10.

11. The process according to claim 1, wherein the protein comprises SEQ ID NO:2.

* * * * *

UNITED STATES PATENT AND TRADEMARK OFFICE
CERTIFICATE OF CORRECTION

| | | |
|---|---|---|
| PATENT NO. | : 7,939,302 B2 | |
| APPLICATION NO. | : 12/400996 | |
| DATED | : May 10, 2011 | |
| INVENTOR(S) | : Shin-ichi Hashimoto et al. | |

It is certified that error appears in the above-identified patent and that said Letters Patent is hereby corrected as shown below:

COLUMN 2:

Line 10, "exist" should read --exists--.

COLUMN 6:

Line 61, "sequence—which" should read --sequence which--.

COLUMN 18:

Line 2, "Genbank)" should read --GenBank)--.

COLUMN 23:

Line 22, "can not" should read --cannot--.

COLUMN 24:

Line 54, "are" should read --is--; and
Line 56, "are" should read --is--.

COLUMN 28:

Line 5, "a" should read --an--.

COLUMN 39:

Line 34, "a" should read --an--; and
Line 37, "a" should read --an--.

Signed and Sealed this
Thirtieth Day of August, 2011

David J. Kappos
*Director of the United States Patent and Trademark Office*

CERTIFICATE OF CORRECTION (continued)
U.S. Pat. No. 7,939,302 B2

COLUMN 53:

Line 14, "pKml aroFm-18" should read --pKmlaroFm-18--.

COLUMN 62:

Line 10, "an" should read --a--.

COLUMN 68:

Line 48, "acids" should read --acid--.

COLUMN 72:

Line 29, "gene" should read --gene which--.

COLUMN 115:

SEQ 14, "
```
act gca aag tat gcg tta tcg gta
Thr Ala Lys Tyr Ala Leu Ser Val
```
" should read --
```
act gca aag tat gcg tta tcg gta
Thr Ala Lys Tyr Ala Leu Ser Val
465                 470
```
--.

COLUMN 117:

SEQ 15, "
```
act gca aag tat gcg tta ccg gta
Thr Ala Lys Tyr Ala Leu Pro Val
```
" should read --
```
act gca aag tat gcg tta ccg gta
Thr Ala Lys Tyr Ala Leu Pro Val
465                 470
```
--.

COLUMN 227:

Line 55, "NO ID" should be deleted.

SEQUENCE LISTING

```
<160> NUMBER OF SEQ ID NOS: 132

<210> SEQ ID NO 1
<211> LENGTH: 472
<212> TYPE: PRT
<213> ORGANISM: Bacillus subtilis
```

<400> SEQUENCE: 1

```
Met Glu Arg Lys Thr Val Leu Val Ile Ala Asp Leu Gly Gly Cys Pro
 1               5                  10                  15

Pro His Met Phe Tyr Lys Ser Ala Ala Glu Lys Tyr Asn Leu Val Ser
            20                  25                  30

Phe Ile Pro Arg Pro Phe Ala Ile Thr Ala Ser His Ala Ala Leu Ile
        35                  40                  45

Glu Lys Tyr Ser Val Ala Val Ile Lys Asp Lys Asp Tyr Phe Lys Ser
    50                  55                  60

Leu Ala Asp Phe Glu His Pro Asp Ser Ile Tyr Trp Ala His Glu Asp
65                  70                  75                  80

His Asn Lys Pro Glu Glu Val Val Glu Gln Ile Val Lys Val Ala
                85                  90                  95

Glu Met Phe Gly Ala Asp Ala Ile Thr Thr Asn Asn Glu Leu Phe Ile
                100                 105                 110

Ala Pro Met Ala Lys Ala Cys Glu Arg Leu Gly Leu Arg Gly Ala Gly
            115                 120                 125

Val Gln Ala Ala Glu Asn Ala Arg Asp Lys Asn Lys Met Arg Asp Ala
130                 135                 140

Phe Asn Lys Ala Gly Val Lys Ser Ile Lys Asn Lys Arg Val Thr Thr
145                 150                 155                 160

Leu Glu Asp Phe Arg Ala Ala Leu Glu Glu Ile Gly Thr Pro Leu Ile
                165                 170                 175

Leu Lys Pro Thr Tyr Leu Ala Ser Ser Ile Gly Val Thr Leu Ile Thr
            180                 185                 190

Asp Thr Glu Thr Ala Glu Asp Glu Phe Asn Arg Val Asn Asp Tyr Leu
        195                 200                 205

Lys Ser Ile Asn Val Pro Lys Ala Val Thr Phe Glu Ala Pro Phe Ile
    210                 215                 220

Ala Glu Glu Phe Leu Gln Gly Glu Tyr Gly Asp Trp Tyr Gln Thr Glu
225                 230                 235                 240

Gly Tyr Ser Asp Tyr Ile Ser Ile Glu Gly Ile Met Ala Asp Gly Glu
                245                 250                 255

Tyr Phe Pro Ile Ala Ile His Asp Lys Thr Pro Gln Ile Gly Phe Thr
            260                 265                 270

Glu Thr Ser His Ile Thr Pro Ser Ile Leu Asp Glu Glu Ala Lys Lys
        275                 280                 285

Lys Ile Val Glu Ala Ala Lys Lys Ala Asn Glu Gly Leu Gly Leu Gln
    290                 295                 300

Asn Cys Ala Thr His Thr Glu Ile Lys Leu Met Lys Asn Arg Glu Pro
305                 310                 315                 320

Gly Leu Ile Glu Ser Ala Ala Arg Phe Ala Gly Trp Asn Met Ile Pro
                325                 330                 335

Asn Ile Lys Lys Val Phe Gly Leu Asp Met Ala Gln Leu Leu Leu Asp
            340                 345                 350

Val Leu Cys Phe Gly Lys Asp Ala Asp Leu Pro Asp Gly Leu Leu Asp
        355                 360                 365

Gln Glu Pro Tyr Tyr Val Ala Asp Cys His Leu Tyr Pro Gln His Phe
    370                 375                 380

Lys Gln Asn Gly Gln Ile Pro Glu Thr Ala Glu Asp Leu Val Ile Glu
385                 390                 395                 400

Ala Ile Asp Ile Pro Asp Gly Leu Leu Lys Gly Asp Thr Glu Ile Val
                405                 410                 415
```

```
Ser Phe Ser Ala Ala Ala Pro Gly Thr Ser Val Asp Leu Thr Leu Phe
            420                 425                 430

Glu Ala Phe Asn Ser Ile Ala Ala Phe Glu Leu Lys Gly Ser Asn Ser
        435                 440                 445

Gln Asp Val Ala Glu Ser Ile Arg Gln Ile Gln Gln His Ala Lys Leu
    450                 455                 460

Thr Ala Lys Tyr Val Leu Pro Val
465                 470

<210> SEQ ID NO 2
<211> LENGTH: 472
<212> TYPE: PRT
<213> ORGANISM: Bacillus subtilis

<400> SEQUENCE: 2

Met Glu Arg Lys Thr Val Leu Val Ile Ala Asp Leu Gly Gly Cys Pro
 1               5                  10                  15

Pro His Met Phe Tyr Lys Ser Ala Ala Glu Lys Tyr Asn Leu Val Ser
            20                  25                  30

Phe Ile Pro Arg Pro Phe Ala Ile Thr Ala Ser His Ala Ala Leu Ile
        35                  40                  45

Glu Lys Tyr Ser Val Ala Val Ile Lys Asp Lys Asp Tyr Phe Gln Ser
    50                  55                  60

Leu Ala Asp Phe Glu His Pro Asp Ser Ile Tyr Trp Ala His Glu Asp
 65                 70                  75                  80

His Asp Lys Pro Glu Glu Glu Val Val Glu Gln Ile Val Lys Val Ala
                85                  90                  95

Gln Met Phe Glu Ala Asp Ala Ile Thr Thr Asn Asn Glu Leu Phe Ile
            100                 105                 110

Ala Pro Met Ala Lys Ala Cys Glu Arg Leu Gly Leu Arg Gly Ala Gly
        115                 120                 125

Val Gln Ala Ala Glu Asn Ala Arg Asp Lys Asn Lys Met Arg Asp Ala
    130                 135                 140

Phe Asn Lys Ala Gly Val Lys Ser Ile Lys Asn Lys Arg Val Thr Thr
145                 150                 155                 160

Leu Glu Asp Phe Arg Ala Ala Leu Glu Glu Ile Gly Thr Pro Leu Ile
                165                 170                 175

Leu Lys Pro Thr Tyr Leu Ala Ser Ser Ile Gly Val Thr Leu Ile Thr
            180                 185                 190

Asp Thr Glu Thr Ala Glu Asp Glu Phe Asn Arg Val Asn Asp Tyr Leu
        195                 200                 205

Lys Ser Ile Asn Val Pro Lys Ala Val Thr Phe Glu Ala Pro Phe Ile
    210                 215                 220

Ala Glu Glu Phe Leu Gln Gly Glu Tyr Gly Asp Trp Tyr Gln Thr Glu
225                 230                 235                 240

Gly Tyr Ser Asp Tyr Ile Ser Ile Glu Gly Ile Met Ala Asp Gly Glu
                245                 250                 255

Tyr Phe Pro Ile Ala Ile His Asp Lys Thr Pro Gln Ile Gly Phe Thr
            260                 265                 270

Glu Thr Ser His Ile Thr Pro Ser Ile Leu Asp Glu Glu Ala Lys Lys
        275                 280                 285

Lys Ile Val Glu Ala Ala Lys Lys Ala Asn Glu Gly Leu Gly Leu Gln
    290                 295                 300

Asn Cys Ala Thr His Thr Glu Ile Lys Leu Met Lys Asn Arg Glu Pro
305                 310                 315                 320
```

```
Gly Leu Ile Glu Ser Ala Ala Arg Phe Ala Gly Trp Asn Met Ile Pro
                325                 330                 335

Asn Ile Lys Lys Val Phe Gly Leu Asp Met Ala Gln Leu Leu Leu Asp
            340                 345                 350

Val Leu Cys Phe Gly Lys Asp Ala Asp Leu Pro Asp Gly Leu Leu Asp
        355                 360                 365

Gln Glu Pro Tyr Tyr Val Ala Asp Cys His Leu Tyr Pro Gln His Phe
    370                 375                 380

Lys Gln Asn Gly Gln Ile Pro Glu Thr Ala Glu Asp Leu Val Ile Glu
385                 390                 395                 400

Ala Ile Asp Ile Pro Asp Gly Leu Leu Lys Gly Asp Thr Glu Ile Val
                405                 410                 415

Thr Phe Ser Ala Ala Pro Gly Thr Ser Val Asp Leu Thr Leu Phe
            420                 425                 430

Glu Ala Phe Asn Ser Ile Ala Ala Phe Glu Leu Lys Gly Ser Asn Ser
        435                 440                 445

Gln Asp Val Ala Glu Ser Ile Arg Gln Ile Gln Gln His Ala Lys Leu
    450                 455                 460

Thr Ala Lys Tyr Val Leu Pro Val
465                 470

<210> SEQ ID NO 3
<211> LENGTH: 472
<212> TYPE: PRT
<213> ORGANISM: Bacillus subtilis

<400> SEQUENCE: 3

Met Glu Arg Lys Thr Val Leu Val Ile Ala Asp Leu Gly Gly Cys Pro
  1               5                  10                  15

Pro His Met Phe Tyr Lys Ser Ala Ala Glu Lys Tyr Asn Leu Val Ser
             20                  25                  30

Phe Ile Pro Arg Pro Phe Ala Ile Thr Ala Ser His Ala Ala Leu Ile
         35                  40                  45

Glu Lys Tyr Ser Val Ala Val Ile Lys Asp Lys Asp Tyr Phe Lys Ser
     50                  55                  60

Leu Ala Asp Phe Glu His Pro Asp Ser Ile Tyr Trp Ala His Glu Asp
 65                  70                  75                  80

His Asn Lys Pro Glu Glu Val Val Glu Gln Ile Val Lys Val Ala
                 85                  90                  95

Glu Met Phe Gly Ala Asp Ala Ile Thr Thr Asn Asn Glu Leu Phe Ile
            100                 105                 110

Ala Pro Met Ala Lys Ala Cys Glu Arg Leu Gly Leu Arg Gly Ala Gly
        115                 120                 125

Val Gln Ala Ala Glu Asn Ala Arg Asp Lys Asn Lys Met Arg Asp Ala
    130                 135                 140

Phe Asn Lys Ala Gly Val Lys Ser Ile Lys Asn Lys Arg Val Thr Thr
145                 150                 155                 160

Leu Glu Asp Phe Arg Ala Ala Leu Glu Glu Ile Gly Thr Pro Leu Ile
                165                 170                 175

Leu Lys Pro Thr Tyr Leu Ala Ser Ser Ile Gly Val Thr Leu Ile Thr
            180                 185                 190

Asp Thr Glu Thr Ala Glu Asp Glu Phe Asn Arg Val Asn Asp Tyr Leu
        195                 200                 205

Lys Ser Ile Asn Val Pro Lys Ala Val Thr Phe Glu Ala Pro Phe Ile
    210                 215                 220
```

```
Ala Glu Glu Phe Leu Gln Gly Glu Tyr Gly Asp Trp Tyr Gln Thr Glu
225                 230                 235                 240

Gly Tyr Ser Asp Tyr Ile Ser Ile Glu Gly Ile Met Ala Asp Gly Glu
            245                 250                 255

Tyr Phe Pro Ile Ala Ile His Asp Lys Thr Pro Gln Ile Gly Phe Thr
        260                 265                 270

Glu Thr Ser His Ile Thr Pro Ser Ile Leu Asp Glu Glu Ala Lys Lys
    275                 280                 285

Lys Ile Val Glu Ala Ala Lys Lys Ala Asn Glu Gly Leu Gly Leu Gln
290                 295                 300

Asn Cys Ala Thr His Thr Glu Ile Lys Leu Met Lys Asn Arg Glu Pro
305                 310                 315                 320

Gly Leu Ile Glu Ser Ala Ala Arg Phe Ala Gly Trp Asn Met Ile Pro
            325                 330                 335

Asn Ile Lys Lys Val Phe Gly Leu Asp Met Ala Gln Leu Leu Leu Asp
        340                 345                 350

Val Leu Cys Phe Gly Lys Asp Ala Asp Leu Pro Asp Gly Leu Leu Asp
    355                 360                 365

Gln Glu Pro Tyr Tyr Val Ala Asp Cys His Leu Tyr Pro Gln His Phe
370                 375                 380

Lys Gln Asn Gly Gln Ile Pro Glu Thr Ala Glu Asp Leu Val Ile Glu
385                 390                 395                 400

Ala Ile Asp Leu Pro Asp Gly Leu Leu Lys Gly Asp Thr Glu Ile Val
            405                 410                 415

Ser Phe Ser Ala Ala Pro Gly Thr Ser Val Asp Leu Thr Leu Phe
        420                 425                 430

Glu Ala Phe Asn Ser Ile Ala Ala Phe Glu Leu Lys Gly Ser Asn Ser
    435                 440                 445

Gln Asp Val Ala Glu Ser Ile Arg Gln Ile Gln Gln His Ala Lys Leu
450                 455                 460

Thr Ala Lys Tyr Val Leu Pro Val
465                 470

<210> SEQ ID NO 4
<211> LENGTH: 472
<212> TYPE: PRT
<213> ORGANISM: Bacillus subtilis

<400> SEQUENCE: 4

Met Glu Arg Lys Thr Val Leu Val Ile Ala Asp Leu Gly Gly Cys Pro
  1               5                  10                  15

Pro His Met Phe Tyr Lys Ser Ala Ala Glu Lys Tyr Asn Leu Val Ser
             20                  25                  30

Phe Ile Pro Arg Pro Phe Ala Ile Thr Ala Ser His Ala Ala Leu Ile
         35                  40                  45

Glu Lys Tyr Ser Val Ala Val Val Lys Asp Lys Asp Tyr Phe Lys Ser
     50                  55                  60

Leu Ala Asp Phe Glu His Pro Asp Ser Ile Tyr Trp Ala His Glu Asp
 65                  70                  75                  80

His Asn Lys Pro Glu Glu Glu Val Val Glu Gln Ile Val Lys Val Ala
                 85                  90                  95

Glu Met Phe Gly Ala Asp Ala Ile Thr Thr Asn Asn Glu Leu Phe Ile
            100                 105                 110

Ala Pro Met Ala Lys Ala Cys Glu Arg Leu Gly Leu Arg Gly Ala Gly
        115                 120                 125
```

```
Val Gln Ala Ala Glu Asn Ala Arg Asp Lys Asn Lys Met Arg Asp Ala
    130                 135                 140

Phe Asn Lys Ala Gly Val Lys Ser Ile Lys Asn Lys Arg Val Thr Thr
145                 150                 155                 160

Leu Glu Asp Phe Arg Ala Ala Leu Glu Glu Ile Gly Thr Pro Leu Ile
                165                 170                 175

Leu Lys Pro Thr Tyr Leu Ala Ser Ser Ile Gly Val Thr Leu Ile Thr
            180                 185                 190

Asp Thr Glu Thr Ala Glu Asp Glu Phe Asn Arg Val Asn Asp Tyr Leu
        195                 200                 205

Lys Ser Ile Asn Val Pro Lys Ala Val Thr Phe Glu Ala Pro Phe Ile
    210                 215                 220

Ala Glu Glu Phe Leu Gln Gly Leu Tyr Gly Asp Trp Tyr Gln Thr Glu
225                 230                 235                 240

Gly Tyr Ser Asp Tyr Ile Ser Ile Glu Gly Ile Met Ala Asp Gly Glu
                245                 250                 255

Tyr Phe Pro Ile Ala Ile His Asp Lys Thr Pro Gln Ile Gly Phe Thr
            260                 265                 270

Glu Thr Ser His Ile Thr Pro Ser Ile Leu Asp Glu Ala Lys Lys
        275                 280                 285

Lys Ile Val Glu Ala Ala Lys Lys Ala Asn Glu Gly Leu Gly Leu Gln
    290                 295                 300

Asn Cys Ala Thr His Thr Glu Val Lys Leu Met Lys Asn Arg Glu Pro
305                 310                 315                 320

Gly Leu Ile Glu Ser Ala Ala Arg Phe Ala Gly Trp Asn Met Ile Pro
                325                 330                 335

Asn Ile Lys Lys Val Phe Gly Leu Asp Met Ala Gln Leu Leu Leu Asp
            340                 345                 350

Val Leu Cys Phe Gly Lys Asp Ala Asp Leu Pro Asp Gly Leu Leu Asp
        355                 360                 365

Gln Glu Pro Tyr Tyr Val Ala Asp Cys His Leu Tyr Pro Gln His Phe
    370                 375                 380

Lys Gln Asn Gly Gln Ile Pro Glu Thr Ala Glu Asp Leu Val Ile Glu
385                 390                 395                 400

Ala Ile Asp Ile Pro Asp Gly Leu Leu Lys Gly Asp Thr Glu Ile Phe
                405                 410                 415

Ser Phe Ser Ala Ala Pro Gly Thr Ser Val Asp Leu Thr Leu Phe
            420                 425                 430

Glu Ala Phe Asn Ser Ile Ala Ala Phe Glu Leu Lys Gly Ser Asn Ser
        435                 440                 445

Gln Asp Val Ala Glu Ser Ile Arg Gln Ile Gln Gln His Ala Lys Leu
    450                 455                 460

Thr Ala Lys Tyr Val Leu Pro Val
465                 470

<210> SEQ ID NO 5
<211> LENGTH: 472
<212> TYPE: PRT
<213> ORGANISM: Bacillus subtilis

<400> SEQUENCE: 5

Met Glu Arg Lys Thr Val Leu Val Ile Ala Asp Leu Gly Gly Cys Pro
1               5                   10                  15

Pro His Met Phe Tyr Lys Ser Ala Ala Glu Lys Tyr Asn Leu Val Ser
            20                  25                  30
```

```
Phe Ile Pro Arg Pro Phe Ala Ile Thr Ala Ser His Ala Ala Leu Ile
            35                  40                  45

Glu Lys Tyr Ser Val Ala Val Ile Lys Asp Lys Asp Tyr Phe Gln Ser
        50                  55                  60

Leu Ala Asp Phe Glu His Pro Asp Ser Ile Tyr Trp Ala His Glu Asp
65                  70                  75                  80

His Asp Lys Pro Glu Glu Val Val Glu Gln Ile Val Lys Val Ala
                85                  90                  95

Gln Met Phe Glu Ala Asp Ala Ile Thr Thr Asn Asn Glu Leu Phe Ile
            100                 105                 110

Ala Pro Met Ala Lys Ala Cys Glu Arg Leu Gly Leu Arg Gly Ala Gly
            115                 120                 125

Val Gln Ala Ala Glu Asn Ala Arg Asp Lys Asn Lys Met Arg Asp Ala
        130                 135                 140

Phe Asn Lys Ala Gly Val Lys Ser Ile Lys Asn Lys Arg Val Thr Thr
145                 150                 155                 160

Leu Glu Asp Phe Arg Ala Ala Leu Glu Glu Ile Gly Thr Pro Leu Ile
                165                 170                 175

Leu Lys Pro Thr Tyr Leu Ala Ser Ser Ile Gly Val Thr Leu Ile Thr
            180                 185                 190

Asp Thr Glu Thr Ala Glu Asp Glu Phe Asn Arg Val Asn Asp Tyr Leu
        195                 200                 205

Lys Ser Ile Asn Val Pro Lys Ala Val Thr Phe Glu Ala Pro Phe Ile
    210                 215                 220

Ala Glu Glu Phe Leu Gln Gly Glu Tyr Gly Asp Trp Tyr Gln Thr Glu
225                 230                 235                 240

Gly Tyr Ser Asp Tyr Ile Ser Ile Glu Gly Ile Met Ala Asp Gly Glu
                245                 250                 255

Tyr Phe Pro Ile Ala Ile His Asp Lys Thr Pro Gln Ile Gly Phe Thr
            260                 265                 270

Glu Thr Ser His Ile Thr Pro Ser Ile Leu Asp Glu Glu Ala Lys Lys
        275                 280                 285

Lys Ile Val Glu Ala Ala Lys Lys Ala Asn Glu Gly Leu Gly Leu Gln
    290                 295                 300

Asn Cys Ala Thr His Thr Glu Ile Lys Leu Met Lys Asn Arg Glu Pro
305                 310                 315                 320

Gly Leu Ile Glu Ser Ala Ala Arg Phe Ala Gly Trp Asn Met Ile Pro
                325                 330                 335

Asn Ile Lys Lys Val Phe Gly Leu Asp Met Ala Gln Leu Leu Leu Asp
            340                 345                 350

Val Leu Cys Phe Gly Lys Asp Ala Asp Leu Pro Asp Gly Leu Leu Asp
        355                 360                 365

Gln Glu Pro Tyr Tyr Val Ala Asp Cys His Leu Tyr Pro Gln His Phe
    370                 375                 380

Lys Gln Asn Gly Gln Ile Pro Glu Thr Ala Glu Asp Leu Val Ile Glu
385                 390                 395                 400

Ala Ile Asp Ile Pro Asp Gly Leu Leu Lys Gly Asp Thr Glu Ile Val
                405                 410                 415

Thr Phe Ser Ala Ala Pro Gly Thr Ser Val Asp Leu Thr Leu Phe
            420                 425                 430

Glu Ala Phe Asn Ser Ile Ala Ala Phe Glu Leu Lys Gly Ser Asn Ser
        435                 440                 445

Gln Asp Val Ala Glu Ser Ile Arg Gln Ile Gln Gln His Ala Lys Leu
```

Thr Ala Lys Tyr Val Leu Pro Val
465                 470

<210> SEQ ID NO 6
<211> LENGTH: 472
<212> TYPE: PRT
<213> ORGANISM: Bacillus subtilis

<400> SEQUENCE: 6

Met Glu Arg Lys Thr Val Leu Val Ile Ala Asp Leu Gly Gly Cys Pro
1               5                   10                  15

Pro His Met Phe Tyr Lys Ser Ala Ala Glu Lys Tyr Asn Leu Val Ser
                20                  25                  30

Phe Ile Pro Arg Pro Phe Ala Ile Thr Ala Ser His Ala Ala Leu Ile
            35                  40                  45

Glu Lys Tyr Ser Ile Ala Val Ile Lys Asp Lys Asp Tyr Phe Lys Ser
        50                  55                  60

Leu Ala Asp Phe Glu His Pro Asp Ser Ile Tyr Trp Ala His Glu Asp
65                  70                  75                  80

His Asp Lys Pro Glu Glu Val Val Glu Ile Val Lys Val Ala
                    85                  90                  95

Asp Met Phe Gly Val Asp Ala Ile Thr Thr Asn Asn Glu Leu Phe Ile
                100                 105                 110

Ala Pro Met Ala Lys Ala Cys Lys Arg Leu Gly Leu Arg Gly Ala Gly
            115                 120                 125

Val Gln Ala Ala Glu Asn Ala Arg Asp Lys Asn Lys Met Arg Ala Ala
        130                 135                 140

Phe Asn Arg Ala Gly Val Lys Ser Ile Lys Asn Lys Arg Val Thr Thr
145                 150                 155                 160

Leu Glu Asp Phe Arg Ala Ala Leu Gln Glu Ile Gly Thr Pro Leu Ile
                165                 170                 175

Leu Lys Pro Thr Tyr Leu Ala Ser Ser Ile Gly Val Thr Leu Ile Lys
            180                 185                 190

Glu Met Glu Thr Ala Glu Ala Glu Phe Asn Arg Val Asn Glu Tyr Leu
        195                 200                 205

Lys Ser Ile Asn Val Pro Lys Ala Val Thr Phe Glu Ala Pro Phe Ile
    210                 215                 220

Ala Glu Glu Phe Leu Gln Gly Glu Tyr Asp Asp Trp Tyr Glu Thr Ser
225                 230                 235                 240

Gly Tyr Ser Asp Tyr Ile Ser Ile Glu Gly Ile Met Ala Asp Gly Glu
                245                 250                 255

Tyr Phe Pro Val Ala Ile His Asp Lys Thr Pro Gln Ile Gly Phe Thr
            260                 265                 270

Glu Thr Ala His Ile Thr Pro Ser Ile Leu Asp Asp Ala Lys Arg
        275                 280                 285

Lys Ile Val Glu Ala Ala Lys Lys Ala Asn Glu Gly Leu Gly Leu Glu
    290                 295                 300

Asn Cys Ala Thr His Thr Glu Ile Lys Leu Met Lys Asn Arg Glu Ala
305                 310                 315                 320

Gly Leu Ile Glu Ser Ala Arg Phe Ala Gly Trp Asn Met Ile Pro
                325                 330                 335

Asn Ile Lys Lys Val Phe Gly Val Asp Met Ala Gln Leu Leu Leu Asp
            340                 345                 350

Val Leu Cys Tyr Gly Lys Glu Ala Asp Leu Pro Lys Gly Leu Leu Glu

```
                       355                 360                 365
Gln Glu Pro Cys Tyr Val Ala Asp Cys His Leu Tyr Pro Gln His Phe
        370                 375                 380
Lys Glu Asn Gly Gln Leu Pro Glu Thr Val Val Asp Phe Val Ile Glu
385                 390                 395                 400
Ser Ile Glu Ile Pro Asp Gly Val Leu Lys Gly Asp Thr Glu Leu Val
                405                 410                 415
Ser Phe Ser Ala Ala Glu Ala Gly Thr Ser Val Asp Leu Arg Leu Phe
            420                 425                 430
Glu Ala Phe Asn Ser Ile Ala Ala Phe Glu Leu Lys Gly Ser Asn Ser
        435                 440                 445
Asn Asp Val Ala Glu Ser Ile Lys Gln Ile Gln Gln Ala Lys Leu
    450                 455                 460
Thr Ala Lys Tyr Ala Leu Ser Val
465                 470

<210> SEQ ID NO 7
<211> LENGTH: 472
<212> TYPE: PRT
<213> ORGANISM: Bacillus amyloliquefaciens

<400> SEQUENCE: 7

Met Glu Arg Lys Thr Val Leu Val Ile Ala Asp Leu Gly Gly Cys Pro
1               5                   10                  15
Pro His Met Phe Tyr Lys Ser Ala Ala Glu Lys Tyr Asn Leu Val Ser
                20                  25                  30
Phe Ile Pro Arg Pro Phe Ala Ile Thr Ala Ser His Ala Ala Leu Ile
            35                  40                  45
Glu Lys Tyr Ser Val Ala Val Ile Lys Asp Lys Asp Tyr Phe Lys Ser
        50                  55                  60
Leu Ala Asp Phe Glu His Pro Asp Ser Ile Tyr Trp Ala His Glu Asp
65                  70                  75                  80
His Asp Lys Pro Glu Glu Val Val Glu Ile Val Lys Val Ala
                85                  90                  95
Gly Met Phe Ala Val Asp Ala Ile Thr Thr Asn Asn Glu Leu Phe Ile
                100                 105                 110
Ala Pro Met Ala Lys Ala Cys Glu Arg Leu Gly Leu Arg Gly Ala Gly
            115                 120                 125
Val Gln Ala Ala Glu Asn Ala Arg Asp Lys Asn Lys Met Arg Ala Ala
130                 135                 140
Phe Asn Arg Ala Gly Val Lys Ser Ile Lys Asn Arg Arg Val Thr Thr
145                 150                 155                 160
Leu Glu Asp Phe Arg Ala Ala Leu Gln Glu Ile Gly Thr Pro Leu Ile
                165                 170                 175
Leu Lys Pro Thr Tyr Leu Ala Ser Ser Ile Gly Val Thr Leu Ile Lys
                180                 185                 190
Glu Arg Glu Thr Ala Gly Ala Glu Phe Asn Arg Val Asn Gly Tyr Leu
            195                 200                 205
Lys Ser Ile Asn Val Pro Lys Ala Val Thr Phe Glu Ala Pro Phe Ile
        210                 215                 220
Ala Glu Glu Phe Leu Gln Gly Gly Tyr Asp Asp Trp Tyr Glu Thr Ser
225                 230                 235                 240
Gly Tyr Ser Asp Tyr Ile Ser Ile Glu Gly Ile Met Ala Asp Gly Glu
                245                 250                 255
Tyr Phe Pro Val Ala Ile His Asp Lys Thr Pro Gln Ile Gly Phe Thr
```

```
                        260                 265                 270
Glu Thr Ser His Ile Thr Pro Ser Ile Leu Asp Asp Ala Lys Arg
                275                 280                 285
Lys Ile Val Glu Ala Ala Lys Lys Ala Asn Glu Gly Leu Gly Leu Glu
290                 295                 300
Asn Cys Ala Thr His Thr Glu Ile Lys Leu Met Lys Asn Arg Glu Ala
305                 310                 315                 320
Gly Leu Ile Glu Ser Ala Ala Arg Phe Ala Gly Trp Asn Met Ile Pro
                325                 330                 335
Asn Ile Lys Lys Val Phe Gly Val Asp Met Ala Gln Leu Leu Leu Asp
                340                 345                 350
Val Leu Cys Phe Gly Lys Glu Ala Asp Leu Pro Lys Gly Leu Leu Glu
                355                 360                 365
Gln Glu Pro Cys Tyr Val Ala Asp Cys His Leu Tyr Pro Gln His Phe
                370                 375                 380
Lys Glu Asn Gly Gln Leu Pro Glu Thr Ala Val Asp Phe Val Ile Glu
385                 390                 395                 400
Ser Ile Asp Ile Pro Asp Gly Val Leu Lys Gly Asp Thr Glu Ile Val
                405                 410                 415
Ser Phe Ser Ala Ala Glu Ala Gly Thr Ser Val Asp Leu Arg Leu Phe
                420                 425                 430
Glu Ala Phe Asn Ser Ile Ala Ala Phe Glu Leu Lys Gly Ser Asn Ser
                435                 440                 445
Gly Asp Val Ala Glu Ser Ile Lys Gln Ile Gln Gln Ala Lys Leu
                450                 455                 460
Thr Ala Lys Tyr Ala Leu Pro Val
465                 470

<210> SEQ ID NO 8
<211> LENGTH: 476
<212> TYPE: PRT
<213> ORGANISM: Bacillus pumilus

<400> SEQUENCE: 8

Val Leu Ser Leu Ser Lys Lys Thr Val Leu Val Ile Ala Asp Leu Gly
  1               5                  10                  15
Gly Cys Pro Pro His Met Phe Tyr Glu Ser Val Ala Ala Ser Tyr His
                 20                  25                  30
Ile Val Ser Tyr Ile Pro Arg Pro Phe Ala Ile Thr Lys Gly His Ala
                 35                  40                  45
Glu Leu Ile Glu Lys Tyr Ser Ile Ala Val Ile Lys Asp Arg Asp Tyr
             50                  55                  60
Phe Glu Thr His Pro Ser Phe Glu His Pro Asp Ser Ile Tyr Trp Ala
 65                  70                  75                  80
His Asp Asp Tyr Pro Lys Ser Glu Glu Glu Val Val Glu Asp Phe Ile
                 85                  90                  95
Arg Val Ala Ser Phe Phe Lys Ala Asp Ala Ile Thr Thr Asn Asn Glu
                100                 105                 110
Leu Phe Ile Ala Pro Met Ala Lys Ala Ala Glu Arg Leu Gly Leu Arg
                115                 120                 125
Gly Ala Gly Val Lys Ala Ala Glu Met Ala Arg Asp Lys Ser Gln Met
                130                 135                 140
Arg Ala Ala Phe Asn Ala Ser Gly Val Lys Ala Val Lys Thr Gln Pro
145                 150                 155                 160
Val Thr Thr Leu Ser Asp Phe Gln Gln Ala Ile Glu Ser Ile Gly Thr
```

```
                    165                 170                 175
Pro Leu Ile Leu Lys Pro Thr Tyr Leu Ala Ser Ser Ile Gly Val Thr
                180                 185                 190

Leu Phe His Asp Lys Ala Gly Ser Asp Leu Phe Leu Gln Val Gln
            195                 200                 205

Ser Tyr Leu Glu Thr Ile Pro Val Pro Asp Ala Val Thr Tyr Glu Ala
        210                 215                 220

Pro Phe Val Ala Glu Thr Tyr Leu Glu Gly Ala Tyr Glu Asp Trp Tyr
225                 230                 235                 240

Glu Asp Glu Gly Tyr Ala Asp Tyr Val Ser Val Glu Gly Leu Val Val
                245                 250                 255

Glu Gly Glu Tyr Leu Pro Phe Val Ile His Asp Lys Thr Pro Gln Ile
                260                 265                 270

Gly Phe Thr Glu Thr Ala His Ile Thr Pro Thr Ile Leu Asp Asn Glu
            275                 280                 285

Ala Lys Gln Ile Ile Glu Ala Ala Arg Lys Ala Asn Glu Gly Leu
        290                 295                 300

Gly Leu Glu His Cys Ala Thr His Thr Glu Ile Lys Leu Met Lys Asn
305                 310                 315                 320

Arg Glu Thr Gly Leu Ile Glu Ala Ala Arg Phe Ala Gly Trp Asn
                325                 330                 335

Met Ile Pro Asn Ile Lys Lys Val Phe Gly Val Asp Met Ala Lys Leu
                340                 345                 350

Leu Ile Asp Val Leu Val Asp Gly Lys Lys Ala Val Leu Pro Lys Gln
            355                 360                 365

Leu Leu Ser Gly His Thr Phe Tyr Val Ala Asp Cys His Leu Tyr Pro
        370                 375                 380

Gln His Phe Lys Glu Ser Gly Leu Ile Pro Pro Glu Ala Thr His Ile
385                 390                 395                 400

Thr Ile Asp His Val Ser Ile Pro Gln Glu Ala Phe Val Gly Asp Thr
                405                 410                 415

Ala Ile Val Ser Gln Ser Phe Pro Ala Lys Gly Thr Ile Val Asp Leu
            420                 425                 430

Glu Leu Phe Glu Ala Phe Asn Gly Ile Val Ser Leu Glu Leu Lys Gly
        435                 440                 445

Ser Ser Ser Gln Asp Val Ala Ala Ser Ile Arg Asn Ile Gln Lys Gln
        450                 455                 460

Ala Thr Ile Gln Leu Met Asp Glu Leu Val Lys Gly
465                 470                 475

<210> SEQ ID NO 9
<211> LENGTH: 1416
<212> TYPE: DNA
<213> ORGANISM: Bacillus subtilis

<400> SEQUENCE: 9 atg gag aga aaa aca gta ttg gtc atc gct gat ctt gga ggc tgc ccg    48
Met Glu Arg Lys Thr Val Leu Val Ile Ala Asp Leu Gly Gly Cys Pro
  1               5                  10                  15 ccg cac atg ttt tat aaa agc gct gct gaa aaa tat aac ctg gtc agc    96
Pro His Met Phe Tyr Lys Ser Ala Ala Glu Lys Tyr Asn Leu Val Ser
                 20                  25                  30 ttt att cca aga cct ttt gca att aca gcc tcc cat gca gca ttg att   144
Phe Ile Pro Arg Pro Phe Ala Ile Thr Ala Ser His Ala Ala Leu Ile
             35                  40                  45 gaa aaa tac tcg gtc gcg gtc ata aaa gat aaa gac tat ttt aag agt   192
```

```
       Glu Lys Tyr Ser Val Ala Val Ile Lys Asp Lys Asp Tyr Phe Lys Ser
            50                  55                  60 tta gct gat ttt gaa cac cct gat tcc att tat tgg gcg cat gaa gat      240
Leu Ala Asp Phe Glu His Pro Asp Ser Ile Tyr Trp Ala His Glu Asp
 65                  70                  75                  80 cat aac aag cct gag gaa gag gtc gtc gag caa atc gtc aag gtt gcc      288
His Asn Lys Pro Glu Glu Glu Val Val Glu Gln Ile Val Lys Val Ala
                 85                  90                  95 gaa atg ttt ggg gcg gat gcc atc aca aca aac aat gaa tta ttc att      336
Glu Met Phe Gly Ala Asp Ala Ile Thr Thr Asn Asn Glu Leu Phe Ile
                100                 105                 110 gct ccg atg gcg aaa gcc tgt gaa cgt ctg ggc ttg aga ggt gcc ggc      384
Ala Pro Met Ala Lys Ala Cys Glu Arg Leu Gly Leu Arg Gly Ala Gly
            115                 120                 125 gtg cag gca gcc gaa aat gcc aga gat aaa aat aaa atg agg gac gct      432
Val Gln Ala Ala Glu Asn Ala Arg Asp Lys Asn Lys Met Arg Asp Ala
        130                 135                 140 ttt aat aag gcc gga gtc aaa tcg atc aaa aac aaa cga gtc aca act      480
Phe Asn Lys Ala Gly Val Lys Ser Ile Lys Asn Lys Arg Val Thr Thr
145                 150                 155                 160 ctt gaa gat ttc cgt gct gct ctt gaa gag atc ggc aca cct ctt atc      528
Leu Glu Asp Phe Arg Ala Ala Leu Glu Glu Ile Gly Thr Pro Leu Ile
                165                 170                 175 tta aag cct aca tac tta gcg agt tct atc ggt gta acg ctg att acg      576
Leu Lys Pro Thr Tyr Leu Ala Ser Ser Ile Gly Val Thr Leu Ile Thr
                180                 185                 190 gac act gag acg gca gaa gat gaa ttt aac aga gtc aat gac tat ctg      624
Asp Thr Glu Thr Ala Glu Asp Glu Phe Asn Arg Val Asn Asp Tyr Leu
            195                 200                 205 aaa tca att aac gtg cca aag gcg gtt acg ttt gaa gcg ccg ttt atc      672
Lys Ser Ile Asn Val Pro Lys Ala Val Thr Phe Glu Ala Pro Phe Ile
        210                 215                 220 gct gaa gaa ttt tta cag ggt gag tac gga gac tgg tat caa aca gaa      720
Ala Glu Glu Phe Leu Gln Gly Glu Tyr Gly Asp Trp Tyr Gln Thr Glu
225                 230                 235                 240 ggg tac tcc gac tat atc agt ata gaa ggc atc atg gct gac ggt gag      768
Gly Tyr Ser Asp Tyr Ile Ser Ile Glu Gly Ile Met Ala Asp Gly Glu
                245                 250                 255 tat ttc ccg atc gcc att cat gat aaa acg ccg caa atc ggg ttt aca      816
Tyr Phe Pro Ile Ala Ile His Asp Lys Thr Pro Gln Ile Gly Phe Thr
                260                 265                 270 gag aca tcc cac att acg ccg tcc att ctg gat gaa gag gca aaa aag      864
Glu Thr Ser His Ile Thr Pro Ser Ile Leu Asp Glu Glu Ala Lys Lys
            275                 280                 285 aaa att gtc gaa gct gcc aaa aag gca aat gaa ggg ctt gga ctg caa      912
Lys Ile Val Glu Ala Ala Lys Lys Ala Asn Glu Gly Leu Gly Leu Gln
        290                 295                 300 aat tgc gca aca cat aca gag atc aag cta atg aaa aac aga gaa ccg      960
Asn Cys Ala Thr His Thr Glu Ile Lys Leu Met Lys Asn Arg Glu Pro
305                 310                 315                 320 ggt tta ata gag tcg gca gcc aga ttt gcc ggc tgg aat atg atc ccc     1008
Gly Leu Ile Glu Ser Ala Ala Arg Phe Ala Gly Trp Asn Met Ile Pro
                325                 330                 335 aat att aaa aag gtc ttt ggc ctt gat atg gcg caa tta tta tta gat     1056
Asn Ile Lys Lys Val Phe Gly Leu Asp Met Ala Gln Leu Leu Leu Asp
                340                 345                 350 gtc ctc tgt ttc gga aaa gac gcc gat ctg ccg gac gga tta ttg gat     1104
Val Leu Cys Phe Gly Lys Asp Ala Asp Leu Pro Asp Gly Leu Leu Asp
            355                 360                 365 caa gag cct tat tat gtt gcc gac tgc cat ttg tac ccg cag cat ttc     1152
```

```
Gln Glu Pro Tyr Tyr Val Ala Asp Cys His Leu Tyr Pro Gln His Phe
        370                 375                 380 aaa caa aat ggc caa att cct gaa act gct gag gat ttg gtc att gaa      1200
Lys Gln Asn Gly Gln Ile Pro Glu Thr Ala Glu Asp Leu Val Ile Glu
385                 390                 395                 400 gcg atc gat att ccg gac ggg ctt tta aaa ggg gat act gaa atc gtt      1248
Ala Ile Asp Ile Pro Asp Gly Leu Leu Lys Gly Asp Thr Glu Ile Val
                405                 410                 415 tct ttt tcg gcc gca gca cca ggc act tca gtt gat ttg aca ttg ttt      1296
Ser Phe Ser Ala Ala Pro Gly Thr Ser Val Asp Leu Thr Leu Phe
                420                 425                 430 gaa gct ttc aat tcc att gct gca ttt gaa ctg aaa ggc agt aat tca      1344
Glu Ala Phe Asn Ser Ile Ala Ala Phe Glu Leu Lys Gly Ser Asn Ser
                435                 440                 445 cag gat gtg gct gaa tca atc aga caa att cag cag cat gcg aag ctg      1392
Gln Asp Val Ala Glu Ser Ile Arg Gln Ile Gln Gln His Ala Lys Leu
450                 455                 460 acg gca aag tat gtg ctg cca gta                                      1416
Thr Ala Lys Tyr Val Leu Pro Val
465                 470

<210> SEQ ID NO 10
<211> LENGTH: 1416
<212> TYPE: DNA
<213> ORGANISM: Bacillus subtilis

<400> SEQUENCE: 10 atg gag aga aaa aca gta ttg gtc atc gct gat ctt gga ggc tgc ccg      48
Met Glu Arg Lys Thr Val Leu Val Ile Ala Asp Leu Gly Gly Cys Pro
1               5                   10                  15 ccg cac atg ttt tat aaa agc gct gct gaa aaa tat aac ctg gtt agc      96
Pro His Met Phe Tyr Lys Ser Ala Ala Glu Lys Tyr Asn Leu Val Ser
                20                  25                  30 ttt att ccg aga cct ttt gca ata aca gcc tcc cat gca gca ctg att      144
Phe Ile Pro Arg Pro Phe Ala Ile Thr Ala Ser His Ala Ala Leu Ile
            35                  40                  45 gaa aaa tac tcg gtc gcg gta ata aaa gat aaa gac tat ttt cag agc      192
Glu Lys Tyr Ser Val Ala Val Ile Lys Asp Lys Asp Tyr Phe Gln Ser
        50                  55                  60 tta gct gat ttt gag cat ccc gat tca att tat tgg gcg cat gag gat      240
Leu Ala Asp Phe Glu His Pro Asp Ser Ile Tyr Trp Ala His Glu Asp
65                  70                  75                  80 cat gac aag cct gaa gaa gag gtt gtc gag caa atc gtc aag gtt gcc      288
His Asp Lys Pro Glu Glu Glu Val Val Glu Gln Ile Val Lys Val Ala
                85                  90                  95 caa atg ttt gag gcg gac gcc atc aca aca aac aat gaa tta ttc att      336
Gln Met Phe Glu Ala Asp Ala Ile Thr Thr Asn Asn Glu Leu Phe Ile
                100                 105                 110 gcc ccg atg gcg aaa gcc tgt gaa cgc ctt ggc ctg agg ggc gcc gga      384
Ala Pro Met Ala Lys Ala Cys Glu Arg Leu Gly Leu Arg Gly Ala Gly
            115                 120                 125 gtg cag gca gcg gaa aat gcc aga gat aaa aat aaa atg agg gac gct      432
Val Gln Ala Ala Glu Asn Ala Arg Asp Lys Asn Lys Met Arg Asp Ala
        130                 135                 140 ttt aat aag gcg gga gtc aaa tcg atc aaa aac aaa cga gtc aca act      480
Phe Asn Lys Ala Gly Val Lys Ser Ile Lys Asn Lys Arg Val Thr Thr
145                 150                 155                 160 ctt gag gat ttt cgt gct gca ctt gaa gag atc ggc aca cct cta atc      528
Leu Glu Asp Phe Arg Ala Ala Leu Glu Glu Ile Gly Thr Pro Leu Ile
                165                 170                 175 tta aag cct aca tac tta gcg agt tca atc ggc gta acg ctg att acc      576
```

```
                    Leu Lys Pro Thr Tyr Leu Ala Ser Ser Ile Gly Val Thr Leu Ile Thr
                                    180                 185                 190 gac acg gag acg gca gaa gat gaa ttt aac aga gtc aat gac tac ctg        624
Asp Thr Glu Thr Ala Glu Asp Glu Phe Asn Arg Val Asn Asp Tyr Leu
            195                 200                 205 aaa tcg att aac gtg ccg aag gcg gtc aca ttt gaa gca ccg ttt att        672
Lys Ser Ile Asn Val Pro Lys Ala Val Thr Phe Glu Ala Pro Phe Ile
        210                 215                 220 gct gag gaa ttt tta cag ggt gag tac gga gac tgg tat caa aca gaa        720
Ala Glu Glu Phe Leu Gln Gly Glu Tyr Gly Asp Trp Tyr Gln Thr Glu
225                 230                 235                 240 ggg tac tcc gac tat atc agc ata gaa ggc att atg gca gat ggt gag        768
Gly Tyr Ser Asp Tyr Ile Ser Ile Glu Gly Ile Met Ala Asp Gly Glu
                245                 250                 255 tat ttt ccg atc gcc att cat gac aaa acg ccg caa att gga ttt aca        816
Tyr Phe Pro Ile Ala Ile His Asp Lys Thr Pro Gln Ile Gly Phe Thr
            260                 265                 270 gag aca tca cat att acg cca tcc att ctg gat gaa gag gcg aaa aag        864
Glu Thr Ser His Ile Thr Pro Ser Ile Leu Asp Glu Glu Ala Lys Lys
        275                 280                 285 aaa att gtc gaa gcg gct aaa aag gca aat gaa ggg ctt gga ctg caa        912
Lys Ile Val Glu Ala Ala Lys Lys Ala Asn Glu Gly Leu Gly Leu Gln
290                 295                 300 aat tgc gca aca cat aca gaa atc aag cta atg aaa aac aga gaa ccg        960
Asn Cys Ala Thr His Thr Glu Ile Lys Leu Met Lys Asn Arg Glu Pro
305                 310                 315                 320 ggt tta ata gag tcg gct gcc aga ttc gca ggc tgg aat atg att cct       1008
Gly Leu Ile Glu Ser Ala Ala Arg Phe Ala Gly Trp Asn Met Ile Pro
                325                 330                 335 aac att aaa aag gtt ttc ggc ctt gat atg gcg caa tta tta tta gat       1056
Asn Ile Lys Lys Val Phe Gly Leu Asp Met Ala Gln Leu Leu Leu Asp
            340                 345                 350 gtt ctc tgt ttc gga aaa gat gct gat ctg ccg gac ggg tta ttg gat       1104
Val Leu Cys Phe Gly Lys Asp Ala Asp Leu Pro Asp Gly Leu Leu Asp
        355                 360                 365 caa gag cct tac tat gtt gct gac tgc cat ctg tac cct cag cat ttc       1152
Gln Glu Pro Tyr Tyr Val Ala Asp Cys His Leu Tyr Pro Gln His Phe
370                 375                 380 aaa caa aat ggc cag atc cct gaa act gcc gag gat ttg gta atc gaa       1200
Lys Gln Asn Gly Gln Ile Pro Glu Thr Ala Glu Asp Leu Val Ile Glu
385                 390                 395                 400 gcg atc gat att ccg gat ggg ctt ttg aag ggt gat aca gaa atc gtt       1248
Ala Ile Asp Ile Pro Asp Gly Leu Leu Lys Gly Asp Thr Glu Ile Val
                405                 410                 415 act ttt tcg gct gcg gca cca gga aca tca gtt gat ttg aca ctg ttt       1296
Thr Phe Ser Ala Ala Ala Pro Gly Thr Ser Val Asp Leu Thr Leu Phe
            420                 425                 430 gaa gcc ttc aac tcc att gct gca ttt gaa ctg aaa ggc agc aat tca       1344
Glu Ala Phe Asn Ser Ile Ala Ala Phe Glu Leu Lys Gly Ser Asn Ser
        435                 440                 445 cag gat gtg gct gaa tca atc aga caa att cag cag cat gcg aag ctg       1392
Gln Asp Val Ala Glu Ser Ile Arg Gln Ile Gln Gln His Ala Lys Leu
450                 455                 460 acg gca aag tat gtg ctg cca gta                                        1416
Thr Ala Lys Tyr Val Leu Pro Val
465                 470

<210> SEQ ID NO 11
<211> LENGTH: 1416
<212> TYPE: DNA
<213> ORGANISM: Bacillus subtilis
```

-continued

```
<400> SEQUENCE: 11 atg gag aga aaa aca gta ttg gtc atc gct gat ctt gga ggc tgc ccg      48
Met Glu Arg Lys Thr Val Leu Val Ile Ala Asp Leu Gly Gly Cys Pro
1               5                   10                  15 ccg cac atg ttt tat aaa agc gct gct gaa aaa tat aac ctg gtc agc      96
Pro His Met Phe Tyr Lys Ser Ala Ala Glu Lys Tyr Asn Leu Val Ser
                20                  25                  30 ttt att cca aga cct ttt gca att aca gcc tcc cat gca gca ttg att     144
Phe Ile Pro Arg Pro Phe Ala Ile Thr Ala Ser His Ala Ala Leu Ile
            35                  40                  45 gaa aaa tac tcg gtc gcg gtc ata aaa gat aaa gac tat ttt aag agt     192
Glu Lys Tyr Ser Val Ala Val Ile Lys Asp Lys Asp Tyr Phe Lys Ser
    50                  55                  60 tta gct gat ttt gag cat cct gac tcc att tat tgg gcg cat gag gat     240
Leu Ala Asp Phe Glu His Pro Asp Ser Ile Tyr Trp Ala His Glu Asp
65                  70                  75                  80 cat aac aag cct gag gaa gag gtc gtc gag caa atc gtc aag gtt gcc     288
His Asn Lys Pro Glu Glu Glu Val Val Glu Gln Ile Val Lys Val Ala
                85                  90                  95 gaa atg ttt ggg gcg gat gcc atc aca aca aac aat gaa tta ttc att     336
Glu Met Phe Gly Ala Asp Ala Ile Thr Thr Asn Asn Glu Leu Phe Ile
                100                 105                 110 gct ccg atg gcg aaa gcc tgt gaa cgt ctg ggc ctg aga ggt gcc ggc     384
Ala Pro Met Ala Lys Ala Cys Glu Arg Leu Gly Leu Arg Gly Ala Gly
            115                 120                 125 gtg cag gca gcc gaa aat gcc aga gat aaa aat aaa atg agg gac gct     432
Val Gln Ala Ala Glu Asn Ala Arg Asp Lys Asn Lys Met Arg Asp Ala
130                 135                 140 ttt aat aag gcc gga gtc aaa tcg atc aaa aac aaa cga gtc aca act     480
Phe Asn Lys Ala Gly Val Lys Ser Ile Lys Asn Lys Arg Val Thr Thr
145                 150                 155                 160 ctc gaa gat ttc cgt gct gct ctt gaa gag atc ggc aca cct ctt atc     528
Leu Glu Asp Phe Arg Ala Ala Leu Glu Glu Ile Gly Thr Pro Leu Ile
                165                 170                 175 tta aag cct aca tac tta gcg agt tca atc ggt gta acg ctg att acg     576
Leu Lys Pro Thr Tyr Leu Ala Ser Ser Ile Gly Val Thr Leu Ile Thr
            180                 185                 190 gac act gag acg gca gaa gat gaa ttt aac aga gtc aat gac tat ctg     624
Asp Thr Glu Thr Ala Glu Asp Glu Phe Asn Arg Val Asn Asp Tyr Leu
        195                 200                 205 aaa tca att aac gtg cca aag gcg gtt acg ttt gaa gcg ccg ttt atc     672
Lys Ser Ile Asn Val Pro Lys Ala Val Thr Phe Glu Ala Pro Phe Ile
    210                 215                 220 gct gaa gaa ttt tta cag ggt gag tac gga gac tgg tat caa aca gaa     720
Ala Glu Glu Phe Leu Gln Gly Glu Tyr Gly Asp Trp Tyr Gln Thr Glu
225                 230                 235                 240 ggg tac tcc gac tat atc agt ata gaa ggc atc atg gct gac ggt gag     768
Gly Tyr Ser Asp Tyr Ile Ser Ile Glu Gly Ile Met Ala Asp Gly Glu
                245                 250                 255 tat ttc ccg atc gcc att cat gat aaa acg ccg caa atc ggg ttt aca     816
Tyr Phe Pro Ile Ala Ile His Asp Lys Thr Pro Gln Ile Gly Phe Thr
            260                 265                 270 gag aca tcc cac att acg ccg tcc att ctg gat gaa gag gca aaa aag     864
Glu Thr Ser His Ile Thr Pro Ser Ile Leu Asp Glu Glu Ala Lys Lys
        275                 280                 285 aaa att gtc gaa gct gcc aaa aag gca aat gaa ggt ctt ggc ctg caa     912
Lys Ile Val Glu Ala Ala Lys Lys Ala Asn Glu Gly Leu Gly Leu Gln
    290                 295                 300 aat tgc gca aca cat aca gag atc aag cta atg aaa aat aga gaa ccg     960
```

```
        Asn Cys Ala Thr His Thr Glu Ile Lys Leu Met Lys Asn Arg Glu Pro
        305                 310                 315                 320 ggt tta att gaa tcg gca gcc aga ttc gcc ggc tgg aat atg atc ccc         1008
Gly Leu Ile Glu Ser Ala Ala Arg Phe Ala Gly Trp Asn Met Ile Pro
            325                 330                 335 aat att aaa aag gtc ttt ggc ctt gat atg gcg caa tta tta tta gat         1056
Asn Ile Lys Lys Val Phe Gly Leu Asp Met Ala Gln Leu Leu Leu Asp
                340                 345                 350 gtc ctt tgt ttc gga aaa gac gcc gat ctg ccg gac gga tta ttg gat         1104
Val Leu Cys Phe Gly Lys Asp Ala Asp Leu Pro Asp Gly Leu Leu Asp
            355                 360                 365 caa gag cct tat tat gtt gcc gac tgc cat ttg tac ccg caa cat ttc         1152
Gln Glu Pro Tyr Tyr Val Ala Asp Cys His Leu Tyr Pro Gln His Phe
        370                 375                 380 aaa caa aat ggc cag att cca gaa act gct gag gat ttg gtc att gaa         1200
Lys Gln Asn Gly Gln Ile Pro Glu Thr Ala Glu Asp Leu Val Ile Glu
385                 390                 395                 400 gcg atc gat ctg cct gac ggg ctt tta aaa ggg gat act gag atc gtt         1248
Ala Ile Asp Leu Pro Asp Gly Leu Leu Lys Gly Asp Thr Glu Ile Val
                405                 410                 415 tct ttt tcg gcc gca gca cca gga act tca gtt gat ttg aca ttg ttt         1296
Ser Phe Ser Ala Ala Ala Pro Gly Thr Ser Val Asp Leu Thr Leu Phe
            420                 425                 430 gaa gct ttc aat tcc att gct gca ttt gaa ctg aaa ggc agt aat tca         1344
Glu Ala Phe Asn Ser Ile Ala Ala Phe Glu Leu Lys Gly Ser Asn Ser
        435                 440                 445 cag gat gtg gct gaa tca atc aga caa att cag cag cat gcg aag ctg         1392
Gln Asp Val Ala Glu Ser Ile Arg Gln Ile Gln Gln His Ala Lys Leu
450                 455                 460 acg gca aag tat gtg ctg cca gta                                         1416
Thr Ala Lys Tyr Val Leu Pro Val
465                 470

<210> SEQ ID NO 12
<211> LENGTH: 1416
<212> TYPE: DNA
<213> ORGANISM: Bacillus subtilis

<400> SEQUENCE: 12 atg gag aga aaa aca gta ttg gtc atc gct gat ctt gga ggc tgc ccg         48
Met Glu Arg Lys Thr Val Leu Val Ile Ala Asp Leu Gly Gly Cys Pro
1               5                   10                  15 ccg cac atg ttt tat aaa agc gct gct gaa aaa tat aac ctg gtc agc         96
Pro His Met Phe Tyr Lys Ser Ala Ala Glu Lys Tyr Asn Leu Val Ser
            20                  25                  30 ttt att cca aga cct ttt gca att aca gcc tcc cat gca gca ttg att         144
Phe Ile Pro Arg Pro Phe Ala Ile Thr Ala Ser His Ala Ala Leu Ile
        35                  40                  45 gaa aaa tac tcg gtc gcg gtc gta aaa gat aaa gac tat ttt aag agt         192
Glu Lys Tyr Ser Val Ala Val Val Lys Asp Lys Asp Tyr Phe Lys Ser
    50                  55                  60 tta gct gat ttt gag cat cct gac tcc att tat tgg gcg cat gag gat         240
Leu Ala Asp Phe Glu His Pro Asp Ser Ile Tyr Trp Ala His Glu Asp
65                  70                  75                  80 cat aac aag cct gag gaa gag gtc gtc gag caa atc gtc aag gtt gcc         288
His Asn Lys Pro Glu Glu Glu Val Val Glu Gln Ile Val Lys Val Ala
                85                  90                  95 gaa atg ttc ggg gcg gat gcc atc aca aca aac aat gaa tta ttc att         336
Glu Met Phe Gly Ala Asp Ala Ile Thr Thr Asn Asn Glu Leu Phe Ile
            100                 105                 110 gct ccg atg gcg aaa gcc tgt gaa cgt ctg ggc ttg aga ggt gcc ggc         384
```

```
                Ala Pro Met Ala Lys Ala Cys Glu Arg Leu Gly Leu Arg Gly Ala Gly
                        115                 120                 125 gtg cag gca gcc gaa aat gcc aga gat aaa aat aaa atg agg gac gct              432
Val Gln Ala Ala Glu Asn Ala Arg Asp Lys Asn Lys Met Arg Asp Ala
130                 135                 140 ttt aat aag gcc gga gtc aaa tcg atc aaa aac aaa cga gtc aca act              480
Phe Asn Lys Ala Gly Val Lys Ser Ile Lys Asn Lys Arg Val Thr Thr
145                 150                 155                 160 ctt gaa gat ttc cgt gct gct ctt gaa gag atc ggc aca cct ctt atc              528
Leu Glu Asp Phe Arg Ala Ala Leu Glu Glu Ile Gly Thr Pro Leu Ile
                165                 170                 175 tta aag cct aca tac tta gcg agt tct atc ggt gta acg ctg att acg              576
Leu Lys Pro Thr Tyr Leu Ala Ser Ser Ile Gly Val Thr Leu Ile Thr
                180                 185                 190 gac act gag acg gca gaa gat gaa ttt aac aga gtc aat gac tat ctg              624
Asp Thr Glu Thr Ala Glu Asp Glu Phe Asn Arg Val Asn Asp Tyr Leu
                195                 200                 205 aaa tca att aac gtg cca aag gcg gtt acg ttt gaa gcg ccg ttt atc              672
Lys Ser Ile Asn Val Pro Lys Ala Val Thr Phe Glu Ala Pro Phe Ile
210                 215                 220 gct gaa gaa ttt tta cag ggt gag tac gga gac tgg tat caa aca gaa              720
Ala Glu Glu Phe Leu Gln Gly Glu Tyr Gly Asp Trp Tyr Gln Thr Glu
225                 230                 235                 240 ggg tac tcc gac tat atc agt ata gaa ggc atc atg gct gac ggt gag              768
Gly Tyr Ser Asp Tyr Ile Ser Ile Glu Gly Ile Met Ala Asp Gly Glu
                245                 250                 255 tat ttc ccg atc gcc att cat gat aaa acg ccg caa atc ggg ttt aca              816
Tyr Phe Pro Ile Ala Ile His Asp Lys Thr Pro Gln Ile Gly Phe Thr
                260                 265                 270 gag aca tcc cac att acg ccg tcc att ctg gat gaa gag gca aaa aag              864
Glu Thr Ser His Ile Thr Pro Ser Ile Leu Asp Glu Glu Ala Lys Lys
                275                 280                 285 aaa att gtc gaa gct gcc aaa aag gca aat gaa ggg ctt ggc ctg caa              912
Lys Ile Val Glu Ala Ala Lys Lys Ala Asn Glu Gly Leu Gly Leu Gln
290                 295                 300 aat tgc gca aca cat aca gag gtc aag cta atg aaa aac aga gaa ccg              960
Asn Cys Ala Thr His Thr Glu Val Lys Leu Met Lys Asn Arg Glu Pro
305                 310                 315                 320 ggt tta att gaa tcg gca gcc aga ttt gcc ggc tgg aat atg atc cct             1008
Gly Leu Ile Glu Ser Ala Ala Arg Phe Ala Gly Trp Asn Met Ile Pro
                325                 330                 335 aac att aaa aag gtt ttc ggc ctt gat atg gcg caa tta tta tta gat             1056
Asn Ile Lys Lys Val Phe Gly Leu Asp Met Ala Gln Leu Leu Leu Asp
                340                 345                 350 gtc ctc tgt ttc gga aaa gat gcc gat ctg ccg gac gga tta ttg gat             1104
Val Leu Cys Phe Gly Lys Asp Ala Asp Leu Pro Asp Gly Leu Leu Asp
                355                 360                 365 caa gag cct tac tat gtc gcc gac tgc cat ttg tac ccg cag cat ttc             1152
Gln Glu Pro Tyr Tyr Val Ala Asp Cys His Leu Tyr Pro Gln His Phe
370                 375                 380 aaa caa aat ggc cag att cca gaa acc gct gag gat ttg gtc att gaa             1200
Lys Gln Asn Gly Gln Ile Pro Glu Thr Ala Glu Asp Leu Val Ile Glu
385                 390                 395                 400 gcg atc gat att ccg gac ggg ctt tta aaa ggg gat act gaa atc ttt             1248
Ala Ile Asp Ile Pro Asp Gly Leu Leu Lys Gly Asp Thr Glu Ile Phe
                405                 410                 415 tct ttt tcg gcc gca gca cca ggc act tca gtt gat ttg aca ttg ttt             1296
Ser Phe Ser Ala Ala Ala Pro Gly Thr Ser Val Asp Leu Thr Leu Phe
                420                 425                 430 gaa gct ttc aat tcc att gct gca ttt gaa ctg aaa ggc agt aat tca             1344
```

```
Glu Ala Phe Asn Ser Ile Ala Ala Phe Glu Leu Lys Gly Ser Asn Ser
        435                 440                 445 cag gat gtg gct gaa tca atc aga caa att cag cag cat gcg aag ctg      1392
Gln Asp Val Ala Glu Ser Ile Arg Gln Ile Gln Gln His Ala Lys Leu
    450                 455                 460 acg gca aag tat gtg ctg cca gta                                      1416
Thr Ala Lys Tyr Val Leu Pro Val
465                 470

<210> SEQ ID NO 13
<211> LENGTH: 1416
<212> TYPE: DNA
<213> ORGANISM: Bacillus subtilis

<400> SEQUENCE: 13 atg gag aga aaa aca gta ttg gtc atc gct gat ctt gga ggc tgc ccg       48
Met Glu Arg Lys Thr Val Leu Val Ile Ala Asp Leu Gly Gly Cys Pro
  1               5                  10                  15 ccg cac atg ttt tat aaa agc gct gct gaa aaa tat aac ctg gtt agc       96
Pro His Met Phe Tyr Lys Ser Ala Ala Glu Lys Tyr Asn Leu Val Ser
             20                  25                  30 ttt att ccg aga cct ttt gca ata aca gcc tcc cat gca gca ctg att      144
Phe Ile Pro Arg Pro Phe Ala Ile Thr Ala Ser His Ala Ala Leu Ile
         35                  40                  45 gaa aaa tac tcg gtc gcg gta ata aaa gat aaa gac tat ttt cag agc      192
Glu Lys Tyr Ser Val Ala Val Ile Lys Asp Lys Asp Tyr Phe Gln Ser
     50                  55                  60 tta gct gat ttt gag cat ccc gat tca att tat tgg gcg cat gag gat      240
Leu Ala Asp Phe Glu His Pro Asp Ser Ile Tyr Trp Ala His Glu Asp
 65                  70                  75                  80 cat gac aag cct gaa gaa gag gtt gtc gag caa atc gtc aag gtt gcc      288
His Asp Lys Pro Glu Glu Glu Val Val Glu Gln Ile Val Lys Val Ala
                 85                  90                  95 caa atg ttt gag gcg gac gcc atc aca aca aac aat gaa tta ttc att      336
Gln Met Phe Glu Ala Asp Ala Ile Thr Thr Asn Asn Glu Leu Phe Ile
            100                 105                 110 gcc ccg atg gcg aaa gcc tgt gaa cgc ctt ggc ctg agg ggc gcc gga      384
Ala Pro Met Ala Lys Ala Cys Glu Arg Leu Gly Leu Arg Gly Ala Gly
        115                 120                 125 gtg cag gca gcg gaa aat gcc aga gat aaa aat aaa atg agg gac gct      432
Val Gln Ala Ala Glu Asn Ala Arg Asp Lys Asn Lys Met Arg Asp Ala
    130                 135                 140 ttt aat aag gcg gga gtc aaa tcg atc aaa aac aaa cga gtc aca act      480
Phe Asn Lys Ala Gly Val Lys Ser Ile Lys Asn Lys Arg Val Thr Thr
145                 150                 155                 160 ctt gag gat ttt cgt gct gca ctt gaa gag atc ggc aca cct cta atc      528
Leu Glu Asp Phe Arg Ala Ala Leu Glu Glu Ile Gly Thr Pro Leu Ile
                165                 170                 175 tta aag cct aca tac tta gcg agt tca atc ggc gta acg ctg att acc      576
Leu Lys Pro Thr Tyr Leu Ala Ser Ser Ile Gly Val Thr Leu Ile Thr
            180                 185                 190 gac acg gag acg gca gaa gat gaa ttt aac aga gtc aat gac tac ctg      624
Asp Thr Glu Thr Ala Glu Asp Glu Phe Asn Arg Val Asn Asp Tyr Leu
        195                 200                 205 aaa tcg att aac gtg ccg aag gcg gtc aca ttt gaa gca ccg ttt att      672
Lys Ser Ile Asn Val Pro Lys Ala Val Thr Phe Glu Ala Pro Phe Ile
    210                 215                 220 gct gag gaa ttt tta cag ggt gag tac gga gac tgg tat caa aca gaa      720
Ala Glu Glu Phe Leu Gln Gly Glu Tyr Gly Asp Trp Tyr Gln Thr Glu
225                 230                 235                 240 ggg tac tcc gac tat atc agc ata gaa ggc att atg gca gat ggt gag      768
```

```
Gly Tyr Ser Asp Tyr Ile Ser Ile Glu Gly Ile Met Ala Asp Gly Glu
            245                 250                 255 tat ttt ccg atc gcc att cat gac aaa acg ccg caa att gga ttt aca        816
Tyr Phe Pro Ile Ala Ile His Asp Lys Thr Pro Gln Ile Gly Phe Thr
            260                 265                 270 gag aca tca cat att acg cca tcc att ctg gat gaa gag gcg aaa aag        864
Glu Thr Ser His Ile Thr Pro Ser Ile Leu Asp Glu Glu Ala Lys Lys
            275                 280                 285 aaa att gtc gaa gcg gct aaa aag gca aat gaa ggg ctt gga ctg caa        912
Lys Ile Val Glu Ala Ala Lys Lys Ala Asn Glu Gly Leu Gly Leu Gln
            290                 295                 300 aat tgc gca aca cat aca gaa atc aag cta atg aaa aac aga gaa ccg        960
Asn Cys Ala Thr His Thr Glu Ile Lys Leu Met Lys Asn Arg Glu Pro
305                 310                 315                 320 ggt tta ata gag tcg gct gcc aga ttc gca ggc tgg aat atg att cct       1008
Gly Leu Ile Glu Ser Ala Ala Arg Phe Ala Gly Trp Asn Met Ile Pro
            325                 330                 335 aac att aaa aag gtt ttc ggc ctt gat atg gcg caa tta tta tta gat       1056
Asn Ile Lys Lys Val Phe Gly Leu Asp Met Ala Gln Leu Leu Leu Asp
            340                 345                 350 gtt ctc tgt ttc gga aaa gat gct gat ctg ccg gac ggg tta ttg gat       1104
Val Leu Cys Phe Gly Lys Asp Ala Asp Leu Pro Asp Gly Leu Leu Asp
            355                 360                 365 caa gag cct tac tat gtt gct gac tgc cat ctg tac cct cag cat ttc       1152
Gln Glu Pro Tyr Tyr Val Ala Asp Cys His Leu Tyr Pro Gln His Phe
            370                 375                 380 aaa caa aat ggc cag atc cct gaa act gcc gag gat ttg gta atc gaa       1200
Lys Gln Asn Gly Gln Ile Pro Glu Thr Ala Glu Asp Leu Val Ile Glu
385                 390                 395                 400 gcg atc gat att ccg gat ggg ctt ttg aag ggt gat aca gaa atc gtt       1248
Ala Ile Asp Ile Pro Asp Gly Leu Leu Lys Gly Asp Thr Glu Ile Val
            405                 410                 415 act ttt tcg gct gcg gca cca gga aca tca gtt gat ttg aca ctg ttt       1296
Thr Phe Ser Ala Ala Ala Pro Gly Thr Ser Val Asp Leu Thr Leu Phe
            420                 425                 430 gaa gcc ttc aac tcc att gct gca ttt gaa ctg aaa ggc agc aat tca       1344
Glu Ala Phe Asn Ser Ile Ala Ala Phe Glu Leu Lys Gly Ser Asn Ser
            435                 440                 445 cag gat gtg gct gaa tca atc aga caa att cag cag cat gcg aag ctg       1392
Gln Asp Val Ala Glu Ser Ile Arg Gln Ile Gln Gln His Ala Lys Leu
            450                 455                 460 acg gca aag tat gtg ctg cca gta                                        1416
Thr Ala Lys Tyr Val Leu Pro Val
465                 470

<210> SEQ ID NO 14
<211> LENGTH: 1416
<212> TYPE: DNA
<213> ORGANISM: Bacillus subtilis

<400> SEQUENCE: 14 atg gag aga aaa aca gta ttg gtt atc gct gat ctt ggg ggc tgc ccg         48
Met Glu Arg Lys Thr Val Leu Val Ile Ala Asp Leu Gly Gly Cys Pro
1               5                   10                  15 ccg cat atg ttt tac aaa agc gca gcc gaa aaa tac aac ctc gtc agc         96
Pro His Met Phe Tyr Lys Ser Ala Ala Glu Lys Tyr Asn Leu Val Ser
            20                  25                  30 ttt att ccg aga ccc ttt gca att aca gcc tct cat gcg gcc tta att        144
Phe Ile Pro Arg Pro Phe Ala Ile Thr Ala Ser His Ala Ala Leu Ile
            35                  40                  45 gaa aaa tac tcg att gcg gtc att aaa gat aaa gac tat ttt aag agt        192
Glu Lys Tyr Ser Ile Ala Val Ile Lys Asp Lys Asp Tyr Phe Lys Ser
```

-continued

| | | |
|---|---|---|
| Glu Lys Tyr Ser Ile Ala Val Ile Lys Asp Lys Asp Tyr Phe Lys Ser<br>     50                       55                      60 | | |
| ctg gct gat ttt gaa cat ccc gat tcg att tat tgg gct cat gaa gat<br>Leu Ala Asp Phe Glu His Pro Asp Ser Ile Tyr Trp Ala His Glu Asp<br> 65                    70                      75                    80 | | 240 |
| cat gac aaa cct gag gaa gaa gtc gtc gaa gaa atc gtg aaa gtg gcc<br>His Asp Lys Pro Glu Glu Glu Val Val Glu Glu Ile Val Lys Val Ala<br>                   85                      90                    95 | | 288 |
| gac atg ttt ggg gtt gac gcc att acg acc aac aat gaa ctg ttt atc<br>Asp Met Phe Gly Val Asp Ala Ile Thr Thr Asn Asn Glu Leu Phe Ile<br>           100                      105                      110 | | 336 |
| gct ccg atg gca aaa gcg tgt aaa cgt ctc ggc ctg cgg gga gcg ggc<br>Ala Pro Met Ala Lys Ala Cys Lys Arg Leu Gly Leu Arg Gly Ala Gly<br>               115                      120                      125 | | 384 |
| gta cag gcc gct gaa aac gcc aga gat aaa aat aaa atg aga gcc gcc<br>Val Gln Ala Ala Glu Asn Ala Arg Asp Lys Asn Lys Met Arg Ala Ala<br>       130                      135                      140 | | 432 |
| ttc aac cgg gcc ggc gtc aaa tcc atc aaa aac aaa cgg gtg acg acc<br>Phe Asn Arg Ala Gly Val Lys Ser Ile Lys Asn Lys Arg Val Thr Thr<br>145                      150                      155                    160 | | 480 |
| ctg gaa gat ttc cgc gcc gcg ctt cag gaa atc gga acg ccg ctt att<br>Leu Glu Asp Phe Arg Ala Ala Leu Gln Glu Ile Gly Thr Pro Leu Ile<br>               165                      170                      175 | | 528 |
| ctg aag cct aca tat ctg gca agc tcg atc ggc gtg acg ctt att aaa<br>Leu Lys Pro Thr Tyr Leu Ala Ser Ser Ile Gly Val Thr Leu Ile Lys<br>               180                      185                      190 | | 576 |
| gag atg gaa acg gcc gaa gct gaa ttc aac aga gtc aat gag tac ttg<br>Glu Met Glu Thr Ala Glu Ala Glu Phe Asn Arg Val Asn Glu Tyr Leu<br>           195                      200                      205 | | 624 |
| aaa tcg att aat gta ccg aaa gcg gtg acg ttt gaa gcg ccg ttt atc<br>Lys Ser Ile Asn Val Pro Lys Ala Val Thr Phe Glu Ala Pro Phe Ile<br>210                      215                      220 | | 672 |
| gcg gaa gaa ttc ttg cag ggc gag tat gat gac tgg tac gaa aca agc<br>Ala Glu Glu Phe Leu Gln Gly Glu Tyr Asp Asp Trp Tyr Glu Thr Ser<br>225                      230                      235                    240 | | 720 |
| ggt tat tcc gac tat atc agc atc gaa ggc atc atg gcc gac gga gaa<br>Gly Tyr Ser Asp Tyr Ile Ser Ile Glu Gly Ile Met Ala Asp Gly Glu<br>                      245                      250                      255 | | 768 |
| tac ttc ccc gtt gcg atc cat gat aaa aca ccg caa atc gga ttc acg<br>Tyr Phe Pro Val Ala Ile His Asp Lys Thr Pro Gln Ile Gly Phe Thr<br>               260                      265                      270 | | 816 |
| gag aca gcg cat att acg ccg tcc atc ctg gat gat gac gcc aag cgg<br>Glu Thr Ala His Ile Thr Pro Ser Ile Leu Asp Asp Asp Ala Lys Arg<br>       275                      280                      285 | | 864 |
| aaa atc gtc gaa gct gcc aag aag gcg aat gaa gga ctc ggc ctc gaa<br>Lys Ile Val Glu Ala Ala Lys Lys Ala Asn Glu Gly Leu Gly Leu Glu<br>     290                      295                      300 | | 912 |
| aac tgt gca acg cat aca gaa ata aaa tta atg aaa aac cgg gaa gcc<br>Asn Cys Ala Thr His Thr Glu Ile Lys Leu Met Lys Asn Arg Glu Ala<br>305                      310                      315                    320 | | 960 |
| gga ctg att gag tca gcg gcc aga ttc gcg gga tgg aat atg att ccg<br>Gly Leu Ile Glu Ser Ala Ala Arg Phe Ala Gly Trp Asn Met Ile Pro<br>                      325                      330                      335 | | 1008 |
| aat att aaa aag gtc ttc ggc gtt gat atg gcg cag cta tta ttg gat<br>Asn Ile Lys Lys Val Phe Gly Val Asp Met Ala Gln Leu Leu Leu Asp<br>               340                      345                      350 | | 1056 |
| gtt ctc tgt tac gga aaa gaa gct gat ctg ccg aaa gga tta ttg gag<br>Val Leu Cys Tyr Gly Lys Glu Ala Asp Leu Pro Lys Gly Leu Leu Glu<br>       355                      360                      365 | | 1104 |
| cag gag cca tgc tat gtc gca gac tgc cac ttg tat cct cag cat ttc | | 1152 |

```
                Gln Glu Pro Cys Tyr Val Ala Asp Cys His Leu Tyr Pro Gln His Phe
                    370                 375                 380 aaa gag aac ggc cag ctg cct gag acg gtt gtc gat ttc gtc att gaa       1200
Lys Glu Asn Gly Gln Leu Pro Glu Thr Val Val Asp Phe Val Ile Glu
385                 390                 395                 400 agc att gaa att cct gac ggc gtc tta aag gga gac act gaa ctc gtt       1248
Ser Ile Glu Ile Pro Asp Gly Val Leu Lys Gly Asp Thr Glu Leu Val
                405                 410                 415 tct ttc tca gcg gct gag gcg ggt acg tca gtg gat ctg cgg ctg ttc       1296
Ser Phe Ser Ala Ala Glu Ala Gly Thr Ser Val Asp Leu Arg Leu Phe
            420                 425                 430 gaa gcg ttc aac agc att gcg gcg ttt gag ctg aaa gga agc aat tcg       1344
Glu Ala Phe Asn Ser Ile Ala Ala Phe Glu Leu Lys Gly Ser Asn Ser
        435                 440                 445 aac gac gtg gcc gaa tca atc aaa caa att cag cag cag gcg aag ctg       1392
Asn Asp Val Ala Glu Ser Ile Lys Gln Ile Gln Gln Gln Ala Lys Leu
    450                 455                 460 act gca aag tat gcg tta tcg gta                                       1416
Thr Ala Lys Tyr Ala Leu Ser Val <210> SEQ ID NO 15
<211> LENGTH: 1416
<212> TYPE: DNA
<213> ORGANISM: Bacillus amyloliquefaciens

<400> SEQUENCE: 15 atg gag aga aaa aca gta ttg gtt atc gct gac ctt ggg gga tgc ccg         48
Met Glu Arg Lys Thr Val Leu Val Ile Ala Asp Leu Gly Gly Cys Pro
1               5                   10                  15 ccg cat atg ttt tac aaa agc gca gcc gaa aaa tac aac ctc gtc agc         96
Pro His Met Phe Tyr Lys Ser Ala Ala Glu Lys Tyr Asn Leu Val Ser
                20                  25                  30 ttt att ccg aga cct ttt gca att aca gcc tct cat gcg gca tta att        144
Phe Ile Pro Arg Pro Phe Ala Ile Thr Ala Ser His Ala Ala Leu Ile
            35                  40                  45 gaa aaa tac tcg gtc gcg gtc ata aaa gat aaa gac tat ttt aag agt        192
Glu Lys Tyr Ser Val Ala Val Ile Lys Asp Lys Asp Tyr Phe Lys Ser
        50                  55                  60 ctg gct gat ttt gag cat ccc gat tcg att tac tgg gct cat gaa gat        240
Leu Ala Asp Phe Glu His Pro Asp Ser Ile Tyr Trp Ala His Glu Asp
65                  70                  75                  80 cat gac aaa cct gag gaa gaa gta gtc gaa gaa atc gtc aag gtg gcc        288
His Asp Lys Pro Glu Glu Glu Val Val Glu Glu Ile Val Lys Val Ala
                85                  90                  95 ggc atg ttc gcg gtt gac gcc att acg acc aac aat gaa ctg ttt atc        336
Gly Met Phe Ala Val Asp Ala Ile Thr Thr Asn Asn Glu Leu Phe Ile
                100                 105                 110 gct ccg atg gca aaa gcg tgt gaa cgt ctc ggc ctg cgg gga gcg ggc        384
Ala Pro Met Ala Lys Ala Cys Glu Arg Leu Gly Leu Arg Gly Ala Gly
            115                 120                 125 gta cag gcc gct gaa aat gcc aga gat aaa aac aaa atg aga gcc gct        432
Val Gln Ala Ala Glu Asn Ala Arg Asp Lys Asn Lys Met Arg Ala Ala
        130                 135                 140 ttc aac cgg gcc ggc gtc aag tct atc aaa aac aga cgg gtg acg acg        480
Phe Asn Arg Ala Gly Val Lys Ser Ile Lys Asn Arg Arg Val Thr Thr
145                 150                 155                 160 ctg gaa gat ttc cgc gcc gcg ctt cag gaa atc gga acg ccg ctc att        528
Leu Glu Asp Phe Arg Ala Ala Leu Gln Glu Ile Gly Thr Pro Leu Ile
                165                 170                 175 ctg aag cct aca tat ctg gcg agc tcc atc ggc gtg acg ctc atc aaa        576
Leu Lys Pro Thr Tyr Leu Ala Ser Ser Ile Gly Val Thr Leu Ile Lys
```

|   |   |   |   |   |   |   |   |   |   |   |   |   |   |   |   |   |
|---|---|---|---|---|---|---|---|---|---|---|---|---|---|---|---|---|
|   |   |   | 180 |   |   |   |   | 185 |   |   |   |   | 190 |   |   |   |
| gag | agg | gaa | acg | gcc | gaa | gcc | gaa | ttt | aac | aga | gtc | aat | gaa | tac | ctg | 624 |
| Glu | Arg | Glu | Thr | Ala | Glu | Ala | Glu | Phe | Asn | Arg | Val | Asn | Glu | Tyr | Leu |   |
|   | 195 |   |   |   |   | 200 |   |   |   |   | 205 |   |   |   |   |   |
| aag | tcg | atc | aac | gta | ccg | aaa | gcg | gtc | acg | ttt | gaa | gcg | ccg | ttt | atc | 672 |
| Lys | Ser | Ile | Asn | Val | Pro | Lys | Ala | Val | Thr | Phe | Glu | Ala | Pro | Phe | Ile |   |
| 210 |   |   |   |   | 215 |   |   |   |   | 220 |   |   |   |   |   |   |
| gcg | gaa | gaa | ttt | ttg | cag | ggc | gag | tat | gac | gac | tgg | tac | gaa | aca | agc | 720 |
| Ala | Glu | Glu | Phe | Leu | Gln | Gly | Glu | Tyr | Asp | Asp | Trp | Tyr | Glu | Thr | Ser |   |
| 225 |   |   |   |   | 230 |   |   |   |   | 235 |   |   |   |   | 240 |   |
| ggt | tat | tcc | gac | tat | atc | agc | ata | gaa | ggc | atc | atg | gcc | gac | gga | gaa | 768 |
| Gly | Tyr | Ser | Asp | Tyr | Ile | Ser | Ile | Glu | Gly | Ile | Met | Ala | Asp | Gly | Glu |   |
|   |   |   |   | 245 |   |   |   |   | 250 |   |   |   |   | 255 |   |   |
| tac | ttc | cct | gtc | gca | att | cat | gat | aaa | aca | ccg | caa | atc | gga | ttc | acg | 816 |
| Tyr | Phe | Pro | Val | Ala | Ile | His | Asp | Lys | Thr | Pro | Gln | Ile | Gly | Phe | Thr |   |
|   |   |   | 260 |   |   |   |   | 265 |   |   |   |   | 270 |   |   |   |
| gag | aca | tcg | cat | att | acg | ccg | tcc | atc | ctg | gat | gat | gac | gcg | aag | cgg | 864 |
| Glu | Thr | Ser | His | Ile | Thr | Pro | Ser | Ile | Leu | Asp | Asp | Asp | Ala | Lys | Arg |   |
|   | 275 |   |   |   |   | 280 |   |   |   |   | 285 |   |   |   |   |   |
| aaa | atc | gtc | gaa | gca | gcc | aaa | aag | gcg | aat | gaa | gga | ctc | ggc | ctc | gaa | 912 |
| Lys | Ile | Val | Glu | Ala | Ala | Lys | Lys | Ala | Asn | Glu | Gly | Leu | Gly | Leu | Glu |   |
| 290 |   |   |   |   | 295 |   |   |   |   | 300 |   |   |   |   |   |   |
| aac | tgc | gca | acc | cat | aca | gag | att | aaa | tta | atg | aaa | aac | cgg | gaa | gcc | 960 |
| Asn | Cys | Ala | Thr | His | Thr | Glu | Ile | Lys | Leu | Met | Lys | Asn | Arg | Glu | Ala |   |
| 305 |   |   |   |   | 310 |   |   |   |   | 315 |   |   |   |   | 320 |   |
| gga | ctg | att | gaa | tca | gcg | gca | cga | ttt | gcg | ggc | tgg | aac | atg | att | ccg | 1008 |
| Gly | Leu | Ile | Glu | Ser | Ala | Ala | Arg | Phe | Ala | Gly | Trp | Asn | Met | Ile | Pro |   |
|   |   |   |   | 325 |   |   |   |   | 330 |   |   |   |   | 335 |   |   |
| aat | att | aaa | aag | gtc | ttc | ggc | gtc | gat | atg | gcg | cag | ctg | tta | ttg | gat | 1056 |
| Asn | Ile | Lys | Lys | Val | Phe | Gly | Val | Asp | Met | Ala | Gln | Leu | Leu | Leu | Asp |   |
|   |   |   | 340 |   |   |   |   | 345 |   |   |   |   | 350 |   |   |   |
| gtt | ctc | tgt | ttc | gga | aaa | gaa | gcc | gat | ctg | ccg | aaa | gga | tta | ttg | gag | 1104 |
| Val | Leu | Cys | Phe | Gly | Lys | Glu | Ala | Asp | Leu | Pro | Lys | Gly | Leu | Leu | Glu |   |
|   | 355 |   |   |   |   | 360 |   |   |   |   | 365 |   |   |   |   |   |
| cag | gag | ccg | tgc | tat | gtc | gcc | gac | tgc | cac | ttg | tat | cct | cag | cat | ttc | 1152 |
| Gln | Glu | Pro | Cys | Tyr | Val | Ala | Asp | Cys | His | Leu | Tyr | Pro | Gln | His | Phe |   |
| 370 |   |   |   |   | 375 |   |   |   |   | 380 |   |   |   |   |   |   |
| aaa | gag | aac | ggc | cag | ctg | cct | gag | acg | gct | gtc | gat | ttc | gtc | att | gaa | 1200 |
| Lys | Glu | Asn | Gly | Gln | Leu | Pro | Glu | Thr | Ala | Val | Asp | Phe | Val | Ile | Glu |   |
| 385 |   |   |   |   | 390 |   |   |   |   | 395 |   |   |   |   | 400 |   |
| agc | att | gac | att | ccc | gac | ggc | gtc | tta | aag | gga | gac | acc | gaa | atc | gtt | 1248 |
| Ser | Ile | Asp | Ile | Pro | Asp | Gly | Val | Leu | Lys | Gly | Asp | Thr | Glu | Ile | Val |   |
|   |   |   |   | 405 |   |   |   |   | 410 |   |   |   |   | 415 |   |   |
| tct | ttc | tcg | gcg | gcc | gag | gcg | ggt | aca | tcc | gtg | gat | ctg | cgg | ctg | ttc | 1296 |
| Ser | Phe | Ser | Ala | Ala | Glu | Ala | Gly | Thr | Ser | Val | Asp | Leu | Arg | Leu | Phe |   |
|   |   |   | 420 |   |   |   |   | 425 |   |   |   |   | 430 |   |   |   |
| gaa | gcg | ttc | aac | agc | att | gcg | gcg | ttc | gag | ctg | aaa | gga | agc | aat | tcg | 1344 |
| Glu | Ala | Phe | Asn | Ser | Ile | Ala | Ala | Phe | Glu | Leu | Lys | Gly | Ser | Asn | Ser |   |
|   | 435 |   |   |   |   | 440 |   |   |   |   | 445 |   |   |   |   |   |
| ggt | gac | gtg | gcc | gaa | tca | atc | aaa | caa | att | cag | cag | cag | gcg | aag | ctg | 1392 |
| Gly | Asp | Val | Ala | Glu | Ser | Ile | Lys | Gln | Ile | Gln | Gln | Gln | Ala | Lys | Leu |   |
| 450 |   |   |   |   | 455 |   |   |   |   | 460 |   |   |   |   |   |   |
| act | gca | aag | tat | gcg | tta | ccg | gta |   |   |   |   |   |   |   |   | 1416 |
| Thr | Ala | Lys | Tyr | Ala | Leu | Pro | Val |   |   |   |   |   |   |   |   |   |

<210> SEQ ID NO 16
<211> LENGTH: 1428
<212> TYPE: DNA
<213> ORGANISM: Bacillus pumilus

<400> SEQUENCE: 16

-continued

| | |
|---|---|
| gtg ctt tca ttg agt aaa aaa act gta ctt gtc att gct gac tta gga<br>Val Leu Ser Leu Ser Lys Lys Thr Val Leu Val Ile Ala Asp Leu Gly<br>1                       5                    10                  15 | 48 |
| ggg tgc ccg ccc cat atg ttt tat gaa agc gtg gcg gca tca tac cat<br>Gly Cys Pro Pro His Met Phe Tyr Glu Ser Val Ala Ala Ser Tyr His<br>                  20                    25                    30 | 96 |
| atc gtt tct tat atc cca aga ccc ttt gcg att aca aag gga cat gcc<br>Ile Val Ser Tyr Ile Pro Arg Pro Phe Ala Ile Thr Lys Gly His Ala<br>        35                    40                    45 | 144 |
| gag cta atc gaa aaa tac tcc att gcc gtc atc aaa gac cgt gat tat<br>Glu Leu Ile Glu Lys Tyr Ser Ile Ala Val Ile Lys Asp Arg Asp Tyr<br>    50                    55                    60 | 192 |
| ttt gag aca cac cct tct ttt gaa cac cct gat tct att tac tgg gca<br>Phe Glu Thr His Pro Ser Phe Glu His Pro Asp Ser Ile Tyr Trp Ala<br>65                      70                    75                  80 | 240 |
| cat gat gat tat cca aaa tca gaa gaa gaa gtt gtg gaa gac ttc att<br>His Asp Asp Tyr Pro Lys Ser Glu Glu Glu Val Val Glu Asp Phe Ile<br>                  85                    90                    95 | 288 |
| cga gta gct tcc ttt ttc aaa gca gat gca atc acg acc aat aat gaa<br>Arg Val Ala Ser Phe Phe Lys Ala Asp Ala Ile Thr Thr Asn Asn Glu<br>              100                   105                110 | 336 |
| tta ttc att gca ccg atg gca aag gcc gct gaa cgt ctt ggg cta cga<br>Leu Phe Ile Ala Pro Met Ala Lys Ala Ala Glu Arg Leu Gly Leu Arg<br>     115                    120                  125 | 384 |
| ggt gcc ggt gtc aag gca gcc gaa atg gcg cgt gat aaa agc caa atg<br>Gly Ala Gly Val Lys Ala Ala Glu Met Ala Arg Asp Lys Ser Gln Met<br>130                      135                    140 | 432 |
| agg gct gca ttc aat gcc tct ggc gtc aaa gcg gtg aaa act cag cct<br>Arg Ala Ala Phe Asn Ala Ser Gly Val Lys Ala Val Lys Thr Gln Pro<br>145                      150                    155                  160 | 480 |
| gtc acg act tta tct gat ttc caa caa gcc att gag tct atc gga aca<br>Val Thr Thr Leu Ser Asp Phe Gln Gln Ala Ile Glu Ser Ile Gly Thr<br>                  165                    170                175 | 528 |
| ccg ctc att tta aag cct aca tat tta gcc agt tct att ggc gtc acc<br>Pro Leu Ile Leu Lys Pro Thr Tyr Leu Ala Ser Ser Ile Gly Val Thr<br>               180                   185                190 | 576 |
| ttg ttt cat gac aaa gcc gga agt gat gac ttg ttt tta caa gta caa<br>Leu Phe His Asp Lys Ala Gly Ser Asp Asp Leu Phe Leu Gln Val Gln<br>             195                   200                205 | 624 |
| tcg tat ttg gaa acc ata cca gtc cca gac gct gtc acg tat gaa gca<br>Ser Tyr Leu Glu Thr Ile Pro Val Pro Asp Ala Val Thr Tyr Glu Ala<br>210                      215                    220 | 672 |
| ccg ttt gtc gct gaa aca tat tta gag ggt gct tac gaa gat tgg tat<br>Pro Phe Val Ala Glu Thr Tyr Leu Glu Gly Ala Tyr Glu Asp Trp Tyr<br>225                      230                    235                  240 | 720 |
| gaa gac gaa gga tat gct gat tat gtc agt gta gaa ggg ctg gtc gta<br>Glu Asp Glu Gly Tyr Ala Asp Tyr Val Ser Val Glu Gly Leu Val Val<br>                  245                    250                255 | 768 |
| gag ggc gaa tat ctc cct ttt gtc ata cat gat aaa acc cct caa atc<br>Glu Gly Glu Tyr Leu Pro Phe Val Ile His Asp Lys Thr Pro Gln Ile<br>             260                   265                270 | 816 |
| ggc ttt aca gaa acg gct cat atc act ccg acg atc tta gac aat gaa<br>Gly Phe Thr Glu Thr Ala His Ile Thr Pro Thr Ile Leu Asp Asn Glu<br>          275                    280                    285 | 864 |
| gcc aag caa atc atc att gaa gca gca agg aag gca aat gaa ggg cta<br>Ala Lys Gln Ile Ile Ile Glu Ala Ala Arg Lys Ala Asn Glu Gly Leu<br>    290                    295                    300 | 912 |
| ggt ctt gaa cat tgt gca acc cat aca gaa atc aaa ctc atg aaa aat<br>Gly Leu Glu His Cys Ala Thr His Thr Glu Ile Lys Leu Met Lys Asn<br>305                      310                    315                  320 | 960 |

```
cga aac act gga ctg atc gag gca gcg gct cga ttc gct ggc tgg aat   1008
Arg Glu Thr Gly Leu Ile Glu Ala Ala Ala Arg Phe Ala Gly Trp Asn
                325                 330                 335 atg atc ccg aat att aaa aaa gtc ttt ggc gtc gat atg gcg aag cta   1056
Met Ile Pro Asn Ile Lys Lys Val Phe Gly Val Asp Met Ala Lys Leu
            340                 345                 350 ttg att gat gta tta gtt gat ggt aaa aag gct gta ctg cca aaa cag   1104
Leu Ile Asp Val Leu Val Asp Gly Lys Lys Ala Val Leu Pro Lys Gln
        355                 360                 365 ctg ctt tct gga cat aca ttt tat gta gcg gac tgc cac ctg tac cct   1152
Leu Leu Ser Gly His Thr Phe Tyr Val Ala Asp Cys His Leu Tyr Pro
    370                 375                 380 cag cat ttt aaa gag agt ggg ctt atc ccg cct gaa gcc aca cat att   1200
Gln His Phe Lys Glu Ser Gly Leu Ile Pro Pro Glu Ala Thr His Ile
385                 390                 395                 400 acc att gat cat gtg tct att ccg cag gaa gca ttc gtt gga gat act   1248
Thr Ile Asp His Val Ser Ile Pro Gln Glu Ala Phe Val Gly Asp Thr
                405                 410                 415 gcg att gtc agt caa tca ttc cct gcc aaa ggg act att gtg gat ctt   1296
Ala Ile Val Ser Gln Ser Phe Pro Ala Lys Gly Thr Ile Val Asp Leu
            420                 425                 430 gaa tta ttt gaa gct ttt aat gga atc gta tct ctt gaa tta aaa gga   1344
Glu Leu Phe Glu Ala Phe Asn Gly Ile Val Ser Leu Glu Leu Lys Gly
        435                 440                 445 tca tcc tca caa gat gtt gcc gcg tcc atc cgc aac att cag aaa cag   1392
Ser Ser Ser Gln Asp Val Ala Ala Ser Ile Arg Asn Ile Gln Lys Gln
    450                 455                 460 gca acg att cag tta atg gat gaa tta gtg aag gga                   1428
Ala Thr Ile Gln Leu Met Asp Glu Leu Val Lys Gly
465                 470                 475

<210> SEQ ID NO 17
<211> LENGTH: 93
<212> TYPE: PRT
<213> ORGANISM: Bacillus subtilis

<400> SEQUENCE: 17

Gly Ala Gly Val Gln Ala Ala Glu Asn Ala Arg Asp Lys Asn Lys Met
1               5                   10                  15

Arg Asp Ala Phe Asn Lys Ala Gly Val Lys Ser Ile Lys Asn Lys Arg
            20                  25                  30

Val Thr Thr Leu Glu Asp Phe Arg Ala Ala Leu Glu Glu Ile Gly Thr
        35                  40                  45

Pro Leu Ile Leu Lys Pro Thr Tyr Leu Ala Ser Ser Ile Gly Val Thr
    50                  55                  60

Leu Ile Thr Asp Thr Glu Thr Ala Glu Asp Glu Phe Asn Arg Val Asn
65                  70                  75                  80

Asp Tyr Leu Lys Ser Ile Asn Val Pro Lys Ala Val Thr
                85                  90

<210> SEQ ID NO 18
<211> LENGTH: 279
<212> TYPE: DNA
<213> ORGANISM: Bacillus subtilis

<400> SEQUENCE: 18 ggt gcc ggc gtg cag gca gcc gaa aat gcc aga gat aaa aat aaa atg   48
Gly Ala Gly Val Gln Ala Ala Glu Asn Ala Arg Asp Lys Asn Lys Met
1               5                   10                  15 agg gac gct ttt aat aag gcc gga gtc aaa tcg atc aaa aac aaa cga   96
```

```
Arg Asp Ala Phe Asn Lys Ala Gly Val Lys Ser Ile Lys Asn Lys Arg
            20                  25                  30 gtc aca act ctt gaa gat ttc cgt gct gct ctt gaa gag atc ggc aca    144
Val Thr Thr Leu Glu Asp Phe Arg Ala Ala Leu Glu Glu Ile Gly Thr
        35                  40                  45 cct ctt atc tta aag cct aca tac tta gcg agt tct atc ggt gta acg    192
Pro Leu Ile Leu Lys Pro Thr Tyr Leu Ala Ser Ser Ile Gly Val Thr
 50                  55                  60 ctg att acg gac act gag acg gca gaa gat gaa ttt aac aga gtc aat    240
Leu Ile Thr Asp Thr Glu Thr Ala Glu Asp Glu Phe Asn Arg Val Asn
 65                  70                  75                  80 gac tat ctg aaa tca att aac gtg cca aag gcg gtt acg                279
Asp Tyr Leu Lys Ser Ile Asn Val Pro Lys Ala Val Thr
                 85                  90

<210> SEQ ID NO 19
<211> LENGTH: 30
<212> TYPE: DNA
<213> ORGANISM: Artificial Sequence
<220> FEATURE:
<223> OTHER INFORMATION: Synthetic DNA

<400> SEQUENCE: 19
attctcgagt agagaaggag tgttttacat                                    30

<210> SEQ ID NO 20
<211> LENGTH: 30
<212> TYPE: DNA
<213> ORGANISM: Artificial Sequence
<220> FEATURE:
<223> OTHER INFORMATION: Synthetic DNA

<400> SEQUENCE: 20
ttaggatcct catactggca gcacatactt                                    30

<210> SEQ ID NO 21
<211> LENGTH: 24
<212> TYPE: DNA
<213> ORGANISM: Artificial Sequence
<220> FEATURE:
<223> OTHER INFORMATION: Synthetic DNA

<400> SEQUENCE: 21
caagaattct catgtttgac agct                                          24

<210> SEQ ID NO 22
<211> LENGTH: 28
<212> TYPE: DNA
<213> ORGANISM: Artificial Sequence
<220> FEATURE:
<223> OTHER INFORMATION: Synthetic DNA

<400> SEQUENCE: 22
taactcgaga ttccctttttt acgtgaac                                     28

<210> SEQ ID NO 23
<211> LENGTH: 27
<212> TYPE: DNA
<213> ORGANISM: Artificial Sequence
<220> FEATURE:
<223> OTHER INFORMATION: Synthetic DNA

<400> SEQUENCE: 23
ttaaccatgg agagaaaaac agtattg                                       27
```

```
<210> SEQ ID NO 24
<211> LENGTH: 30
<212> TYPE: DNA
<213> ORGANISM: Artificial Sequence
<220> FEATURE:
<223> OTHER INFORMATION: Synthetic DNA

<400> SEQUENCE: 24
atatggatcc tactggcagc acatactttg                                    30

<210> SEQ ID NO 25
<211> LENGTH: 21
<212> TYPE: DNA
<213> ORGANISM: Artificial Sequence
<220> FEATURE:
<223> OTHER INFORMATION: Synthetic DNA

<400> SEQUENCE: 25
caccgcagac ggaggataca c                                             21

<210> SEQ ID NO 26
<211> LENGTH: 22
<212> TYPE: DNA
<213> ORGANISM: Artificial Sequence
<220> FEATURE:
<223> OTHER INFORMATION: Synthetic DNA

<400> SEQUENCE: 26
cggacgtcac ccaataatcg tg                                            22

<210> SEQ ID NO 27
<211> LENGTH: 23
<212> TYPE: DNA
<213> ORGANISM: Artificial Sequence
<220> FEATURE:
<223> OTHER INFORMATION: Synthetic DNA

<400> SEQUENCE: 27
ccgatggcra aagcstgtra acg                                           23

<210> SEQ ID NO 28
<211> LENGTH: 21
<212> TYPE: DNA
<213> ORGANISM: Artificial Sequence
<220> FEATURE:
<223> OTHER INFORMATION: Synthetic DNA

<400> SEQUENCE: 28
cggcagatcr gcdtcttttc c                                             21

<210> SEQ ID NO 29
<211> LENGTH: 26
<212> TYPE: DNA
<213> ORGANISM: Artificial Sequence
<220> FEATURE:
<223> OTHER INFORMATION: Synthetic DNA

<400> SEQUENCE: 29
gctaggtctt gaacattgtg caaccc                                        26

<210> SEQ ID NO 30
<211> LENGTH: 23
<212> TYPE: DNA
<213> ORGANISM: Artificial Sequence
<220> FEATURE:
<223> OTHER INFORMATION: Synthetic DNA

<400> SEQUENCE: 30
```

-continued

```
ggtgttccga tagactcaat ggc                                          23

<210> SEQ ID NO 31
<211> LENGTH: 44
<212> TYPE: DNA
<213> ORGANISM: Artificial Sequence
<220> FEATURE:
<223> OTHER INFORMATION: Synthetic DNA

<400> SEQUENCE: 31
catgccatgg agaaaaaaac tgtacttgtc attgctgact tagg                    44

<210> SEQ ID NO 32
<211> LENGTH: 38
<212> TYPE: DNA
<213> ORGANISM: Artificial Sequence
<220> FEATURE:
<223> OTHER INFORMATION: Synthetic DNA

<400> SEQUENCE: 32
cgcggatccc ttcactaatt catccattaa ctgaatcg                           38

<210> SEQ ID NO 33
<211> LENGTH: 12
<212> TYPE: PRT
<213> ORGANISM: Artificial Sequence
<220> FEATURE:
<223> OTHER INFORMATION: Synthetic Protein
<220> FEATURE:
<221> NAME/KEY: UNSURE
<222> LOCATION: (3)
<223> OTHER INFORMATION: Xaa is Ala, Arg, Asn, Asp, Cys, Glu, Gln, Gly,
      His, Ile, Leu, Lys, Met, Phe, Pro, Ser, Thr, Trp, Tyr or Val
<220> FEATURE:
<221> NAME/KEY: UNSURE
<222> LOCATION: (4)
<223> OTHER INFORMATION: Xaa is Ala, Arg, Asn, Asp, Cys, Glu, Gln, Gly,
      His, Ile, Leu, Lys, Met, Phe, Pro, Ser, Thr, Trp, Tyr or Val
<220> FEATURE:
<221> NAME/KEY: UNSURE
<222> LOCATION: (9)
<223> OTHER INFORMATION: Xaa is Ala, Arg, Asn, Asp, Cys, Glu, Gln, Gly,
      His, Ile, Leu, Lys, Met, Phe, Pro, Ser, Thr, Trp, Tyr or Val
<220> FEATURE:
<221> NAME/KEY: UNSURE
<222> LOCATION: (10)
<223> OTHER INFORMATION: Xaa is Leu, Ile, Val, Met or Ala
<220> FEATURE:
<221> NAME/KEY: UNSURE
<222> LOCATION: (11)
<223> OTHER INFORMATION: Xaa is Glu, Ser or Ala
<220> FEATURE:
<221> NAME/KEY: UNSURE
<222> LOCATION: (12)
<223> OTHER INFORMATION: Xaa is Gly, Ser or Ala
<220> FEATURE:
<223> OTHER INFORMATION: Amino acid sequence used for data base search

<400> SEQUENCE: 33

His Gly Xaa Xaa Gly Gln Asp Gly Xaa Xaa Xaa Xaa
               5                  10

<210> SEQ ID NO 34
<211> LENGTH: 28
<212> TYPE: PRT
<213> ORGANISM: Artificial Sequence
<220> FEATURE:
<223> OTHER INFORMATION: Synthetic Protein
<220> FEATURE:
<221> NAME/KEY: UNSURE
<222> LOCATION: (1)
<223> OTHER INFORMATION: Xaa is Leu Ile or Val
```

```
<220> FEATURE:
<221> NAME/KEY: UNSURE
<222> LOCATION: (2)
<223> OTHER INFORMATION: Xaa is Ala, Arg, Asn, Asp, Cys, Glu, Gln, Gly,
      His, Ile, Leu, Lys, Met, Phe, Pro, Ser, Thr, Trp, Tyr or Val
<220> FEATURE:
<221> NAME/KEY: UNSURE
<222> LOCATION: (3)
<223> OTHER INFORMATION: Xaa is Ala, Arg, Asn, Asp, Cys, Glu, Gln, Gly,
      His, Ile, Leu, Lys, Met, Phe, Pro, Ser, Thr, Trp, Tyr or Val
<220> FEATURE:
<221> NAME/KEY: UNSURE
<222> LOCATION: (4)
<223> OTHER INFORMATION: Xaa is Ala, Arg, Asn, Asp, Cys, Glu, Gln, Gly,
      His, Ile, Leu, Lys, Met, Phe, Pro, Ser, Thr, Trp, Tyr or Val
<220> FEATURE:
<221> NAME/KEY: UNSURE
<222> LOCATION: (5)
<223> OTHER INFORMATION: Xaa is Gly or Ala
<220> FEATURE:
<221> NAME/KEY: UNSURE
<222> LOCATION: (6)
<223> OTHER INFORMATION: Xaa is Ala, Arg, Asn, Asp, Cys, Glu, Gln, Gly,
      His, Ile, Leu, Lys, Met, Phe, Pro, Ser, Thr, Trp, Tyr or Val
<220> FEATURE:
<221> NAME/KEY: UNSURE
<222> LOCATION: (7)
<223> OTHER INFORMATION: Xaa is Gly, Ser, Ala, Ile or Val
<220> FEATURE:
<221> NAME/KEY: UNSURE
<222> LOCATION: (9)
<223> OTHER INFORMATION: Xaa is Leu, Ile, Val, Met, Cys or Ala
<220> FEATURE:
<221> NAME/KEY: UNSURE
<222> LOCATION: (11)
<223> OTHER INFORMATION: Xaa is Leu, Ile, Val, Met, Phe or Ala
<220> FEATURE:
<221> NAME/KEY: UNSURE
<222> LOCATION: (12)
<223> OTHER INFORMATION: Xaa is Leu, Ile, Val, Met, Phe or Ala
<220> FEATURE:
<221> NAME/KEY: UNSURE
<222> LOCATION: (13)
<223> OTHER INFORMATION: Xaa is Ala, Arg, Asn, Asp, Cys, Glu, Gln, Gly,
      His, Ile, Leu, Lys, Met, Phe, Pro, Ser, Thr, Trp, Tyr or Val
<220> FEATURE:
<221> NAME/KEY: UNSURE
<222> LOCATION: (14)
<223> OTHER INFORMATION: Xaa is Ala, Arg, Asn, Asp, Cys, Glu, Gln, Gly,
      His, Ile, Leu, Lys, Met, Phe, Pro, Ser, Thr, Trp, Tyr or Val
<220> FEATURE:
<221> NAME/KEY: UNSURE
<222> LOCATION: (15)
<223> OTHER INFORMATION: Xaa is Ala, Arg, Asn, Asp, Cys, Glu, Gln, Gly,
      His, Ile, Leu, Lys, Met, Phe, Pro, Ser, Thr, Trp, Tyr or Val
<220> FEATURE:
<221> NAME/KEY: UNSURE
<222> LOCATION: (16)
<223> OTHER INFORMATION: Xaa is Ala, Arg, Asn, Asp, Cys, Glu, Gln, Gly,
      His, Ile, Leu, Lys, Met, Phe, Pro, Ser, Thr, Trp, Tyr or Val
<220> FEATURE:
<221> NAME/KEY: UNSURE
<222> LOCATION: (17)
<223> OTHER INFORMATION: Xaa is Ala, Arg, Asn, Asp, Cys, Glu, Gln, Gly,
      His, Ile, Leu, Lys, Met, Phe, Pro, Ser, Thr, Trp, Tyr or Val
<220> FEATURE:
<221> NAME/KEY: UNSURE
<222> LOCATION: (18)
<223> OTHER INFORMATION: Xaa is Ala, Arg, Asn, Asp, Cys, Glu, Gln, Gly,
      His, Ile, Leu, Lys, Met, Phe, Pro, Ser, Thr, Trp, Tyr or Val
<220> FEATURE:
<221> NAME/KEY: UNSURE
<222> LOCATION: (19)
<223> OTHER INFORMATION: Xaa is Ala, Arg, Asn, Asp, Cys, Glu, Gln, Gly,
      His, Ile, Leu, Lys, Met, Phe, Pro, Ser, Thr, Trp, Tyr or Val
<220> FEATURE:
<221> NAME/KEY: UNSURE
<222> LOCATION: (20)
<223> OTHER INFORMATION: Xaa is Leu, Ile or Val
<220> FEATURE:
```

```
<221> NAME/KEY: UNSURE
<222> LOCATION: (21)
<223> OTHER INFORMATION: Xaa is Ala, Arg, Asn, Asp, Cys, Glu, Gln, Gly,
      His, Ile, Leu, Lys, Met, Phe, Pro, Ser, Thr, Trp, Tyr or Val
<220> FEATURE:
<221> NAME/KEY: UNSURE
<222> LOCATION: (23)
<223> OTHER INFORMATION: Xaa is Leu, Ile, Val, Ala or Pro
<220> FEATURE:
<221> NAME/KEY: UNSURE
<222> LOCATION: (25)
<223> OTHER INFORMATION: Xaa is Ser, Thr or Pro
<220> FEATURE:
<221> NAME/KEY: UNSURE
<222> LOCATION: (26)
<223> OTHER INFORMATION: Xaa is Ala, Arg, Asn, Asp, Cys, Glu, Gln, Gly,
      His, Ile, Leu, Lys, Met, Phe, Pro, Ser, Thr, Trp, Tyr or Val
<220> FEATURE:
<221> NAME/KEY: UNSURE
<222> LOCATION: (28)
<223> OTHER INFORMATION: Xaa is Gly or Ala
<220> FEATURE:
<223> OTHER INFORMATION: Amino acid sequence used for data base search

<400> SEQUENCE: 34

Xaa Xaa Xaa Xaa Xaa Xaa Xaa Arg Xaa Asp Xaa Xaa Xaa Xaa Xaa Xaa
                 5                  10                  15

Xaa Xaa Xaa Xaa Xaa Gln Xaa Asn Xaa Xaa Pro Xaa
            20                  25

<210> SEQ ID NO 35
<211> LENGTH: 30
<212> TYPE: PRT
<213> ORGANISM: Artificial Sequence
<220> FEATURE:
<223> OTHER INFORMATION: Synthetic Protein
<220> FEATURE:
<221> NAME/KEY: UNSURE
<222> LOCATION: (1)
<223> OTHER INFORMATION: Xaa is Leu, Ile or Val
<220> FEATURE:
<221> NAME/KEY: UNSURE
<222> LOCATION: (2)
<223> OTHER INFORMATION: Xaa is Ala, Arg, Asn, Asp, Cys, Glu, Gln, Gly,
      His, Ile, Leu, Lys, Met, Phe, Pro, Ser, Thr, Trp, Tyr or Val
<220> FEATURE:
<221> NAME/KEY: UNSURE
<222> LOCATION: (3)
<223> OTHER INFORMATION: Xaa is Ala, Arg, Asn, Asp, Cys, Glu, Gln, Gly,
      His, Ile, Leu, Lys, Met, Phe, Pro, Ser, Thr, Trp, Tyr or Val
<220> FEATURE:
<221> NAME/KEY: UNSURE
<222> LOCATION: (4)
<223> OTHER INFORMATION: Xaa is Ala, Arg, Asn, Asp, Cys, Glu, Gln, Gly,
      His, Ile, Leu, Lys, Met, Phe, Pro, Ser, Thr, Trp, Tyr or Val
<220> FEATURE:
<221> NAME/KEY: UNSURE
<222> LOCATION: (5)
<223> OTHER INFORMATION: Xaa is Gly or Ala
<220> FEATURE:
<221> NAME/KEY: UNSURE
<222> LOCATION: (6)
<223> OTHER INFORMATION: Xaa is Ala, Arg, Asn, Asp, Cys, Glu, Gln, Gly,
      His, Ile, Leu, Lys, Met, Phe, Pro, Ser, Thr, Trp, Tyr or Val
<220> FEATURE:
<221> NAME/KEY: UNSURE
<222> LOCATION: (7)
<223> OTHER INFORMATION: Xaa is Gly, Ser, Ala, Ile or Val
<220> FEATURE:
<221> NAME/KEY: UNSURE
<222> LOCATION: (9)
<223> OTHER INFORMATION: Xaa is Leu, Ile, Val, Met, Cys or Ala
<220> FEATURE:
<221> NAME/KEY: UNSURE
<222> LOCATION: (11)
<223> OTHER INFORMATION: Xaa is Leu, Ile, Val, Met, Phe or Ala
<220> FEATURE:
```

```
<221> NAME/KEY: UNSURE
<222> LOCATION: (12)
<223> OTHER INFORMATION: Xaa is Leu, Ile, Val, Met, Phe or Ala
<220> FEATURE:
<221> NAME/KEY: UNSURE
<222> LOCATION: (13)
<223> OTHER INFORMATION: Xaa is Ala, Arg, Asn, Asp, Cys, Glu, Gln, Gly,
      His, Ile, Leu, Lys, Met, Phe, Pro, Ser, Thr, Trp, Tyr or Val
<220> FEATURE:
<221> NAME/KEY: UNSURE
<222> LOCATION: (14)
<223> OTHER INFORMATION: Xaa is Ala, Arg, Asn, Asp, Cys, Glu, Gln, Gly,
      His, Ile, Leu, Lys, Met, Phe, Pro, Ser, Thr, Trp, Tyr or Val
<220> FEATURE:
<221> NAME/KEY: UNSURE
<222> LOCATION: (15)
<223> OTHER INFORMATION: Xaa is Ala, Arg, Asn, Asp, Cys, Glu, Gln, Gly,
      His, Ile, Leu, Lys, Met, Phe, Pro, Ser, Thr, Trp, Tyr or Val
<220> FEATURE:
<221> NAME/KEY: UNSURE
<222> LOCATION: (16)
<223> OTHER INFORMATION: Xaa is Ala, Arg, Asn, Asp, Cys, Glu, Gln, Gly,
      His, Ile, Leu, Lys, Met, Phe, Pro, Ser, Thr, Trp, Tyr or Val
<220> FEATURE:
<221> NAME/KEY: UNSURE
<222> LOCATION: (17)
<223> OTHER INFORMATION: Xaa is Ala, Arg, Asn, Asp, Cys, Glu, Gln, Gly,
      His, Ile, Leu, Lys, Met, Phe, Pro, Ser, Thr, Trp, Tyr or Val
<220> FEATURE:
<221> NAME/KEY: UNSURE
<222> LOCATION: (18)
<223> OTHER INFORMATION: Xaa is Ala, Arg, Asn, Asp, Cys, Glu, Gln, Gly,
      His, Ile, Leu, Lys, Met, Phe, Pro, Ser, Thr, Trp, Tyr or Val
<220> FEATURE:
<221> NAME/KEY: UNSURE
<222> LOCATION: (19)
<223> OTHER INFORMATION: Xaa is Ala, Arg, Asn, Asp, Cys, Glu, Gln, Gly,
      His, Ile, Leu, Lys, Met, Phe, Pro, Ser, Thr, Trp, Tyr or Val
<220> FEATURE:
<221> NAME/KEY: UNSURE
<222> LOCATION: (20)
<223> OTHER INFORMATION: Xaa is Ala, Arg, Asn, Asp, Cys, Glu, Gln, Gly,
      His, Ile, Leu, Lys, Met, Phe, Pro, Ser, Thr, Trp, Tyr or Val
<220> FEATURE:
<221> NAME/KEY: UNSURE
<222> LOCATION: (21)
<223> OTHER INFORMATION: Xaa is Ala, Arg, Asn, Asp, Cys, Glu, Gln, Gly,
      His, Ile, Leu, Lys, Met, Phe, Pro, Ser, Thr, Trp, Tyr or Val
<220> FEATURE:
<221> NAME/KEY: UNSURE
<222> LOCATION: (22)
<223> OTHER INFORMATION: Xaa is Leu, Ile or Val
<220> FEATURE:
<221> NAME/KEY: UNSURE
<222> LOCATION: (23)
<223> OTHER INFORMATION: Xaa is Ala, Arg, Asn, Asp, Cys, Glu, Gln, Gly,
      His, Ile, Leu, Lys, Met, Phe, Pro, Ser, Thr, Trp, Tyr or Val
<220> FEATURE:
<221> NAME/KEY: UNSURE
<222> LOCATION: (25)
<223> OTHER INFORMATION: Xaa is Leu, Ile, Val, Ala or Pro
<220> FEATURE:
<221> NAME/KEY: UNSURE
<222> LOCATION: (27)
<223> OTHER INFORMATION: Xaa is Ser, Thr or Pro
<220> FEATURE:
<221> NAME/KEY: UNSURE
<222> LOCATION: (28)
<223> OTHER INFORMATION: Xaa is Ala, Arg, Asn, Asp, Cys, Glu, Gln, Gly,
      His, Ile, Leu, Lys, Met, Phe, Pro, Ser, Thr, Trp, Tyr or Val
<220> FEATURE:
<221> NAME/KEY: UNSURE
<222> LOCATION: (30)
<223> OTHER INFORMATION: Xaa is Gly or Ala
<220> FEATURE:
<223> OTHER INFORMATION: Amino acid sequence used for data base search

<400> SEQUENCE: 35

Xaa Xaa Xaa Xaa Xaa Xaa Xaa Arg Xaa Asp Xaa Xaa Xaa Xaa Xaa Xaa
```

```
                      5                  10                  15
Xaa Xaa Xaa Xaa Xaa Xaa Xaa Gln Xaa Asn Xaa Xaa Pro Xaa
                 20                  25                  30

<210> SEQ ID NO 36
<211> LENGTH: 1416
<212> TYPE: DNA
<213> ORGANISM: Bacillus subtilis

<400> SEQUENCE: 36 atg gag aga aaa aca gta ttg gtc atc gct gat ctt gga ggc tgc ccg      48
Met Glu Arg Lys Thr Val Leu Val Ile Ala Asp Leu Gly Gly Cys Pro
1               5                   10                  15 ccg cac atg ttt tat aaa agc gct gct gaa aaa tat aac ctg gtc agc      96
Pro His Met Phe Tyr Lys Ser Ala Ala Glu Lys Tyr Asn Leu Val Ser
                20                  25                  30 ttt att cca aga cct ttt gca att aca gcc tcc cat gca gca ttg att     144
Phe Ile Pro Arg Pro Phe Ala Ile Thr Ala Ser His Ala Ala Leu Ile
            35                  40                  45 gaa aaa tac tcg gtc gcg gtc ata aaa gat aaa gac tat ttt aag agt     192
Glu Lys Tyr Ser Val Ala Val Ile Lys Asp Lys Asp Tyr Phe Lys Ser
        50                  55                  60 tta gct gat ttt gag cat cct gat tcc att tat tgg gcg cat gag gat     240
Leu Ala Asp Phe Glu His Pro Asp Ser Ile Tyr Trp Ala His Glu Asp
65                  70                  75                  80 cat aac aag cct gag gaa gag gtc gtc gag caa atc gtc aag gtt gcc     288
His Asn Lys Pro Glu Glu Glu Val Val Glu Gln Ile Val Lys Val Ala
                85                  90                  95 gaa atg ttt ggg gcg gat gcc atc aca aca aac aat gaa tta ttc att     336
Glu Met Phe Gly Ala Asp Ala Ile Thr Thr Asn Asn Glu Leu Phe Ile
                100                 105                 110 gct ccg atg gcg aaa gcc tgt gaa cgt ctg ggc ctg aga ggt gcc ggc     384
Ala Pro Met Ala Lys Ala Cys Glu Arg Leu Gly Leu Arg Gly Ala Gly
            115                 120                 125 gtg cag gca gcc gaa aat gcc aga gat aaa aat aaa atg agg gac gct     432
Val Gln Ala Ala Glu Asn Ala Arg Asp Lys Asn Lys Met Arg Asp Ala
        130                 135                 140 ttt aat aag gcc gga gtc aaa tcg atc aaa aac aaa cga gtc aca act     480
Phe Asn Lys Ala Gly Val Lys Ser Ile Lys Asn Lys Arg Val Thr Thr
145                 150                 155                 160 ctt gaa gat ttc cgt gct gct ctt gaa gag atc ggc aca cct ctt atc     528
Leu Glu Asp Phe Arg Ala Ala Leu Glu Glu Ile Gly Thr Pro Leu Ile
                165                 170                 175 tta aag cct aca tac tta gcg agt tca atc ggt gta acg ctg att acg     576
Leu Lys Pro Thr Tyr Leu Ala Ser Ser Ile Gly Val Thr Leu Ile Thr
                180                 185                 190 gac act gag acg gca gaa gat gaa ttt aac aga gtc aat gac tat ctg     624
Asp Thr Glu Thr Ala Glu Asp Glu Phe Asn Arg Val Asn Asp Tyr Leu
            195                 200                 205 aaa tca att aac gtg cca aag gcg gtt acg ttt gaa gcg ccg ttt atc     672
Lys Ser Ile Asn Val Pro Lys Ala Val Thr Phe Glu Ala Pro Phe Ile
        210                 215                 220 gct gaa gaa ttt tta cag ggt gag tac gga gac tgg tat caa aca gaa     720
Ala Glu Glu Phe Leu Gln Gly Glu Tyr Gly Asp Trp Tyr Gln Thr Glu
225                 230                 235                 240 ggg tac tcc gac tat atc agt ata gaa ggc atc atg gct gac ggt gag     768
Gly Tyr Ser Asp Tyr Ile Ser Ile Glu Gly Ile Met Ala Asp Gly Glu
                245                 250                 255 tat ttc ccg atc gcc att cat gat aaa acg ccg caa atc ggg ttt aca     816
Tyr Phe Pro Ile Ala Ile His Asp Lys Thr Pro Gln Ile Gly Phe Thr
                260                 265                 270
```

```
gag aca tcc cac att acg ccg tcc att ctg gat gaa gag gca aaa aag      864
Glu Thr Ser His Ile Thr Pro Ser Ile Leu Asp Glu Glu Ala Lys Lys
        275                 280                 285 aaa att gtc gaa gct gcc aaa aag gca aat gaa ggg ctt ggc ctg caa      912
Lys Ile Val Glu Ala Ala Lys Lys Ala Asn Glu Gly Leu Gly Leu Gln
290                 295                 300 aat tgc gca aca cat aca gag atc aag cta atg aaa aac aga gaa ccg      960
Asn Cys Ala Thr His Thr Glu Ile Lys Leu Met Lys Asn Arg Glu Pro
305                 310                 315                 320 ggt tta ata gag tcg gca gcc aga ttc gca ggc tgg aat atg att cct     1008
Gly Leu Ile Glu Ser Ala Ala Arg Phe Ala Gly Trp Asn Met Ile Pro
                325                 330                 335 aat att aaa aag gtc ttt ggc ctt gat atg gcg caa tta tta tta gat     1056
Asn Ile Lys Lys Val Phe Gly Leu Asp Met Ala Gln Leu Leu Leu Asp
        340                 345                 350 gtc ctc tgt ttc gga aaa gac gcc gat ctg ccg gac gga tta ttg gat     1104
Val Leu Cys Phe Gly Lys Asp Ala Asp Leu Pro Asp Gly Leu Leu Asp
            355                 360                 365 caa gag cct tat tat gtt gcc gac tgc cat ttg tac ccg cag cat ttc     1152
Gln Glu Pro Tyr Tyr Val Ala Asp Cys His Leu Tyr Pro Gln His Phe
370                 375                 380 aaa caa aat ggc cag att cca gaa acc gct gag gat ttg gtc att gaa     1200
Lys Gln Asn Gly Gln Ile Pro Glu Thr Ala Glu Asp Leu Val Ile Glu
385                 390                 395                 400 gcg atc gat att ccg gac ggg ctt tta aaa ggg gat act gaa atc gtt     1248
Ala Ile Asp Ile Pro Asp Gly Leu Leu Lys Gly Asp Thr Glu Ile Val
                405                 410                 415 tca ttt tca gcc gca gca cca ggc act tca gtt gat ttg aca ttg ttt     1296
Ser Phe Ser Ala Ala Ala Pro Gly Thr Ser Val Asp Leu Thr Leu Phe
            420                 425                 430 gaa gct ttc aat tcc att gct gca ttt gaa ctg aaa ggc agt aat tca     1344
Glu Ala Phe Asn Ser Ile Ala Ala Phe Glu Leu Lys Gly Ser Asn Ser
                435                 440                 445 cag gat gtg gct gaa tca atc aga caa att cag cag cat gca aag ctg     1392
Gln Asp Val Ala Glu Ser Ile Arg Gln Ile Gln Gln His Ala Lys Leu
450                 455                 460 acg gca aag tat gtg ctg cca gta                                     1416
Thr Ala Lys Tyr Val Leu Pro Val
465                 470
```

<210> SEQ ID NO 37
<211> LENGTH: 239
<212> TYPE: PRT
<213> ORGANISM: Streptomyces noursei

<400> SEQUENCE: 37

```
Met Leu Ala Gly Leu Val Pro Ala Pro Asp His Gly Met Arg Glu Glu
 1               5                  10                  15

Ile Leu Gly Asp Arg Ser Arg Leu Ile Arg Gln Arg Gly Glu His Ala
             20                  25                  30

Leu Ile Gly Ile Ser Ala Gly Asn Ser Tyr Phe Ser Gln Lys Asn Thr
         35                  40                  45

Val Met Leu Leu Gln Trp Ala Gly Gln Arg Phe Glu Arg Thr Asp Val
     50                  55                  60

Val Tyr Val Asp Thr His Ile Asp Glu Met Leu Ile Ala Asp Gly Arg
 65                  70                  75                  80

Ser Ala Gln Glu Ala Glu Arg Ser Val Lys Arg Thr Leu Lys Asp Leu
                 85                  90                  95

Arg Arg Arg Leu Arg Arg Ser Leu Glu Ser Val Gly Asp His Ala Glu
```

```
            100                 105                 110
Arg Phe Arg Val Arg Ser Leu Ser Glu Leu Gln Glu Thr Pro Glu Tyr
        115                 120                 125

Arg Ala Val Arg Glu Arg Thr Asp Arg Ala Phe Glu Glu Asp Ala Glu
        130                 135                 140

Phe Ala Thr Ala Cys Glu Asp Met Val Arg Ala Val Val Met Asn Arg
145                 150                 155                 160

Pro Gly Asp Gly Val Gly Ile Ser Ala Glu His Leu Arg Ala Gly Leu
                165                 170                 175

Asn Tyr Val Leu Ala Glu Ala Pro Leu Phe Ala Asp Ser Pro Gly Val
            180                 185                 190

Phe Ser Val Pro Ser Ser Val Leu Cys Tyr His Ile Asp Thr Pro Ile
        195                 200                 205

Thr Ala Phe Leu Ser Arg Arg Glu Thr Gly Phe Arg Ala Ala Glu Gly
210                 215                 220

Gln Ala Tyr Val Val Arg Pro Gln Glu Leu Ala Asp Ala Ala
225                 230                 235

<210> SEQ ID NO 38
<211> LENGTH: 239
<212> TYPE: PRT
<213> ORGANISM: Streptomyces alborus

<400> SEQUENCE: 38

Met Leu Ala Gly Leu Val Pro Ala Leu Asp His Ser Met Arg Glu Glu
1               5                   10                  15

Ile Leu Gly Asn Arg Gly Arg Lys Ile Arg Gln Arg Gly Glu His Ala
                20                  25                  30

Leu Ile Gly Ile Ser Ala Gly Asn Ser Tyr Phe Ser Gln Lys Asn Val
            35                  40                  45

Thr Met Leu Leu Gln Trp Ala Gly Gln His Phe Glu Arg Thr Asp Val
        50                  55                  60

Val Tyr Val Asp Thr His Ile Asp Asp Met Leu Met Ala Asp Gly Arg
65                  70                  75                  80

Ser Ala Gln Glu Ala Glu Lys Ser Val Lys Arg Thr Leu Lys Asp Leu
                85                  90                  95

Arg Arg Arg Leu Arg Arg Ser Leu Glu Ser Val Gly Asp His Ser Glu
            100                 105                 110

Arg Phe Arg Val Arg Ser Leu Ser Glu Ile Gln Glu Thr Pro Glu Tyr
        115                 120                 125

Arg Ala Ala Arg Glu Ser Thr Asp Arg Ala Phe Arg Glu Asp Gly Glu
        130                 135                 140

Phe Ala Thr Val Cys Glu Glu Met Val Arg Ala Val Val Met Asn Arg
145                 150                 155                 160

Pro Gly Asp Gly Val Asp Ile Ser Glu Glu His Leu Arg Ala Gly Leu
                165                 170                 175

Asn Tyr Val Leu Ala Glu Ala Pro Leu Phe Ala Asp Ser Pro Gly Val
            180                 185                 190

Phe Ser Val Pro Ser Ser Val Leu Cys Tyr His Ile Pro Thr Pro Val
        195                 200                 205

Ser Thr Phe Leu Ala His Arg Glu Thr Gly Phe Gln Ala Ala Gln Gly
        210                 215                 220

Gln Ala Tyr Val Val Arg Pro Gln Glu Leu Ala Asp Ala Ala
225                 230                 235
```

<210> SEQ ID NO 39
<211> LENGTH: 717
<212> TYPE: DNA
<213> ORGANISM: Streptomyces noursei

<400> SEQUENCE: 39

| | | | | | | | | | | | | | | | | |
|---|---|---|---|---|---|---|---|---|---|---|---|---|---|---|---|---|
| atg | ctt | gca | ggc | tta | gtt | ccc | gcg | ccg | gac | cac | gga | atg | cgg | gaa | gaa | 48 |
| Met | Leu | Ala | Gly | Leu | Val | Pro | Ala | Pro | Asp | His | Gly | Met | Arg | Glu | Glu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ata | ctt | ggc | gac | cgc | agc | cga | ttg | atc | cgg | caa | cgc | ggt | gag | cac | gcc | 96 |
| Ile | Leu | Gly | Asp | Arg | Ser | Arg | Leu | Ile | Arg | Gln | Arg | Gly | Glu | His | Ala | |
| | | | 20 | | | | | 25 | | | | | 30 | | | |

| | | | | | | | | | | | | | | | | |
|---|---|---|---|---|---|---|---|---|---|---|---|---|---|---|---|---|
| ctc | atc | gga | atc | agt | gcg | ggc | aac | agt | tat | ttc | agc | cag | aag | aac | acc | 144 |
| Leu | Ile | Gly | Ile | Ser | Ala | Gly | Asn | Ser | Tyr | Phe | Ser | Gln | Lys | Asn | Thr | |
| | | 35 | | | | | 40 | | | | | 45 | | | | |

| | | | | | | | | | | | | | | | | |
|---|---|---|---|---|---|---|---|---|---|---|---|---|---|---|---|---|
| gtc | atg | ctg | ctg | caa | tgg | gcc | ggg | cag | cgt | ttc | gag | cgc | acc | gat | gtc | 192 |
| Val | Met | Leu | Leu | Gln | Trp | Ala | Gly | Gln | Arg | Phe | Glu | Arg | Thr | Asp | Val | |
| 50 | | | | | 55 | | | | | 60 | | | | | | |

| | | | | | | | | | | | | | | | | |
|---|---|---|---|---|---|---|---|---|---|---|---|---|---|---|---|---|
| gtc | tat | gtc | gac | acc | cac | atc | gac | gag | atg | ctg | atc | gcc | gac | ggc | cgc | 240 |
| Val | Tyr | Val | Asp | Thr | His | Ile | Asp | Glu | Met | Leu | Ile | Ala | Asp | Gly | Arg | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| agc | gcg | cag | gag | gcc | gag | cgg | tcg | gtc | aaa | cgc | acg | ctc | aag | gat | ctg | 288 |
| Ser | Ala | Gln | Glu | Ala | Glu | Arg | Ser | Val | Lys | Arg | Thr | Leu | Lys | Asp | Leu | |
| | | | | 85 | | | | | 90 | | | | | 95 | | |

| | | | | | | | | | | | | | | | | |
|---|---|---|---|---|---|---|---|---|---|---|---|---|---|---|---|---|
| cgg | cgc | aga | ctc | cgg | cgc | tcg | ctg | gag | agc | gtg | ggc | gac | cac | gcc | gag | 336 |
| Arg | Arg | Arg | Leu | Arg | Arg | Ser | Leu | Glu | Ser | Val | Gly | Asp | His | Ala | Glu | |
| | | | 100 | | | | | 105 | | | | | 110 | | | |

| | | | | | | | | | | | | | | | | |
|---|---|---|---|---|---|---|---|---|---|---|---|---|---|---|---|---|
| cgg | ttc | cgt | gtc | cgg | tcc | ctg | tcc | gag | ctc | cag | gag | acc | cct | gag | tac | 384 |
| Arg | Phe | Arg | Val | Arg | Ser | Leu | Ser | Glu | Leu | Gln | Glu | Thr | Pro | Glu | Tyr | |
| | | 115 | | | | | 120 | | | | | 125 | | | | |

| | | | | | | | | | | | | | | | | |
|---|---|---|---|---|---|---|---|---|---|---|---|---|---|---|---|---|
| cgg | gcc | gta | cgc | gag | cgc | acc | gac | cgg | gcc | ttc | gag | gag | gac | gcc | gaa | 432 |
| Arg | Ala | Val | Arg | Glu | Arg | Thr | Asp | Arg | Ala | Phe | Glu | Glu | Asp | Ala | Glu | |
| 130 | | | | | 135 | | | | | 140 | | | | | | |

| | | | | | | | | | | | | | | | | |
|---|---|---|---|---|---|---|---|---|---|---|---|---|---|---|---|---|
| ttc | gcc | acc | gcc | tgc | gag | gac | atg | gtg | cgg | gcc | gtg | gtg | atg | aac | cgg | 480 |
| Phe | Ala | Thr | Ala | Cys | Glu | Asp | Met | Val | Arg | Ala | Val | Val | Met | Asn | Arg | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| ccc | ggt | gac | ggc | gtc | ggc | atc | tcc | gcg | gaa | cac | ctg | cgg | gcc | ggt | ctg | 528 |
| Pro | Gly | Asp | Gly | Val | Gly | Ile | Ser | Ala | Glu | His | Leu | Arg | Ala | Gly | Leu | |
| | | | | 165 | | | | | 170 | | | | | 175 | | |

| | | | | | | | | | | | | | | | | |
|---|---|---|---|---|---|---|---|---|---|---|---|---|---|---|---|---|
| aac | tac | gtg | ctg | gcc | gag | gcc | ccg | ctc | ttc | gcg | gac | tcg | ccc | gga | gtc | 576 |
| Asn | Tyr | Val | Leu | Ala | Glu | Ala | Pro | Leu | Phe | Ala | Asp | Ser | Pro | Gly | Val | |
| | | | 180 | | | | | 185 | | | | | 190 | | | |

| | | | | | | | | | | | | | | | | |
|---|---|---|---|---|---|---|---|---|---|---|---|---|---|---|---|---|
| ttc | tcc | gtc | ccc | tcc | tcg | gtg | ctc | tgc | tac | cac | atc | gac | acc | ccg | atc | 624 |
| Phe | Ser | Val | Pro | Ser | Ser | Val | Leu | Cys | Tyr | His | Ile | Asp | Thr | Pro | Ile | |
| | | 195 | | | | | 200 | | | | | 205 | | | | |

| | | | | | | | | | | | | | | | | |
|---|---|---|---|---|---|---|---|---|---|---|---|---|---|---|---|---|
| acg | gcg | ttc | ctg | tcc | cgg | cgc | gag | acc | ggt | ttc | cgg | gcg | gcc | gag | gga | 672 |
| Thr | Ala | Phe | Leu | Ser | Arg | Arg | Glu | Thr | Gly | Phe | Arg | Ala | Ala | Glu | Gly | |
| | | 210 | | | | | 215 | | | | | 220 | | | | |

| | | | | | | | | | | | | | | |
|---|---|---|---|---|---|---|---|---|---|---|---|---|---|---|
| cag | gcg | tac | gtc | gtc | gtc | agg | ccc | cag | gag | ctg | gcc | gac | gcg | gcc | 717 |
| Gln | Ala | Tyr | Val | Val | Val | Arg | Pro | Gln | Glu | Leu | Ala | Asp | Ala | Ala | |
| 225 | | | | | 230 | | | | | 235 | | | | | |

<210> SEQ ID NO 40
<211> LENGTH: 717
<212> TYPE: DNA
<213> ORGANISM: Streptomyces alborus

<400> SEQUENCE: 40

| | | | | | | | | | | | | | | | | |
|---|---|---|---|---|---|---|---|---|---|---|---|---|---|---|---|---|
| atg | ctt | gca | ggc | tta | gtt | ccc | gcg | ctg | gac | cac | agc | atg | cgg | gaa | gaa | 48 |
| Met | Leu | Ala | Gly | Leu | Val | Pro | Ala | Leu | Asp | His | Ser | Met | Arg | Glu | Glu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ata | ctt | ggc | aat | cgc | ggc | cga | aag | atc | cgg | caa | cgc | ggt | gag | cac | gct | 96 |

```
                Ile Leu Gly Asn Arg Gly Arg Lys Ile Arg Gln Arg Gly Glu His Ala
                                 20                  25                  30 ctc att gga atc agt gcg ggc aac agt tat ttc agc cag aag aac gtc         144
Leu Ile Gly Ile Ser Ala Gly Asn Ser Tyr Phe Ser Gln Lys Asn Val
             35                  40                  45 acc atg ctg ctg caa tgg gcc ggg cag cat ttc gag cgc acg gat gtc         192
Thr Met Leu Leu Gln Trp Ala Gly Gln His Phe Glu Arg Thr Asp Val
 50                  55                  60 gtc tac gtg gac acg cac atc gac gac atg ctg atg gcg gac ggc cgc         240
Val Tyr Val Asp Thr His Ile Asp Asp Met Leu Met Ala Asp Gly Arg
 65                  70                  75                  80 agc gcg cag gaa gcc gag aag tcg gtc aag cgc acg ctc aag gat ctg         288
Ser Ala Gln Glu Ala Glu Lys Ser Val Lys Arg Thr Leu Lys Asp Leu
             85                  90                  95 cgg cgc agg ctg cgg cgc tcg ttg gaa agc gtg ggc gac cac agc gag         336
Arg Arg Arg Leu Arg Arg Ser Leu Glu Ser Val Gly Asp His Ser Glu
            100                 105                 110 cgg ttc cgc gtc cgg tcc ctg tcc gag atc cag gag acc cct gag tac         384
Arg Phe Arg Val Arg Ser Leu Ser Glu Ile Gln Glu Thr Pro Glu Tyr
        115                 120                 125 cgg gcc gca cgc gag tcc acc gac cgg gcc ttc cgc gag gac ggc gag         432
Arg Ala Ala Arg Glu Ser Thr Asp Arg Ala Phe Arg Glu Asp Gly Glu
    130                 135                 140 ttc gcc acc gtc tgc gag gag atg gtg cgc gcc gtg gtg atg aac cgg         480
Phe Ala Thr Val Cys Glu Glu Met Val Arg Ala Val Val Met Asn Arg
145                 150                 155                 160 ccc ggt gac ggc gtc gac atc tcg gag gaa cac ctg cgg gcc ggt ctg         528
Pro Gly Asp Gly Val Asp Ile Ser Glu Glu His Leu Arg Ala Gly Leu
                165                 170                 175 aac tac gtg ctc gcc gag gcc ccg ctc ttc gcg gac tcg ccc ggc gtg         576
Asn Tyr Val Leu Ala Glu Ala Pro Leu Phe Ala Asp Ser Pro Gly Val
            180                 185                 190 ttc tcc gtc ccc tcg tcg gtg ctc tgc tac cac atc ccc acc ccg gta         624
Phe Ser Val Pro Ser Ser Val Leu Cys Tyr His Ile Pro Thr Pro Val
        195                 200                 205 tcg acg ttc ctg gcc cat cgc gag acc ggt ttc cag gcg gct cag ggt         672
Ser Thr Phe Leu Ala His Arg Glu Thr Gly Phe Gln Ala Ala Gln Gly
    210                 215                 220 cag gca tac gtc gtc gtc agg ccg cag gag ctg gcc gac gcg gcc             717
Gln Ala Tyr Val Val Val Arg Pro Gln Glu Leu Ala Asp Ala Ala
225                 230                 235

<210> SEQ ID NO 41
<211> LENGTH: 32
<212> TYPE: DNA
<213> ORGANISM: Artificial Sequence
<220> FEATURE:
<223> OTHER INFORMATION: Synthetic DNA

<400> SEQUENCE: 41
agagccatgg gacttgcagg cttagttccc gc                                      32

<210> SEQ ID NO 42
<211> LENGTH: 29
<212> TYPE: DNA
<213> ORGANISM: Artificial Sequence
<220> FEATURE:
<223> OTHER INFORMATION: Synthetic DNA

<400> SEQUENCE: 42
agagagatct ggccgcgtcg gccagctcc                                          29
```

```
<210> SEQ ID NO 43
<211> LENGTH: 1078
<212> TYPE: PRT
<213> ORGANISM: Brevibacillus brevis

<400> SEQUENCE: 43

Met Leu Asn Ser Ser Lys Ser Ile Leu Ile His Ala Gln Asn Lys Asn
 1               5                  10                  15

Gly Thr His Glu Glu Gln Tyr Leu Phe Ala Val Asn Asn Thr Lys
             20                  25                  30

Ala Glu Tyr Pro Arg Asp Lys Thr Ile His Gln Leu Phe Glu Glu Gln
         35                  40                  45

Val Ser Lys Arg Pro Asn Asn Val Ala Ile Val Cys Glu Asn Glu Gln
     50                  55                  60

Leu Thr Tyr His Glu Leu Asn Val Lys Ala Asn Gln Leu Ala Arg Ile
 65                  70                  75                  80

Phe Ile Glu Lys Gly Ile Gly Lys Asp Thr Leu Val Gly Ile Met Met
                 85                  90                  95

Glu Lys Ser Ile Asp Leu Phe Ile Gly Ile Leu Ala Val Leu Lys Ala
            100                 105                 110

Gly Gly Ala Tyr Val Pro Ile Asp Ile Glu Tyr Pro Lys Glu Val His
        115                 120                 125

Leu Ile His Asn Ile Gln Phe Asn Gly Gln Val Glu Ile Phe Glu Glu
    130                 135                 140

Asp Thr Ile Lys Ile Arg Glu Gly Thr Asn Leu His Val Pro Ser Lys
145                 150                 155                 160

Ser Thr Asp Leu Ala Tyr Val Ile Tyr Thr Ser Gly Thr Thr Gly Asn
                165                 170                 175

Pro Lys Gly Thr Met Leu Glu His Lys Gly Ile Ser Asn Leu Lys Val
            180                 185                 190

Phe Phe Glu Asn Ser Leu Asn Val Thr Glu Lys Asp Arg Ile Gly Gln
        195                 200                 205

Phe Ala Ser Ile Ser Phe Asp Ala Ser Val Trp Glu Met Phe Met Ala
    210                 215                 220

Leu Leu Thr Gly Ala Ser Leu Tyr Ile Ile Leu Lys Asp Thr Ile Asn
225                 230                 235                 240

Asp Phe Val Lys Phe Glu Gln Tyr Ile Asn Gln Lys Glu Ile Thr Val
                245                 250                 255

Ile Thr Leu Pro Pro Thr Tyr Val Val His Leu Asp Pro Glu Arg Ile
            260                 265                 270

Leu Ser Ile Gln Thr Leu Ile Thr Ala Gly Ser Ala Thr Ser Pro Ser
        275                 280                 285

Leu Val Asn Lys Trp Lys Glu Lys Val Thr Tyr Ile Asn Ala Tyr Gly
    290                 295                 300

Pro Thr Glu Thr Thr Ile Cys Ala Thr Thr Cys Val Ala Thr Lys Glu
305                 310                 315                 320

Thr Ile Gly His Ser Val Pro Ile Gly Ala Pro Ile Gln Asn Thr Gln
                325                 330                 335

Ile Tyr Ile Val Asp Glu Asn Leu Gln Leu Lys Ser Val Gly Glu Ala
            340                 345                 350

Gly Glu Leu Cys Ile Gly Gly Glu Gly Leu Ala Arg Gly Tyr Trp Lys
        355                 360                 365

Arg Pro Glu Leu Thr Ser Gln Lys Phe Val Asp Asn Pro Phe Val Pro
    370                 375                 380

Gly Glu Lys Leu Tyr Lys Thr Gly Asp Gln Ala Arg Trp Leu Ser Asp
```

```
               385                 390                 395                 400
Gly Asn Ile Glu Tyr Leu Gly Arg Ile Asp Asn Gln Val Lys Ile Arg
                405                 410                 415
Gly His Arg Val Glu Leu Glu Val Glu Ser Ile Leu Leu Lys His
                420                 425                 430
Met Tyr Ile Ser Glu Thr Ala Val Ser Val His Lys Asp His Gln Glu
                435                 440                 445
Gln Pro Tyr Leu Cys Ala Tyr Phe Val Ser Glu Lys His Ile Pro Leu
    450                 455                 460
Glu Gln Leu Arg Gln Phe Ser Ser Glu Leu Pro Thr Tyr Met Ile
465                 470                 475                 480
Pro Ser Tyr Phe Ile Gln Leu Asp Lys Met Pro Leu Thr Ser Asn Gly
                485                 490                 495
Lys Ile Asp Arg Lys Gln Leu Pro Glu Pro Asp Leu Thr Phe Gly Met
                500                 505                 510
Arg Val Asp Tyr Glu Ala Pro Arg Asn Glu Ile Glu Glu Thr Leu Val
                515                 520                 525
Thr Ile Trp Gln Asp Val Leu Gly Ile Glu Lys Ile Gly Ile Lys Asp
            530                 535                 540
Asn Phe Tyr Ala Leu Gly Gly Asp Ser Ile Lys Ala Ile Gln Val Ala
545                 550                 555                 560
Ala Arg Leu His Ser Tyr Gln Leu Lys Leu Glu Thr Lys Asp Leu Leu
                565                 570                 575
Lys Tyr Pro Thr Ile Asp Gln Leu Val His Tyr Ile Lys Asp Ser Lys
                580                 585                 590
Arg Arg Ser Glu Gln Gly Ile Val Glu Gly Glu Ile Gly Leu Thr Pro
                595                 600                 605
Ile Gln His Trp Phe Phe Glu Gln Gln Phe Thr Asn Met His His Trp
    610                 615                 620
Asn Gln Ser Tyr Met Leu Tyr Arg Pro Asn Gly Phe Asp Lys Glu Ile
625                 630                 635                 640
Leu Leu Arg Val Phe Asn Lys Ile Val Glu His His Asp Ala Leu Arg
                645                 650                 655
Met Ile Tyr Lys His His Asn Gly Lys Ile Val Gln Ile Asn Arg Gly
                660                 665                 670
Leu Glu Gly Thr Leu Phe Asp Phe Tyr Thr Phe Asp Leu Thr Ala Asn
            675                 680                 685
Asp Asn Glu Gln Gln Val Ile Cys Glu Glu Ser Ala Arg Leu Gln Asn
690                 695                 700
Ser Ile Asn Leu Glu Val Gly Pro Leu Val Lys Ile Ala Leu Phe His
705                 710                 715                 720
Thr Gln Asn Gly Asp His Leu Phe Met Ala Ile His Leu Val Val
            725                 730                 735
Asp Gly Ile Ser Trp Arg Ile Leu Phe Glu Asp Leu Ala Thr Ala Tyr
            740                 745                 750
Glu Gln Ala Met His Gln Gln Thr Ile Ala Leu Pro Glu Lys Thr Asp
        755                 760                 765
Ser Phe Lys Asp Trp Ser Ile Glu Leu Glu Lys Tyr Ala Asn Ser Glu
    770                 775                 780
Leu Phe Leu Glu Glu Ala Glu Tyr Trp His His Leu Asn Tyr Tyr Thr
785                 790                 795                 800
Glu Asn Val Gln Ile Lys Lys Asp Tyr Val Thr Met Asn Asn Lys Gln
                805                 810                 815
```

-continued

| | | | | | | | | | | | | |
|---|---|---|---|---|---|---|---|---|---|---|---|---|
|Lys|Asn|Ile|Arg|Tyr|Val|Gly|Met|Glu|Leu|Thr|Ile|Glu|Glu|Thr|Glu|
| | | |820| | |825| | | |830| | | |

Lys Leu Leu Lys Asn Val Asn Lys Ala Tyr Arg Thr Glu Ile Asn Asp
            835                 840                 845

Ile Leu Leu Thr Ala Leu Gly Phe Ala Leu Lys Glu Trp Ala Asp Ile
850                 855                 860

Asp Lys Ile Val Ile Asn Leu Glu Gly His Gly Arg Glu Glu Ile Leu
865                 870                 875                 880

Glu Gln Met Asn Ile Ala Arg Thr Val Gly Trp Phe Thr Ser Gln Tyr
                885                 890                 895

Pro Val Val Leu Asp Met Gln Lys Ser Asp Leu Ser Tyr Gln Ile
            900                 905                 910

Lys Leu Met Lys Glu Asn Leu Arg Arg Ile Pro Asn Lys Gly Ile Gly
            915                 920                 925

Tyr Glu Ile Phe Lys Tyr Leu Thr Thr Glu Tyr Leu Arg Pro Val Leu
            930                 935                 940

Pro Phe Thr Leu Lys Pro Glu Ile Asn Phe Asn Tyr Leu Gly Gln Phe
945                 950                 955                 960

Asp Thr Asp Val Lys Thr Glu Leu Phe Thr Arg Ser Pro Tyr Ser Met
                965                 970                 975

Gly Asn Ser Leu Gly Pro Asp Gly Lys Asn Asn Leu Ser Pro Glu Gly
            980                 985                 990

Glu Ser Tyr Phe Val Leu Asn Ile Asn Gly Phe Ile Glu Glu Gly Lys
            995                 1000                1005

Leu His Ile Thr Phe Ser Tyr Asn Glu Gln Gln Tyr Lys Glu Asp Thr
    1010                1015                1020

Ile Gln Gln Leu Ser Arg Ser Tyr Lys Gln His Leu Leu Ala Ile Ile
1025                1030                1035                1040

Glu His Cys Val Gln Lys Glu Asp Thr Glu Leu Thr Pro Ser Asp Phe
                1045                1050                1055

Ser Phe Lys Glu Leu Glu Leu Glu Glu Met Asp Asp Ile Phe Asp Leu
            1060                1065                1070

Leu Ala Asp Ser Leu Thr
        1075

<210> SEQ ID NO 44
<211> LENGTH: 3234
<212> TYPE: DNA
<213> ORGANISM: Brevibacillus brevis

<400> SEQUENCE: 44

```
atg tta aac agt tct aaa agt ata ttg att cat gct caa aat aaa aat      48
Met Leu Asn Ser Ser Lys Ser Ile Leu Ile His Ala Gln Asn Lys Asn
  1               5                  10                  15 gga acg cat gaa gag gag cag tat ctc ttt gct gtg aac aac acc aaa      96
Gly Thr His Glu Glu Glu Gln Tyr Leu Phe Ala Val Asn Asn Thr Lys
             20                  25                  30 gcg gag tat cca cgt gat aag acg atc cat cag tta ttt gaa gag cag     144
Ala Glu Tyr Pro Arg Asp Lys Thr Ile His Gln Leu Phe Glu Glu Gln
         35                  40                  45 gtt agt aag aga cca aac aat gta gcc att gta tgt gaa aat gag caa     192
Val Ser Lys Arg Pro Asn Asn Val Ala Ile Val Cys Glu Asn Glu Gln
     50                  55                  60 ctt acc tac cat gag ctt aat gtg aaa gcc aat caa cta gca cgg att     240
Leu Thr Tyr His Glu Leu Asn Val Lys Ala Asn Gln Leu Ala Arg Ile
 65                  70                  75                  80 ttt ata gaa aaa ggg att gga aaa gac act ctt gtt gga att atg atg     288
```

-continued

```
                Phe Ile Glu Lys Gly Ile Gly Lys Asp Thr Leu Val Gly Ile Met Met
                                 85                  90                  95 gag aaa tct atc gat tta ttt ata ggc ata tta gcc gtt tta aaa gca        336
Glu Lys Ser Ile Asp Leu Phe Ile Gly Ile Leu Ala Val Leu Lys Ala
            100                 105                 110 ggt gga gca tat gtt ccg att gat att gaa tat cct aag gaa gtt cat        384
Gly Gly Ala Tyr Val Pro Ile Asp Ile Glu Tyr Pro Lys Glu Val His
            115                 120                 125 tta att cat aat att caa ttt aat ggg caa gtg gaa att ttt gaa gaa        432
Leu Ile His Asn Ile Gln Phe Asn Gly Gln Val Glu Ile Phe Glu Glu
            130                 135                 140 gat act atc aaa att aga gaa gga act aat cta cat gta cca agt aaa        480
Asp Thr Ile Lys Ile Arg Glu Gly Thr Asn Leu His Val Pro Ser Lys
145                 150                 155                 160 tca acc gat ctt gct tat gtt att tat act tct ggt aca aca ggc aat        528
Ser Thr Asp Leu Ala Tyr Val Ile Tyr Thr Ser Gly Thr Thr Gly Asn
                165                 170                 175 cca aaa ggt aca atg ctg gag cat aaa gga ata agt aat cta aag gta        576
Pro Lys Gly Thr Met Leu Glu His Lys Gly Ile Ser Asn Leu Lys Val
            180                 185                 190 ttt ttc gaa aat agt ctt aac gtg act gaa aag gat aga att ggt caa        624
Phe Phe Glu Asn Ser Leu Asn Val Thr Glu Lys Asp Arg Ile Gly Gln
            195                 200                 205 ttt gcc agc atc tct ttt gat gca tct gta tgg gag atg ttt atg gct        672
Phe Ala Ser Ile Ser Phe Asp Ala Ser Val Trp Glu Met Phe Met Ala
            210                 215                 220 ttg tta acg ggg gct agc ctg tat att atc ctg aag gat aca atc aat        720
Leu Leu Thr Gly Ala Ser Leu Tyr Ile Ile Leu Lys Asp Thr Ile Asn
225                 230                 235                 240 gat ttt gtg aag ttt gaa caa tac att aac caa aag gaa atc act gtt        768
Asp Phe Val Lys Phe Glu Gln Tyr Ile Asn Gln Lys Glu Ile Thr Val
                245                 250                 255 att acg tta cca cct acc tat gta gtt cat ctt gat cca gaa cgt att        816
Ile Thr Leu Pro Pro Thr Tyr Val Val His Leu Asp Pro Glu Arg Ile
            260                 265                 270 tta tcg ata caa acg tta att aca gca ggc tca gct acc tcg cct tcc        864
Leu Ser Ile Gln Thr Leu Ile Thr Ala Gly Ser Ala Thr Ser Pro Ser
            275                 280                 285 tta gta aac aag tgg aag gag aaa gta act tac ata aat gcc tat ggc        912
Leu Val Asn Lys Trp Lys Glu Lys Val Thr Tyr Ile Asn Ala Tyr Gly
            290                 295                 300 cct acg gaa aca act att tgt gcg act aca tgc gta gcc acc aaa gaa        960
Pro Thr Glu Thr Thr Ile Cys Ala Thr Thr Cys Val Ala Thr Lys Glu
305                 310                 315                 320 aca ata ggt cat tca gtt cca atc gga gca cca att caa aat aca caa       1008
Thr Ile Gly His Ser Val Pro Ile Gly Ala Pro Ile Gln Asn Thr Gln
                325                 330                 335 att tat att gtc gat gaa aat ctt caa tta aaa tcg gtt ggt gaa gct       1056
Ile Tyr Ile Val Asp Glu Asn Leu Gln Leu Lys Ser Val Gly Glu Ala
            340                 345                 350 ggt gaa ttg tgt att ggt gga gaa ggg tta gca agg gga tat tgg aag       1104
Gly Glu Leu Cys Ile Gly Gly Glu Gly Leu Ala Arg Gly Tyr Trp Lys
            355                 360                 365 cga ccg gaa tta act tcc cag aag ttc gtt gat aac ccg ttt gtt cca       1152
Arg Pro Glu Leu Thr Ser Gln Lys Phe Val Asp Asn Pro Phe Val Pro
            370                 375                 380 gga gag aag ttg tat aaa aca gga gat cag gca aga tgg cta tct gat       1200
Gly Glu Lys Leu Tyr Lys Thr Gly Asp Gln Ala Arg Trp Leu Ser Asp
385                 390                 395                 400 gga aat att gaa tat ctc gga aga ata gat aac cag gta aag att aga       1248
```

|  |  |  |  |  |  |  |  |  |  |  |  |  |  |  |  |  |
|---|---|---|---|---|---|---|---|---|---|---|---|---|---|---|---|---|
| Gly | Asn | Ile | Glu | Tyr | Leu | Gly | Arg | Ile | Asp | Asn | Gln | Val | Lys | Ile | Arg | |
|  |  |  | 405 |  |  |  |  | 410 |  |  |  |  | 415 |  |  | |

```
ggt cac cga gtt gaa cta gaa gaa gtt gag tct att ctt cta aag cat         1296
Gly His Arg Val Glu Leu Glu Glu Val Glu Ser Ile Leu Leu Lys His
            420                 425                 430 atg tat att agc gaa act gca gta agt gtg cat aaa gat cac caa gaa         1344
Met Tyr Ile Ser Glu Thr Ala Val Ser Val His Lys Asp His Gln Glu
        435                 440                 445 cag ccg tat ttg tgc gct tat ttt gta tcg gaa aag cat ata cca cta         1392
Gln Pro Tyr Leu Cys Ala Tyr Phe Val Ser Glu Lys His Ile Pro Leu
    450                 455                 460 gaa cag tta aga caa ttc tca tca gaa gaa ctg cca acg tat atg atc         1440
Glu Gln Leu Arg Gln Phe Ser Ser Glu Glu Leu Pro Thr Tyr Met Ile
465                 470                 475                 480 cct tct tat ttt atc cag tta gac aaa atg ccg ctt aca tca aat ggg         1488
Pro Ser Tyr Phe Ile Gln Leu Asp Lys Met Pro Leu Thr Ser Asn Gly
                485                 490                 495 aag att gat cga aag cag ttg ccg gaa cct gat tta act ttc ggg atg         1536
Lys Ile Asp Arg Lys Gln Leu Pro Glu Pro Asp Leu Thr Phe Gly Met
            500                 505                 510 agg gta gac tat gaa gcg ccg cga aat gaa atc gag gaa acg ctt gtt         1584
Arg Val Asp Tyr Glu Ala Pro Arg Asn Glu Ile Glu Glu Thr Leu Val
        515                 520                 525 act atc tgg cag gat gta tta ggt att gag aaa atc ggt att aaa gat         1632
Thr Ile Trp Gln Asp Val Leu Gly Ile Glu Lys Ile Gly Ile Lys Asp
    530                 535                 540 aat ttc tat gca tta ggt gga gat tct att aaa gca ata cag gtt gct         1680
Asn Phe Tyr Ala Leu Gly Gly Asp Ser Ile Lys Ala Ile Gln Val Ala
545                 550                 555                 560 gct cgc ctg cat tcc tac caa tta aag cta gaa aca aaa gat tta tta         1728
Ala Arg Leu His Ser Tyr Gln Leu Lys Leu Glu Thr Lys Asp Leu Leu
                565                 570                 575 aag tat cca aca atc gat caa ctc gtt cat tat ata aaa gat agt aaa         1776
Lys Tyr Pro Thr Ile Asp Gln Leu Val His Tyr Ile Lys Asp Ser Lys
            580                 585                 590 aga aga agt gag caa ggt att gtg gaa ggt gag att gga ctt aca cct         1824
Arg Arg Ser Glu Gln Gly Ile Val Glu Gly Glu Ile Gly Leu Thr Pro
        595                 600                 605 att cag cat tgg ttc ttt gaa caa caa ttt aca aat atg cac cat tgg         1872
Ile Gln His Trp Phe Phe Glu Gln Gln Phe Thr Asn Met His His Trp
    610                 615                 620 aac caa tcg tat atg ttg tat aga cca aat ggg ttt gat aaa gag atc         1920
Asn Gln Ser Tyr Met Leu Tyr Arg Pro Asn Gly Phe Asp Lys Glu Ile
625                 630                 635                 640 ttg cta agg gta ttt aat aaa att gtt gag cat cat gat gca tta cgt         1968
Leu Leu Arg Val Phe Asn Lys Ile Val Glu His His Asp Ala Leu Arg
                645                 650                 655 atg ata tac aaa cat cat aac gga aag atc gtg cag ata aat cgg ggg         2016
Met Ile Tyr Lys His His Asn Gly Lys Ile Val Gln Ile Asn Arg Gly
            660                 665                 670 ctt gaa ggt acg ttg ttt gat ttt tat acc ttt gat tta act gca aat         2064
Leu Glu Gly Thr Leu Phe Asp Phe Tyr Thr Phe Asp Leu Thr Ala Asn
        675                 680                 685 gat aat gag caa cag gtg att tgt gaa gaa tct gct cga tta caa aat         2112
Asp Asn Glu Gln Gln Val Ile Cys Glu Glu Ser Ala Arg Leu Gln Asn
690                 695                 700 agt ata aac ttg gaa gta ggc cct cta gta aag ata gcg ctg ttt cat         2160
Ser Ile Asn Leu Glu Val Gly Pro Leu Val Lys Ile Ala Leu Phe His
705                 710                 715                 720 act cag aat gga gat cac ctg ttt atg gct att cat cat ttg gtt gtg         2208
Thr Gln Asn Gly Asp His Leu Phe Met Ala Ile His His Leu Val Val
```

```
Thr Gln Asn Gly Asp His Leu Phe Met Ala Ile His His Leu Val Val
                725                 730                 735 gat ggt att tct tgg agg att ttg ttt gag gat ttg gcc aca gct tat      2256
Asp Gly Ile Ser Trp Arg Ile Leu Phe Glu Asp Leu Ala Thr Ala Tyr
                740                 745                 750 gaa caa gca atg cat cag caa acg att gct tta cca gag aaa aca gat      2304
Glu Gln Ala Met His Gln Gln Thr Ile Ala Leu Pro Glu Lys Thr Asp
                755                 760                 765 tca ttt aag gac tgg tct att gaa tta gaa aaa tat gcg aac agc gaa      2352
Ser Phe Lys Asp Trp Ser Ile Glu Leu Glu Lys Tyr Ala Asn Ser Glu
        770                 775                 780 tta ttc cta gaa gaa gct gaa tat tgg cat cat ttg aat tat tat acc      2400
Leu Phe Leu Glu Glu Ala Glu Tyr Trp His His Leu Asn Tyr Tyr Thr
785                 790                 795                 800 gag aac gtt caa att aag aaa gat tat gtc acc atg aac aat aaa caa      2448
Glu Asn Val Gln Ile Lys Lys Asp Tyr Val Thr Met Asn Asn Lys Gln
                805                 810                 815 aag aat ata cgt tat gta gga atg gag tta aca ata gaa gag aca gaa      2496
Lys Asn Ile Arg Tyr Val Gly Met Glu Leu Thr Ile Glu Glu Thr Glu
                820                 825                 830 aaa tta ttg aaa aat gta aat aaa gcg tat cga aca gaa att aat gat      2544
Lys Leu Leu Lys Asn Val Asn Lys Ala Tyr Arg Thr Glu Ile Asn Asp
                835                 840                 845 att tta tta acg gca ctt ggc ttt gca ctc aaa gaa tgg gcc gat att      2592
Ile Leu Leu Thr Ala Leu Gly Phe Ala Leu Lys Glu Trp Ala Asp Ile
        850                 855                 860 gat aaa att gta att aac tta gag gga cac gga cgg gaa gaa ata ctg      2640
Asp Lys Ile Val Ile Asn Leu Glu Gly His Gly Arg Glu Glu Ile Leu
865                 870                 875                 880 gaa cag atg aac att gca agg acg gta ggc tgg ttt act tcc cag tat      2688
Glu Gln Met Asn Ile Ala Arg Thr Val Gly Trp Phe Thr Ser Gln Tyr
                885                 890                 895 cct gtt gta ctt gat atg caa aaa tcg gat gat ttg tct tat caa atc      2736
Pro Val Val Leu Asp Met Gln Lys Ser Asp Asp Leu Ser Tyr Gln Ile
                900                 905                 910 aaa tta atg aaa gaa aat tta cgc aga ata cct aac aaa gga atc gga      2784
Lys Leu Met Lys Glu Asn Leu Arg Arg Ile Pro Asn Lys Gly Ile Gly
                915                 920                 925 tat gaa att ttt aag tat tta aca act gaa tat tta cgg cct gtt tta      2832
Tyr Glu Ile Phe Lys Tyr Leu Thr Thr Glu Tyr Leu Arg Pro Val Leu
        930                 935                 940 ccc ttt aca tta aag ccg gaa att aac ttt aac tac tta gga cag ttc      2880
Pro Phe Thr Leu Lys Pro Glu Ile Asn Phe Asn Tyr Leu Gly Gln Phe
945                 950                 955                 960 gat acg gac gtg aag act gaa ttg ttt act cgt tct cct tat agc atg      2928
Asp Thr Asp Val Lys Thr Glu Leu Phe Thr Arg Ser Pro Tyr Ser Met
                965                 970                 975 ggt aat tca tta gga cca gat gga aaa aat aat tta agc cca gaa ggg      2976
Gly Asn Ser Leu Gly Pro Asp Gly Lys Asn Asn Leu Ser Pro Glu Gly
                980                 985                 990 gaa agt tat ttt gta ctc aat att aat ggt ttt att gaa gaa ggt aag      3024
Glu Ser Tyr Phe Val Leu Asn Ile Asn Gly Phe Ile Glu Glu Gly Lys
                995                 1000                1005 ctt cac atc acc ttt tct tat aat gaa cag cag tat aag gag gat acc      3072
Leu His Ile Thr Phe Ser Tyr Asn Glu Gln Gln Tyr Lys Glu Asp Thr
        1010                1015                1020 att cag caa ttg agc cgg agc tat aag caa cat ctt ttg gcc atc att      3120
Ile Gln Gln Leu Ser Arg Ser Tyr Lys Gln His Leu Leu Ala Ile Ile
1025                1030                1035                1040 gaa cat tgt gta cag aag gaa gat act gag tta act cca agt gat ttc      3168
```

```
                                        Glu His Cys Val Gln Lys Glu Asp Thr Glu Leu Thr Pro Ser Asp Phe
                                                    1045                1050                1055 agt ttc aag gaa ctt gaa tta gaa gag atg gat gat att ttc gat ttg         3216
Ser Phe Lys Glu Leu Glu Leu Glu Glu Met Asp Asp Ile Phe Asp Leu
        1060                1065                1070 ttg gcc gat tca tta acg                                                 3234
Leu Ala Asp Ser Leu Thr
        1075

<210> SEQ ID NO 45
<211> LENGTH: 503
<212> TYPE: PRT
<213> ORGANISM: Escherichia coli

<400> SEQUENCE: 45

Met Glu Phe Ser Val Lys Ser Gly Ser Pro Glu Lys Gln Arg Ser Ala
 1               5                  10                  15

Cys Ile Val Val Gly Val Phe Glu Pro Arg Arg Leu Ser Pro Ile Ala
             20                  25                  30

Glu Gln Leu Asp Lys Ile Ser Asp Gly Tyr Ile Ser Ala Leu Leu Arg
         35                  40                  45

Arg Gly Glu Leu Glu Gly Lys Pro Gly Gln Thr Leu Leu His His
     50                  55                  60

Val Pro Asn Val Leu Ser Glu Arg Ile Leu Ile Gly Cys Gly Lys
 65                  70                  75                  80

Glu Arg Glu Leu Asp Glu Arg Gln Tyr Lys Gln Val Ile Gln Lys Thr
                 85                  90                  95

Ile Asn Thr Leu Asn Asp Thr Gly Ser Met Glu Ala Val Cys Phe Leu
            100                 105                 110

Thr Glu Leu His Val Lys Gly Arg Asn Asn Tyr Trp Lys Val Arg Gln
        115                 120                 125

Ala Val Glu Thr Ala Lys Glu Thr Leu Tyr Ser Phe Asp Gln Leu Lys
    130                 135                 140

Thr Asn Lys Ser Glu Pro Arg Arg Pro Leu Arg Lys Met Val Phe Asn
145                 150                 155                 160

Val Pro Thr Arg Arg Glu Leu Thr Ser Gly Glu Arg Ala Ile Gln His
                165                 170                 175

Gly Leu Ala Ile Ala Ala Gly Ile Lys Ala Lys Asp Leu Gly Asn
            180                 185                 190

Met Pro Pro Asn Ile Cys Asn Ala Ala Tyr Leu Ala Ser Gln Ala Arg
        195                 200                 205

Gln Leu Ala Asp Ser Tyr Ser Lys Asn Val Ile Thr Arg Val Ile Gly
    210                 215                 220

Glu Gln Gln Met Lys Glu Leu Gly Met His Ser Tyr Leu Ala Val Gly
225                 230                 235                 240

Gln Gly Ser Gln Asn Glu Ser Leu Met Ser Val Ile Glu Tyr Lys Gly
                245                 250                 255

Asn Ala Ser Glu Asp Ala Arg Pro Ile Val Leu Val Gly Lys Gly Leu
            260                 265                 270

Thr Phe Asp Ser Gly Gly Ile Ser Ile Lys Pro Ser Glu Gly Met Asp
        275                 280                 285

Glu Met Lys Tyr Asp Met Cys Gly Ala Ala Val Tyr Gly Val Met
    290                 295                 300

Arg Met Val Ala Glu Leu Gln Leu Pro Ile Asn Val Ile Gly Val Leu
305                 310                 315                 320

Ala Gly Cys Glu Asn Met Pro Gly Gly Arg Ala Tyr Arg Pro Gly Asp
```

```
                        325                 330                 335
Val Leu Thr Thr Met Ser Gly Gln Thr Val Glu Val Leu Asn Thr Asp
                    340                 345                 350

Ala Glu Gly Arg Leu Val Leu Cys Asp Val Leu Thr Tyr Val Glu Arg
                355                 360                 365

Phe Glu Pro Glu Ala Val Ile Asp Val Ala Thr Leu Thr Gly Ala Cys
            370                 375                 380

Val Ile Ala Leu Gly His His Ile Thr Gly Leu Met Ala Asn His Asn
385                 390                 395                 400

Pro Leu Ala His Glu Leu Ile Ala Ala Ser Glu Gln Ser Gly Asp Arg
                405                 410                 415

Ala Trp Arg Leu Pro Leu Gly Asp Glu Tyr Gln Glu Gln Leu Glu Ser
                420                 425                 430

Asn Phe Ala Asp Met Ala Asn Ile Gly Gly Arg Pro Gly Ala Ile
            435                 440                 445

Thr Ala Gly Cys Phe Leu Ser Arg Phe Thr Arg Lys Tyr Asn Trp Ala
        450                 455                 460

His Leu Asp Ile Ala Gly Thr Ala Trp Arg Ser Gly Lys Ala Lys Gly
465                 470                 475                 480

Ala Thr Gly Arg Pro Val Ala Leu Leu Ala Gln Phe Leu Leu Asn Arg
                485                 490                 495

Ala Gly Phe Asn Gly Glu Glu
            500

<210> SEQ ID NO 46
<211> LENGTH: 427
<212> TYPE: PRT
<213> ORGANISM: Escherichia coli

<400> SEQUENCE: 46

Met Thr Glu Ala Met Lys Ile Thr Leu Ser Thr Gln Pro Ala Asp Ala
1               5                   10                  15

Arg Trp Gly Glu Lys Ala Thr Tyr Ser Ile Asn Asn Asp Gly Ile Thr
            20                  25                  30

Leu His Leu Asn Gly Ala Asp Asp Leu Gly Leu Ile Gln Arg Ala Ala
        35                  40                  45

Arg Lys Ile Asp Gly Leu Gly Ile Lys His Val Gln Leu Ser Gly Glu
    50                  55                  60

Gly Trp Asp Ala Asp Arg Cys Trp Ala Phe Trp Gln Gly Tyr Lys Ala
65                  70                  75                  80

Pro Lys Gly Thr Arg Lys Val Val Trp Pro Asp Leu Asp Asp Ala Gln
                85                  90                  95

Arg Gln Glu Leu Asp Asn Arg Leu Met Ile Ile Asp Trp Val Arg Asp
            100                 105                 110

Thr Ile Asn Ala Pro Ala Glu Glu Leu Gly Pro Ser Gln Leu Ala Gln
        115                 120                 125

Arg Ala Val Asp Leu Ile Ser Asn Val Ala Gly Asp Arg Val Thr Tyr
    130                 135                 140

Arg Ile Thr Lys Gly Glu Asp Leu Arg Glu Gln Gly Tyr Met Gly Leu
145                 150                 155                 160

His Thr Val Gly Arg Gly Ser Glu Arg Ser Pro Val Leu Leu Ala Leu
                165                 170                 175

Asp Tyr Asn Pro Thr Gly Asp Lys Glu Ala Pro Val Tyr Ala Cys Leu
            180                 185                 190

Val Gly Lys Gly Ile Thr Phe Asp Ser Gly Gly Tyr Ser Ile Lys Gln
```

```
                195                 200                 205
Thr Ala Phe Met Asp Ser Met Lys Ser Asp Met Gly Gly Ala Ala Thr
            210                 215                 220

Val Thr Gly Ala Leu Ala Phe Ala Ile Thr Arg Gly Leu Asn Lys Arg
225                 230                 235                 240

Val Lys Leu Phe Leu Cys Cys Ala Asp Asn Leu Ile Ser Gly Asn Ala
                245                 250                 255

Phe Lys Leu Gly Asp Ile Ile Thr Tyr Arg Asn Gly Lys Lys Val Glu
            260                 265                 270

Val Met Asn Thr Asp Ala Glu Gly Arg Leu Val Leu Ala Asp Gly Leu
        275                 280                 285

Ile Asp Ala Ser Ala Gln Lys Pro Glu Met Ile Ile Asp Ala Ala Thr
    290                 295                 300

Leu Thr Gly Ala Ala Lys Thr Ala Leu Gly Asn Asp Tyr His Ala Leu
305                 310                 315                 320

Phe Ser Phe Asp Asp Ala Leu Ala Gly Arg Leu Leu Ala Ser Ala Ala
                325                 330                 335

Gln Glu Asn Glu Pro Phe Trp Arg Leu Pro Leu Ala Glu Phe His Arg
            340                 345                 350

Ser Gln Leu Pro Ser Asn Phe Ala Glu Leu Asn Asn Thr Gly Ser Ala
        355                 360                 365

Ala Tyr Pro Ala Gly Ala Ser Thr Ala Ala Gly Phe Leu Ser His Phe
    370                 375                 380

Val Glu Asn Tyr Gln Gln Gly Trp Leu His Ile Asp Cys Ser Ala Thr
385                 390                 395                 400

Tyr Arg Lys Ala Pro Val Glu Gln Trp Ser Ala Gly Ala Thr Gly Leu
                405                 410                 415

Gly Val Arg Thr Ile Ala Asn Leu Leu Thr Ala
            420                 425

<210> SEQ ID NO 47
<211> LENGTH: 485
<212> TYPE: PRT
<213> ORGANISM: Escherichia coli

<400> SEQUENCE: 47

Met Ser Glu Leu Ser Gln Leu Ser Pro Gln Pro Leu Trp Asp Ile Phe
  1               5                  10                  15

Ala Lys Ile Cys Ser Ile Pro His Pro Ser Tyr His Glu Glu Gln Leu
                 20                  25                  30

Ala Glu Tyr Ile Val Gly Trp Ala Lys Glu Lys Gly Phe His Val Glu
             35                  40                  45

Arg Asp Gln Val Gly Asn Ile Leu Ile Arg Lys Pro Ala Thr Ala Gly
         50                  55                  60

Met Glu Asn Arg Lys Pro Val Val Leu Gln Ala His Leu Asp Met Val
 65                  70                  75                  80

Pro Gln Lys Asn Asn Asp Thr Val His Asp Phe Thr Lys Asp Pro Ile
                 85                  90                  95

Gln Pro Tyr Ile Asp Gly Glu Trp Val Lys Ala Arg Gly Thr Thr Leu
            100                 105                 110

Gly Ala Asp Asn Gly Ile Gly Met Ala Ser Ala Leu Ala Val Leu Ala
        115                 120                 125

Asp Glu Asn Val Val His Gly Pro Leu Glu Val Leu Leu Thr Met Thr
    130                 135                 140

Glu Glu Ala Gly Met Asp Gly Ala Phe Gly Leu Gln Gly Asn Trp Leu
```

```
145                 150                 155                 160
Gln Ala Asp Ile Leu Ile Asn Thr Asp Ser Glu Glu Gly Glu Ile
                165                 170                 175
Tyr Met Gly Cys Ala Gly Gly Ile Asp Phe Thr Ser Asn Leu His Leu
            180                 185                 190
Asp Arg Glu Ala Val Pro Ala Gly Phe Glu Thr Phe Lys Leu Thr Leu
        195                 200                 205
Lys Gly Leu Lys Gly Gly His Ser Gly Gly Glu Ile His Val Gly Leu
    210                 215                 220
Gly Asn Ala Asn Lys Leu Leu Val Arg Phe Leu Ala Gly His Ala Glu
225                 230                 235                 240
Glu Leu Asp Leu Arg Leu Ile Asp Phe Asn Gly Gly Thr Leu Arg Asn
                245                 250                 255
Ala Ile Pro Arg Glu Ala Phe Ala Thr Ile Ala Val Ala Ala Asp Lys
            260                 265                 270
Val Asp Val Leu Lys Ser Leu Val Asn Thr Tyr Gln Glu Ile Leu Lys
        275                 280                 285
Asn Glu Leu Ala Glu Lys Glu Lys Asn Leu Ala Leu Leu Leu Asp Ser
    290                 295                 300
Val Ala Asn Asp Lys Ala Ala Leu Ile Ala Lys Ser Arg Asp Thr Phe
305                 310                 315                 320
Ile Arg Leu Leu Asn Ala Thr Pro Asn Gly Val Ile Arg Asn Ser Asp
                325                 330                 335
Val Ala Lys Gly Val Val Glu Thr Ser Leu Asn Val Gly Val Val Thr
            340                 345                 350
Met Thr Asp Asn Asn Val Glu Ile His Cys Leu Ile Arg Ser Leu Ile
        355                 360                 365
Asp Ser Gly Lys Asp Tyr Val Val Ser Met Leu Asp Ser Leu Gly Lys
    370                 375                 380
Leu Ala Gly Ala Lys Thr Glu Ala Lys Gly Ala Tyr Pro Gly Trp Gln
385                 390                 395                 400
Pro Asp Ala Asn Ser Pro Val Met His Leu Val Arg Glu Thr Tyr Gln
                405                 410                 415
Arg Leu Phe Asn Lys Thr Pro Asn Ile Gln Ile Ile His Ala Gly Leu
            420                 425                 430
Glu Cys Gly Leu Phe Lys Lys Pro Tyr Pro Glu Met Asp Met Val Ser
        435                 440                 445
Ile Gly Pro Thr Ile Thr Gly Pro His Ser Pro Asp Glu Gln Val His
    450                 455                 460
Ile Glu Ser Val Gly His Tyr Trp Thr Leu Leu Thr Glu Leu Leu Lys
465                 470                 475                 480
Glu Ile Pro Ala Lys
                485

<210> SEQ ID NO 48
<211> LENGTH: 870
<212> TYPE: PRT
<213> ORGANISM: Escherichia coli

<400> SEQUENCE: 48

Met Thr Gln Gln Pro Gln Ala Lys Tyr Arg His Asp Tyr Arg Ala Pro
1               5                   10                  15
Asp Tyr Gln Ile Thr Asp Ile Asp Leu Thr Phe Asp Leu Asp Ala Gln
                20                  25                  30
Lys Thr Val Val Thr Ala Val Ser Gln Ala Val Arg His Gly Ala Ser
```

```
                35                  40                  45
Asp Ala Pro Leu Arg Leu Asn Gly Glu Asp Leu Lys Leu Val Ser Val
            50                  55                  60
His Ile Asn Asp Glu Pro Trp Thr Ala Trp Lys Glu Glu Gly Ala
 65                  70                  75                  80
Leu Val Ile Ser Asn Leu Pro Glu Arg Phe Thr Leu Lys Ile Ile Asn
                85                  90                  95
Glu Ile Ser Pro Ala Ala Asn Thr Ala Leu Glu Gly Leu Tyr Gln Ser
               100                 105                 110
Gly Asp Ala Leu Cys Thr Gln Cys Glu Ala Glu Gly Phe Arg His Ile
               115                 120                 125
Thr Tyr Tyr Leu Asp Arg Pro Asp Val Leu Ala Arg Phe Thr Thr Lys
               130                 135                 140
Ile Ile Ala Asp Lys Ile Lys Tyr Pro Phe Leu Leu Ser Asn Gly Asn
145                 150                 155                 160
Arg Val Ala Gln Gly Glu Leu Glu Asn Gly Arg His Trp Val Gln Trp
               165                 170                 175
Gln Asp Pro Phe Pro Lys Pro Cys Tyr Leu Phe Ala Leu Val Ala Gly
               180                 185                 190
Asp Phe Asp Val Leu Arg Asp Thr Phe Thr Thr Arg Ser Gly Arg Glu
               195                 200                 205
Val Ala Leu Glu Leu Tyr Val Asp Arg Gly Asn Leu Asp Arg Ala Pro
               210                 215                 220
Trp Ala Met Thr Ser Leu Lys Asn Ser Met Lys Trp Asp Glu Glu Arg
225                 230                 235                 240
Phe Gly Leu Glu Tyr Asp Leu Asp Ile Tyr Met Ile Val Ala Val Asp
               245                 250                 255
Phe Phe Asn Met Gly Ala Met Glu Asn Lys Gly Leu Asn Ile Phe Asn
               260                 265                 270
Ser Lys Tyr Val Leu Ala Arg Thr Asp Thr Ala Thr Asp Lys Asp Tyr
               275                 280                 285
Leu Asp Ile Glu Arg Val Ile Gly His Glu Tyr Phe His Asn Trp Thr
               290                 295                 300
Gly Asn Arg Val Thr Cys Arg Asp Trp Phe Gln Leu Ser Leu Lys Glu
305                 310                 315                 320
Gly Leu Thr Val Phe Arg Asp Gln Glu Phe Ser Ser Asp Leu Gly Ser
               325                 330                 335
Arg Ala Val Asn Arg Ile Asn Asn Val Arg Thr Met Arg Gly Leu Gln
               340                 345                 350
Phe Ala Glu Asp Ala Ser Pro Met Ala His Pro Ile Arg Pro Asp Met
               355                 360                 365
Val Ile Glu Met Asn Asn Phe Tyr Thr Leu Thr Val Tyr Glu Lys Gly
               370                 375                 380
Ala Glu Val Ile Arg Met Ile His Thr Leu Leu Gly Glu Glu Asn Phe
385                 390                 395                 400
Gln Lys Gly Met Gln Leu Tyr Phe Glu Arg His Asp Gly Ser Ala Ala
               405                 410                 415
Thr Cys Asp Asp Phe Val Gln Ala Met Glu Asp Ala Ser Asn Val Asp
               420                 425                 430
Leu Ser His Phe Arg Arg Trp Tyr Ser Gln Ser Gly Thr Pro Ile Val
               435                 440                 445
Thr Val Lys Asp Asp Tyr Asn Pro Glu Thr Glu Gln Tyr Thr Leu Thr
               450                 455                 460
```

```
Ile Ser Gln Arg Thr Pro Ala Thr Pro Asp Gln Ala Glu Lys Gln Pro
465                 470                 475                 480

Leu His Ile Pro Phe Ala Ile Glu Leu Tyr Asp Asn Glu Gly Lys Val
                485                 490                 495

Ile Pro Leu Gln Lys Gly Gly His Pro Val Asn Ser Val Leu Asn Val
            500                 505                 510

Thr Gln Ala Glu Gln Thr Phe Val Phe Asp Asn Val Tyr Phe Gln Pro
        515                 520                 525

Val Pro Ala Leu Leu Cys Glu Phe Ser Ala Pro Val Lys Leu Glu Tyr
    530                 535                 540

Lys Trp Ser Asp Gln Gln Leu Thr Phe Leu Met Arg His Ala Arg Asn
545                 550                 555                 560

Asp Phe Ser Arg Trp Asp Ala Ala Gln Ser Leu Leu Ala Thr Tyr Ile
                565                 570                 575

Lys Leu Asn Val Ala Arg His Gln Gln Gly Gln Pro Leu Ser Leu Pro
            580                 585                 590

Val His Val Ala Asp Ala Phe Arg Ala Val Leu Leu Asp Glu Lys Ile
        595                 600                 605

Asp Pro Ala Leu Ala Ala Glu Ile Leu Thr Leu Pro Ser Val Asn Glu
    610                 615                 620

Met Ala Glu Leu Phe Asp Ile Ile Asp Pro Ile Ala Ile Ala Glu Val
625                 630                 635                 640

Arg Glu Ala Leu Thr Arg Thr Leu Ala Thr Glu Leu Ala Asp Glu Leu
                645                 650                 655

Leu Ala Ile Tyr Asn Ala Asn Tyr Gln Ser Glu Tyr Arg Val Glu His
            660                 665                 670

Glu Asp Ile Ala Lys Arg Thr Leu Arg Asn Ala Cys Leu Arg Phe Leu
        675                 680                 685

Ala Phe Gly Glu Thr His Leu Ala Asp Val Leu Val Ser Lys Gln Phe
    690                 695                 700

His Glu Ala Asn Asn Met Thr Asp Ala Leu Ala Ala Leu Ser Ala Ala
705                 710                 715                 720

Val Ala Ala Gln Leu Pro Cys Arg Asp Ala Leu Met Gln Glu Tyr Asp
                725                 730                 735

Asp Lys Trp His Gln Asn Gly Leu Val Met Asp Lys Trp Phe Ile Leu
            740                 745                 750

Gln Ala Thr Ser Pro Ala Ala Asn Val Leu Glu Thr Val Arg Gly Leu
        755                 760                 765

Leu Gln His Arg Ser Phe Thr Met Ser Asn Pro Asn Arg Ile Arg Ser
    770                 775                 780

Leu Ile Gly Ala Phe Ala Gly Ser Asn Pro Ala Ala Phe His Ala Glu
785                 790                 795                 800

Asp Gly Ser Gly Tyr Leu Phe Leu Val Glu Met Leu Thr Asp Leu Asn
                805                 810                 815

Ser Arg Asn Pro Gln Val Ala Ser Arg Leu Ile Glu Pro Leu Ile Arg
            820                 825                 830

Leu Lys Arg Tyr Asp Ala Lys Arg Gln Glu Lys Met Arg Ala Ala Leu
        835                 840                 845

Glu Gln Leu Lys Gly Leu Glu Asn Leu Ser Gly Asp Leu Tyr Glu Lys
    850                 855                 860

Ile Thr Lys Ala Leu Ala
865                 870

<210> SEQ ID NO 49
```

```
<211> LENGTH: 535
<212> TYPE: PRT
<213> ORGANISM: Escherichia coli

<400> SEQUENCE: 49

Met Arg Ile Ser Leu Lys Lys Ser Gly Met Leu Lys Leu Gly Leu Ser
 1               5                  10                  15

Leu Val Ala Met Thr Val Ala Ala Ser Val Gln Ala Lys Thr Leu Val
            20                  25                  30

Tyr Cys Ser Glu Gly Ser Pro Glu Gly Phe Asn Pro Gln Leu Phe Thr
        35                  40                  45

Ser Gly Thr Thr Tyr Asp Ala Ser Ser Val Pro Leu Tyr Asn Arg Leu
    50                  55                  60

Val Glu Phe Lys Ile Gly Thr Thr Glu Val Ile Pro Gly Leu Ala Glu
65                  70                  75                  80

Lys Trp Glu Val Ser Glu Asp Gly Lys Thr Tyr Thr Phe His Leu Arg
                85                  90                  95

Lys Gly Val Lys Trp His Asp Asn Lys Glu Phe Lys Pro Thr Arg Glu
            100                 105                 110

Leu Asn Ala Asp Asp Val Val Phe Ser Phe Asp Arg Gln Lys Asn Ala
        115                 120                 125

Gln Asn Pro Tyr His Lys Val Ser Gly Gly Ser Tyr Glu Tyr Phe Glu
    130                 135                 140

Gly Met Gly Leu Pro Glu Leu Ile Ser Glu Val Lys Lys Val Asp Asp
145                 150                 155                 160

Asn Thr Val Gln Phe Val Leu Thr Arg Pro Glu Ala Pro Phe Leu Ala
                165                 170                 175

Asp Leu Ala Met Asp Phe Ala Ser Ile Leu Ser Lys Glu Tyr Ala Asp
            180                 185                 190

Ala Met Met Lys Ala Gly Thr Pro Glu Lys Leu Asp Leu Asn Pro Ile
        195                 200                 205

Gly Thr Gly Pro Phe Gln Leu Gln Gln Tyr Gln Lys Asp Ser Arg Ile
    210                 215                 220

Arg Tyr Lys Ala Phe Asp Gly Tyr Trp Gly Thr Lys Pro Gln Ile Asp
225                 230                 235                 240

Thr Leu Val Phe Ser Ile Thr Pro Asp Ala Ser Val Arg Tyr Ala Lys
                245                 250                 255

Leu Gln Lys Asn Glu Cys Gln Val Met Pro Tyr Pro Asn Pro Ala Asp
            260                 265                 270

Ile Ala Arg Met Lys Gln Asp Lys Ser Ile Asn Leu Met Glu Met Pro
        275                 280                 285

Gly Leu Asn Val Gly Tyr Leu Ser Tyr Asn Val Gln Lys Lys Pro Leu
    290                 295                 300

Asp Asp Val Lys Val Arg Gln Ala Leu Thr Tyr Ala Val Asn Lys Asp
305                 310                 315                 320

Ala Ile Ile Lys Ala Val Tyr Gln Gly Ala Gly Val Ser Ala Lys Asn
                325                 330                 335

Leu Ile Pro Pro Thr Met Trp Gly Tyr Asn Asp Asp Val Gln Asp Tyr
            340                 345                 350

Thr Tyr Asp Pro Glu Lys Ala Lys Ala Leu Leu Lys Glu Ala Gly Leu
        355                 360                 365

Glu Lys Gly Phe Ser Ile Asp Leu Trp Ala Met Pro Val Gln Arg Pro
    370                 375                 380

Tyr Asn Pro Asn Ala Arg Arg Met Ala Glu Met Ile Gln Ala Asp Trp
385                 390                 395                 400
```

```
Ala Lys Val Gly Val Gln Ala Lys Ile Val Thr Tyr Glu Trp Gly Glu
            405                 410                 415

Tyr Leu Lys Arg Ala Lys Asp Gly Glu His Gln Thr Val Met Met Gly
            420                 425                 430

Trp Thr Gly Asp Asn Gly Asp Pro Asp Asn Phe Phe Ala Thr Leu Phe
            435                 440                 445

Ser Cys Ala Ala Ser Glu Gln Gly Ser Asn Tyr Ser Lys Trp Cys Tyr
            450                 455                 460

Lys Pro Phe Glu Asp Leu Ile Gln Pro Ala Arg Ala Thr Asp Asp His
465                 470                 475                 480

Asn Lys Arg Val Glu Leu Tyr Lys Gln Ala Gln Val Val Met His Asp
                485                 490                 495

Gln Ala Pro Ala Leu Ile Ile Ala His Ser Thr Val Phe Glu Pro Val
            500                 505                 510

Arg Lys Glu Val Lys Gly Tyr Val Val Asp Pro Leu Gly Lys His His
            515                 520                 525

Phe Glu Asn Val Ser Ile Glu
            530                 535

<210> SEQ ID NO 50
<211> LENGTH: 339
<212> TYPE: PRT
<213> ORGANISM: Escherichia coli

<400> SEQUENCE: 50

Met Leu Gln Phe Ile Leu Arg Arg Leu Gly Leu Val Ile Pro Thr Phe
1               5                   10                  15

Ile Gly Ile Thr Leu Leu Thr Phe Ala Phe Val His Met Ile Pro Gly
            20                  25                  30

Asp Pro Val Met Ile Met Ala Gly Glu Arg Gly Ile Ser Pro Glu Arg
        35                  40                  45

His Ala Gln Leu Leu Ala Glu Leu Gly Leu Asp Lys Pro Met Trp Gln
    50                  55                  60

Gln Tyr Leu His Tyr Ile Trp Gly Val Met His Gly Asp Leu Gly Ile
65                  70                  75                  80

Ser Met Lys Ser Arg Ile Pro Val Trp Glu Glu Phe Val Pro Arg Phe
                85                  90                  95

Gln Ala Thr Leu Glu Leu Gly Val Cys Ala Met Ile Phe Ala Thr Ala
            100                 105                 110

Val Gly Ile Pro Val Gly Val Leu Ala Ala Val Lys Arg Gly Ser Ile
            115                 120                 125

Phe Asp His Thr Ala Val Gly Leu Ala Leu Thr Gly Tyr Ser Met Pro
        130                 135                 140

Ile Phe Trp Trp Gly Met Met Leu Ile Met Leu Val Ser Val His Trp
145                 150                 155                 160

Asn Leu Thr Pro Val Ser Gly Arg Val Ser Asp Met Val Phe Leu Asp
                165                 170                 175

Asp Ser Asn Pro Leu Thr Gly Phe Met Leu Ile Asp Thr Ala Ile Trp
            180                 185                 190

Gly Glu Asp Gly Asn Phe Ile Asp Ala Val Ala His Met Ile Leu Pro
        195                 200                 205

Ala Ile Val Leu Gly Thr Ile Pro Leu Ala Val Ile Val Arg Met Thr
    210                 215                 220

Arg Ser Ser Met Leu Glu Val Leu Gly Glu Asp Tyr Ile Arg Thr Ala
225                 230                 235                 240
```

```
Arg Ala Lys Gly Leu Thr Arg Met Arg Val Ile Ile Val His Ala Leu
                245                 250                 255

Arg Asn Ala Met Leu Pro Val Val Thr Val Ile Gly Leu Gln Val Gly
            260                 265                 270

Thr Leu Leu Ala Gly Ala Ile Leu Thr Glu Thr Ile Phe Ser Trp Pro
        275                 280                 285

Gly Leu Gly Arg Trp Leu Ile Asp Ala Leu Gln Arg Arg Asp Tyr Pro
    290                 295                 300

Val Val Gln Gly Gly Val Leu Val Ala Thr Met Ile Ile Leu Val
305                 310                 315                 320

Asn Leu Leu Val Asp Leu Leu Tyr Gly Val Val Asn Pro Arg Ile Arg
                325                 330                 335

His Lys Lys

<210> SEQ ID NO 51
<211> LENGTH: 300
<212> TYPE: PRT
<213> ORGANISM: Escherichia coli

<400> SEQUENCE: 51

Met Ser Gln Val Thr Glu Asn Lys Val Ile Ser Ala Pro Val Pro Met
 1               5                  10                  15

Thr Pro Leu Gln Glu Phe Trp His Tyr Phe Lys Arg Asn Lys Gly Ala
                20                  25                  30

Val Val Gly Leu Val Tyr Val Val Ile Val Leu Phe Ile Ala Ile Phe
            35                  40                  45

Ala Asn Trp Ile Ala Pro Tyr Asn Pro Ala Glu Gln Phe Arg Asp Ala
        50                  55                  60

Leu Leu Ala Pro Pro Ala Trp Gln Glu Gly Ser Met Ala His Leu
65                  70                  75                  80

Leu Gly Thr Asp Asp Val Gly Arg Asp Val Leu Ser Arg Leu Met Tyr
                85                  90                  95

Gly Ala Arg Leu Ser Leu Leu Val Gly Cys Leu Val Val Val Leu Ser
            100                 105                 110

Leu Ile Met Gly Val Ile Leu Gly Leu Ile Ala Gly Tyr Phe Gly Gly
        115                 120                 125

Leu Val Asp Asn Ile Ile Met Arg Val Val Asp Ile Met Leu Ala Leu
    130                 135                 140

Pro Ser Leu Leu Leu Ala Leu Val Leu Val Ala Ile Phe Gly Pro Ser
145                 150                 155                 160

Ile Gly Asn Ala Ala Leu Ala Leu Thr Phe Val Ala Leu Pro His Tyr
                165                 170                 175

Val Arg Leu Thr Arg Ala Ala Val Leu Val Glu Val Asn Arg Asp Tyr
            180                 185                 190

Val Thr Ala Ser Arg Val Ala Gly Ala Gly Ala Met Arg Gln Met Phe
        195                 200                 205

Ile Asn Ile Phe Pro Asn Cys Leu Ala Pro Leu Ile Val Gln Ala Ser
    210                 215                 220

Leu Gly Phe Ser Asn Ala Ile Leu Asp Met Ala Ala Leu Gly Phe Leu
225                 230                 235                 240

Gly Met Gly Ala Gln Pro Pro Thr Pro Glu Trp Gly Thr Met Leu Ser
                245                 250                 255

Asp Val Leu Gln Phe Ala Gln Ser Ala Trp Trp Val Val Thr Phe Pro
            260                 265                 270
```

```
Gly Leu Ala Ile Leu Leu Thr Val Leu Ala Phe Asn Leu Met Gly Asp
        275                 280                 285

Gly Leu Arg Asp Ala Leu Asp Pro Lys Leu Lys Gln
    290                 295                 300

<210> SEQ ID NO 52
<211> LENGTH: 327
<212> TYPE: PRT
<213> ORGANISM: Escherichia coli

<400> SEQUENCE: 52

Met Ala Leu Leu Asn Val Asp Lys Leu Ser Val His Phe Gly Asp Glu
  1               5                  10                  15

Ser Ala Pro Phe Arg Ala Val Asp Arg Ile Ser Tyr Ser Val Lys Gln
                 20                  25                  30

Gly Glu Val Val Gly Ile Val Gly Glu Ser Gly Ser Gly Lys Ser Val
             35                  40                  45

Ser Ser Leu Ala Ile Met Gly Leu Ile Asp Tyr Pro Gly Arg Val Met
     50                  55                  60

Ala Glu Lys Leu Glu Phe Asn Gly Gln Asp Leu Gln Arg Ile Ser Glu
 65                  70                  75                  80

Lys Glu Arg Arg Asn Leu Val Gly Ala Glu Val Ala Met Ile Phe Gln
                 85                  90                  95

Asp Pro Met Thr Ser Leu Asn Pro Cys Tyr Thr Val Gly Phe Gln Ile
                100                 105                 110

Met Glu Ala Ile Lys Val His Gln Gly Gly Asn Lys Ser Thr Arg Arg
            115                 120                 125

Gln Arg Ala Ile Asp Leu Leu Asn Gln Val Gly Ile Pro Asp Pro Ala
        130                 135                 140

Ser Arg Leu Asp Val Tyr Pro His Gln Leu Ser Gly Gly Met Ser Gln
145                 150                 155                 160

Arg Val Met Ile Ala Met Ala Ile Ala Cys Arg Pro Lys Leu Leu Ile
                165                 170                 175

Ala Asp Glu Pro Thr Thr Ala Leu Asp Val Thr Ile Gln Ala Gln Ile
            180                 185                 190

Ile Glu Leu Leu Leu Glu Leu Gln Gln Lys Glu Asn Met Ala Leu Val
        195                 200                 205

Leu Ile Thr His Asp Leu Ala Leu Val Ala Glu Ala His Lys Ile
    210                 215                 220

Ile Val Met Tyr Ala Gly Gln Val Val Glu Thr Gly Asp Ala His Ala
225                 230                 235                 240

Ile Phe His Ala Pro Arg His Pro Tyr Thr Gln Ala Leu Leu Arg Ala
                245                 250                 255

Leu Pro Glu Phe Ala Gln Asp Lys Glu Arg Leu Ala Ser Leu Pro Gly
            260                 265                 270

Val Val Pro Gly Lys Tyr Asp Arg Pro Asn Gly Cys Leu Leu Asn Pro
        275                 280                 285

Arg Cys Pro Tyr Ala Thr Asp Arg Cys Arg Ala Glu Glu Pro Ala Leu
    290                 295                 300

Asn Met Leu Ala Asp Gly Arg Gln Ser Lys Cys His Tyr Pro Leu Asp
305                 310                 315                 320

Asp Ala Gly Arg Pro Thr Leu
                325

<210> SEQ ID NO 53
<211> LENGTH: 334
```

```
<212> TYPE: PRT
<213> ORGANISM: Escherichia coli

<400> SEQUENCE: 53

Met Ser Thr Gln Glu Ala Thr Leu Gln Gln Pro Leu Leu Ala Ile
 1               5                  10                  15

Asp Leu Lys Lys His Tyr Pro Val Lys Gly Met Phe Ala Pro Glu
            20                  25                  30

Arg Leu Val Lys Ala Leu Asp Gly Val Ser Phe Asn Leu Glu Arg Gly
        35                  40                  45

Lys Thr Leu Ala Val Val Gly Glu Ser Gly Cys Gly Lys Ser Thr Leu
    50                  55                  60

Gly Arg Leu Leu Thr Met Ile Glu Met Pro Thr Gly Gly Leu Tyr
65                  70                  75                  80

Tyr Gln Gly Gln Asp Leu Leu Lys His Asp Pro Gln Ala Gln Lys Leu
                85                  90                  95

Arg Arg Gln Lys Ile Gln Ile Val Phe Gln Asn Pro Tyr Gly Ser Leu
            100                 105                 110

Asn Pro Arg Lys Lys Val Gly Gln Ile Leu Glu Glu Pro Leu Leu Ile
        115                 120                 125

Asn Thr Ser Leu Ser Lys Glu Gln Arg Arg Glu Lys Ala Leu Ser Met
    130                 135                 140

Met Ala Lys Val Gly Leu Lys Thr Glu His Tyr Asp Arg Tyr Pro His
145                 150                 155                 160

Met Phe Ser Gly Gly Gln Arg Gln Arg Ile Ala Ile Ala Arg Gly Leu
                165                 170                 175

Met Leu Asp Pro Asp Val Val Ile Ala Asp Glu Pro Val Ser Ala Leu
            180                 185                 190

Asp Val Ser Val Arg Ala Gln Val Leu Asn Leu Met Met Asp Leu Gln
        195                 200                 205

Gln Glu Leu Gly Leu Ser Tyr Val Phe Ile Ser His Asp Leu Ser Val
    210                 215                 220

Val Glu His Ile Ala Asp Glu Val Met Val Met Tyr Leu Gly Arg Cys
225                 230                 235                 240

Val Glu Lys Gly Thr Lys Asp Gln Ile Phe Asn Asn Pro Arg His Pro
                245                 250                 255

Tyr Thr Gln Ala Leu Leu Ser Ala Thr Pro Arg Leu Asn Pro Asp Asp
            260                 265                 270

Arg Arg Glu Arg Ile Lys Leu Ser Gly Glu Leu Pro Ser Pro Leu Asn
        275                 280                 285

Pro Pro Pro Gly Cys Ala Phe Asn Ala Arg Cys Arg Arg Phe Gly
    290                 295                 300

Pro Cys Thr Gln Leu Gln Pro Gln Leu Lys Asp Tyr Gly Gly Gln Leu
305                 310                 315                 320

Val Ala Cys Phe Ala Val Asp Gln Asp Glu Asn Pro Gln Arg
                325                 330

<210> SEQ ID NO 54
<211> LENGTH: 34
<212> TYPE: DNA
<213> ORGANISM: Artificial Sequence
<220> FEATURE:
<223> OTHER INFORMATION: Synthetic DNA

<400> SEQUENCE: 54
gaagttccta tactttctag agaataggaa cttc                          34
```

```
<210> SEQ ID NO 55
<211> LENGTH: 1509
<212> TYPE: DNA
<213> ORGANISM: Escherichia coli

<400> SEQUENCE: 55 atg gag ttt agt gta aaa agc ggt agc ccg gag aaa cag cgg agt gcc      48
Met Glu Phe Ser Val Lys Ser Gly Ser Pro Glu Lys Gln Arg Ser Ala
 1               5                  10                  15 tgc atc gtc gtg ggc gtc ttc gaa cca cgt cgc ctt tct ccg att gca      96
Cys Ile Val Val Gly Val Phe Glu Pro Arg Arg Leu Ser Pro Ile Ala
             20                  25                  30 gaa cag ctc gat aaa atc agc gat ggg tac atc agc gcc ctg cta cgt     144
Glu Gln Leu Asp Lys Ile Ser Asp Gly Tyr Ile Ser Ala Leu Leu Arg
         35                  40                  45 cgg ggc gaa ctg gaa gga aaa ccg ggg cag aca ttg ttg ctg cac cat     192
Arg Gly Glu Leu Glu Gly Lys Pro Gly Gln Thr Leu Leu Leu His His
     50                  55                  60 gtt ccg aat gta ctt tcc gag cga att ctc ctt att ggt tgc ggc aaa     240
Val Pro Asn Val Leu Ser Glu Arg Ile Leu Leu Ile Gly Cys Gly Lys
 65                  70                  75                  80 gaa cgt gag ctg gat gag cgt cag tac aag cag gtt att cag aaa acc     288
Glu Arg Glu Leu Asp Glu Arg Gln Tyr Lys Gln Val Ile Gln Lys Thr
                 85                  90                  95 att aat acg ctg aat gat act ggc tca atg gaa gcg gtc tgc ttt ctg     336
Ile Asn Thr Leu Asn Asp Thr Gly Ser Met Glu Ala Val Cys Phe Leu
            100                 105                 110 act gag ctg cac gtt aaa ggc cgt aac aac tac tgg aaa gtg cgt cag     384
Thr Glu Leu His Val Lys Gly Arg Asn Asn Tyr Trp Lys Val Arg Gln
        115                 120                 125 gct gtc gag acg gca aaa gag acg ctc tac agt ttc gat cag ctg aaa     432
Ala Val Glu Thr Ala Lys Glu Thr Leu Tyr Ser Phe Asp Gln Leu Lys
    130                 135                 140 acg aac aag agc gaa ccg cgt cgt ccg ctg cgt aag atg gtg ttc aac     480
Thr Asn Lys Ser Glu Pro Arg Arg Pro Leu Arg Lys Met Val Phe Asn
145                 150                 155                 160 gtg ccg acc cgc cgt gaa ctg acc agc ggt gag cgc gcg atc cag cac     528
Val Pro Thr Arg Arg Glu Leu Thr Ser Gly Glu Arg Ala Ile Gln His
                165                 170                 175 ggt ctg gcg att gcc gcc ggg att aaa gca gca aaa gat ctc ggc aat     576
Gly Leu Ala Ile Ala Ala Gly Ile Lys Ala Ala Lys Asp Leu Gly Asn
            180                 185                 190 atg ccg ccg aat atc tgt aac gcc gct tac ctc gct tca caa gcg cgc     624
Met Pro Pro Asn Ile Cys Asn Ala Ala Tyr Leu Ala Ser Gln Ala Arg
        195                 200                 205 cag ctg gct gac agc tac agc aag aat gtc atc acc cgc gtt atc ggc     672
Gln Leu Ala Asp Ser Tyr Ser Lys Asn Val Ile Thr Arg Val Ile Gly
    210                 215                 220 gaa cag cag atg aaa gag ctg ggg atg cat tcc tat ctg gcg gtc ggt     720
Glu Gln Gln Met Lys Glu Leu Gly Met His Ser Tyr Leu Ala Val Gly
225                 230                 235                 240 cag ggt tcg caa aac gaa tcg ctg atg tcg gtg att gag tac aaa ggc     768
Gln Gly Ser Gln Asn Glu Ser Leu Met Ser Val Ile Glu Tyr Lys Gly
                245                 250                 255 aac gcg tcg gaa gat gca cgc cca atc gtg ctg gtg ggt aaa ggt tta     816
Asn Ala Ser Glu Asp Ala Arg Pro Ile Val Leu Val Gly Lys Gly Leu
            260                 265                 270 acc ttc gac tcc ggc ggt atc tcg atc aag cct tca gaa ggc atg gat     864
Thr Phe Asp Ser Gly Gly Ile Ser Ile Lys Pro Ser Glu Gly Met Asp
        275                 280                 285
```

```
gag atg aag tac gat atg tgc ggt gcg gca gcg gtt tac ggc gtg atg         912
Glu Met Lys Tyr Asp Met Cys Gly Ala Ala Ala Val Tyr Gly Val Met
    290             295                 300 cgg atg gtc gcg gag cta caa ctg ccg att aac gtt atc ggc gtg ttg         960
Arg Met Val Ala Glu Leu Gln Leu Pro Ile Asn Val Ile Gly Val Leu
305                 310                 315                 320 gca ggc tgc gaa aac atg cct ggc gga cga gcc tat cgt ccg ggc gat        1008
Ala Gly Cys Glu Asn Met Pro Gly Gly Arg Ala Tyr Arg Pro Gly Asp
                325                 330                 335 gtg tta acc acc atg tcc ggt caa acc gtt gaa gtg ctg aac acc gac        1056
Val Leu Thr Thr Met Ser Gly Gln Thr Val Glu Val Leu Asn Thr Asp
            340                 345                 350 gct gaa ggc cgc ctg gta ctg tgc gac gtg tta act tac gtt gag cgt        1104
Ala Glu Gly Arg Leu Val Leu Cys Asp Val Leu Thr Tyr Val Glu Arg
        355                 360                 365 ttt gag ccg gaa gcg gtg att gac gtg gcg acg ctg acc ggt gcc tgc        1152
Phe Glu Pro Glu Ala Val Ile Asp Val Ala Thr Leu Thr Gly Ala Cys
    370                 375                 380 gtg atc gcg ctg ggt cat cat att act ggt ctg atg gcg aac cat aat        1200
Val Ile Ala Leu Gly His His Ile Thr Gly Leu Met Ala Asn His Asn
385                 390                 395                 400 ccg ctg gcc cat gaa ctg att gcc gcg tct gaa caa tcc ggt gac cgc        1248
Pro Leu Ala His Glu Leu Ile Ala Ala Ser Glu Gln Ser Gly Asp Arg
                405                 410                 415 gca tgg cgc tta ccg ctg ggt gac gag tat cag gaa caa ctg gag tcc        1296
Ala Trp Arg Leu Pro Leu Gly Asp Glu Tyr Gln Glu Gln Leu Glu Ser
            420                 425                 430 aat ttt gcc gat atg gcg aac att ggc ggt cgt cct ggt ggg gcg att        1344
Asn Phe Ala Asp Met Ala Asn Ile Gly Gly Arg Pro Gly Gly Ala Ile
        435                 440                 445 acc gca ggt tgc ttc ctg tca cgc ttt acc cgt aag tac aac tgg gcg        1392
Thr Ala Gly Cys Phe Leu Ser Arg Phe Thr Arg Lys Tyr Asn Trp Ala
    450                 455                 460 cac ctg gat atc gcc ggt acc gcc tgg cgt tct ggt aaa gca aaa ggc        1440
His Leu Asp Ile Ala Gly Thr Ala Trp Arg Ser Gly Lys Ala Lys Gly
465                 470                 475                 480 gcc acc ggt cgt ccg gta gcg ttg ctg gca cag ttc ctg tta aac cgc        1488
Ala Thr Gly Arg Pro Val Ala Leu Leu Ala Gln Phe Leu Leu Asn Arg
                485                 490                 495 gct ggg ttt aac ggc gaa gag                                            1509
Ala Gly Phe Asn Gly Glu Glu
            500

<210> SEQ ID NO 56
<211> LENGTH: 1281
<212> TYPE: DNA
<213> ORGANISM: Escherichia coli

<400> SEQUENCE: 56 atg aca gaa gcg atg aag att acc ctc tct acc caa cct gcc gac gcg          48
Met Thr Glu Ala Met Lys Ile Thr Leu Ser Thr Gln Pro Ala Asp Ala
1               5                   10                  15 cgc tgg gga gaa aaa gca act tac agc att aat aat gac ggc att acc          96
Arg Trp Gly Glu Lys Ala Thr Tyr Ser Ile Asn Asn Asp Gly Ile Thr
                20                  25                  30 ctg cat ttg aac ggg gca gac gat ctg ggg ctg atc cag cgt gcg gcg         144
Leu His Leu Asn Gly Ala Asp Asp Leu Gly Leu Ile Gln Arg Ala Ala
            35                  40                  45 cgc aag att gac ggt ctg ggc atc aag cat gtt cag tta agc ggt gaa         192
Arg Lys Ile Asp Gly Leu Gly Ile Lys His Val Gln Leu Ser Gly Glu
        50                  55                  60
```

| | | |
|---|---|---|
| ggc tgg gat gcg gat cgc tgc tgg gca ttc tgg caa ggt tac aaa gcc<br>Gly Trp Asp Ala Asp Arg Cys Trp Ala Phe Trp Gln Gly Tyr Lys Ala<br>65                          70                     75                   80 | 240 | |
| ccg aaa ggc acg cgt aaa gtg gtg tgg ccg gat ctg gac gat gcc cag<br>Pro Lys Gly Thr Arg Lys Val Val Trp Pro Asp Leu Asp Asp Ala Gln<br>                     85                     90                     95 | 288 | |
| cgc cag gaa ctg gat aac cgc ctg atg atc atc gac tgg gtg cgt gac<br>Arg Gln Glu Leu Asp Asn Arg Leu Met Ile Ile Asp Trp Val Arg Asp<br>          100                    105                   110 | 336 | |
| acc atc aac gca ccg gca gaa gaa ttg gga cca tcg caa ctg gca cag<br>Thr Ile Asn Ala Pro Ala Glu Glu Leu Gly Pro Ser Gln Leu Ala Gln<br>          115                    120                   125 | 384 | |
| cgt gct gtt gat ctg atc agc aac gtc gcg ggc gat cgt gtg act tat<br>Arg Ala Val Asp Leu Ile Ser Asn Val Ala Gly Asp Arg Val Thr Tyr<br>130                         135                    140 | 432 | |
| cgg atc acc aaa ggc gaa gat ctg cgt gag caa ggt tat atg ggg ctg<br>Arg Ile Thr Lys Gly Glu Asp Leu Arg Glu Gln Gly Tyr Met Gly Leu<br>145                         150                   155                   160 | 480 | |
| cac aca gtc gga cgc ggt tca gaa cgt tct ccg gta ttg ctg gcg ctg<br>His Thr Val Gly Arg Gly Ser Glu Arg Ser Pro Val Leu Leu Ala Leu<br>                   165                    170                   175 | 528 | |
| gat tac aac cca act ggc gat aaa gaa gcg cca gtg tac gcg tgc ctg<br>Asp Tyr Asn Pro Thr Gly Asp Lys Glu Ala Pro Val Tyr Ala Cys Leu<br>                   180                    185                   190 | 576 | |
| gta ggt aaa ggt atc act ttt gac tcc ggc ggc tac agc atc aaa cag<br>Val Gly Lys Gly Ile Thr Phe Asp Ser Gly Gly Tyr Ser Ile Lys Gln<br>          195                    200                   205 | 624 | |
| act gcg ttt atg gac tcg atg aag tcg gac atg ggc ggc gcg gca acg<br>Thr Ala Phe Met Asp Ser Met Lys Ser Asp Met Gly Gly Ala Ala Thr<br>210                         215                    220 | 672 | |
| gtt acc ggg gcg ctg gca ttt gcc att acg cgc gga ctg aac aag cgc<br>Val Thr Gly Ala Leu Ala Phe Ala Ile Thr Arg Gly Leu Asn Lys Arg<br>225                         230                    235                   240 | 720 | |
| gtg aag ctg ttc ctc tgc tgt gcg gat aac ctg att agc ggc aat gcg<br>Val Lys Leu Phe Leu Cys Cys Ala Asp Asn Leu Ile Ser Gly Asn Ala<br>                   245                    250                   255 | 768 | |
| ttc aag ctg ggc gat atc atc acc tat cgc aac ggt aaa aaa gtt gaa<br>Phe Lys Leu Gly Asp Ile Ile Thr Tyr Arg Asn Gly Lys Lys Val Glu<br>                   260                    265                   270 | 816 | |
| gtg atg aac act gat gcc gaa ggg cgt ctg gtg ctt gcc gat ggt ctg<br>Val Met Asn Thr Asp Ala Glu Gly Arg Leu Val Leu Ala Asp Gly Leu<br>          275                    280                   285 | 864 | |
| att gat gcc agt gcg cag aaa ccg gaa atg atc att gat gcg gcg acc<br>Ile Asp Ala Ser Ala Gln Lys Pro Glu Met Ile Ile Asp Ala Ala Thr<br>290                         295                    300 | 912 | |
| ctc acc ggg gcg gcg aaa act gcg ctg ggt aat gat tat cac gcg ctg<br>Leu Thr Gly Ala Ala Lys Thr Ala Leu Gly Asn Asp Tyr His Ala Leu<br>305                         310                    315                   320 | 960 | |
| ttc agt ttt gac gat gcg ctg gcc ggt cgc ttg ctg gcg agt gcc gcg<br>Phe Ser Phe Asp Asp Ala Leu Ala Gly Arg Leu Leu Ala Ser Ala Ala<br>                   325                    330                   335 | 1008 | |
| cag gag aac gaa ccg ttc tgg cgt ctg ccg ctg gcg gag ttc cac cgc<br>Gln Glu Asn Glu Pro Phe Trp Arg Leu Pro Leu Ala Glu Phe His Arg<br>          340                    345                   350 | 1056 | |
| agc cag ctg ccg tct aac ttt gcc gaa ctg aac aat acc gga agc gcg<br>Ser Gln Leu Pro Ser Asn Phe Ala Glu Leu Asn Asn Thr Gly Ser Ala<br>          355                    360                   365 | 1104 | |
| gcg tat ccg gca ggc gcg agc acg gcg gcg ggc ttc ctg tcg cac ttt<br>Ala Tyr Pro Ala Gly Ala Ser Thr Ala Ala Gly Phe Leu Ser His Phe<br>370                         375                    380 | 1152 | |

```
gtt gag aac tat cag caa ggc tgg ctg cat atc gac tgc tcg gcg act      1200
Val Glu Asn Tyr Gln Gln Gly Trp Leu His Ile Asp Cys Ser Ala Thr
385                 390                 395                 400 tac cgt aaa gcg ccg gtt gaa cag tgg tct gcg ggc gct acg gga ctt      1248
Tyr Arg Lys Ala Pro Val Glu Gln Trp Ser Ala Gly Ala Thr Gly Leu
            405                 410                 415 ggt gtg cgc acg ata gct aat ctg tta acg gcg                          1281
Gly Val Arg Thr Ile Ala Asn Leu Leu Thr Ala
        420                 425

<210> SEQ ID NO 57
<211> LENGTH: 1455
<212> TYPE: DNA
<213> ORGANISM: Escherichia coli

<400> SEQUENCE: 57 gtg tct gaa ctg tct caa tta tct cca cag ccg ctg tgg gat att ttt        48
Val Ser Glu Leu Ser Gln Leu Ser Pro Gln Pro Leu Trp Asp Ile Phe
  1               5                  10                  15 gcc aaa atc tgt tct att cct cac ccg tcc tat cat gaa gag caa ctc        96
Ala Lys Ile Cys Ser Ile Pro His Pro Ser Tyr His Glu Glu Gln Leu
                 20                  25                  30 gct gaa tac att gtt ggt tgg gca aaa gag aaa ggt ttc cat gtc gaa       144
Ala Glu Tyr Ile Val Gly Trp Ala Lys Glu Lys Gly Phe His Val Glu
             35                  40                  45 cgc gat cag gta ggt aat atc ctg att cgt aaa cct gct acc gca ggt       192
Arg Asp Gln Val Gly Asn Ile Leu Ile Arg Lys Pro Ala Thr Ala Gly
         50                  55                  60 atg gaa aat cgt aaa ccg gtc gtc tta cag gcc cac ctc gat atg gtg       240
Met Glu Asn Arg Lys Pro Val Val Leu Gln Ala His Leu Asp Met Val
 65                  70                  75                  80 ccg cag aaa aat aac gac acc gtg cat gac ttc acg aaa gat cct atc       288
Pro Gln Lys Asn Asn Asp Thr Val His Asp Phe Thr Lys Asp Pro Ile
                 85                  90                  95 cag cct tat att gat ggc gaa tgg gtt aaa gcg cgc ggc acc acg ctg       336
Gln Pro Tyr Ile Asp Gly Glu Trp Val Lys Ala Arg Gly Thr Thr Leu
            100                 105                 110 ggt gcg gat aac ggc att ggt atg gcc tct gcg ctg gcg gtt ctg gct       384
Gly Ala Asp Asn Gly Ile Gly Met Ala Ser Ala Leu Ala Val Leu Ala
        115                 120                 125 gac gaa aac gtg gtt cac ggc ccg ctg gaa gtg ctg ctg acc atg acc       432
Asp Glu Asn Val Val His Gly Pro Leu Glu Val Leu Leu Thr Met Thr
    130                 135                 140 gaa gaa gcc ggt atg gac ggt gcg ttc ggc tta cag ggc aac tgg ttg       480
Glu Glu Ala Gly Met Asp Gly Ala Phe Gly Leu Gln Gly Asn Trp Leu
145                 150                 155                 160 cag gct gat att ctg att aac acc gac tcc gaa gaa gaa ggt gaa atc       528
Gln Ala Asp Ile Leu Ile Asn Thr Asp Ser Glu Glu Glu Gly Glu Ile
                165                 170                 175 tac atg ggt tgt gcg ggg ggt atc gac ttc acc tcc aac ctg cat tta       576
Tyr Met Gly Cys Ala Gly Gly Ile Asp Phe Thr Ser Asn Leu His Leu
            180                 185                 190 gat cgt gaa gcg gtt cca gct ggt ttt gaa acc ttc aag tta acc tta       624
Asp Arg Glu Ala Val Pro Ala Gly Phe Glu Thr Phe Lys Leu Thr Leu
        195                 200                 205 aaa ggt ctg aaa ggc ggt cac tcc ggc ggg gaa atc cac gtt ggg ctg       672
Lys Gly Leu Lys Gly Gly His Ser Gly Gly Glu Ile His Val Gly Leu
    210                 215                 220 ggt aat gcc aac aaa ctg ctg gtg cgc ttc ctg gcg ggt cat gcg gaa       720
Gly Asn Ala Asn Lys Leu Leu Val Arg Phe Leu Ala Gly His Ala Glu
225                 230                 235                 240
```

```
gaa ctg gat ctg cgc ctt atc gat ttc aac ggc ggc aca ctg cgt aac        768
Glu Leu Asp Leu Arg Leu Ile Asp Phe Asn Gly Gly Thr Leu Arg Asn
            245                 250                 255 gcc atc ccg cgt gaa gcc ttt gcg acc att gct gtc gca gct gat aaa        816
Ala Ile Pro Arg Glu Ala Phe Ala Thr Ile Ala Val Ala Ala Asp Lys
        260                 265                 270 gtc gac gtc ctg aaa tct ctg gtg aat acc tat cag gag atc ctg aaa        864
Val Asp Val Leu Lys Ser Leu Val Asn Thr Tyr Gln Glu Ile Leu Lys
    275                 280                 285 aac gag ctg gca gaa aaa gag aaa aat ctg gcc ttg ttg ctg gac tct        912
Asn Glu Leu Ala Glu Lys Glu Lys Asn Leu Ala Leu Leu Leu Asp Ser
290                 295                 300 gta gcg aac gat aaa gct gcc ctg att gcg aaa tct cgc gat acc ttt        960
Val Ala Asn Asp Lys Ala Ala Leu Ile Ala Lys Ser Arg Asp Thr Phe
305                 310                 315                 320 att cgt ctg ctg aac gcc acc ccg aac ggt gtg att cgt aac tcc gat       1008
Ile Arg Leu Leu Asn Ala Thr Pro Asn Gly Val Ile Arg Asn Ser Asp
            325                 330                 335 gta gcc aaa ggt gtg gtt gaa acc tcc ctg aac gtc ggt gtg gtg acc       1056
Val Ala Lys Gly Val Val Glu Thr Ser Leu Asn Val Gly Val Val Thr
        340                 345                 350 atg act gac aat aac gta gaa att cac tgc ctg atc cgt tca ctg atc       1104
Met Thr Asp Asn Asn Val Glu Ile His Cys Leu Ile Arg Ser Leu Ile
    355                 360                 365 gac agc ggt aaa gac tac gtg gtg agc atg ctg gat tcg ctg ggt aaa       1152
Asp Ser Gly Lys Asp Tyr Val Val Ser Met Leu Asp Ser Leu Gly Lys
370                 375                 380 ctg gct ggc gcg aaa acc gaa gcg aaa ggc gca tat cct ggc tgg cag       1200
Leu Ala Gly Ala Lys Thr Glu Ala Lys Gly Ala Tyr Pro Gly Trp Gln
385                 390                 395                 400 ccg gac gct aat tct ccg gtg atg cat ctg gta cgt gaa acc tat cag       1248
Pro Asp Ala Asn Ser Pro Val Met His Leu Val Arg Glu Thr Tyr Gln
            405                 410                 415 cgc ctg ttc aac aag acg ccg aac atc cag att atc cac gcg ggc ctg       1296
Arg Leu Phe Asn Lys Thr Pro Asn Ile Gln Ile Ile His Ala Gly Leu
        420                 425                 430 gaa tgt ggt ctg ttc aaa aaa ccg tat ccg gaa atg gac atg gtt tct       1344
Glu Cys Gly Leu Phe Lys Lys Pro Tyr Pro Glu Met Asp Met Val Ser
    435                 440                 445 atc ggg cca act atc acc ggt cca cac tct ccg gat gag caa gtt cac       1392
Ile Gly Pro Thr Ile Thr Gly Pro His Ser Pro Asp Glu Gln Val His
450                 455                 460 atc gaa agc gta ggt cat tac tgg aca ctg ctg act gaa ctg ctg aaa       1440
Ile Glu Ser Val Gly His Tyr Trp Thr Leu Leu Thr Glu Leu Leu Lys
465                 470                 475                 480 gaa att ccg gcg aag                                                    1455
Glu Ile Pro Ala Lys
            485

<210> SEQ ID NO 58
<211> LENGTH: 2610
<212> TYPE: DNA
<213> ORGANISM: Escherichia coli

<400> SEQUENCE: 58 atg act caa cag cca caa gcc aaa tac cgt cac gat tat cgt gcg ccg         48
Met Thr Gln Gln Pro Gln Ala Lys Tyr Arg His Asp Tyr Arg Ala Pro
1               5                   10                  15 gat tac cag att act gat att gac ttg acc ttt gac ctc gac gcg caa         96
Asp Tyr Gln Ile Thr Asp Ile Asp Leu Thr Phe Asp Leu Asp Ala Gln
            20                  25                  30
```

```
aag acg gtc gtt acc gcg gtc agc cag gct gtc cgt cat ggt gca tca    144
Lys Thr Val Val Thr Ala Val Ser Gln Ala Val Arg His Gly Ala Ser
         35                  40                  45 gat gct ccc ctt cgt ctc aac ggc gaa gac ctc aaa ctg gtt tct gtt    192
Asp Ala Pro Leu Arg Leu Asn Gly Glu Asp Leu Lys Leu Val Ser Val
 50                  55                  60 cat att aat gat gag ccg tgg acc gcc tgg aaa gaa gaa gag ggc gca    240
His Ile Asn Asp Glu Pro Trp Thr Ala Trp Lys Glu Glu Glu Gly Ala
 65                  70                  75                  80 ctg gtt atc agt aat ttg ccg gag cgt ttt acg ctt aag atc att aat    288
Leu Val Ile Ser Asn Leu Pro Glu Arg Phe Thr Leu Lys Ile Ile Asn
                 85                  90                  95 gaa ata agc ccg gcg gcg aat acc gcg ctg gaa ggg ctt tat cag tca    336
Glu Ile Ser Pro Ala Ala Asn Thr Ala Leu Glu Gly Leu Tyr Gln Ser
100                 105                 110 ggc gat gcg ctt tgc acc cag tgt gaa gcc gaa ggt ttc cgc cat att    384
Gly Asp Ala Leu Cys Thr Gln Cys Glu Ala Glu Gly Phe Arg His Ile
            115                 120                 125 acg tat tat ctc gac cgc ccg gac gtg ctg gcg cgt ttt acc acc aaa    432
Thr Tyr Tyr Leu Asp Arg Pro Asp Val Leu Ala Arg Phe Thr Thr Lys
130                 135                 140 att att gcc gat aaa atc aaa tat ccc ttc ctg ctt tcc aat ggt aac    480
Ile Ile Ala Asp Lys Ile Lys Tyr Pro Phe Leu Leu Ser Asn Gly Asn
145                 150                 155                 160 cgc gtt gcg caa ggc gaa ctg gaa aac gga cgc cat tgg gta cag tgg    528
Arg Val Ala Gln Gly Glu Leu Glu Asn Gly Arg His Trp Val Gln Trp
                165                 170                 175 cag gac ccg ttc ccg aaa ccg tgc tac ctg ttt gcg ctg gtg gca ggc    576
Gln Asp Pro Phe Pro Lys Pro Cys Tyr Leu Phe Ala Leu Val Ala Gly
            180                 185                 190 gac ttt gat gta ctg cgc gat acc ttt acc acg cgt tct ggt cgc gaa    624
Asp Phe Asp Val Leu Arg Asp Thr Phe Thr Thr Arg Ser Gly Arg Glu
        195                 200                 205 gta gca ctg gag ctg tac gtc gat cgc ggc aac ctt gat cgc gcg ccg    672
Val Ala Leu Glu Leu Tyr Val Asp Arg Gly Asn Leu Asp Arg Ala Pro
210                 215                 220 tgg gcg atg acc tcg ctg aaa aac tcc atg aaa tgg gat gaa gaa cgc    720
Trp Ala Met Thr Ser Leu Lys Asn Ser Met Lys Trp Asp Glu Glu Arg
225                 230                 235                 240 ttt ggc ctg gag tat gac ctc gac atc tat atg atc gtc gcg gtg gat    768
Phe Gly Leu Glu Tyr Asp Leu Asp Ile Tyr Met Ile Val Ala Val Asp
                245                 250                 255 ttc ttc aat atg ggc gca atg gag aat aag ggg ctg aat atc ttt aac    816
Phe Phe Asn Met Gly Ala Met Glu Asn Lys Gly Leu Asn Ile Phe Asn
            260                 265                 270 tcc aaa tat gtg ctg gcc cgc acc gac acc gcc acc gac aaa gat tac    864
Ser Lys Tyr Val Leu Ala Arg Thr Asp Thr Ala Thr Asp Lys Asp Tyr
        275                 280                 285 ctc gat att gaa cgc gtt atc ggc cat gaa tat ttc cat aac tgg acc    912
Leu Asp Ile Glu Arg Val Ile Gly His Glu Tyr Phe His Asn Trp Thr
290                 295                 300 ggt aac cga gtg acc tgt cgc gac tgg ttc cag ctc agc ctg aaa gaa    960
Gly Asn Arg Val Thr Cys Arg Asp Trp Phe Gln Leu Ser Leu Lys Glu
305                 310                 315                 320 ggt tta acc gtc ttc cgc gat cag gag ttc agc tct gac ctt ggt tcc   1008
Gly Leu Thr Val Phe Arg Asp Gln Glu Phe Ser Ser Asp Leu Gly Ser
                325                 330                 335 cgc gca gtt aac cgc atc aat aat gta cgc acc atg cgc gga ttg cag   1056
Arg Ala Val Asn Arg Ile Asn Asn Val Arg Thr Met Arg Gly Leu Gln
            340                 345                 350
```

```
ttt gca gaa gac gcc agc ccg atg gcg cac ccg atc cgc ccg gat atg       1104
Phe Ala Glu Asp Ala Ser Pro Met Ala His Pro Ile Arg Pro Asp Met
        355                 360                 365 gtc att gag atg aac aac ttc tac acc ctg acc gtt tac gag aag ggc       1152
Val Ile Glu Met Asn Asn Phe Tyr Thr Leu Thr Val Tyr Glu Lys Gly
370                 375                 380 gcg gaa gtg att cgc atg atc cac acc ctg ctt ggc gaa gaa aac ttc       1200
Ala Glu Val Ile Arg Met Ile His Thr Leu Leu Gly Glu Glu Asn Phe
385                 390                 395                 400 cag aaa ggg atg cag ctt tat ttc gag cgt cat gat ggt agt gca gcg       1248
Gln Lys Gly Met Gln Leu Tyr Phe Glu Arg His Asp Gly Ser Ala Ala
                405                 410                 415 acc tgt gac gac ttt gtg cag gcg atg gaa gat gcg tcg aat gtc gat       1296
Thr Cys Asp Asp Phe Val Gln Ala Met Glu Asp Ala Ser Asn Val Asp
            420                 425                 430 ctc tcc cat ttc cgc cgt tgg tac agc cag tcc ggt aca ccg att gtg       1344
Leu Ser His Phe Arg Arg Trp Tyr Ser Gln Ser Gly Thr Pro Ile Val
        435                 440                 445 acc gtc aaa gac gac tac aat ccg gaa acc gag cag tac acc ctg acc       1392
Thr Val Lys Asp Asp Tyr Asn Pro Glu Thr Glu Gln Tyr Thr Leu Thr
450                 455                 460 atc agc cag cgc acg cca gcc acg ccg gat cag gca gaa aaa cag ccg       1440
Ile Ser Gln Arg Thr Pro Ala Thr Pro Asp Gln Ala Glu Lys Gln Pro
465                 470                 475                 480 ctg cat att ccg ttt gcc atc gaa ctg tat gat aac gaa ggc aaa gtg       1488
Leu His Ile Pro Phe Ala Ile Glu Leu Tyr Asp Asn Glu Gly Lys Val
                485                 490                 495 atc ccg ttg cag aaa ggc ggt cat ccg gtg aat tcc gtg ctg aac gtc       1536
Ile Pro Leu Gln Lys Gly Gly His Pro Val Asn Ser Val Leu Asn Val
            500                 505                 510 act cag gcg gaa cag acc ttt gtc ttt gat aat gtc tac ttc cag ccg       1584
Thr Gln Ala Glu Gln Thr Phe Val Phe Asp Asn Val Tyr Phe Gln Pro
        515                 520                 525 gtg cct gcg ctg ctg tgc gaa ttc tct gcg cca gtg aaa ctg gaa tat       1632
Val Pro Ala Leu Leu Cys Glu Phe Ser Ala Pro Val Lys Leu Glu Tyr
530                 535                 540 aag tgg agc gat cag caa ctg acc ttc ctg atg cgt cat gcg cgt aat       1680
Lys Trp Ser Asp Gln Gln Leu Thr Phe Leu Met Arg His Ala Arg Asn
545                 550                 555                 560 gat ttc tcc cgc tgg gat gcg gcg caa agt ttg ctg gca acc tac atc       1728
Asp Phe Ser Arg Trp Asp Ala Ala Gln Ser Leu Leu Ala Thr Tyr Ile
                565                 570                 575 aag ctg aac gtc gcg cgt cat cag caa ggt cag ccg ctg tct ctg ccg       1776
Lys Leu Asn Val Ala Arg His Gln Gln Gly Gln Pro Leu Ser Leu Pro
            580                 585                 590 gtg cat gtg gct gat gct ttc cgc gcg gta ctg ctt gat gag aag att       1824
Val His Val Ala Asp Ala Phe Arg Ala Val Leu Leu Asp Glu Lys Ile
        595                 600                 605 gat cca gcg ctg gcg gca gaa atc ctg acg ctg cct tct gtc aat gaa       1872
Asp Pro Ala Leu Ala Ala Glu Ile Leu Thr Leu Pro Ser Val Asn Glu
610                 615                 620 atg gct gaa ttg ttc gat atc atc gac ccg att gct att gcc gaa gta       1920
Met Ala Glu Leu Phe Asp Ile Ile Asp Pro Ile Ala Ile Ala Glu Val
625                 630                 635                 640 cgc gaa gca ctc act cgt act ctg gcg act gaa ctg gcg gat gag cta       1968
Arg Glu Ala Leu Thr Arg Thr Leu Ala Thr Glu Leu Ala Asp Glu Leu
                645                 650                 655 ctg gct att tac aac gcg aat tac cag agc gag tac cgt gtt gag cat       2016
Leu Ala Ile Tyr Asn Ala Asn Tyr Gln Ser Glu Tyr Arg Val Glu His
            660                 665                 670
```

| | | | | | | | | | | | | | | | | |
|---|---|---|---|---|---|---|---|---|---|---|---|---|---|---|---|---|
|gaa|gat|att|gca|aaa|cgc|act|ctg|cgt|aat|gcc|tgc|ctg|cgt|ttc|ctc|2064|
|Glu|Asp|Ile|Ala|Lys|Arg|Thr|Leu|Arg|Asn|Ala|Cys|Leu|Arg|Phe|Leu| |
| | | |675| | |680| | | |685| | | | | | |

| | | | | | | | | | | | | | | | | |
|---|---|---|---|---|---|---|---|---|---|---|---|---|---|---|---|---|
|gct|ttt|ggt|gaa|acg|cat|ctg|gct|gat|gtg|ctg|gtg|agc|aag|cag|ttc|2112|
|Ala|Phe|Gly|Glu|Thr|His|Leu|Ala|Asp|Val|Leu|Val|Ser|Lys|Gln|Phe| |
| |690| | | |695| | | |700| | | | | | | |

| | | | | | | | | | | | | | | | | |
|---|---|---|---|---|---|---|---|---|---|---|---|---|---|---|---|---|
|cac|gaa|gca|aac|aat|atg|act|gat|gcg|ctg|gcg|gcg|ctt|tct|gcg|gcg|2160|
|His|Glu|Ala|Asn|Asn|Met|Thr|Asp|Ala|Leu|Ala|Ala|Leu|Ser|Ala|Ala| |
|705| | | | |710| | | |715| | | | | |720| |

| | | | | | | | | | | | | | | | | |
|---|---|---|---|---|---|---|---|---|---|---|---|---|---|---|---|---|
|gtt|gcc|gca|cag|ctg|cct|tgc|cgt|gac|gcg|ctg|atg|cag|gag|tac|gac|2208|
|Val|Ala|Ala|Gln|Leu|Pro|Cys|Arg|Asp|Ala|Leu|Met|Gln|Glu|Tyr|Asp| |
| | | | |725| | | | |730| | | | |735| | |

| | | | | | | | | | | | | | | | | |
|---|---|---|---|---|---|---|---|---|---|---|---|---|---|---|---|---|
|gac|aag|tgg|cat|cag|aac|ggt|ctg|gtg|atg|gat|aaa|tgg|ttt|atc|ctg|2256|
|Asp|Lys|Trp|His|Gln|Asn|Gly|Leu|Val|Met|Asp|Lys|Trp|Phe|Ile|Leu| |
| | | |740| | | |745| | | |750| | | | | |

| | | | | | | | | | | | | | | | | |
|---|---|---|---|---|---|---|---|---|---|---|---|---|---|---|---|---|
|caa|gcc|acc|agc|ccg|gcg|gcg|aat|gtg|ctg|gag|acg|gtg|cgc|ggc|ctg|2304|
|Gln|Ala|Thr|Ser|Pro|Ala|Ala|Asn|Val|Leu|Glu|Thr|Val|Arg|Gly|Leu| |
| | |755| | | |760| | | |765| | | | | | |

| | | | | | | | | | | | | | | | | |
|---|---|---|---|---|---|---|---|---|---|---|---|---|---|---|---|---|
|ttg|cag|cat|cgc|tca|ttt|acc|atg|agc|aac|ccg|aac|cgt|att|cgt|tcg|2352|
|Leu|Gln|His|Arg|Ser|Phe|Thr|Met|Ser|Asn|Pro|Asn|Arg|Ile|Arg|Ser| |
| |770| | | |775| | | |780| | | | | | | |

| | | | | | | | | | | | | | | | | |
|---|---|---|---|---|---|---|---|---|---|---|---|---|---|---|---|---|
|ttg|att|ggc|gcg|ttt|gcg|ggc|agc|aat|ccg|gca|gcg|ttc|cat|gcc|gaa|2400|
|Leu|Ile|Gly|Ala|Phe|Ala|Gly|Ser|Asn|Pro|Ala|Ala|Phe|His|Ala|Glu| |
|785| | | |790| | | |795| | | |800| | | | |

| | | | | | | | | | | | | | | | | |
|---|---|---|---|---|---|---|---|---|---|---|---|---|---|---|---|---|
|gat|ggc|agc|ggt|tac|ctg|ttc|ctg|gtg|gaa|atg|ctt|acc|gac|ctc|aac|2448|
|Asp|Gly|Ser|Gly|Tyr|Leu|Phe|Leu|Val|Glu|Met|Leu|Thr|Asp|Leu|Asn| |
| | | |805| | | |810| | | |815| | | | | |

| | | | | | | | | | | | | | | | | |
|---|---|---|---|---|---|---|---|---|---|---|---|---|---|---|---|---|
|agc|cgt|aac|ccg|cag|gtg|gct|tca|cgt|ctg|att|gaa|ccg|ctg|att|cgc|2496|
|Ser|Arg|Asn|Pro|Gln|Val|Ala|Ser|Arg|Leu|Ile|Glu|Pro|Leu|Ile|Arg| |
| | | |820| | | |825| | | |830| | | | | |

| | | | | | | | | | | | | | | | | |
|---|---|---|---|---|---|---|---|---|---|---|---|---|---|---|---|---|
|ctg|aaa|cgt|tac|gat|gcc|aaa|cgt|cag|gag|aaa|atg|cgc|gcg|gcg|ctg|2544|
|Leu|Lys|Arg|Tyr|Asp|Ala|Lys|Arg|Gln|Glu|Lys|Met|Arg|Ala|Ala|Leu| |
| | |835| | | |840| | | |845| | | | | | |

| | | | | | | | | | | | | | | | | |
|---|---|---|---|---|---|---|---|---|---|---|---|---|---|---|---|---|
|gaa|cag|ttg|aaa|ggg|ctg|gaa|aat|ctc|tct|ggc|gat|ctg|tac|gag|aag|2592|
|Glu|Gln|Leu|Lys|Gly|Leu|Glu|Asn|Leu|Ser|Gly|Asp|Leu|Tyr|Glu|Lys| |
| |850| | | |855| | | |860| | | | | | | |

| | | | | |
|---|---|---|---|---|---|
|ata|act|aaa|gca|ctg|gct|2610|
|Ile|Thr|Lys|Ala|Leu|Ala| |
|865| | | |870| | |

<210> SEQ ID NO 59
<211> LENGTH: 1605
<212> TYPE: DNA
<213> ORGANISM: Escherichia coli

<400> SEQUENCE: 59

| | | | | | | | | | | | | | | | | |
|---|---|---|---|---|---|---|---|---|---|---|---|---|---|---|---|---|
|atg|cgt|att|tcc|ttg|aaa|aag|tca|ggg|atg|ctg|aag|ctt|ggt|ctc|agc|48|
|Met|Arg|Ile|Ser|Leu|Lys|Lys|Ser|Gly|Met|Leu|Lys|Leu|Gly|Leu|Ser| |
|1| | | |5| | | |10| | | |15| | | | |

| | | | | | | | | | | | | | | | | |
|---|---|---|---|---|---|---|---|---|---|---|---|---|---|---|---|---|
|ctg|gtg|gct|atg|acc|gtc|gca|gca|agt|gtt|cag|gct|aaa|act|ctg|gtt|96|
|Leu|Val|Ala|Met|Thr|Val|Ala|Ala|Ser|Val|Gln|Ala|Lys|Thr|Leu|Val| |
| | | |20| | | |25| | | |30| | | | | |

| | | | | | | | | | | | | | | | | |
|---|---|---|---|---|---|---|---|---|---|---|---|---|---|---|---|---|
|tat|tgc|tca|gaa|gga|tct|ccg|gaa|ggg|ttt|aac|ccg|cag|ctg|ttt|acc|144|
|Tyr|Cys|Ser|Glu|Gly|Ser|Pro|Glu|Gly|Phe|Asn|Pro|Gln|Leu|Phe|Thr| |
| | |35| | | |40| | | |45| | | | | | |

| | | | | | | | | | | | | | | | | |
|---|---|---|---|---|---|---|---|---|---|---|---|---|---|---|---|---|
|tcc|ggc|acc|acc|tat|gac|gcc|tct|tcc|gtc|ccg|ctt|tat|aac|cgt|ctg|192|
|Ser|Gly|Thr|Thr|Tyr|Asp|Ala|Ser|Ser|Val|Pro|Leu|Tyr|Asn|Arg|Leu| |
| |50| | | |55| | | |60| | | | | | | |

| | | | | | | | | | | | | | | | | |
|---|---|---|---|---|---|---|---|---|---|---|---|---|---|---|---|---|
|gtt|gaa|ttt|aaa|atc|ggc|acc|acc|gaa|gtg|atc|ccg|ggc|ctc|gct|gaa|240|
|Val|Glu|Phe|Lys|Ile|Gly|Thr|Thr|Glu|Val|Ile|Pro|Gly|Leu|Ala|Glu| |
|65| | | |70| | | |75| | | |80| | | | |

| | | |
|---|---|---|
| aag tgg gaa gtc agc gaa gac ggt aaa acc tat acc ttc cat ctg cgt<br>Lys Trp Glu Val Ser Glu Asp Gly Lys Thr Tyr Thr Phe His Leu Arg<br>85 90 95 | | 288 |
| aaa ggt gtg aag tgg cac gac aat aaa gaa ttc aaa ccg acg cgt gaa<br>Lys Gly Val Lys Trp His Asp Asn Lys Glu Phe Lys Pro Thr Arg Glu<br>100 105 110 | | 336 |
| ctg aac gcc gat gat gtg gtg ttc tcg ttc gat cgt cag aaa aac gcg<br>Leu Asn Ala Asp Asp Val Val Phe Ser Phe Asp Arg Gln Lys Asn Ala<br>115 120 125 | | 384 |
| caa aac ccg tac cat aaa gtt tct ggc ggc agc tac gaa tac ttc gaa<br>Gln Asn Pro Tyr His Lys Val Ser Gly Gly Ser Tyr Glu Tyr Phe Glu<br>130 135 140 | | 432 |
| ggc atg ggc ttg cca gag ctg atc agt gaa gtg aaa aag gtg gac gac<br>Gly Met Gly Leu Pro Glu Leu Ile Ser Glu Val Lys Lys Val Asp Asp<br>145 150 155 160 | | 480 |
| aac acc gtt cag ttt gtg ctg act cgc ccg gaa gcg ccg ttc ctc gct<br>Asn Thr Val Gln Phe Val Leu Thr Arg Pro Glu Ala Pro Phe Leu Ala<br>165 170 175 | | 528 |
| gac ctg gca atg gac ttc gcc tct att ctg tca aaa gaa tat gct gat<br>Asp Leu Ala Met Asp Phe Ala Ser Ile Leu Ser Lys Glu Tyr Ala Asp<br>180 185 190 | | 576 |
| gcg atg atg aaa gcc ggt aca ccg gaa aaa ctg gac ctc aac cca atc<br>Ala Met Met Lys Ala Gly Thr Pro Glu Lys Leu Asp Leu Asn Pro Ile<br>195 200 205 | | 624 |
| gga acc ggt ccg ttc cag tta cag cag tat caa aaa gat tcc cgt atc<br>Gly Thr Gly Pro Phe Gln Leu Gln Gln Tyr Gln Lys Asp Ser Arg Ile<br>210 215 220 | | 672 |
| cgc tac aaa gcg ttt gat ggc tac tgg ggc acc aaa ccg cag atc gat<br>Arg Tyr Lys Ala Phe Asp Gly Tyr Trp Gly Thr Lys Pro Gln Ile Asp<br>225 230 235 240 | | 720 |
| acg ctg gtt ttc tct att acc cct gac gct tcc gtg cgt tac gcg aaa<br>Thr Leu Val Phe Ser Ile Thr Pro Asp Ala Ser Val Arg Tyr Ala Lys<br>245 250 255 | | 768 |
| ttg cag aag aat gaa tgc cag gtg atg ccg tac ccg aac ccg gca gat<br>Leu Gln Lys Asn Glu Cys Gln Val Met Pro Tyr Pro Asn Pro Ala Asp<br>260 265 270 | | 816 |
| atc gct cgc atg aag cag gat aaa tcc atc aat ctg atg gaa atg ccg<br>Ile Ala Arg Met Lys Gln Asp Lys Ser Ile Asn Leu Met Glu Met Pro<br>275 280 285 | | 864 |
| ggg ctg aac gtc ggt tat ctc tcg tat aac gtg cag aaa aaa cca ctc<br>Gly Leu Asn Val Gly Tyr Leu Ser Tyr Asn Val Gln Lys Lys Pro Leu<br>290 295 300 | | 912 |
| gat gac gtg aaa gtt cgc cag gct ctg acc tac gcg gtg aac aaa gac<br>Asp Asp Val Lys Val Arg Gln Ala Leu Thr Tyr Ala Val Asn Lys Asp<br>305 310 315 320 | | 960 |
| gcg atc atc aaa gcg gtt tat cag ggc gcg ggc gta tca gcg aaa aac<br>Ala Ile Ile Lys Ala Val Tyr Gln Gly Ala Gly Val Ser Ala Lys Asn<br>325 330 335 | | 1008 |
| ctg atc ccg cca acc atg tgg ggc tat aac gac gac gtt cag gac tac<br>Leu Ile Pro Pro Thr Met Trp Gly Tyr Asn Asp Asp Val Gln Asp Tyr<br>340 345 350 | | 1056 |
| acc tac gat cct gaa aaa gcg aaa gcc ttg ctg aaa gaa gcg ggt ctg<br>Thr Tyr Asp Pro Glu Lys Ala Lys Ala Leu Leu Lys Glu Ala Gly Leu<br>355 360 365 | | 1104 |
| gaa aaa ggt ttc tcc atc gac ctg tgg gcg atg ccg gta caa cgt ccg<br>Glu Lys Gly Phe Ser Ile Asp Leu Trp Ala Met Pro Val Gln Arg Pro<br>370 375 380 | | 1152 |
| tat aac ccg aac gct cgc cgc atg gcg gag atg att cag gca gac tgg<br>Tyr Asn Pro Asn Ala Arg Arg Met Ala Glu Met Ile Gln Ala Asp Trp<br>385 390 395 400 | | 1200 |

| | | |
|---|---|---|
| gcg aaa gtc ggc gtg cag gcc aaa att gtc acc tac gaa tgg ggt gag<br>Ala Lys Val Gly Val Gln Ala Lys Ile Val Thr Tyr Glu Trp Gly Glu<br>405 410 415 | | 1248 |
| tac ctc aag cgt gcg aaa gat ggc gag cac cag acg gta atg atg ggc<br>Tyr Leu Lys Arg Ala Lys Asp Gly Glu His Gln Thr Val Met Met Gly<br>420 425 430 | | 1296 |
| tgg act ggc gat aac ggg gat ccg gat aac ttc ttc gcc acc ctg ttc<br>Trp Thr Gly Asp Asn Gly Asp Pro Asp Asn Phe Phe Ala Thr Leu Phe<br>435 440 445 | | 1344 |
| agc tgc gcc gcc tct gaa caa ggc tcc aac tac tca aaa tgg tgc tac<br>Ser Cys Ala Ala Ser Glu Gln Gly Ser Asn Tyr Ser Lys Trp Cys Tyr<br>450 455 460 | | 1392 |
| aaa ccg ttt gaa gat ctg att caa ccg gcg cgt gct acc gac gac cac<br>Lys Pro Phe Glu Asp Leu Ile Gln Pro Ala Arg Ala Thr Asp Asp His<br>465 470 475 480 | | 1440 |
| aat aaa cgc gtt gaa ctg tac aaa caa gcg cag gtg gtg atg cac gat<br>Asn Lys Arg Val Glu Leu Tyr Lys Gln Ala Gln Val Val Met His Asp<br>485 490 495 | | 1488 |
| cag gct ccg gca ctg atc atc gct cac tcc acc gtg ttt gaa ccg gta<br>Gln Ala Pro Ala Leu Ile Ile Ala His Ser Thr Val Phe Glu Pro Val<br>500 505 510 | | 1536 |
| cgt aaa gaa gtt aaa ggc tat gtg gtt gat cca tta ggc aaa cat cac<br>Arg Lys Glu Val Lys Gly Tyr Val Val Asp Pro Leu Gly Lys His His<br>515 520 525 | | 1584 |
| ttc gaa aac gtc tct atc gaa<br>Phe Glu Asn Val Ser Ile Glu<br>530 535 | | 1605 |

<210> SEQ ID NO 60
<211> LENGTH: 1017
<212> TYPE: DNA
<213> ORGANISM: Escherichia coli

<400> SEQUENCE: 60

| | | |
|---|---|---|
| atg ttg cag ttt att ctc cga cgt ttg gga ctc gtc atc ccc acg ttt<br>Met Leu Gln Phe Ile Leu Arg Arg Leu Gly Leu Val Ile Pro Thr Phe<br>1 5 10 15 | | 48 |
| atc ggt att acc ctt ctc aca ttt gcc ttt gtc cac atg atc ccg ggc<br>Ile Gly Ile Thr Leu Leu Thr Phe Ala Phe Val His Met Ile Pro Gly<br>20 25 30 | | 96 |
| gat ccg gtg atg atc atg gcg ggc gaa cgt ggg atc tcc cca gag cgt<br>Asp Pro Val Met Ile Met Ala Gly Glu Arg Gly Ile Ser Pro Glu Arg<br>35 40 45 | | 144 |
| cac gcg cag ctg ctg gct gaa ctc ggc tta gat aaa ccg atg tgg cag<br>His Ala Gln Leu Leu Ala Glu Leu Gly Leu Asp Lys Pro Met Trp Gln<br>50 55 60 | | 192 |
| cag tat ctc cat tac att tgg ggc gtt atg cat ggc gat cta ggc att<br>Gln Tyr Leu His Tyr Ile Trp Gly Val Met His Gly Asp Leu Gly Ile<br>65 70 75 80 | | 240 |
| tca atg aaa agc cgc atc ccg gtt tgg gaa gag ttc gtg ccg cgc ttc<br>Ser Met Lys Ser Arg Ile Pro Val Trp Glu Glu Phe Val Pro Arg Phe<br>85 90 95 | | 288 |
| cag gcc acg ctg gaa ctt ggc gtc tgc gcg atg att ttt gct acg gca<br>Gln Ala Thr Leu Glu Leu Gly Val Cys Ala Met Ile Phe Ala Thr Ala<br>100 105 110 | | 336 |
| gtc ggt att ccg gtc ggc gtg ctg gct gcg gtt aaa cgc ggt tcc att<br>Val Gly Ile Pro Val Gly Val Leu Ala Ala Val Lys Arg Gly Ser Ile<br>115 120 125 | | 384 |
| ttc gat cac aca gcg gtt ggc ctg gcg ctg aca ggt tat tca atg cct<br>Phe Asp His Thr Ala Val Gly Leu Ala Leu Thr Gly Tyr Ser Met Pro<br>130 135 140 | | 432 |

```
atc ttc tgg tgg ggc atg atg ctg atc atg ctg gtt tcg gtg cac tgg      480
Ile Phe Trp Trp Gly Met Met Leu Ile Met Leu Val Ser Val His Trp
145                 150                 155                 160 aac ctg acg ccc gtc tcc ggt cgc gtg agc gat atg gtg ttc ctc gat      528
Asn Leu Thr Pro Val Ser Gly Arg Val Ser Asp Met Val Phe Leu Asp
                165                 170                 175 gac tcc aat ccg tta acc ggt ttt atg cta atc gac acc gcc atc tgg      576
Asp Ser Asn Pro Leu Thr Gly Phe Met Leu Ile Asp Thr Ala Ile Trp
            180                 185                 190 ggt gaa gac ggc aac ttt atc gat gcc gtc gcc cat atg atc ttg cct      624
Gly Glu Asp Gly Asn Phe Ile Asp Ala Val Ala His Met Ile Leu Pro
        195                 200                 205 gcc att gtg ctg ggt act att ccg ctg gcg gtc att gtg cgt atg aca      672
Ala Ile Val Leu Gly Thr Ile Pro Leu Ala Val Ile Val Arg Met Thr
    210                 215                 220 cgc tcc tcg atg ctg gaa gtg ctg ggc gag gat tac atc cgc acc gcg      720
Arg Ser Ser Met Leu Glu Val Leu Gly Glu Asp Tyr Ile Arg Thr Ala
225                 230                 235                 240 cgc gcc aaa ggg cta acc cgc atg cgg gtg att atc gtc cat gcg ctg      768
Arg Ala Lys Gly Leu Thr Arg Met Arg Val Ile Ile Val His Ala Leu
                245                 250                 255 cgt aac gcg atg ctg ccg gtg gtg acc gtt atc ggc ctg cag gtg gga      816
Arg Asn Ala Met Leu Pro Val Val Thr Val Ile Gly Leu Gln Val Gly
            260                 265                 270 aca ttg ctg gcg ggg gcg att ctg acc gaa acc atc ttc tcg tgg ccc      864
Thr Leu Leu Ala Gly Ala Ile Leu Thr Glu Thr Ile Phe Ser Trp Pro
        275                 280                 285 ggt ctg gga cgc tgg ttg att gac gca ctg caa cgc cgc gac tat ccg      912
Gly Leu Gly Arg Trp Leu Ile Asp Ala Leu Gln Arg Arg Asp Tyr Pro
    290                 295                 300 gta gtg cag ggc ggc gta ttg ctg gtg gcg acg atg att atc ctc gtc      960
Val Val Gln Gly Gly Val Leu Leu Val Ala Thr Met Ile Ile Leu Val
305                 310                 315                 320 aac ttg ctg gtc gat ctg ctg tac ggc gtg gtg aac ccg cgt att cgt     1008
Asn Leu Leu Val Asp Leu Leu Tyr Gly Val Val Asn Pro Arg Ile Arg
                325                 330                 335 cat aag aag                                                         1017
His Lys Lys <210> SEQ ID NO 61
<211> LENGTH: 900
<212> TYPE: DNA
<213> ORGANISM: Escherichia coli

<400> SEQUENCE: 61 atg tca cag gtt act gaa aat aaa gtg att agc gca ccg gtg ccg atg       48
Met Ser Gln Val Thr Glu Asn Lys Val Ile Ser Ala Pro Val Pro Met
1               5                   10                  15 acc ccg tta cag gag ttc tgg cac tat ttt aaa cgc aac aaa ggc gcg       96
Thr Pro Leu Gln Glu Phe Trp His Tyr Phe Lys Arg Asn Lys Gly Ala
            20                  25                  30 gtc gtc ggg ctg gtt tac gtc gtc atc gtg ctg ttc atc gcg atc ttt      144
Val Val Gly Leu Val Tyr Val Val Ile Val Leu Phe Ile Ala Ile Phe
        35                  40                  45 gcc aac tgg att gca ccc tat aac ccg gcg gaa cag ttc cgc gat gca      192
Ala Asn Trp Ile Ala Pro Tyr Asn Pro Ala Glu Gln Phe Arg Asp Ala
    50                  55                  60 ctg ctc gcc ccg cca gcc tgg cag gaa ggc ggc agc atg gcg cac ttg      240
Leu Leu Ala Pro Pro Ala Trp Gln Glu Gly Gly Ser Met Ala His Leu
65                  70                  75                  80 ctg ggc acc gat gac gta ggc cgt gat gtg ctg tcg cgc ctg atg tac      288
```

```
                Leu Gly Thr Asp Asp Val Gly Arg Asp Val Leu Ser Arg Leu Met Tyr
                                85                  90                  95 ggt gcg cgc ctg tcg ctg ctg gtt ggc tgt ctg gta gtt gtg tta tcg       336
Gly Ala Arg Leu Ser Leu Leu Val Gly Cys Leu Val Val Val Leu Ser
            100                 105                 110 ctg att atg ggc gtt att ctc ggc ctg atc gcc ggt tac ttt ggc ggc       384
Leu Ile Met Gly Val Ile Leu Gly Leu Ile Ala Gly Tyr Phe Gly Gly
            115                 120                 125 ctg gtc gat aac atc att atg cgc gtc gtc gat atc atg ctg gcg ctg       432
Leu Val Asp Asn Ile Ile Met Arg Val Val Asp Ile Met Leu Ala Leu
130                 135                 140 cca agt ctg ctg ctg gcg ctg gtg ctg gtg gca att ttc ggc ccg tcg       480
Pro Ser Leu Leu Leu Ala Leu Val Leu Val Ala Ile Phe Gly Pro Ser
145                 150                 155                 160 att ggt aac gcc gcg ctg gca ctg acc ttc gtt gcc ttg ccg cac tat       528
Ile Gly Asn Ala Ala Leu Ala Leu Thr Phe Val Ala Leu Pro His Tyr
                165                 170                 175 gtg cgc tta acc cgc gcc gcc gtg ctg gtg gaa gtt aac cgc gat tac       576
Val Arg Leu Thr Arg Ala Ala Val Leu Val Glu Val Asn Arg Asp Tyr
            180                 185                 190 gtc acc gcg tct cgc gtg gcg ggt gcc ggg gcg atg cgt cag atg ttt       624
Val Thr Ala Ser Arg Val Ala Gly Ala Gly Ala Met Arg Gln Met Phe
            195                 200                 205 att aac atc ttc ccg aac tgc ctt gcg ccg ctg att gtt cag gcg tcg       672
Ile Asn Ile Phe Pro Asn Cys Leu Ala Pro Leu Ile Val Gln Ala Ser
210                 215                 220 ctc ggt ttc tct aac gcc att ctc gat atg gct gct ctt ggt ttc ctc       720
Leu Gly Phe Ser Asn Ala Ile Leu Asp Met Ala Ala Leu Gly Phe Leu
225                 230                 235                 240 ggc atg ggg gca cag ccg cca acg cct gag tgg ggc acc atg ctc tcc       768
Gly Met Gly Ala Gln Pro Pro Thr Pro Glu Trp Gly Thr Met Leu Ser
                245                 250                 255 gac gtg ttg cag ttc gcg caa agc gcc tgg tgg gtc gtg acc ttc ccg       816
Asp Val Leu Gln Phe Ala Gln Ser Ala Trp Trp Val Val Thr Phe Pro
            260                 265                 270 ggt ctg gcg atc ctg ctg acg gtg ctg gca ttt aac ctg atg ggt gac       864
Gly Leu Ala Ile Leu Leu Thr Val Leu Ala Phe Asn Leu Met Gly Asp
            275                 280                 285 ggt ctg cgt gac gcg ctc gat ccc aaa ctg aag cag                       900
Gly Leu Arg Asp Ala Leu Asp Pro Lys Leu Lys Gln
290                 295                 300

<210> SEQ ID NO 62
<211> LENGTH: 981
<212> TYPE: DNA
<213> ORGANISM: Escherichia coli

<400> SEQUENCE: 62 atg gcg tta tta aat gta gat aaa tta tcg gtg cat ttc ggc gac gaa        48
Met Ala Leu Leu Asn Val Asp Lys Leu Ser Val His Phe Gly Asp Glu
1               5                   10                  15 agc gcg ccg ttc cgc gcc gta gac cgc atc agc tac agc gta aaa cag        96
Ser Ala Pro Phe Arg Ala Val Asp Arg Ile Ser Tyr Ser Val Lys Gln
                20                  25                  30 ggc gaa gtg gtc ggg att gtg ggt gag tcc ggc tcc ggt aag tcg gtc       144
Gly Glu Val Val Gly Ile Val Gly Glu Ser Gly Ser Gly Lys Ser Val
            35                  40                  45 agt tca ctg gcg att atg ggg ctg att gat tat ccg ggc cgc gta atg       192
Ser Ser Leu Ala Ile Met Gly Leu Ile Asp Tyr Pro Gly Arg Val Met
50                  55                  60 gca gaa aaa ctg gag ttt aac ggc cag gat ttg cag cgt atc tca gaa       240
```

```
Ala Glu Lys Leu Glu Phe Asn Gly Gln Asp Leu Gln Arg Ile Ser Glu
 65                  70                  75                  80 aaa gag cgc cgc aac ctg gtg ggt gcc gaa gtg gcg atg atc ttc cag      288
Lys Glu Arg Arg Asn Leu Val Gly Ala Glu Val Ala Met Ile Phe Gln
                 85                  90                  95 gac ccg atg acc agc ctt aac ccg tgc tac acc gtg ggt ttc cag att      336
Asp Pro Met Thr Ser Leu Asn Pro Cys Tyr Thr Val Gly Phe Gln Ile
            100                 105                 110 atg gaa gcg att aag gtg cat cag ggc aac aaa agt acc cgc cgt          384
Met Glu Ala Ile Lys Val His Gln Gly Gly Asn Lys Ser Thr Arg Arg
        115                 120                 125 cag cga gcg att gac ctg ctg aat cag gtc ggt att ccc gat ccg gca      432
Gln Arg Ala Ile Asp Leu Leu Asn Gln Val Gly Ile Pro Asp Pro Ala
    130                 135                 140 tcg cgt ctg gat gtt tac ccg cat cag ctt tcc ggc ggc atg agc cag      480
Ser Arg Leu Asp Val Tyr Pro His Gln Leu Ser Gly Gly Met Ser Gln
145                 150                 155                 160 cgc gtg atg atc gcc atg gcg att gcc tgt cgg cca aaa ctg ctg att      528
Arg Val Met Ile Ala Met Ala Ile Ala Cys Arg Pro Lys Leu Leu Ile
                165                 170                 175 gcc gat gaa ccg acc acc gcg ctg gac gtg acc att cag gcg caa atc      576
Ala Asp Glu Pro Thr Thr Ala Leu Asp Val Thr Ile Gln Ala Gln Ile
            180                 185                 190 atc gaa cta ctg ctg gag cta cag cag aaa gag aac atg gcg ctg gtg      624
Ile Glu Leu Leu Leu Glu Leu Gln Gln Lys Glu Asn Met Ala Leu Val
        195                 200                 205 tta att acc cat gac ctg gcg ctg gtg gcg gaa gcg gca cat aaa atc      672
Leu Ile Thr His Asp Leu Ala Leu Val Ala Glu Ala Ala His Lys Ile
    210                 215                 220 atc gtg atg tat gca ggc cag gtg gtg gaa acc ggt gat gcg cac gcc      720
Ile Val Met Tyr Ala Gly Gln Val Val Glu Thr Gly Asp Ala His Ala
225                 230                 235                 240 atc ttc cat gcg ccg cgt cac ccg tat act cag gca ttg ctg cgt gcg      768
Ile Phe His Ala Pro Arg His Pro Tyr Thr Gln Ala Leu Leu Arg Ala
                245                 250                 255 ctg cca gaa ttt gct cag gac aaa gaa cgt ctg gcg tcg ttg cca ggt      816
Leu Pro Glu Phe Ala Gln Asp Lys Glu Arg Leu Ala Ser Leu Pro Gly
            260                 265                 270 gtc gtt ccc ggc aag tac gac cgc ccg aac ggc tgc ctg ctt aac ccg      864
Val Val Pro Gly Lys Tyr Asp Arg Pro Asn Gly Cys Leu Leu Asn Pro
        275                 280                 285 cgc tgc ccc tat gcc act gac aga tgt cgc gct gaa gaa ccg gcg ctg      912
Arg Cys Pro Tyr Ala Thr Asp Arg Cys Arg Ala Glu Glu Pro Ala Leu
    290                 295                 300 aat atg ctc gct gac ggg cgt cag tcc aaa tgc cat tac cca ctt gat      960
Asn Met Leu Ala Asp Gly Arg Gln Ser Lys Cys His Tyr Pro Leu Asp
305                 310                 315                 320 gat gcc ggg agg ccg aca cta                                          981
Asp Ala Gly Arg Pro Thr Leu
                325

<210> SEQ ID NO 63
<211> LENGTH: 1002
<212> TYPE: DNA
<213> ORGANISM: Escherichia coli

<400> SEQUENCE: 63 atg agt acg caa gag gcc acc ctg caa caa ccg ctg ttg cag gct atc       48
Met Ser Thr Gln Glu Ala Thr Leu Gln Gln Pro Leu Leu Gln Ala Ile
  1               5                  10                  15 gac ctg aaa aaa cat tat ccg gtg aag aaa ggc atg ttc gcg ccg gaa       96
```

```
                  -continued

Asp Leu Lys Lys His Tyr Pro Val Lys Lys Gly Met Phe Ala Pro Glu
             20                  25                  30 cgt ctg gtt aaa gcg ctg gat ggc gtt tcg ttt aac ctt gaa cgt ggc    144
Arg Leu Val Lys Ala Leu Asp Gly Val Ser Phe Asn Leu Glu Arg Gly
         35                  40                  45 aaa acg ctg gca gta gtg ggc gaa tct ggc tgc ggt aaa tcg acc ctc    192
Lys Thr Leu Ala Val Val Gly Glu Ser Gly Cys Gly Lys Ser Thr Leu
     50                  55                  60 ggt cgg ttg ctg acg atg att gaa atg ccc acc ggt ggc gag ctg tat    240
Gly Arg Leu Leu Thr Met Ile Glu Met Pro Thr Gly Gly Glu Leu Tyr
 65                  70                  75                  80 tac cag ggg cag gat ctg ctt aag cac gat ccg cag gcg cag aag ctg    288
Tyr Gln Gly Gln Asp Leu Leu Lys His Asp Pro Gln Ala Gln Lys Leu
                 85                  90                  95 cgt cgg cag aaa atc cag atc gtc ttc cag aac cct tac ggt tcg ctg    336
Arg Arg Gln Lys Ile Gln Ile Val Phe Gln Asn Pro Tyr Gly Ser Leu
            100                 105                 110 aat ccg cgt aaa aaa gtc ggg caa att ctt gaa gag ccg ctg ctg atc    384
Asn Pro Arg Lys Lys Val Gly Gln Ile Leu Glu Glu Pro Leu Leu Ile
        115                 120                 125 aac acc agc tta agc aaa gaa cag cgt cgg gaa aaa gcc ctg tcg atg    432
Asn Thr Ser Leu Ser Lys Glu Gln Arg Arg Glu Lys Ala Leu Ser Met
    130                 135                 140 atg gcg aaa gtc ggc ctg aaa acc gag cac tat gac cgc tat ccg cat    480
Met Ala Lys Val Gly Leu Lys Thr Glu His Tyr Asp Arg Tyr Pro His
145                 150                 155                 160 atg ttc tcc ggc ggt cag cgt cag cgt atc gcc atc gcc cgt ggt ctg    528
Met Phe Ser Gly Gly Gln Arg Gln Arg Ile Ala Ile Ala Arg Gly Leu
                165                 170                 175 atg ctc gac ccg gat gtg gtg att gcc gat gaa ccg gtt tcc gcg ctg    576
Met Leu Asp Pro Asp Val Val Ile Ala Asp Glu Pro Val Ser Ala Leu
            180                 185                 190 gat gtt tca gtg cgc gcg cag gtg ctg aat ctg atg atg gat ttg cag    624
Asp Val Ser Val Arg Ala Gln Val Leu Asn Leu Met Met Asp Leu Gln
        195                 200                 205 cag gag ttg ggg ctg tct tat gtc ttt atc tcc cac gac ctg tcg gtg    672
Gln Glu Leu Gly Leu Ser Tyr Val Phe Ile Ser His Asp Leu Ser Val
    210                 215                 220 gtg gag cac att gct gat gaa gtg atg gtg atg tac ctg ggc cgc tgc    720
Val Glu His Ile Ala Asp Glu Val Met Val Met Tyr Leu Gly Arg Cys
225                 230                 235                 240 gtg gag aag gga acg aaa gac caa atc ttc aat aac ccg cgc cat ccg    768
Val Glu Lys Gly Thr Lys Asp Gln Ile Phe Asn Asn Pro Arg His Pro
                245                 250                 255 tac act cag gcg cta ctt tcc gcg acg ccg cgc ctg aac ccg gac gat    816
Tyr Thr Gln Ala Leu Leu Ser Ala Thr Pro Arg Leu Asn Pro Asp Asp
            260                 265                 270 cgc cgc gag cgc atc aag ctc agc ggt gaa cta cca agc cca ctg aat    864
Arg Arg Glu Arg Ile Lys Leu Ser Gly Glu Leu Pro Ser Pro Leu Asn
        275                 280                 285 cca ccg ccg ggt tgc gcc ttc aac gcc cgc tgt cgt cgg cgc ttc ggc    912
Pro Pro Pro Gly Cys Ala Phe Asn Ala Arg Cys Arg Arg Arg Phe Gly
    290                 295                 300 ccc tgc acc cag ttg cag ccg cag cta aaa gac tac ggc ggt caa ctg    960
Pro Cys Thr Gln Leu Gln Pro Gln Leu Lys Asp Tyr Gly Gly Gln Leu
305                 310                 315                 320 gta gct tgt ttt gct gtt gat cag gat gaa aat ccg cag cgt           1002
Val Ala Cys Phe Ala Val Asp Gln Asp Glu Asn Pro Gln Arg
                325                 330
```

<210> SEQ ID NO 64
<211> LENGTH: 56
<212> TYPE: DNA
<213> ORGANISM: Artificial Sequence
<220> FEATURE:
<223> OTHER INFORMATION: Synthetic DNA

<400> SEQUENCE: 64
ctaaccctgt gacctgcaat actgttttgc gggtgagtgt aggctggagc tgcttc    56

<210> SEQ ID NO 65
<211> LENGTH: 56
<212> TYPE: DNA
<213> ORGANISM: Artificial Sequence
<220> FEATURE:
<223> OTHER INFORMATION: Synthetic DNA

<400> SEQUENCE: 65
gaaactgccg gaaggcgatt aaacgccatc cggcagcata tgaatatcct ccttag    56

<210> SEQ ID NO 66
<211> LENGTH: 56
<212> TYPE: DNA
<213> ORGANISM: Artificial Sequence
<220> FEATURE:
<223> OTHER INFORMATION: Synthetic DNA

<400> SEQUENCE: 66
ttacgcaaca ggaatagact gaacaccaga ctctatgtgt aggctggagc tgcttc    56

<210> SEQ ID NO 67
<211> LENGTH: 56
<212> TYPE: DNA
<213> ORGANISM: Artificial Sequence
<220> FEATURE:
<223> OTHER INFORMATION: Synthetic DNA

<400> SEQUENCE: 67
agaaaacagg ggtaaattcc ccgaatggcg gcgctacata tgaatatcct ccttag    56

<210> SEQ ID NO 68
<211> LENGTH: 56
<212> TYPE: DNA
<213> ORGANISM: Artificial Sequence
<220> FEATURE:
<223> OTHER INFORMATION: Synthetic DNA

<400> SEQUENCE: 68
atggagttta gtgtaaaaag cggtagcccg gagaaagtgt aggctggagc tgcttc    56

<210> SEQ ID NO 69
<211> LENGTH: 56
<212> TYPE: DNA
<213> ORGANISM: Artificial Sequence
<220> FEATURE:
<223> OTHER INFORMATION: Synthetic DNA

<400> SEQUENCE: 69
ttactcttcg ccgttaaacc cagcgcggtt taacagcata tgaatatcct ccttag    56

<210> SEQ ID NO 70
<211> LENGTH: 56
<212> TYPE: DNA
<213> ORGANISM: Artificial Sequence
<220> FEATURE:
<223> OTHER INFORMATION: Synthetic DNA

<400> SEQUENCE: 70
atgacagaag cgatgaagat taccctctct acccaagtgt aggctggagc tgcttc      56

<210> SEQ ID NO 71
<211> LENGTH: 56
<212> TYPE: DNA
<213> ORGANISM: Artificial Sequence
<220> FEATURE:
<223> OTHER INFORMATION: Synthetic DNA

<400> SEQUENCE: 71
ttacgccgtt aacagattag ctatcgtgcg cacacccata tgaatatcct ccttag      56

<210> SEQ ID NO 72
<211> LENGTH: 56
<212> TYPE: DNA
<213> ORGANISM: Artificial Sequence
<220> FEATURE:
<223> OTHER INFORMATION: Synthetic DNA

<400> SEQUENCE: 72
gcatccccac ctcataacgt tgacccgacc gggcaagtgt aggctggagc tgcttc      56

<210> SEQ ID NO 73
<211> LENGTH: 56
<212> TYPE: DNA
<213> ORGANISM: Artificial Sequence
<220> FEATURE:
<223> OTHER INFORMATION: Synthetic DNA

<400> SEQUENCE: 73
ctgtacggca ttttgctatg cttgtcgcca ctgttgcata tgaatatcct ccttag      56

<210> SEQ ID NO 74
<211> LENGTH: 21
<212> TYPE: DNA
<213> ORGANISM: Artificial Sequence
<220> FEATURE:
<223> OTHER INFORMATION: Synthetic DNA

<400> SEQUENCE: 74
gtgtctgaac tgtctcaatt a                                            21

<210> SEQ ID NO 75
<211> LENGTH: 21
<212> TYPE: DNA
<213> ORGANISM: Artificial Sequence
<220> FEATURE:
<223> OTHER INFORMATION: Synthetic DNA

<400> SEQUENCE: 75
cggaatttct ttcagcagtt c                                            21

<210> SEQ ID NO 76
<211> LENGTH: 21
<212> TYPE: DNA
<213> ORGANISM: Artificial Sequence
<220> FEATURE:
<223> OTHER INFORMATION: Synthetic DNA

<400> SEQUENCE: 76
atgactcaac agccacaagc c                                            21

<210> SEQ ID NO 77
<211> LENGTH: 21
<212> TYPE: DNA
<213> ORGANISM: Artificial Sequence

```
<220> FEATURE:
<223> OTHER INFORMATION: Synthetic DNA

<400> SEQUENCE: 77
tgctttagtt atcttctcgt a                                        21

<210> SEQ ID NO 78
<211> LENGTH: 21
<212> TYPE: DNA
<213> ORGANISM: Artificial Sequence
<220> FEATURE:
<223> OTHER INFORMATION: Synthetic DNA

<400> SEQUENCE: 78
agtgcctgca tcgtcgtggg c                                        21

<210> SEQ ID NO 79
<211> LENGTH: 21
<212> TYPE: DNA
<213> ORGANISM: Artificial Sequence
<220> FEATURE:
<223> OTHER INFORMATION: Synthetic DNA

<400> SEQUENCE: 79
ggcgcctttt gctttaccag a                                        21

<210> SEQ ID NO 80
<211> LENGTH: 21
<212> TYPE: DNA
<213> ORGANISM: Artificial Sequence
<220> FEATURE:
<223> OTHER INFORMATION: Synthetic DNA

<400> SEQUENCE: 80
gacgcgcgct ggggagaaaa a                                        21

<210> SEQ ID NO 81
<211> LENGTH: 21
<212> TYPE: DNA
<213> ORGANISM: Artificial Sequence
<220> FEATURE:
<223> OTHER INFORMATION: Synthetic DNA

<400> SEQUENCE: 81
cgtagcgccc gcagaccact g                                        21

<210> SEQ ID NO 82
<211> LENGTH: 21
<212> TYPE: DNA
<213> ORGANISM: Artificial Sequence
<220> FEATURE:
<223> OTHER INFORMATION: Synthetic DNA

<400> SEQUENCE: 82
atgcgtattt ccttgaaaaa g                                        21

<210> SEQ ID NO 83
<211> LENGTH: 21
<212> TYPE: DNA
<213> ORGANISM: Artificial Sequence
<220> FEATURE:
<223> OTHER INFORMATION: Synthetic DNA

<400> SEQUENCE: 83
ttattcgata gagacgtttt c                                        21
```

<210> SEQ ID NO 84
<211> LENGTH: 29
<212> TYPE: DNA
<213> ORGANISM: Artificial Sequence
<220> FEATURE:
<223> OTHER INFORMATION: Synthetic DNA

<400> SEQUENCE: 84
tacactcgag attaaagagg agaaattaa                                29

<210> SEQ ID NO 85
<211> LENGTH: 30
<212> TYPE: DNA
<213> ORGANISM: Artificial Sequence
<220> FEATURE:
<223> OTHER INFORMATION: Synthetic DNA

<400> SEQUENCE: 85
ttaggatcct catactggca gcacatactt                               30

<210> SEQ ID NO 86
<211> LENGTH: 24
<212> TYPE: DNA
<213> ORGANISM: Artificial Sequence
<220> FEATURE:
<223> OTHER INFORMATION: Synthetic DNA

<400> SEQUENCE: 86
caagaattct catgtttgac agct                                     24

<210> SEQ ID NO 87
<211> LENGTH: 28
<212> TYPE: DNA
<213> ORGANISM: Artificial Sequence
<220> FEATURE:
<223> OTHER INFORMATION: Synthetic DNA

<400> SEQUENCE: 87
taactcgaga ttccctttt acgtgaac                                  28

<210> SEQ ID NO 88
<211> LENGTH: 56
<212> TYPE: DNA
<213> ORGANISM: Artificial Sequence
<220> FEATURE:
<223> OTHER INFORMATION: Synthetic DNA

<400> SEQUENCE: 88
gttgagcggc tgccagagcc tttagccgag gaatcagtgt aggctggagc tgcttc   56

<210> SEQ ID NO 89
<211> LENGTH: 56
<212> TYPE: DNA
<213> ORGANISM: Artificial Sequence
<220> FEATURE:
<223> OTHER INFORMATION: Synthetic DNA

<400> SEQUENCE: 89
ctgccagctt gcccgcacca gttcacgctc tgcggtcata tgaatatcct ccttag   56

<210> SEQ ID NO 90
<211> LENGTH: 56
<212> TYPE: DNA
<213> ORGANISM: Artificial Sequence
<220> FEATURE:
<223> OTHER INFORMATION: Synthetic DNA

<400> SEQUENCE: 90

```
ctggacgatg tccgcgaagc actggccgaa gtcggtgtgt aggctggagc tgcttc          56
```

<210> SEQ ID NO 91
<211> LENGTH: 56
<212> TYPE: DNA
<213> ORGANISM: Artificial Sequence
<220> FEATURE:
<223> OTHER INFORMATION: Synthetic DNA

<400> SEQUENCE: 91

```
tgccgcgtcg tcctcttcac cggtacggat gcgaatcata tgaatatcct ccttag          56
```

<210> SEQ ID NO 92
<211> LENGTH: 27
<212> TYPE: DNA
<213> ORGANISM: Artificial Sequence
<220> FEATURE:
<223> OTHER INFORMATION: Synthetic DNA

<400> SEQUENCE: 92

```
agccaaccgc cgcaggccga cgaatgg                                          27
```

<210> SEQ ID NO 93
<211> LENGTH: 27
<212> TYPE: DNA
<213> ORGANISM: Artificial Sequence
<220> FEATURE:
<223> OTHER INFORMATION: Synthetic DNA

<400> SEQUENCE: 93

```
ggtcagcgcc atcgcttcct gctcttc                                          27
```

<210> SEQ ID NO 94
<211> LENGTH: 27
<212> TYPE: DNA
<213> ORGANISM: Artificial Sequence
<220> FEATURE:
<223> OTHER INFORMATION: Synthetic DNA

<400> SEQUENCE: 94

```
tcccgacacg agctggatgc aaacgat                                          27
```

<210> SEQ ID NO 95
<211> LENGTH: 27
<212> TYPE: DNA
<213> ORGANISM: Artificial Sequence
<220> FEATURE:
<223> OTHER INFORMATION: Synthetic DNA

<400> SEQUENCE: 95

```
atggaaacat ccggcaaccc ttgacgc                                          27
```

<210> SEQ ID NO 96
<211> LENGTH: 30
<212> TYPE: DNA
<213> ORGANISM: Artificial Sequence
<220> FEATURE:
<223> OTHER INFORMATION: Synthetic DNA

<400> SEQUENCE: 96

```
aaaggatccc atatacagga ggagacagat                                       30
```

<210> SEQ ID NO 97
<211> LENGTH: 30
<212> TYPE: DNA
<213> ORGANISM: Artificial Sequence

```
<220> FEATURE:
<223> OTHER INFORMATION: Synthetic DNA

<400> SEQUENCE: 97
tatggatcct taagcacccg ccacagatga                              30

<210> SEQ ID NO 98
<211> LENGTH: 33
<212> TYPE: DNA
<213> ORGANISM: Artificial Sequence
<220> FEATURE:
<223> OTHER INFORMATION: Synthetic DNA

<400> SEQUENCE: 98
tatatcgatc aaaaaggcaa cactatgaca tcg                           33

<210> SEQ ID NO 99
<211> LENGTH: 33
<212> TYPE: DNA
<213> ORGANISM: Artificial Sequence
<220> FEATURE:
<223> OTHER INFORMATION: Synthetic DNA

<400> SEQUENCE: 99
ttaggatcct catcaggttg gatcaacagg cac                           33

<210> SEQ ID NO 100
<211> LENGTH: 30
<212> TYPE: DNA
<213> ORGANISM: Artificial Sequence
<220> FEATURE:
<223> OTHER INFORMATION: Synthetic DNA

<400> SEQUENCE: 100
actagatcta acaggatcgc catcatgcaa                              30

<210> SEQ ID NO 101
<211> LENGTH: 33
<212> TYPE: DNA
<213> ORGANISM: Artificial Sequence
<220> FEATURE:
<223> OTHER INFORMATION: Synthetic DNA

<400> SEQUENCE: 101
ataggatcct taagccacgc gagccgtcag ctg                           33

<210> SEQ ID NO 102
<211> LENGTH: 30
<212> TYPE: DNA
<213> ORGANISM: Artificial Sequence
<220> FEATURE:
<223> OTHER INFORMATION: Synthetic DNA

<400> SEQUENCE: 102
attatcgata acaggatcgc catcatgcaa                              30

<210> SEQ ID NO 103
<211> LENGTH: 30
<212> TYPE: DNA
<213> ORGANISM: Artificial Sequence
<220> FEATURE:
<223> OTHER INFORMATION: Synthetic DNA

<400> SEQUENCE: 103
ttagcatgct tattactggc gattgtcatt                              30
```

```
<210> SEQ ID NO 104
<211> LENGTH: 56
<212> TYPE: DNA
<213> ORGANISM: Artificial Sequence
<220> FEATURE:
<223> OTHER INFORMATION: Synthetic DNA

<400> SEQUENCE: 104
ggtctcaatt tattgacgaa gaggattaag tatctcgtgt aggctggagc tgcttc        56

<210> SEQ ID NO 105
<211> LENGTH: 56
<212> TYPE: DNA
<213> ORGANISM: Artificial Sequence
<220> FEATURE:
<223> OTHER INFORMATION: Synthetic DNA

<400> SEQUENCE: 105
tgcggcgtga acgccttatc cggcctacaa gttcgtcata tgaatatcct ccttag        56

<210> SEQ ID NO 106
<211> LENGTH: 27
<212> TYPE: DNA
<213> ORGANISM: Artificial Sequence
<220> FEATURE:
<223> OTHER INFORMATION: Synthetic DNA

<400> SEQUENCE: 106
gacggtcgtt accaggtgaa tcgcgga                                        27

<210> SEQ ID NO 107
<211> LENGTH: 27
<212> TYPE: DNA
<213> ORGANISM: Artificial Sequence
<220> FEATURE:
<223> OTHER INFORMATION: Synthetic DNA

<400> SEQUENCE: 107
gaactctttc aacttctgct gctcgcc                                        27

<210> SEQ ID NO 108
<211> LENGTH: 30
<212> TYPE: DNA
<213> ORGANISM: Artificial Sequence
<220> FEATURE:
<223> OTHER INFORMATION: Synthetic DNA

<400> SEQUENCE: 108
aatatcgata aagacaggat tgggtaaatg                                     30

<210> SEQ ID NO 109
<211> LENGTH: 36
<212> TYPE: DNA
<213> ORGANISM: Artificial Sequence
<220> FEATURE:
<223> OTHER INFORMATION: Synthetic DNA

<400> SEQUENCE: 109
ttagcatgct tagaggacgc cctgctcggc gaagat                              36

<210> SEQ ID NO 110
<211> LENGTH: 29
<212> TYPE: DNA
<213> ORGANISM: Artificial Sequence
<220> FEATURE:
<223> OTHER INFORMATION: Synthetic DNA

<400> SEQUENCE: 110
```
ccgcaagatc tcgtaaaaag ggtatcgat                                29

<210> SEQ ID NO 111
<211> LENGTH: 24
<212> TYPE: DNA
<213> ORGANISM: Artificial Sequence
<220> FEATURE:
<223> OTHER INFORMATION: Synthetic DNA

<400> SEQUENCE: 111
caagaattct catgtttgac agct                                     24

<210> SEQ ID NO 112
<211> LENGTH: 30
<212> TYPE: DNA
<213> ORGANISM: Artificial Sequence
<220> FEATURE:
<223> OTHER INFORMATION: Synthetic DNA

<400> SEQUENCE: 112
ttaggatcct catactggca gcacatactt                               30

<210> SEQ ID NO 113
<211> LENGTH: 56
<212> TYPE: DNA
<213> ORGANISM: Artificial Sequence
<220> FEATURE:
<223> OTHER INFORMATION: Synthetic DNA

<400> SEQUENCE: 113
ctttaggcat tccttcgaac aagatgcaag aaaagagtgt aggctggagc tgcttc  56

<210> SEQ ID NO 114
<211> LENGTH: 56
<212> TYPE: DNA
<213> ORGANISM: Artificial Sequence
<220> FEATURE:
<223> OTHER INFORMATION: Synthetic DNA

<400> SEQUENCE: 114
atagttagtt ccccgtcctg aatcttgaga aacagacata tgaatatcct ccttag  56

<210> SEQ ID NO 115
<211> LENGTH: 27
<212> TYPE: DNA
<213> ORGANISM: Artificial Sequence
<220> FEATURE:
<223> OTHER INFORMATION: Synthetic DNA

<400> SEQUENCE: 115
gaagtgactt tcccacatgc cgaagtt                                  27

<210> SEQ ID NO 116
<211> LENGTH: 36
<212> TYPE: DNA
<213> ORGANISM: Artificial Sequence
<220> FEATURE:
<223> OTHER INFORMATION: Synthetic DNA

<400> SEQUENCE: 116
gtgttgctgc cagtcatttt gatttaacgg ctgctg                        36

<210> SEQ ID NO 117
<211> LENGTH: 36
<212> TYPE: DNA
<213> ORGANISM: Artificial Sequence

```
<220> FEATURE:
<223> OTHER INFORMATION: Synthetic DNA

<400> SEQUENCE: 117
cagccgttaa atcaaaatga ctggcagcaa cactgc                                  36

<210> SEQ ID NO 118
<211> LENGTH: 27
<212> TYPE: DNA
<213> ORGANISM: Artificial Sequence
<220> FEATURE:
<223> OTHER INFORMATION: Synthetic DNA

<400> SEQUENCE: 118
gctggctaac atgaggaaat cggggtt                                            27

<210> SEQ ID NO 119
<211> LENGTH: 27
<212> TYPE: DNA
<213> ORGANISM: Artificial Sequence
<220> FEATURE:
<223> OTHER INFORMATION: Synthetic DNA

<400> SEQUENCE: 119
gtaagcccac catcgttaag ccgggta                                            27

<210> SEQ ID NO 120
<211> LENGTH: 27
<212> TYPE: DNA
<213> ORGANISM: Artificial Sequence
<220> FEATURE:
<223> OTHER INFORMATION: Synthetic DNA

<400> SEQUENCE: 120
gaccagaacc ggaccaggac gacctga                                            27

<210> SEQ ID NO 121
<211> LENGTH: 56
<212> TYPE: DNA
<213> ORGANISM: Artificial Sequence
<220> FEATURE:
<223> OTHER INFORMATION: Synthetic DNA

<400> SEQUENCE: 121
ctctacagct tcgaattccc ggaatcaccg ggcgcggtgt aggctggagc tgcttc            56

<210> SEQ ID NO 122
<211> LENGTH: 56
<212> TYPE: DNA
<213> ORGANISM: Artificial Sequence
<220> FEATURE:
<223> OTHER INFORMATION: Synthetic DNA

<400> SEQUENCE: 122
gttccagtac gtacccagcg tgttgaggaa gcgcagcata tgaatatcct ccttag            56

<210> SEQ ID NO 123
<211> LENGTH: 21
<212> TYPE: DNA
<213> ORGANISM: Artificial Sequence
<220> FEATURE:
<223> OTHER INFORMATION: Synthetic DNA

<400> SEQUENCE: 123
gaacagcgtg aagcgttgtt g                                                  21
```

```
<210> SEQ ID NO 124
<211> LENGTH: 36
<212> TYPE: DNA
<213> ORGANISM: Artificial Sequence
<220> FEATURE:
<223> OTHER INFORMATION: Synthetic DNA

<400> SEQUENCE: 124
gttgaggaag cgcaggaacg cgcccggtga ttccgg                            36

<210> SEQ ID NO 125
<211> LENGTH: 36
<212> TYPE: DNA
<213> ORGANISM: Artificial Sequence
<220> FEATURE:
<223> OTHER INFORMATION: Synthetic DNA

<400> SEQUENCE: 125
gaatcaccgg gcgcgttcct gcgcttcctc aacacg                            36

<210> SEQ ID NO 126
<211> LENGTH: 21
<212> TYPE: DNA
<213> ORGANISM: Artificial Sequence
<220> FEATURE:
<223> OTHER INFORMATION: Synthetic DNA

<400> SEQUENCE: 126
tttgagctgg gcgtgtgtgc g                                            21

<210> SEQ ID NO 127
<211> LENGTH: 56
<212> TYPE: DNA
<213> ORGANISM: Artificial Sequence
<220> FEATURE:
<223> OTHER INFORMATION: Synthetic DNA

<400> SEQUENCE: 127
aactctaaaa gcatatcgca ttcatctgga gctgatgtgt aggctggagc tgcttc      56

<210> SEQ ID NO 128
<211> LENGTH: 56
<212> TYPE: DNA
<213> ORGANISM: Artificial Sequence
<220> FEATURE:
<223> OTHER INFORMATION: Synthetic DNA

<400> SEQUENCE: 128
ctggctcatg gtttgggtcc ttgtctcttt tagagccata tgaatatcct ccttag      56

<210> SEQ ID NO 129
<211> LENGTH: 56
<212> TYPE: DNA
<213> ORGANISM: Artificial Sequence
<220> FEATURE:
<223> OTHER INFORMATION: Synthetic DNA

<400> SEQUENCE: 129
aacagccgcg tatgtgcgtt agctcgctgc gtggaagtgt aggctggagc tgcttc      56

<210> SEQ ID NO 130
<211> LENGTH: 56
<212> TYPE: DNA
<213> ORGANISM: Artificial Sequence
<220> FEATURE:
<223> OTHER INFORMATION: Synthetic DNA

<400> SEQUENCE: 130
```

```
gacttctgcg gcacgccaga tattgttcag aacgtgcata tgaatatcct ccttag          56

<210> SEQ ID NO 131
<211> LENGTH: 21
<212> TYPE: DNA
<213> ORGANISM: Artificial Sequence
<220> FEATURE:
<223> OTHER INFORMATION: Synthetic DNA

<400> SEQUENCE: 131
ttcatctgga gctgatttaa t                                                21

<210> SEQ ID NO 132
<211> LENGTH: 21
<212> TYPE: DNA
<213> ORGANISM: Artificial Sequence
<220> FEATURE:
<223> OTHER INFORMATION: Synthetic DNA

<400> SEQUENCE: 132
caggcggcag tggttgcccg t                                                21
```